US012600728B2

(12) United States Patent
Troxler et al.

(10) Patent No.: US 12,600,728 B2
(45) Date of Patent: Apr. 14, 2026

(54) INTERLEUKIN-17 INHIBITORS

(71) Applicant: Novartis AG, Basel (CH)

(72) Inventors: Thomas Josef Troxler, Laufen (CH); David Orain, Hesingue (FR); Pascal Furet, Thann (FR); Klaus Weigand, Riehen (CH); Achim Schlapbach, Basel (CH)

(73) Assignee: NOVARTIS AG, Basel (CH)

( * ) Notice: Subject to any disclaimer, the term of this patent is extended or adjusted under 35 U.S.C. 154(b) by 420 days.

(21) Appl. No.: 18/033,100

(22) PCT Filed: Nov. 1, 2021

(86) PCT No.: PCT/IB2021/060092
§ 371 (c)(1),
(2) Date: Apr. 21, 2023

(87) PCT Pub. No.: WO2022/091056
PCT Pub. Date: May 5, 2022

(65) Prior Publication Data

US 2023/0391782 A1 Dec. 7, 2023

(30) Foreign Application Priority Data

Nov. 2, 2020 (EP) .................................... 20205121

(51) Int. Cl.

| | |
|---|---|
| ***C07D 487/04*** | (2006.01) |
| ***A61K 31/4439*** | (2006.01) |
| ***A61K 31/496*** | (2006.01) |
| ***A61P 17/02*** | (2006.01) |
| ***A61P 17/06*** | (2006.01) |
| ***A61P 37/00*** | (2006.01) |
| ***C07D 401/12*** | (2006.01) |
| ***C07D 405/12*** | (2006.01) |
| ***C07D 413/12*** | (2006.01) |
| ***C07D 417/12*** | (2006.01) |

(52) U.S. Cl.

CPC ........ *C07D 487/04* (2013.01); *A61K 31/4439* (2013.01); *A61K 31/496* (2013.01); *A61P 17/02* (2018.01); *A61P 17/06* (2018.01); *A61P 37/00* (2018.01); *C07D 401/12* (2013.01); *C07D 405/12* (2013.01); *C07D 413/12* (2013.01); *C07D 417/12* (2013.01)

(58) Field of Classification Search

CPC .. C07D 487/04; C07D 401/12; C07D 405/12; C07D 413/12; C07D 417/12

See application file for complete search history.

(56) References Cited

U.S. PATENT DOCUMENTS

2023/0227427 A1* 7/2023 Martin ................. C07D 413/14
514/249

FOREIGN PATENT DOCUMENTS

| | | | |
|---|---|---|---|
| WO | 2018229079 | A1 | 12/2018 |
| WO | 2019138017 | A1 | 7/2019 |
| WO | 2020120141 | A1 | 6/2020 |
| WO | 2020127685 | A1 | 6/2020 |
| WO | 2020163554 | A1 | 8/2020 |
| WO | 2021239743 | A1 | 12/2021 |
| WO | 2021239745 | A1 | 12/2021 |

OTHER PUBLICATIONS

Deng Z, et al. Front Pharmacol. Mar. 23, 2023; 14:1124628. doi: 10.3389/fphar.2023.1124628. (Year: 2023).*
Miossec P, et al. Nat Rev Drug Discov. Oct. 2012;11(10):763-76. doi: 10.1038/nrd3794. (Year: 2012).*
Poddubnyy D. Joint Bone Spine Jan. 2023;90(1):105468. doi: 10.1016/j.jbspin.2022.105468. (Year: 2023).*
Kim BS, et al. Arch Pharm Res. Nov. 2016;39(11):1537-1547. doi: 10. 1007/s12272-016-0823-8. (Year: 2016).*
S. Chakraborty, et al. Ecancermedicalscience. 2012, 14;6:ed16. doi: 10.3332/ecancer.2012.ed16. (Year: 2012).*
Chiricozzi A, et al. Expert Opin Investig Drugs. Aug. 2013;22(8):993-1005. doi: 10.1517/13543784.2013.806483. (Year: 2013).*
W. Wilson, et al. Nat Rev Cancer 11, 393-410 (2011), doi.org/10. 1038/nrc3064, (Year: 2011).*
B. Testa, Current Opinion in Chemical Biology, vol. 13, Issue 3, Jun. 2009, pp. 338-344, doi.org/10.1016/j.cbpa.2009.04.620, (Year: 2009).*
W. Denny, Lancet Oncol. Sep. 2000;1(1):25-9. doi: 10.1016/S1470-2045(00)00006-1. (Year: 2000).*
Denny, Tumor-activated Prodrugs—A New Approach to Cancer Therapy, Cancer Investigation, 2004, 604-619, 22(4).
Krise et al., Prodrugs of Amines, 2007, 102-131.
Testa et al, Prodrugs: bridging pharmacodynamic/pharmacokinetic gaps, Current Opinion in Chemical Biology, May 25, 2009, 338-344, 13.
A study guide for students and cadets of cycles of professional development of state-financed professional educational institutions, Fundamentals of Medical Prophylaxis, 13-21, 2016.
Bastin, et al., Salt Selection and Optimisation Procedures for Pharmaceutical New Chemical Entities, Organic Process Research & Development, 4(5), 427-435, 2000.
Sergeev, A concise course in molecular biology, 10, 1975.
Belikov, Relationship between the chemical structure, properties of compounds and their action on the body, Pharmaceutical Chemistry, chapters 1.1, 1.2, 2.5, 2.6, 2.7, 2007.
Chou, Drug Combination Studies and their Synergy Quantification using the Chou-Talalay Method, Cancer Research, 70(2), 440-446, Jan. 15, 2010.
Gavrilov, Pharmaceutical Engineering. Manufacture of Drugs, 20, 2010.

(Continued)

*Primary Examiner* — James H Alstrum-Acevedo
*Assistant Examiner* — Manahil Mirghani Ali Abdalhameed
(74) *Attorney, Agent, or Firm* — Francine F. Li

(57) ABSTRACT

The present invention relates to novel pyridine-N oxide substituted 2-formamido (N-phenyl and N-pyridyl) acetamide compounds that are Interleukin-17 (IL-17) inhibitors, processes for their preparation, pharmaceutical compositions, and medicaments containing them, and their use in diseases and disorders mediated by IL-17.

4 Claims, No Drawings

Specification includes a Sequence Listing.

(56) References Cited

OTHER PUBLICATIONS

Kearns, et al., Developmental Pharmacology—Drug Disposition, Action, and Therapy in Infants and Children, The New England Journal of Medicine, 349(12), 1157-1167, Sep. 18, 2003.

Kharkevich, Doses and concentrations, Pharmacology, 10, 72-82, 2010.

Kholodov L.E., Clinical Pharmacokinetics, Medicine, 83-98; 134-138; 160; 378-380, 1985, Moscow.

* cited by examiner

SEQUENCE LISTING

```
<160> NUMBER OF SEQ ID NOS: 12

<210> SEQ ID NO 1
<211> LENGTH: 6829
<212> TYPE: DNA
<213> ORGANISM: Artificial Sequence
<220> FEATURE:
<223> OTHER INFORMATION: NPL012065 - SEQ ID NO: 1

<400> SEQUENCE: 1

ttggccatta gccatattat tcattggtta tatagcataa atcaatattg gctattggcc      60

attgcatacg ttgtatctat atcataatat gtacatttat attggctcat gtccaatatg     120

accgccatgt tggcattgat tattgactag ttattaatag taatcaatta cggggtcatt     180

agttcatagc ccatatatgg agttccgcgt tacataactt acggtaaatg gcccgcctgg     240
```

ctgaccgccc aacgaccccc gcccattgac gtcaataatg acgtatgttc ccatagtaac 300
gccaataggg actttccatt gacgtcaatg ggtggagtat ttacggtaaa ctgcccactt 360
ggcagtacat caagtgtatc atatgccaag tccgccccct attgacgtca atgacggtaa 420
atggcccgcc tggcattatg cccagtacat gaccttacgg gactttccta cttggcagta 480
catctacgta ttagtcatcg ctattaccat ggtgatgcgg ttttggcagt acaccaatgg 540
gcgtggatag cggtttgact cacggggatt tccaagtctc caccccattg acgtcaatgg 600
gagtttgttt tggcaccaaa atcaacggga ctttccaaaa tgtcgtaata accccgcccc 660
gttgacgcaa atgggcggta ggcgtgtacg gtgggaggtc tatataagca gagctcgttt 720
agtgaaccgt cagatcgcct ggagacgcca tccacgctgt tttgacctcc atagaagaca 780
ccgggaccga tccagcctcc gcggccggga acggtgcatt ggaacgcgga ttccccgtgc 840
caagagtgac gtaagtaccg cctatagagt ctataggccc acccccttgg cttcgttaga 900
acgcggctac aattaataca taaccttatg tatcatacac atacgattta ggtgacacta 960
tagaataaca tccactttgc ctttctctcc acaggtgtcc actcccaggt ccaactgcac 1020
ggaagcttct gcaggtcgac gccgccacca tgactcctgg gaagacctca ttggtgtcac 1080
tgctactgct gctgagcctg gaggccatag tgaaggcagg aatcacaatc ccacgaaatc 1140
caggatgccc aaattctgag gacaagaact tcccccggac tgtgatggtc aacctgaaca 1200
tccataaccg gaataccaat accaatccca aaaggtcctc agattactac aaccgatcca 1260
cctcaccttg gaatctccac cgcaatgagg accctgagag atatccctct gtgatctggg 1320
aggcaaagtg ccgccacttg ggctgcatca acgctgatgg gaacgtggac taccacatga 1380
actctgtccc catccagcaa gagatcctgg tcctgcgcag ggagcctcca cactgcccca 1440
actccttccg gctggagaag atactggtgt ccgtgggctg cacctgtgtc accccgattg 1500
tcgaattccg tcacgactcc taagcggccg ctctagaggg cccgtttaaa cccgctgatc 1560
agcctcgact gtgccttcta gttgccagcc atctgttgtt tgcccctccc ccgtgccttc 1620
cttgaccctg gaaggtgcca ctcccactgt cctttcctaa taaaatgagg aaattgcatc 1680
gcattgtctg agtaggtgtc attctattct ggggggtggg gtggggcagg acagcaaggg 1740
ggaggattgg gaagacaata gcaggcatgc tggggatgcg gtgggctcta tggcttctga 1800
ggcggaaaga accagctagc tcgaggcagg cagaagtatg caaagcatgc atctcaatta 1860
gtcagcaacc aggtgtggaa agtccccagg ctccccagca ggcagaagta tgcaaagcat 1920
gcatctcaat tagtcagcaa ccatagtccc gcccctaact ccgcccatcc cgcccctaac 1980
tccgcccagt tccgcccatt ctccgcccca tggctgacta attttttta tttatgcaga 2040
ggccgaggcc gcctctgcct ctgagctatt ccagaagtag tgaggaggct tttttggagg 2100
cctaggcttt tgcaaaaagc tcccgggagc ttgtatatcc attttcggat ctgatcagca 2160
cgtgttgaca attaatcatc ggcatagtat atcggcatag tataatacga caaggtgagg 2220
aactaaacca tggccaagtt gaccagtgcc gttccggtgc tcaccgcgcg cgacgtcgcc 2280
ggagcggtcg agttctggac cgaccggctc gggttctccc gggacttcgt ggaggacgac 2340
ttcgccggtg tggtccggga cgacgtgacc ctgttcatca gcgcggtcca ggaccaggtg 2400
gtgccggaca acaccctggc ctgggtgtgg gtgcgcggcc tggacgagct gtacgccgag 2460
tggtcggagg tcgtgtccac gaacttccgg gacgcctccg ggccggccat gaccgagatc 2520
ggcgagcagc cgtgggggcg ggagttcgcc ctgcgcgacc cggccggcaa ctgcgtgcac 2580
ttcgtggccg aggagcagga ctgacacgtg ctacgagatt tcgattccac cgccgccttc 2640

```
tatgaaaggt tgggcttcgg aatcgttttc cgggacgccg gctggatgat cctccagcgc   2700
ggggatctca tgctggagtt cttcgcccac cccaacttgt ttattgcagc ttataatggt   2760
tacaaataaa gcaatagcat cacaaatttc acaaataaag catttttttc actgcattct   2820
agttgtggtt tgtccaaact catcaatgta tcttatcatg tctgaatttt gcattaatga   2880
atcggccaac gcgcggggag aggcggtttg cgtattgggc gctcttccgc ttcctcgctc   2940
actgactcgc tgcgctcggt cgttcggctg cggcgagcgg tatcagctca ctcaaaggcg   3000
gtaatacggt tatccacaga atcaggggat aacgcaggaa agaacatgtg agcaaaaggc   3060
cagcaaaagg ccaggaaccg taaaaaggcc gcgttgctgg cgtttttcca taggctccgc   3120
ccccctgacg agcatcacaa aaatcgacgc tcaagtcaga ggtggcgaaa cccgacagga   3180
ctataaagat accaggcgtt tccccctgga agctccctcg tgcgctctcc tgttccgacc   3240
ctgccgctta ccggatacct gtccgccttt ctcccttcgg gaagcgtggc gctttctcaa   3300
tgctcacgct gtaggtatct cagttcggtg taggtcgttc gctccaagct gggctgtgtg   3360
cacgaacccc ccgttcagcc cgaccgctgc gccttatccg gtaactatcg tcttgagtcc   3420
aacccggtaa gacacgactt atcgccactg gcagcagcca ctggtaacag gattagcaga   3480
gcgaggtatg taggcggtgc tacagagttc ttgaagtggt ggcctaacta cggctacact   3540
agaaggacag tatttggtat ctgcgctctg ctgaagccag ttaccttcgg aaaaagagtt   3600
ggtagctctt gatccggcaa acaaaccacc gctggtagcg gtggtttttt tgtttgcaag   3660
cagcagatta cgcgcagaaa aaaaggatct caagaagatc ctttgatctt ttctacgggg   3720
tctgacgctc agtggaacga aaactcacgt taagggattt tggtcatgag attatcaaaa   3780
aggatcttca cctagatcct tttaaattaa aaatgaagtt ttaaatcaat ctaaagtata   3840
tatgagtaaa cttggtctga cagttaccaa tgcttaatca gtgaggcacc tatctcagcg   3900
atctgtctat ttcgttcatc catagttgcc tgactccccg tcgtgtagat aactacgata   3960
cgggagggct taccatctgg ccccagtgct gcaatgatac cgcgagaccc acgctcaccg   4020
gctccagatt tatcagcaat aaaccagcca gccggaaggg ccgagcgcag aagtggtcct   4080
gcaactttat ccgcctccat ccagtctatt aattgttgcc gggaagctag agtaagtagt   4140
tcgccagtta atagtttgcg caacgttgtt gccattgcta caggcatcgt ggtgtcacgc   4200
tcgtcgtttg gtatggcttc attcagctcc ggttcccaac gatcaaggcg agttacatga   4260
tcccccatgt tgtgcaaaaa agcggttagc tccttcggtc ctccgatcgt tgtcagaagt   4320
aagttggccg cagtgttatc actcatggtt atggcagcac tgcataattc tcttactgtc   4380
atgccatccg taagatgctt ttctgtgact ggtgagtact caaccaagtc attctgagaa   4440
tagtgtatgc ggcgaccgag ttgctcttgc ccggcgtcaa tacgggataa taccgcgcca   4500
catagcagaa ctttaaaagt gctcatcatt ggaaaacgtt cttcggggcg aaaactctca   4560
aggatcttac cgctgttgag atccagttcg atgtaaccca ctcgtgcacc caactgatct   4620
tcagcatctt ttactttcac cagcgtttct gggtgagcaa aaacaggaag gcaaaatgcc   4680
gcaaaaaagg gaataagggc gacacggaaa tgttgaatac tcatactctt cctttttcaa   4740
tattattgaa gcatttatca gggttattgt ctcatgagcg gatacatatt tgaatgtatt   4800
tagaaaaata aacaaatagg ggttccgcgc acatttcccc gaaaagtgcc acctgacgtc   4860
gatcgacgga tcgggagatc cgggacatgt acctcccagg ggcccaggaa gactacggga   4920
ggctacacca acgtcaatca gaggggcctg tgtagctacc gataagcgga ccctcaagag   4980
```

-continued

```
ggcattagca atagtgttta taaggccccc ttgttaaccc taaacgggta gcatatgctt   5040
cccgggtagt agtatatact atccagacta accctaattc aatagcatat gttacccaac   5100
gggaagcata tgctatcgaa ttagggttag taaaagggtc ctaaggaaca gcgatatctc   5160
ccaccccatg agctgtcacg gttttattta catggggtca ggattccacg agggtagtga   5220
accattttag tcacaagggc agtggctgaa gatcaaggag cgggcagtga actctcctga   5280
atcttcgcct gcttcttcat tctccttcgt ttagctaata gaataactgc tgagttgtga   5340
acagtaaggt gtatgtgagg tgctcgaaaa caaggtttca ggtgacgccc ccagaataaa   5400
atttggacgg ggggttcagt ggtggcattg tgctatgaca ccaatataac cctcacaaac   5460
cccttgggca ataaatacta gtgtaggaat gaaacattct gaatatcttt aacaatagaa   5520
atccatgggg tggggacaag ccgtaaagac tggatgtcca tctcacacga atttatggct   5580
atgggcaaca cataatccta gtgcaatatg atactggggt tattaagatg tgtcccaggc   5640
agggaccaag acaggtgaac catgttgtta cactctattt gtaacaaggg gaaagagagt   5700
ggacgccgac agcagcggac tccactggtt gtctctaaca cccccgaaaa ttaaacgggg   5760
ctccacgcca atggggccca taaacaaaga caagtggcca ctcttttttt tgaaattgtg   5820
gagtgggggc acgcgtcagc ccccacacgc cgccctgcgg ttttggactg taaaataagg   5880
gtgtaataac ttggctgatt gtaaccccgc taaccactgc ggtcaaacca cttgcccaca   5940
aaaccactaa tggcaccccg gggaatacct gcataagtag gtgggcgggc caagataggg   6000
gcgcgattgc tgcgatctgg aggacaaatt acacacactt gcgcctgagc gccaagcaca   6060
gggttgttgg tcctcatatt cacgaggtcg ctgagagcac ggtgggctaa tgttgccatg   6120
ggtagcatat actacccaaa tatctggata gcatatgcta tcctaatcta tatctgggta   6180
gcataggcta tcctaatcta tatctgggta gcatatgcta tcctaatcta tatctgggta   6240
gtatatgcta tcctaattta tatctgggta gcataggcta tcctaatcta tatctgggta   6300
gcatatgcta tcctaatcta tatctgggta gtatatgcta tcctaatctg tatccgggta   6360
gcatatgcta tcctaataga gattagggta gtatatgcta tcctaattta tatctgggta   6420
gcatatacta cccaaatatc tggatagcat atgctatcct aatctatatc tgggtagcat   6480
atgctatcct aatctatatc tgggtagcat aggctatcct aatctatatc tgggtagcat   6540
atgctatcct aatctatatc tgggtagtat atgctatcct aatttatatc tgggtagcat   6600
aggctatcct aatctatatc tgggtagcat atgctatcct aatctatatc tgggtagtat   6660
atgctatcct aatctgtatc cgggtagcat atgctatcct catgcatata cagtcagcat   6720
atgataccca gtagtagagt gggagtgcta tcctttgcat atgccgccac ctcccaaggg   6780
ggcgtgaatt ttcgctgctt gtccttttcc tgcatgcgga tcttcaata              6829

<210> SEQ ID NO 2
<211> LENGTH: 16
<212> TYPE: DNA
<213> ORGANISM: Artificial Sequence
<220> FEATURE:
<223> OTHER INFORMATION: Forward primer RS198 - SEQ ID NO: 2

<400> SEQUENCE: 2

catacgattt aggtga                                                    16

<210> SEQ ID NO 3
<211> LENGTH: 74
<212> TYPE: DNA
<213> ORGANISM: Artificial Sequence
```

<220> FEATURE:
<223> OTHER INFORMATION: Reverse primer RS4930 - SEQ ID NO: 3

<400> SEQUENCE: 3
cctctagagc ggccgcttag gagtcgtgac ggaattcggc cacatggtgg acaatcgggg 60
tgacacaggt gcac 74

<210> SEQ ID NO 4
<211> LENGTH: 6841
<212> TYPE: DNA
<213> ORGANISM: Artificial Sequence
<220> FEATURE:
<223> OTHER INFORMATION: NPL016964 - SEQ ID NO: 4
<220> FEATURE:
<221> NAME/KEY: APP tag
<222> LOCATION: (1515)..(1532)
<223> OTHER INFORMATION: encoding APP (a.k.a. APP6) tag.

<400> SEQUENCE: 4
ttggccatta gccatattat tcattggtta tatagcataa atcaatattg gctattggcc 60
attgcatacg ttgtatctat atcataatat gtacatttat attggctcat gtccaatatg 120
accgccatgt tggcattgat tattgactag ttattaatag taatcaatta cggggtcatt 180
agttcatagc ccatatatgg agttccgcgt tacataactt acggtaaatg gcccgcctgg 240
ctgaccgccc aacgaccccc gcccattgac gtcaataatg acgtatgttc ccatagtaac 300
gccaataggg actttccatt gacgtcaatg ggtggagtat ttacggtaaa ctgcccactt 360
ggcagtacat caagtgtatc atatgccaag tccgccccct attgacgtca atgacggtaa 420
atggcccgcc tggcattatg cccagtacat gaccttacgg gactttccta cttggcagta 480
catctacgta ttagtcatcg ctattaccat ggtgatgcgg ttttggcagt acaccaatgg 540
gcgtggatag cggtttgact cacggggatt tccaagtctc caccccattg acgtcaatgg 600
gagtttgttt tggcaccaaa atcaacggga ctttccaaaa tgtcgtaata accccgcccc 660
gttgacgcaa atgggcggta ggcgtgtacg gtgggaggtc tatataagca gagctcgttt 720
agtgaaccgt cagatcgcct ggagacgcca tccacgctgt tttgacctcc atagaagaca 780
ccgggaccga tccagcctcc gcggccggga acggtgcatt ggaacgcgga ttccccgtgc 840
caagagtgac gtaagtaccg cctatagagt ctataggccc acccccttgg cttcgttaga 900
acgcggctac aattaataca taaccttatg tatcatacac atacgattta ggtgacacta 960
tagaataaca tccactttgc ctttctctcc acaggtgtcc actcccaggt ccaactgcac 1020
ggaagcttct gcaggtcgac gccgccacca tgactcctgg gaagacctca ttggtgtcac 1080
tgctactgct gctgagcctg gaggccatag tgaaggcagg aatcacaatc ccacgaaatc 1140
caggatgccc aaattctgag gacaagaact tcccccggac tgtgatggtc aacctgaaca 1200
tccataaccg gaataccaat accaatccca aaaggtcctc agattactac aaccgatcca 1260
cctcaccttg gaatctccac cgcaatgagg accctgagag atatccctct gtgatctggg 1320
aggcaaagtg ccgccacttg ggctgcatca acgctgatgg gaacgtggac taccacatga 1380
actctgtccc catccagcaa gagatcctgg tcctgcgcag ggagcctcca cactgcccca 1440
actccttccg gctggagaag atactggtgt ccgtgggctg cacctgtgtc accccgattg 1500
tccaccatgt ggccgaattc cgtcacgact cctaagcggc cgctctagag ggcccgttta 1560
aacccgctga tcagcctcga ctgtgccttc tagttgccag ccatctgttg tttgcccctc 1620
ccccgtgcct tccttgaccc tggaaggtgc cactcccact gtcctttcct aataaaatga 1680

```
ggaaattgca tcgcattgtc tgagtaggtg tcattctatt ctggggggtg gggtggggca   1740
ggacagcaag ggggaggatt gggaagacaa tagcaggcat gctggggatg cggtgggctc   1800
tatggcttct gaggcggaaa gaaccagcta gctcgaggca ggcagaagta tgcaaagcat   1860
gcatctcaat tagtcagcaa ccaggtgtgg aaagtcccca ggctccccag caggcagaag   1920
tatgcaaagc atgcatctca attagtcagc aaccatagtc ccgcccctaa ctccgcccat   1980
cccgccccta actccgccca gttccgccca ttctccgccc catggctgac taattttttt   2040
tatttatgca gaggccgagg ccgcctctgc ctctgagcta ttccagaagt agtgaggagg   2100
cttttttgga ggcctaggct tttgcaaaaa gctcccggga gcttgtatat ccattttcgg   2160
atctgatcag cacgtgttga caattaatca tcggcatagt atatcggcat agtataatac   2220
gacaaggtga ggaactaaac catggccaag ttgaccagtg ccgttccggt gctcaccgcg   2280
cgcgacgtcg ccggagcggt cgagttctgg accgaccggc tcgggttctc ccgggacttc   2340
gtggaggacg acttcgccgg tgtggtccgg gacgacgtga ccctgttcat cagcgcggtc   2400
caggaccagg tggtgccgga caacaccctg gcctgggtgt gggtgcgcgg cctggacgag   2460
ctgtacgccg agtggtcgga ggtcgtgtcc acgaacttcc gggacgcctc cgggccggcc   2520
atgaccgaga tcggcgagca gccgtggggg cgggagttcg ccctgcgcga cccggccggc   2580
aactgcgtgc acttcgtggc cgaggagcag gactgacacg tgctacgaga tttcgattcc   2640
accgccgcct tctatgaaag gttgggcttc ggaatcgttt tccgggacgc cggctggatg   2700
atcctccagc gcggggatct catgctggag ttcttcgccc accccaactt gtttattgca   2760
gcttataatg gttacaaata aagcaatagc atcacaaatt tcacaaataa agcatttttt   2820
tcactgcatt ctagttgtgg tttgtccaaa ctcatcaatg tatcttatca tgtctgaatt   2880
ttgcattaat gaatcggcca acgcgcgggg agaggcggtt tgcgtattgg gcgctcttcc   2940
gcttcctcgc tcactgactc gctgcgctcg gtcgttcggc tgcggcgagc ggtatcagct   3000
cactcaaagg cggtaatacg gttatccaca gaatcagggg ataacgcagg aaagaacatg   3060
tgagcaaaag gccagcaaaa ggccaggaac cgtaaaaagg ccgcgttgct ggcgtttttc   3120
cataggctcc gcccccctga cgagcatcac aaaaatcgac gctcaagtca gaggtggcga   3180
aacccgacag gactataaag ataccaggcg tttccccctg gaagctccct cgtgcgctct   3240
cctgttccga ccctgccgct taccggatac ctgtccgcct ttctcccttc gggaagcgtg   3300
gcgctttctc aatgctcacg ctgtaggtat ctcagttcgg tgtaggtcgt tcgctccaag   3360
ctgggctgtg tgcacgaacc ccccgttcag cccgaccgct gcgccttatc cggtaactat   3420
cgtcttgagt ccaacccggt aagacacgac ttatcgccac tggcagcagc cactggtaac   3480
aggattagca gagcgaggta tgtaggcggt gctacagagt tcttgaagtg gtggcctaac   3540
tacggctaca ctagaaggac agtatttggt atctgcgctc tgctgaagcc agttaccttc   3600
ggaaaaagag ttggtagctc ttgatccggc aaacaaacca ccgctggtag cggtggtttt   3660
tttgtttgca agcagcagat tacgcgcaga aaaaaaggat ctcaagaaga tcctttgatc   3720
ttttctacgg ggtctgacgc tcagtggaac gaaaactcac gttaagggat tttggtcatg   3780
agattatcaa aaaggatctt cacctagatc cttttaaatt aaaaatgaag ttttaaatca   3840
atctaaagta tatatgagta aacttggtct gacagttacc aatgcttaat cagtgaggca   3900
cctatctcag cgatctgtct atttcgttca tccatagttg cctgactccc cgtcgtgtag   3960
ataactacga tacgggaggg cttaccatct ggccccagtg ctgcaatgat accgcgagac   4020
ccacgctcac cggctccaga tttatcagca ataaaccagc cagccggaag ggccgagcgc   4080
```

-continued agaagtggtc ctgcaacttt atccgcctcc atccagtcta ttaattgttg ccgggaagct 4140
agagtaagta gttcgccagt taatagtttg cgcaacgttg ttgccattgc tacaggcatc 4200
gtggtgtcac gctcgtcgtt tggtatggct tcattcagct ccggttccca acgatcaagg 4260
cgagttacat gatcccccat gttgtgcaaa aaagcggtta gctccttcgg tcctccgatc 4320
gttgtcagaa gtaagttggc cgcagtgtta tcactcatgg ttatggcagc actgcataat 4380
tctcttactg tcatgccatc cgtaagatgc ttttctgtga ctggtgagta ctcaaccaag 4440
tcattctgag aatagtgtat gcggcgaccg agttgctctt gcccggcgtc aatacgggat 4500
aataccgcgc cacatagcag aactttaaaa gtgctcatca ttggaaaacg ttcttcgggg 4560
cgaaaactct caaggatctt accgctgttg agatccagtt cgatgtaacc cactcgtgca 4620
cccaactgat cttcagcatc ttttactttc accagcgttt ctgggtgagc aaaaacagga 4680
aggcaaaatg ccgcaaaaaa gggaataagg gcgacacgga aatgttgaat actcatactc 4740
ttcctttttc aatattattg aagcatttat cagggttatt gtctcatgag cggatacata 4800
tttgaatgta tttagaaaaa taaacaaata ggggttccgc gcacatttcc ccgaaaagtg 4860
ccacctgacg tcgatcgacg gatcgggaga tccgggacat gtacctccca ggggcccagg 4920
aagactacgg gaggctacac caacgtcaat cagaggggcc tgtgtagcta ccgataagcg 4980
gaccctcaag agggcattag caatagtgtt tataaggccc ccttgttaac cctaaacggg 5040
tagcatatgc ttcccgggta gtagtatata ctatccagac taaccctaat tcaatagcat 5100
atgttaccca acgggaagca tatgctatcg aattagggtt agtaaaaggg tcctaaggaa 5160
cagcgatatc tcccacccca tgagctgtca cggttttatt tacatggggt caggattcca 5220
cgagggtagt gaaccatttt agtcacaagg gcagtggctg aagatcaagg agcgggcagt 5280
gaactctcct gaatcttcgc ctgcttcttc attctccttc gtttagctaa tagaataact 5340
gctgagttgt gaacagtaag gtgtatgtga ggtgctcgaa aacaaggttt caggtgacgc 5400
ccccagaata aaatttggac gggggggttca gtggtggcat tgtgctatga caccaatata 5460
accctcacaa accccttggg caataaatac tagtgtagga atgaaacatt ctgaatatct 5520
ttaacaatag aaatccatgg ggtggggaca agccgtaaag actggatgtc catctcacac 5580
gaatttatgg ctatgggcaa cacataatcc tagtgcaata tgatactggg gttattaaga 5640
tgtgtcccag gcagggacca agacaggtga accatgttgt tacactctat ttgtaacaag 5700
gggaaagaga gtggacgccg acagcagcgg actccactgg ttgtctctaa cacccccgaa 5760
aattaaacgg ggctccacgc caatggggcc cataaacaaa gacaagtggc cactcttttt 5820
tttgaaattg tggagtgggg gcacgcgtca gcccccacac gccgccctgc ggttttggac 5880
tgtaaaataa gggtgtaata acttggctga ttgtaacccc gctaaccact gcggtcaaac 5940
cacttgccca caaaaccact aatggcaccc cggggaatac ctgcataagt aggtgggcgg 6000
gccaagatag gggcgcgatt gctgcgatct ggaggacaaa ttacacacac ttgcgcctga 6060
gcgccaagca cagggttgtt ggtcctcata ttcacgaggt cgctgagagc acggtgggct 6120
aatgttgcca tgggtagcat atactaccca aatatctgga tagcatatgc tatcctaatc 6180
tatatctggg tagcataggc tatcctaatc tatatctggg tagcatatgc tatcctaatc 6240
tatatctggg tagtatatgc tatcctaatt tatatctggg tagcataggc tatcctaatc 6300
tatatctggg tagcatatgc tatcctaatc tatatctggg tagtatatgc tatcctaatc 6360
tgtatccggg tagcatatgc tatcctaata gagattaggg tagtatatgc tatcctaatt 6420

```
tatatctggg tagcatatac tacccaaata tctggatagc atatgctatc ctaatctata   6480

tctgggtagc atatgctatc ctaatctata tctgggtagc ataggctatc ctaatctata   6540

tctgggtagc atatgctatc ctaatctata tctgggtagt atatgctatc ctaatttata   6600

tctgggtagc ataggctatc ctaatctata tctgggtagc atatgctatc ctaatctata   6660

tctgggtagt atatgctatc ctaatctgta tccgggtagc atatgctatc ctcatgcata   6720

tacagtcagc atatgatacc cagtagtaga gtgggagtgc tatcctttgc atatgccgcc   6780

acctcccaag gggcgtgaa ttttcgctgc ttgtcctttt cctgcatgcg gatcttcaat   6840

a                                                                   6841
```

<210> SEQ ID NO 5
<211> LENGTH: 3429
<212> TYPE: DNA
<213> ORGANISM: Homo sapiens

<400> SEQUENCE: 5

```
ctgggcccgg gctggaagcc ggaagcgagc aaagtggagc cgactcgaac tccaccgcgg     60

aaaagaaagc ctcagaacgt tcgttcgctg cgtccccagc cggggccgag ccctccgcga    120

cgccagccgg gccatggggg ccgcacgcag cccgccgtcc gctgtcccgg ggcccctgct    180

ggggctgctc ctgctgctcc tgggcgtgct ggccccgggt ggcgcctccc tgcgactcct    240

ggaccaccgg gcgctggtct gctcccagcc ggggctaaac tgcacggtca agaatagtac    300

ctgcctggat gacagctgga ttcaccctcg aaacctgacc ccctcctccc caaaggacct    360

gcagatccag ctgcactttg cccacaccca acaaggagac ctgttccccg tggctcacat    420

cgaatggaca ctgcagacag acgccagcat cctgtacctc gagggtgcag agttatctgt    480

cctgcagctg aacaccaatg aacgtttgtg cgtcaggttt gagtttctgt ccaaactgag    540

gcatcaccac aggcggtggc gttttacctt cagccacttt gtggttgacc ctgaccagga    600

atatgaggtg accgttcacc acctgcccaa gcccatccct gatggggacc caaaccacca    660

gtccaagaat ttccttgtgc ctgactgtga gcacgccagg atgaaggtaa ccacgccatg    720

catgagctca ggcagcctgt gggaccccaa catcaccgtg gagaccctgg aggcccacca    780

gctgcgtgtg agcttcaccc tgtggaacga atctacccat taccagatcc tgctgaccag    840

ttttccgcac atggagaacc acagttgctt tgagcacatg caccacatac ctgcgcccag    900

accagaagag ttccaccagc gatccaacgt cacactcact ctacgcaacc ttaaagggtg    960

ctgtcgccac caagtgcaga tccagccctt cttcagcagc tgcctcaatg actgcctcag   1020

acactccgcg actgtttcct gcccagaaat gccagacact ccagaaccaa ttccggacta   1080

catgcccctg tgggtgtact ggttcatcac gggcatctcc atcctgctgg tgggctccgt   1140

catcctgctc atcgtctgca tgacctggag gctagctggg cctggaagtg aaaaatacag   1200

tgatgacacc aaatacaccg atggcctgcc tgcggctgac ctgatccccc caccgctgaa   1260

gcccaggaag gtctggatca tctactcagc cgaccacccc ctctacgtgg acgtggtcct   1320

gaaattcgcc cagttcctgc tcaccgcctg cggcacggaa gtggccctgg acctgctgga   1380

agagcaggcc atctcggagg caggagtcat gacctgggtg ggccgtcaga agcaggagat   1440

ggtggagagc aactctaaga tcatcgtcct gtgctcccgc ggcacgcgcg ccaagtggca   1500

ggcgctcctg ggccgggggg cgcctgtgcg gctgcgctgc gaccacggaa agcccgtggg   1560

ggacctgttc actgcagcca tgaacatgat cctcccggac ttcaagaggc cagcctgctt   1620

cggcacctac gtagtctgct acttcagcga ggtcagctgt gacggcgacg tccccgacct   1680
```

```
gttcggcgcg gcgccgcggt acccgctcat ggacaggttc gaggaggtgt acttccgcat   1740

ccaggacctg gagatgttcc agccgggccg catgcaccgc gtaggggagc tgtcggggga   1800

caactacctg cggagcccgg gcggcaggca gctccgcgcc gccctggaca ggttccggga   1860

ctggcaggtc cgctgtcccg actggttcga atgtgagaac ctctactcag cagatgacca   1920

ggatgccccg tccctggacg aagaggtgtt tgaggagcca ctgctgcctc cgggaaccgg   1980

catcgtgaag cgggcgcccc tggtgcgcga gcctggctcc caggcctgcc tggccataga   2040

cccgctggtc ggggaggaag gaggagcagc agtggcaaag ctggaacctc acctgcagcc   2100

ccggggtcag ccagcgccgc agcccctcca caccctggtg ctcgccgcag aggagggggc   2160

cctggtggcc gcggtggagc ctgggcccct ggctgacggt gccgcagtcc ggctggcact   2220

ggcggggag ggcgaggcct gcccgctgct gggcagcccg ggcgctgggc gaaatagcgt   2280

cctcttcctc cccgtggacc ccgaggactc gccccttggc agcagcaccc ccatggcgtc   2340

tcctgacctc cttccagagg acgtgaggga gcacctcgaa ggcttgatgc tctcgctctt   2400

cgagcagagt ctgagctgcc aggcccaggg gggctgcagt agacccgcca tggtcctcac   2460

agacccacac acgccctacg aggaggagca gcggcagtca gtgcagtctg accagggcta   2520

catctccagg agctccccgc agccccccga gggactcacg gaaatggagg aagaggagga   2580

agaggagcag gacccaggga agccggccct gccactctct cccgaggacc tggagagcct   2640

gaggagcctc cagcggcagc tgcttttccg ccagctgcag aagaactcgg gctgggacac   2700

gatggggtca gagtcagagg ggcccagtgc atgagggcgg ctccccaggg accgcccaga   2760

tcccagcttt gagagaggag tgtgtgtgca cgtattcatc tgtgtgtaca tgtctgcatg   2820

tgtatatgtt cgtgtgtgaa atgtaggctt taaaatgtaa atgtctggat tttaatccca   2880

ggcatccctc ctaacttttc tttgtgcagc ggtctggtta tcgtctatcc ccaggggaat   2940

ccacacagcc cgctcccagg agctaatggt agagcgtcct tgaggctcca ttattcgttc   3000

attcagcatt tattgtgcac ctactatgtg gcgggcattt gggataccaa gataaattgc   3060

atgcggcatg gccccagcca tgaaggaact taaccgctag tgccgaggac acgttaaacg   3120

aacaggatgg gccgggcacg gtggctcacg cctgtaatcc cagcacactg ggaggccgag   3180

gcaggtggat cactctgagg tcaggagttt gagccagcct ggccaacatg gtgaaacccc   3240

atctccacta aaaatagaaa aattagccgg gcatggtgac acatgcctgt agtcctagct   3300

acttgggagg ctgaggcagg agaattgctt gaatctggga ggcagaggtt gcagtgagcc   3360

gagattgtgc cattgcactg cagcctggat gacagagcga gactctatct caaaaaaaaa   3420

aaaaaaaaa                                                           3429
```

<210> SEQ ID NO 6
<211> LENGTH: 7356
<212> TYPE: DNA
<213> ORGANISM: Artificial Sequence
<220> FEATURE:
<223> OTHER INFORMATION: NPL012271 - SEQ ID NO: 6
<220> FEATURE:
<221> NAME/KEY: APP6-Avi tag
<222> LOCATION: (1527)..(1595)
<223> OTHER INFORMATION: encoding APP6-Avi tag.

<400> SEQUENCE: 6

```
gtattagtca tcgctattac catggtgatg cggttttggc agtacaccaa tgggcgtgga     60

tagcggtttg actcacgggg atttccaagt ctccacccca ttgacgtcaa tgggagtttg    120
```

-continued

```
ttttggcacc aaaatcaacg ggactttcca aaatgtcgta ataaccccgc cccgttgacg    180
caaatgggcg gtaggcgtgt acggtgggag gtctatataa gcagagctcg tttagtgaac    240
cgtcagatcg cctggagacg ccatccacgc tgttttgacc tccatagaag acaccgggac    300
cgatccagcc tccgcggccg ggaacggtgc attggaacgc ggattccccg tgccaagagt    360
gacgtaagta ccgcctatag agtctatagg cccacccct tggcttcgtt agaacgcggc    420
tacaattaat acataacctt atgtatcata cacatacgat ttaggtgaca ctatagaata    480
acatccactt tgcctttctc tccacaggtg tccactccca ggtccaactg cacggaagct    540
tctgcaggtc gaccaattga gatctggtac ctcgatcaac aagtttgtac aaaaaagcag    600
gcttggccgc caccatgccc ctgctcctgc tgctgcccct gctgtgggcc ggagccctgg    660
ccctgcgact cctggaccac cgggcgctgg tctgctccca gccggggcta aactgcacgg    720
tcaagaatag tacctgcctg gatgacagct ggattcaccc tcgaaacctg accccctcct    780
ccccaaagga cctgcagatc cagctgcact ttgcccacac ccaacaagga gacctgttcc    840
ccgtggctca catcgaatgg acactgcaga cagacgccag catcctgtac ctcgagggtg    900
cagagttatc tgtcctgcag ctgaacacca atgaacgttt gtgcgtcagg tttgagtttc    960
tgtccaaact gaggcatcac cacaggcggt ggcgttttac cttcagccac tttgtggttg   1020
accctgacca ggaatatgag gtgaccgttc accacctgcc caagcccatc cctgatgggg   1080
acccaaacca ccagtccaag aatttccttg tgcctgactg tgagcacgcc aggatgaagg   1140
taaccacgcc atgcatgagc tcaggcagcc tgtgggaccc caacatcacc gtggagaccc   1200
tggaggccca ccagctgcgt gtgagcttca ccctgtggaa cgaatctacc cattaccaga   1260
tcctgctgac cagttttccg cacatggaga accacagttg ctttgagcac atgcaccaca   1320
tacctgcgcc cagaccagaa gagttccacc agcgatccaa cgtcacactc actctacgca   1380
accttaaagg gtgctgtcgc caccaagtgc agatccagcc cttcttcagc agctgcctca   1440
atgactgcct cagacactcc gcgactgttt cctgcccaga aatgccagac actccagaac   1500
caattccgga ctacatgccc ctgtgggaat tccgtcacga ctccggcggc ggcctgaacg   1560
atatctttga agcgcagaaa attgagtggc atgaataatg aacccagctt tcttgtacaa   1620
agtggttgat cgatggcggc cgctctagag ggcccgttta aacccgctga tcagcctcga   1680
ctgtgccttc tagttgccag ccatctgttg tttgcccctc ccccgtgcct tccttgaccc   1740
tggaaggtgc cactcccact gtcctttcct aataaaatga ggaaattgca tcgcattgtc   1800
tgagtaggtg tcattctatt ctggggggtg gggtggggca ggacagcaag ggggaggatt   1860
gggaagacaa tagcaggcat gctggggatg cggtgggctc tatggcttct gaggcggaaa   1920
gaaccagcta gctcgaggca ggcagaagta tgcaaagcat gcatctcaat tagtcagcaa   1980
ccatagtccc gcccctaact ccgcccatcc cgcccctaac tccgcccagt tccgcccatt   2040
ctccgcccca tggctgacta atttttttta tttatgcaga ggccgaggcc gcctctgcct   2100
ctgagctatt ccagaagtag tgaggaggct tttttggagg cctaggcttt tgcaaaaagc   2160
tcccgggagc ttgtatatcc attttcggat ctgatcagca cgtgttgaca attaatcatc   2220
ggcatagtat atcggcatag tataatacga caaggtgagg aactaaacca tggccaagtt   2280
gaccagtgcc gttccggtgc tcaccgcgcg cgacgtcgcc ggagcggtcg agttctggac   2340
cgaccggctc gggttctccc gggacttcgt ggaggacgac ttcgccggtg tggtccggga   2400
cgacgtgacc ctgttcatca gcgcggtcca ggaccaggtg gtgccggaca acaccctggc   2460
ctgggtgtgg gtgcgcggcc tggacgagct gtacgccgag tggtcggagg tcgtgtccac   2520
```

gaacttccgg gacgcctccg ggccggccat gaccgagatc ggcgagcagc cgtgggggcg 2580
ggagttcgcc ctgcgcgacc cggccggcaa ctgcgtgcac ttcgtggccg aggagcagga 2640
ctgacacgtg ctacgagatt tcgattccac cgccgccttc tatgaaaggt tgggcttcgg 2700
aatcgttttc cgggacgccg gctggatgat cctccagcgc ggggatctca tgctggagtt 2760
cttcgcccac cccaacttgt ttattgcagc ttataatggt tacaaataaa gcaatagcat 2820
cacaaatttc acaaataaag catttttttc actgcattct agttgtggtt tgtccaaact 2880
catcaatgta tcttatcatg tctgaatttt gcattaatga atcggccaac gcgcggggag 2940
aggcggtttg cgtattgggc gctcttccgc ttcctcgctc actgactcgc tgcgctcggt 3000
cgttcggctg cggcgagcgg tatcagctca ctcaaaggcg gtaatacggt tatccacaga 3060
atcaggggat aacgcaggaa agaacatgtg agcaaaaggc cagcaaaagg ccaggaaccg 3120
taaaaaggcc gcgttgctgg cgtttttcca taggctccgc ccccctgacg agcatcacaa 3180
aaatcgacgc tcaagtcaga ggtggcgaaa cccgacagga ctataaagat accaggcgtt 3240
tccccctgga agctccctcg tgcgctctcc tgttccgacc ctgccgctta ccggatacct 3300
gtccgccttt ctcccttcgg gaagcgtggc gctttctcaa tgctcacgct gtaggtatct 3360
cagttcggtg taggtcgttc gctccaagct gggctgtgtg cacgaacccc ccgttcagcc 3420
cgaccgctgc gccttatccg gtaactatcg tcttgagtcc aacccggtaa gacacgactt 3480
atcgccactg gcagcagcca ctggtaacag gattagcaga gcgaggtatg taggcggtgc 3540
tacagagttc ttgaagtggt ggcctaacta cggctacact agaaggacag tatttggtat 3600
ctgcgctctg ctgaagccag ttaccttcgg aaaaagagtt ggtagctctt gatccggcaa 3660
acaaaccacc gctggtagcg gtggtttttt tgtttgcaag cagcagatta cgcgcagaaa 3720
aaaaggatct caagaagatc ctttgatctt ttctacgggg tctgacgctc agtggaacga 3780
aaactcacgt taagggattt tggtcatgag attatcaaaa aggatcttca cctagatcct 3840
tttaaattaa aaatgaagtt ttaaatcaat ctaaagtata tatgagtaaa cttggtctga 3900
cagttaccaa tgcttaatca gtgaggcacc tatctcagcg atctgtctat ttcgttcatc 3960
catagttgcc tgactccccg tcgtgtagat aactacgata cgggagggct taccatctgg 4020
ccccagtgct gcaatgatac cgcgagaccc acgctcaccg gctccagatt tatcagcaat 4080
aaaccagcca gccggaaggg ccgagcgcag aagtggtcct gcaactttat ccgcctccat 4140
ccagtctatt aattgttgcc gggaagctag agtaagtagt tcgccagtta atagtttgcg 4200
caacgttgtt gccattgcta caggcatcgt ggtgtcacgc tcgtcgtttg gtatggcttc 4260
attcagctcc ggttcccaac gatcaaggcg agttacatga tcccccatgt tgtgcaaaaa 4320
agcggttagc tccttcggtc ctccgatcgt tgtcagaagt aagttggccg cagtgttatc 4380
actcatggtt atggcagcac tgcataattc tcttactgtc atgccatccg taagatgctt 4440
ttctgtgact ggtgagtact caaccaagtc attctgagaa tagtgtatgc ggcgaccgag 4500
ttgctcttgc ccggcgtcaa tacgggataa taccgcgcca catagcagaa ctttaaaagt 4560
gctcatcatt ggaaaacgtt cttcggggcg aaaactctca aggatcttac cgctgttgag 4620
atccagttcg atgtaaccca ctcgtgcacc caactgatct tcagcatctt ttactttcac 4680
cagcgtttct gggtgagcaa aaacaggaag gcaaaatgcc gcaaaaaagg gaataagggc 4740
gacacggaaa tgttgaatac tcatactctt cctttttcaa tattattgaa gcatttatca 4800
gggttattgt ctcatgagcg gatacatatt tgaatgtatt tagaaaaata aacaaatagg 4860
ggttccgcgc acatttcccc gaaaagtgcc acctgacgtc gatcgacgga tcgggagatc 4920
cgggacatgt acctcccagg ggcccaggaa gactacggga ggctacacca acgtcaatca 4980
gaggggcctg tgtagctacc gataagcgga ccctcaagag ggcattagca atagtgttta 5040
taaggccccc ttgttaaccc taaacgggta gcatatgctt cccgggtagt agtatatact 5100
atccagacta accctaattc aatagcatat gttacccaac gggaagcata tgctatcgaa 5160
ttagggttag taaaagggtc ctaaggaaca gcgatatctc ccaccccatg agctgtcacg 5220
gttttattta catggggtca ggattccacg agggtagtga accattttag tcacaagggc 5280
agtggctgaa gatcaaggag cgggcagtga actctcctga atcttcgcct gcttcttcat 5340
tctccttcgt ttagctaata gaataactgc tgagttgtga acagtaaggt gtatgtgagg 5400
tgctcgaaaa caaggtttca ggtgacgccc ccagaataaa atttggacgg ggggttcagt 5460
ggtggcattg tgctatgaca ccaatataac cctcacaaac cccttgggca ataaatacta 5520
gtgtaggaat gaaacattct gaatatcttt aacaatagaa atccatgggg tggggacaag 5580
ccgtaaagac tggatgtcca tctcacacga atttatggct atgggcaaca cataatccta 5640
gtgcaatatg atactggggt tattaagatg tgtcccaggc agggaccaag acaggtgaac 5700
catgttgtta cactctattt gtaacaaggg gaaagagagt ggacgccgac agcagcggac 5760
tccactggtt gtctctaaca cccccgaaaa ttaaacgggg ctccacgcca atggggccca 5820
taaacaaaga caagtggcca ctcttttttt tgaaattgtg gagtgggggc acgcgtcagc 5880
ccccacacgc cgccctgcgg ttttggactg taaaataagg gtgtaataac ttggctgatt 5940
gtaaccccgc taaccactgc ggtcaaacca cttgcccaca aaaccactaa tggcaccccg 6000
gggaatacct gcataagtag gtgggcgggc caagataggg gcgcgattgc tgcgatctgg 6060
aggacaaatt acacacactt gcgcctgagc gccaagcaca gggttgttgg tcctcatatt 6120
cacgaggtcg ctgagagcac ggtgggctaa tgttgccatg ggtagcatat actacccaaa 6180
tatctggata gcatatgcta tcctaatcta tatctgggta gcataggcta tcctaatcta 6240
tatctgggta gcatatgcta tcctaatcta tatctgggta gtatatgcta tcctaattta 6300
tatctgggta gcataggcta tcctaatcta tatctgggta gcatatgcta tcctaatcta 6360
tatctgggta gtatatgcta tcctaatctg tatccgggta gcatatgcta tcctaataga 6420
gattagggta gtatatgcta tcctaattta tatctgggta gcatatacta cccaaatatc 6480
tggatagcat atgctatcct aatctatatc tgggtagcat atgctatcct aatctatatc 6540
tgggtagcat aggctatcct aatctatatc tgggtagcat atgctatcct aatctatatc 6600
tgggtagtat atgctatcct aatttatatc tgggtagcat aggctatcct aatctatatc 6660
tgggtagcat atgctatcct aatctatatc tgggtagtat atgctatcct aatctgtatc 6720
cgggtagcat atgctatcct catgcatata cagtcagcat atgataccca gtagtagagt 6780
gggagtgcta tcctttgcat atgccgccac ctcccaaggg ggcgtgaatt ttcgctgctt 6840
gtccttttcc tgcatgcgga tcttcaatat tggccattag ccatattatt cattggttat 6900
atagcataaa tcaatattgg ctattggcca ttgcatacgt tgtatctata tcataatatg 6960
tacatttata ttggctcatg tccaatatga ccgccatgtt ggcattgatt attgactagt 7020
tattaatagt aatcaattac ggggtcatta gttcatagcc catatatgga gttccgcgtt 7080
acataactta cggtaaatgg cccgcctggc tgaccgccca acgacccccg cccattgacg 7140
tcaataatga cgtatgttcc catagtaacg ccaataggga ctttccattg acgtcaatgg 7200
gtggagtatt tacggtaaac tgcccacttg gcagtacatc aagtgtatca tatgccaagt 7260
ccgcccccta ttgacgtcaa tgacggtaaa tggcccgcct ggcattatgc ccagtacatg 7320
accttacggg actttcctac ttggcagtac atctac 7356

<210> SEQ ID NO 7
<211> LENGTH: 78
<212> TYPE: DNA
<213> ORGANISM: Artificial Sequence
<220> FEATURE:
<223> OTHER INFORMATION: Forward primer 1 RS3766 - SEQ ID NO: 7

<400> SEQUENCE: 7
ccatgcccct gctcctgctg ctgcccctgc tgtgggccgg agccctggcc ctgcgactcc 60
tggaccaccg ggcgctgg 78

<210> SEQ ID NO 8
<211> LENGTH: 74
<212> TYPE: DNA
<213> ORGANISM: Artificial Sequence
<220> FEATURE:
<223> OTHER INFORMATION: Reverse primer 1 RS3768 - SEQ ID NO: 8

<400> SEQUENCE: 8
gcttcaaaga tatcgttcag gccgccgccg gagtcgtgac ggaattccca caggggcatg 60
tagtccggaa ttgg 74

<210> SEQ ID NO 9
<211> LENGTH: 71
<212> TYPE: DNA
<213> ORGANISM: Artificial Sequence
<220> FEATURE:
<223> OTHER INFORMATION: Forward primer 2 RS3767 - SEQ ID NO: 9

<400> SEQUENCE: 9
ggggacaagt ttgtacaaaa aagcaggctt ggccgccacc atgcccctgc tcctgctgct 60
gcccctgctg g 71

<210> SEQ ID NO 10
<211> LENGTH: 79
<212> TYPE: DNA
<213> ORGANISM: Artificial Sequence
<220> FEATURE:
<223> OTHER INFORMATION: Reverse primer 2 RS3769 - SEQ ID NO: 10

<400> SEQUENCE: 10
ggggaccact ttgtacaaga aagctgggtt cattattcat gccactcaat tttctgcgct 60
tcaaagatat cgttcaggc 79

<210> SEQ ID NO 11
<211> LENGTH: 219
<212> TYPE: PRT
<213> ORGANISM: Mus musculus

<400> SEQUENCE: 11

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Asn
                85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 12
<211> LENGTH: 449
<212> TYPE: PRT
<213> ORGANISM: Mus musculus

<400> SEQUENCE: 12

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asn Asp Arg Tyr Tyr Asn Pro Ser
    50                  55                  60

Leu Lys Ser Arg Leu Thr Ile Ser Lys Asp Thr Phe Ser Asn Gln Val
65                  70                  75                  80

Phe Leu Lys Ile Thr Asn Val Asp Thr Ala Asp Thr Ala Thr Tyr Tyr
                85                  90                  95

Cys Ala Arg Ser Pro Met Asn Thr Trp Gly Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205
```

-continued

```
Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys
```

INTERLEUKIN-17 INHIBITORS

SEQUENCE LISTING

The instant application contains a Sequence Listing which has been submitted electronically in ASCII format and is hereby incorporated by reference in its entirety. Said ASCII copy, created on Apr. 14, 2023, is named PAT058979-US-PCT_SL.txt and is 40,960 bytes in size.

FIELD OF THE INVENTION

The present invention relates to pyridine-N oxide substituted 2-formamido (N-phenyl and N-pyridyl) acetamide compounds. The present invention also relates to processes for the preparation of said compounds, pharmaceutical compositions comprising said compounds, and use of said compounds in the treatment of conditions, diseases and disorders mediated by interleukin-17 (IL-17).

BACKGROUND OF THE INVENTION

Interleukin-17 (IL-17) family cytokines are important regulators of inflammatory responses and participate in immune responses to infections. The family consists of six members, IL-17A to IL-17F. IL-17A (frequently cited as IL-17), the prototypic member of the family, was originally identified as a cytokine produced by the subset of CD4+ T-cells that is now termed Th17 (Matsuzaki et al *Microbiol. Immunol.* 2018, 62, 1-13).

IL-17, a T-cell derived cytokine present e.g. in rheumatoid arthritis (RA), acts as a pro-inflammatory cytokine, particularly in conjunction with IL-1 and TNF-α (Chabaud et al *Arthritis Rheum.* 1999, 42, 963-970; Awane M et al *J. Immunol.* 1999, 162, 5337-5344). IL-17 induces MMP production and downregulates TIMP (Jovanovic et al *J. Rheumatol.* 2001, 28, 712-718), and blockage of IL-1 and IL-17 has a synergistic effect on inflammation and bone destruction in vivo (Chabaud et al *Arthritis Rheum* 2001, 44, 1293-1303). Inappropriate or excessive production of IL-17 is associated with the pathology of various diseases and disorders, such as rheumatoid arthritis (Witowski et al *Cell. Mol. Life Sci.* 2004, 61, 567-579), osteoarthritis, loosening of bone implants, acute transplant rejection (Antonysamy et al *J. Immunol.* 1999, 162, 577-584; Van Kooten et al *J.* Am. Soc. Nephrol. 1998, 9, 1526-1534), septicemia, septic or endotoxic shock, allergies, asthma (Molet et al *J. Allergy Clin. Immunol.* 2001, 108, 430-438), bone loss, psoriasis (Teunissen et al *J. Invest. Dermatol.* 1998, 111, 645-649), ischemia, systemic sclerosis (Kurasawa et al *Arthritis Rheum.* 2000, 43, 2455-2463), stroke, and other inflammatory disorders. Antibodies to IL-17 have been proposed for use in the treatment of IL-17 mediated diseases and disorders; see for instance, WO 95/18826 or WO 2006/013107. One of the major problems associated with such antibody-based treatments is that they require repeated subcutaneous injections. Such injections may be associated with pain, bruising of the injected area, skin irritation, or skin infection. Small molecule IL-17 modulators are described in WO2020/127685, Liu et al *Sci. Rep.* 2016, 6, 30859, WO 2013/116682 and WO2014/066726.

There is a need to provide new and/or alternative treatments for IL-17 mediated diseases and/or conditions, which may allow, for example, a different mode of administration (for example oral or topical application) and/or demonstrate improved solubility and/or exposure in vivo.

SUMMARY OF THE INVENTION

The present invention provides compounds of formula (I), or a pharmaceutically acceptable salt thereof, as defined herein below. The compounds of formula (I) inhibit the IL-17 pathway and are therefore potentially useful in the treatment of conditions, diseases and disorders such as psoriasis, psoriatic arthritis, ankylosing spondylitis or non-radiographic axial spondyloarthritis. Inhibition of the IL-17 pathway provides new treatments and therapies for patients suffering from IL-17-related diseases/disorders. The compounds of formula (I) may be suitable for oral or topical application and may further exhibit improved solubility and/or exposure in vivo.

In one aspect of the present invention, a compound of formula (I) is provided, (I)

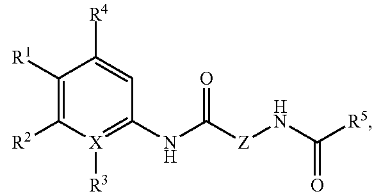

wherein, $R^1$ is

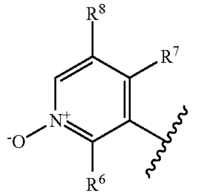

or

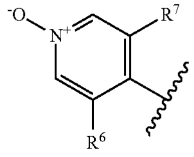

wherein,

- $R^6$ at each occurrence is selected from H, F, Cl, $C_1$-$C_3$alkyl and $C_1$-$C_3$fluoroalkyl;
- $R^7$ at each occurrence is selected from H, F, Cl, $C_1$-$C_3$alkyl and $C_1$-$C_3$fluoroalkyl;
- $R^8$ is selected from H, halo, $C_1$-$C_3$alkyl and hydroxymethyl;
- X is C or N and when X is N, $R^3$ is absent;
- $R^2$ is selected from H and F;
- $R^3$ is selected from H, F and Cl;
- $R^4$ is selected from H and F;
- $R^5$ is a 5-membered heteroaryl comprising 1 or 2 heteroatoms independently selected from N, S, and O, and wherein said heteroaryl is unsubstituted or substituted with one or two groups independently selected from $C_1$-$C_3$alkyl and $C_3$-$C_4$cycloalkyl, wherein said $C_1$-$C_3$alkyl is unsubstituted or substituted with one or more groups independently selected from F, OH, $C_1$-$C_3$alkoxy, —C(O)OH and $NR^{1b}R^{1c}$, wherein $R^{1b}$ and $R^{1c}$ are independently selected from H and $C_1$-$C_3$alkyl; or
- $R^5$ is a 5-membered heteroaryl comprising one N atom wherein said 5-membered heteroaryl is fused to a 6-membered heterocycle comprising one N atom wherein said heterocycle is unsubstituted or substituted with a group selected from $C_1$-$C_3$alkyl, $C_1$-$C_3$alkoxy$C_1$-$C_3$alkyl, —C(O)$C_1$-$C_3$alkyl, $C_3$-$C_4$cycloalkyl and oxetanyl;

Z is

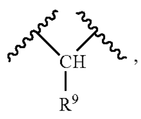

, wherein $R^9$ is selected from (1) monocyclic $C_5$-$C_8$cycloalkyl and $C_6$-bicycloalkyl, each of which is independently unsubstituted or substituted with one or more groups independently selected at each occurrence from fluoro, $C_1$-$C_3$alkyl and $C_1$-$C_3$fluoroalkyl, and wherein said monocyclic $C_5$-$C_8$cycloalkyl is optionally fused to phenyl; wherein said phenyl is unsubstituted or substituted with one or more groups selected from halo, $C_1$-$C_3$alkyl, $C_3$-$C_5$cycloalkyl or $C_1$-$C_3$fluoroalkyl;

(2) monocyclic $C_5$-$C_8$cycloalkenyl, which is unsubstituted or substituted with one or more fluoro;

(3) $C_1$-$C_3$alkyl, which is unsubstituted or substituted with one or two phenyl groups, wherein said phenyl at each occurrence is independently unsubstituted or substituted with one or more halo; or a pharmaceutically acceptable salt thereof.

The present invention relates to compounds of formula (I), or subformulae thereof, and pharmaceutically acceptable salts thereof, as herein defined, which are inhibitors of the IL-17 pathway. Accordingly, compounds of the present invention may therefore be potentially useful in the treatment of psoriasis, psoriatic arthritis, ankylosing spondylitis and non-radiographic axial spondyloarthritis.

In another aspect, the invention provides a composition, in particular, a pharmaceutical composition, which comprises (e.g. a therapeutically effective amount of) a compound of formula (I), or subformulae thereof, or a pharmaceutically acceptable salt thereof, and one or more pharmaceutically acceptable carriers.

In another aspect, the invention provides a combination, in particular a pharmaceutical combination, which comprises (e.g. a therapeutically effective amount of) a compound of formula (I) or subformulae thereof, or a pharmaceutically acceptable salt thereof, and one or more therapeutic agents.

In another aspect, the invention provides compounds of formula (I), or pharmaceutically acceptable salts thereof, for use in methods of treating, preventing, or ameliorating a condition, disease, or disorder treatable by modulating (e.g. inhibiting) IL-17 activity.

In another aspect, the invention provides a compound of formula (I), or subformulae thereof, or a pharmaceutically acceptable salt thereof, for use in the treatment, or prevention of autoimmune diseases and of inflammatory conditions, in particular inflammatory conditions with an etiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarthropathies including ankylosing spondylitis and non-radiographic axial spondyloarthritis, Reiter syndrome, reactive arthritis, psoriatic arthritis, and enterophathis arthritis, osteoarthritis, tendinopathy, hypersensitivity (including both airways hypersensitivity and dermal hypersensitivity) and allergies, including eczema and dermatitis, as well as asthma; in particular autoimmune diseases such as autoimmune hematological disorders (including e.g. hemolytic anemia, aplastic anemia, pure red cell anemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven Johnson syndrome, idiopathic sprue, autoimmune inflammatory bowel disease (including e.g. ulcerative colitis, Crohn's disease and Irritable Bowel Syndrome), endocrine ophthalmopathy, Grave's disease, sarcoidosis, primary biliary cirrhosis, juvenile diabetes (diabetes mellitus type 1), uveitis (anterior and posterior), keratoconjunctivitis sicca and vernal keratoconjunctivitis, Behcet disease, lichen planopilaris, lichen planus, hidradenitis suppurativa, acne, recurrent aphthous stomatitis, and periodontitis, pyoderma gangraenosum, and other neutrophil dermatoses, *Pityriasis rubra* pilaris, bullous pemphigoid and ichthyosis, endometriosis, non-alcoholic steatohepatitis, interstitial lung fibrosis, glomerulonephritis (with and without nephrotic syndrome, e.g. including idiopathic nephrotic syndrome or minimal change nephropathy), tumors, multiple sclerosis, autism, depressiona DNA, Alzheimer's disease, inflammatory disease of skin and cornea, myositis, loosening of bone implants, metabolic disorders, such as atherosclerosis, diabetes, and dislipidemia.

DETAILED DESCRIPTION OF THE INVENTION

Various embodiments of the invention are described herein.

The definition of the substituents applies to compounds of formulae (I), (IA) and (IB) as applicable.

The definition of the substituents applies to the end-products as well as to the corresponding intermediates.

In embodiment 1, the invention therefore provides a compound of formula (I):

(I)

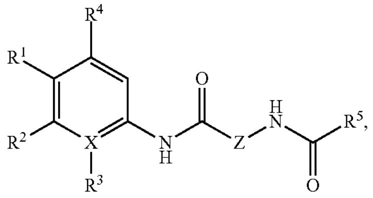

, wherein, $R^1$ is

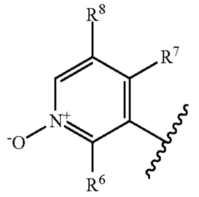

or

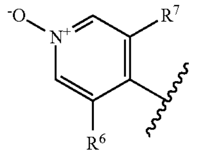

wherein, $R^6$ at each occurrence is selected from H, F, Cl, $C_1$-$C_3$alkyl and $C_1$-$C_3$fluoroalkyl;

$R^7$ at each occurrence is selected from H, F, Cl, $C_1$-$C_3$alkyl and $C_1$-$C_3$fluoroalkyl;

$R^8$ is selected from H, halo, $C_1$-$C_3$alkyl and hydroxymethyl;

X is C or N and when X is N, $R^3$ is absent;

$R^2$ is selected from H and F;

$R^3$ is selected from H, F and Cl;

$R^4$ is selected from H and F;

$R^5$ is a 5-membered heteroaryl comprising 1 or 2 heteroatoms independently selected from N, S, and O, and wherein said heteroaryl is unsubstituted or substituted with one or two groups independently selected from $C_1$-$C_3$alkyl and $C_3$-$C_4$cycloalkyl, wherein said $C_1$-$C_3$alkyl is unsubstituted or substituted with one or more groups independently selected from F, OH, $C_1$-$C_3$alkoxy, —C(O)OH and $NR^{1b}R^{1c}$, wherein $R^{1b}$ and $R^{1c}$ are independently selected from H and $C_1$-$C_3$alkyl; or $R^5$ is a 5-membered heteroaryl comprising one N atom wherein said 5-membered heteroaryl is fused to a 6-membered heterocycle comprising one N atom wherein said heterocycle is unsubstituted or substituted with a group selected from $C_1$-$C_3$alkyl, $C_1$-$C_3$alkoxy$C_1$-$C_3$alkyl, —C(O)$C_1$-$C_3$alkyl, $C_3$-$C_4$cycloalkyl and oxetanyl;

Z is

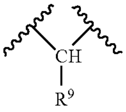, wherein $R^9$ is selected from (1) monocyclic $C_5$-$C_8$cycloalkyl and $C_6$-bicycloalkyl, each of which is independently unsubstituted or substituted with one or more groups independently selected at each occurrence from fluoro, $C_1$-$C_3$alkyl and $C_1$-$C_3$fluoroalkyl,
and wherein said monocyclic $C_5$-$C_8$cycloalkyl is optionally fused to phenyl; wherein said phenyl is unsubstituted or substituted with one or more groups selected from halo, $C_1$-$C_3$alkyl, $C_3$-$C_5$cycloalkyl or $C_1$-$C_3$fluoroalkyl;

(2) monocyclic $C_5$-$C_8$cycloalkenyl, which is unsubstituted or substituted with one or more fluoro;

(3) $C_1$-$C_3$alkyl, which is unsubstituted or substituted with one or two phenyl groups, wherein said phenyl at each occurrence is independently unsubstituted or substituted with one or more halo; or a pharmaceutically acceptable salt thereof.

Definitions

For the purpose of interpreting this specification, the following definitions will apply unless specified otherwise and when appropriate, terms used in the singular will also include the plural and vice versa. It must be noted that as used herein and in the appended claims, the singular forms "a", "an" and "the" include the plural unless the context clearly dictates otherwise. Thus, for example, reference to "the compound" includes reference to one or more compounds, and so forth.

As used herein, the term "$C_1$-$C_3$alkyl" refers to a straight or branched hydrocarbon chain radical consisting solely of carbon and hydrogen atoms, containing no unsaturation, having from one to three carbon atoms, and which is attached to the rest of the molecule by a single bond. Examples of $C_1$-$C_3$alkyl include, but are not limited to, methyl, ethyl, n-propyl and 1-methylethyl (iso-propyl).

As used herein, the term "$C_1$-$C_3$fluoroalkyl" refers to a $C_1$-$C_3$alkyl as defined herein which is substituted with at least one fluorine atom, up to the maximum permitted number of fluorine atoms as substituent positions allow. Examples of $C_1$-$C_3$fluoroalkyl include, but are not limited to, mono-, di- and tri-fluoromethyl.

As used herein, the term "$C_1$-$C_3$alkoxy" refers to the radical —O—$C_1$-$C_3$alkyl, wherein the $C_1$-$C_3$alkyl portion is as defined herein.

As used herein, the term "$C_1$-$C_3$alkoxy$C_1$-$C_3$alkyl" refers to a $C_1$-$C_3$alkyl radical substituted by $C_1$-$C_3$alkoxy. Examples of $C_1$-$C_3$alkoxy$C_1$-$C_3$alkyl include, but are not limited to, methoxymethyl and methoxyethyl.

As used herein, the term "$C_3$-$C_4$cycloalkyl" refers to a stable, saturated hydrocarbon radical consisting solely of carbon and hydrogen atoms, having three or four carbon atoms, i.e. cyclopropyl or cyclobutyl.

As used herein, the term "monocyclic $C_5$-$C_8$cycloalkyl" refers to a stable monocyclic, saturated hydrocarbon radical consisting solely of carbon and hydrogen atoms, having from five to eight carbon atoms. Examples of monocyclic $C_5$-$C_8$cycloalkyl include, but are not limited to, cyclopentyl, cyclohexyl, cycloheptyl and cyclooctyl.

As used herein, the term "monocyclic $C_5$-$C_8$ cycloalkenyl" refers to a stable, monocyclic, partially saturated (i.e. containing at least one double bond) hydrocarbon radical consisting solely of carbon and hydrogen atoms, having from five to eight carbon atoms. Examples of monocyclic $C_5$-$C_8$cycloalkenyl include cyclopentenyl, cyclohexenyl, cycloheptenyl and cyclooctenyl.

As used herein, the term "$C_6$-bicycloalkyl" refers to a stable, saturated hydrocarbon radical consisting solely of carbon and hydrogen atoms, having six carbon atoms and two fused rings. Examples of $C_6$-bicycloalkyl include bicyclo[3.1.0]hexanyl and bicyclo[2.2.0]hexanyl.

As used herein, the term "5-membered heteroaryl comprising 1 or 2 heteroatoms independently selected from N, S, and O", refers to an aromatic ring radical of 5 ring atoms, one or two of which are selected from N, S and O and the rest are carbon. Examples include pyrazolyl (particularly pyrazol-5-yl), isoxazolyl (particularly isoxazol-4-yl), furanyl, pyrrolyl and thiazole. 5-membered heteroaryl comprising one N atom is to be construed accordingly.

As used herein, the term "Halo" refers to bromo, chloro, fluoro or iodo, preferably chloro or fluoro.

Unless specified otherwise, the term "compounds of the present invention" refers to compounds of formula (I), and subformulae thereof, such as compounds of formula (IA) or (IB), as defined herein, and salts thereof, as well as all stereoisomers (including diastereoisomers and enantiomers), rotamers, tautomers and isotopically labeled compounds (including deuterium substitutions), as well as inherently formed moieties. The term "compounds of the (present) invention" or "a compound of the (present) invention" refers to a compound as defined in any one of the embodiments mentioned below.

Various embodiments of the invention are described herein, it will be recognized that features specified in each embodiment may be combined with other specified features to provide further embodiments of the present invention.

FURTHER ENUMERATED EMBODIMENTS

Embodiment 2. A compound of the formula (I), or a pharmaceutically acceptable salt thereof, according to embodiment 1, wherein $R^6$ at each occurrence is selected from H, F, Cl, methyl and difluoromethyl.

Embodiment 3. A compound of the formula (I), or a pharmaceutically acceptable salt thereof, according to embodiment 1 or 2, wherein $R^6$ is methyl.

Embodiment 4. A compound of the formula (I), or a pharmaceutically acceptable salt thereof, according to any one of embodiments 1 to 3, wherein $R^7$ at each occurrence is selected from H, F, Cl, methyl and trifluoromethyl.

Embodiment 5. A compound of the formula (I), or a pharmaceutically acceptable salt thereof, according to any one of embodiments 1 to 4, wherein $R^7$ at each occurrence is selected from Cl, methyl and trifluoromethyl.

Embodiment 6. A compound of formula (I), or a pharmaceutically acceptable salt thereof, according to any one of embodiments 1 to 5, wherein $R^8$ is selected from H, chloro, methyl and hydroxymethyl.

Embodiment 7. A compound of formula (I), or a pharmaceutically acceptable salt thereof, according to any one of embodiments 1 to 6, wherein $R^8$ is H.

Embodiment 8. A compound of formula (I), or a pharmaceutically acceptable salt thereof, according to any one of embodiments 1 to 7, wherein $R^1$ is

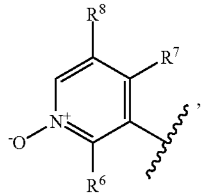

wherein $R^6$, $R^7$ and $R^8$ are as defined in any one of embodiments 1 to 7.

Embodiment 9. A compound of formula (I), or a pharmaceutically acceptable salt thereof, according to any one of embodiments 1 to 8, wherein $R^1$ is

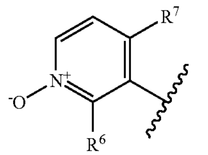

wherein $R^6$ and $R^7$ are as defined in any one of embodiments 1 to 5.

Embodiment 10. A compound of formula (I), or a pharmaceutically acceptable salt thereof, according to any one of embodiments 1 to 9, wherein X is C.

Embodiment 11. A compound of formula (I), or a pharmaceutically acceptable salt thereof, according to any one of embodiments 1 to 10, wherein $R^3$ is H.

Embodiment 12. A compound of formula (I), or a pharmaceutically acceptable salt thereof, according to any one of embodiments 1 to 10, wherein $R^4$ is H.

Embodiment 13. A compound of formula (I), or a pharmaceutically acceptable salt thereof, according to any one of embodiments 1 to 12, wherein $R^5$ is a 5-membered heteroaryl comprising 1 or 2 heteroatoms independently selected from N, S, and O, at least one of which is N, and wherein said heteroaryl is unsubstituted or substituted with one group selected from $C_1$-$C_3$alkyl and $C_3$-$C_4$cycloalkyl, wherein said $C_1$-$C_3$alkyl is unsubstituted or substituted with one group selected from OH, $C_1$-$C_3$alkoxy, —C(O)OH and $NR^{1b}R^{1c}$, wherein $R^{1b}$ and $R^{1c}$ are independently selected from H and $C_1$-$C_3$alkyl;

or $R^5$ is a 5-membered heteroaryl comprising one N atom wherein said 5-membered heteroaryl is fused to a 6-membered heterocycle comprising one N atom wherein said heterocycle is unsubstituted or substituted with one group selected from $C_1$-$C_3$alkyl, $C_1$-$C_3$alkoxy$C_1$-$C_3$alkyl, —C(O)$C_1$-$C_3$alkyl, $C_3$-$C_4$cycloalkyl and oxetanyl.

Embodiment 14. A compound of formula (I), or a pharmaceutically acceptable salt thereof, according to any one of embodiments 1 to 13, wherein $R^5$ is selected from pyrazolyl (particularly pyrazol-5-yl), isoxazolyl (particularly isoxazol-4-yl) and 1,2,3,4-tetrahydropyrrolo[1,2-a]pyrazinyl (particularly 1,2,3,4-tetrahydropyrrolo[1,2-a]pyrazine-6-yl), wherein said pyrazole and isoxazole are each independently substituted with one group selected from $C_1$-$C_3$alkyl and $C_3$-$C_4$cycloalkyl, wherein said $C_1$-$C_3$alkyl is unsubstituted or substituted with one group selected from OH, $C_1$-$C_3$alkoxy, —C(O)OH and $NR^{1b}R^{1c}$, wherein $R^{1b}$ and $R^{1c}$ are independently selected from H and $C_1$-$C_3$alkyl; and said 1,2,3,4-tetrahydropyrrolo[1,2-a]pyrazine is unsubstituted or substituted with one group selected from $C_1$-$C_3$alkyl, $C_1$-$C_3$alkoxy$C_1$-$C_3$alkyl, —C(O)$C_1$-$C_3$alkyl, $C_3$-$C_4$ cycloalkyl and oxetanyl.

Embodiment 15. A compound of formula (I), or a pharmaceutically acceptable salt thereof, according to any one of embodiments 1 to 14, wherein $R^5$ is selected from pyrazolyl (particularly pyrazol-5-yl), isoxazolyl (particularly isoxazol-4-yl) and 1,2,3,4-tetrahydropyrrolo[1,2-a]pyrazinyl (particularly 1,2,3,4-tetrahydropyrrolo[1,2-a]pyrazin-6-yl), wherein said pyrazole and isoxazole are each independently substituted with one group selected from methyl, ethyl, isopropyl, cyclopropyl and cyclobutyl, wherein said methyl and ethyl are each unsubstituted or substituted with one group selected from OH, methoxy, —C(O)OH, $NH_2$ and $N(CH_3)_2$; and said 1,2,3,4-tetrahydropyrrolo[1,2-a]pyrazinyl, is unsubstituted or substituted with one group selected from methyl, methoxyethyl, —C(O)$CH_3$), cyclopropyl and oxetanyl.

Embodiment 16. A compound of formula (I), or a pharmaceutically acceptable salt thereof, according to any one of embodiments 1 to 15, wherein $R^5$ is selected from

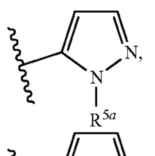

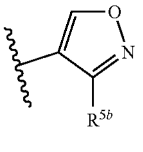

and

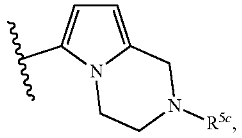

wherein $R^{5a}$ is selected from methyl, ethyl, isopropyl, cyclopropyl, cyclobutyl, —$(CH_2)_2OH$, —$(CH_2)_2OCH_3$, —$CH_2C(O)OH$ and —$(CH_2)_2N(CH_3)_2$;

$R^{5b}$ is selected from methyl, ethyl, —$CH_2OCH_3$, —$CH_2OH$, —$CH_2NH_2$ and —$CH_2N(CH_3)_2$; and $R^{5c}$ is selected from H, methyl, —C(O)$CH_3$, cyclopropyl, oxetanyl and —$(CH_2)_2OCH_3$.

Embodiment 17. A compound of formula (I), or a pharmaceutically acceptable salt thereof, according to any one of embodiments 1 to 16, wherein $R^5$ is selected from

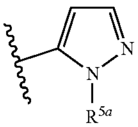
and
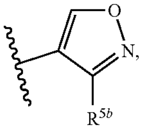

wherein $R^{5a}$ is selected from methyl and ethyl; and $R^{5b}$ is selected from methyl and ethyl.

Embodiment 18. A compound of formula (I), or a pharmaceutically acceptable salt thereof, according to any one of embodiments 1 to 17, wherein $R^9$ is selected from, (1) monocyclic $C_5$-$C_7$cycloalkyl and $C_6$-bicycloalkyl, each of which is independently unsubstituted or substituted with one or two groups independently selected at each occurrence from fluoro, $C_1$-$C_3$alkyl and $C_1$-$C_3$fluoroalkyl, and wherein said monocyclic $C_5$-$C_7$cycloalkyl is optionally fused to unsubstituted phenyl;

(2) monocyclic $C_5$-$C_8$cycloalkenyl, which is unsubstituted or substituted with one fluoro;

(3) methyl, which is unsubstituted or substituted with one or two phenyl groups, wherein said phenyl at each occurrence is independently unsubstituted or substituted with one chloro.

Embodiment 19. A compound of formula (I), or a pharmaceutically acceptable salt thereof, according to any one of embodiments 1 to 18, wherein $R^9$ is selected from cyclopentyl, cyclohexyl, cycloheptyl, 1,2,3,4-tetrahydronaphthalen-1-yl, 1,2,3,4-tetrahydronaphthalen-2-yl, bicyclo[3.1.0]hexanyl, cyclohexenyl, 2-chlorobenzyl and diphenylmethyl, wherein said cyclopentyl, cyclohexyl, cycloheptyl, 1,2,3,4-tetrahydronaphthalen-1-yl, 1,2,3,4-tetrahydronaphthalen-2-yl and bicyclo[3.1.0]hexanyl are independently unsubstituted or substituted with one or two groups independently selected at each occurrence from fluoro, methyl and trifluoromethyl, and wherein said cyclohexenyl is unsubstituted or substituted with one fluoro.

Embodiment 20. A compound of formula (I), or a pharmaceutically acceptable salt thereof, according to any one of embodiments 1 to 19, wherein $R^9$ is selected from cyclopentyl, cyclohexyl, cyclohexenyl and 1,2,3,4-tetrahydronaphthalen-1-yl, wherein said cyclohexyl is unsubstituted or substituted with one group selected from methyl and trifluoromethyl or substituted with two fluoro, and wherein said cyclohexenyl is substituted with one fluoro.

Embodiment 21. A compound of formula (I), or a pharmaceutically acceptable salt thereof, according to any one of embodiments 1 to 20, wherein Z is

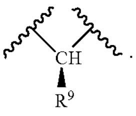
.

Embodiment 22. A compound, or a pharmaceutically acceptable salt thereof, according to any one of embodiments 1 to 19, wherein the compound is of formula (IA):

(IA)

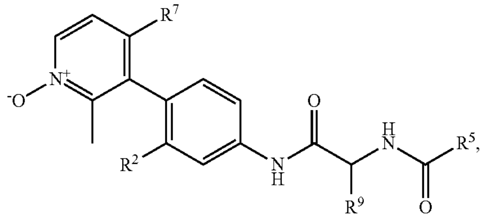

wherein, $R^7$ is selected from Cl, methyl and trifluoromethyl;

$R^2$ is selected from H and F;

$R^5$ is selected from

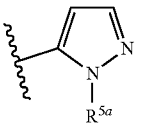
and
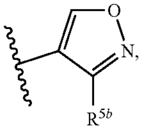

wherein, $R^{5a}$ is selected from methyl and ethyl; and $R^{5b}$ is selected from methyl and ethyl;

$R^9$ is selected from

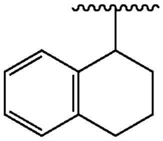
,
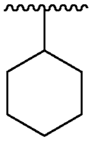
,
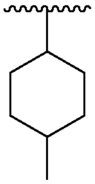
,
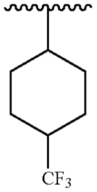
,
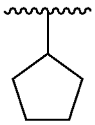
,
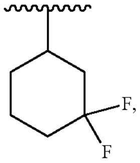
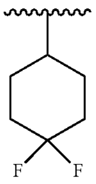
,
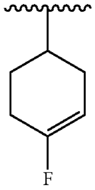
,
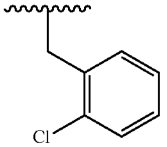
,
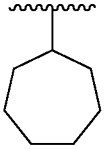
,
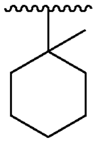
,
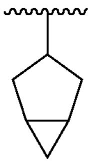
,
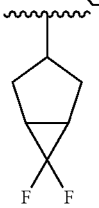
,
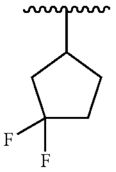
,
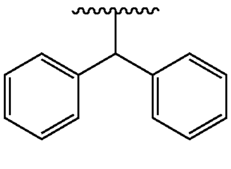
and
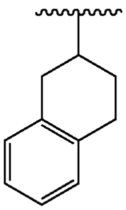
.

Embodiment 23. A compound, or a pharmaceutically acceptable salt thereof, according to embodiment 22, wherein $R^9$ is selected from

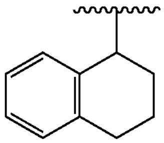, 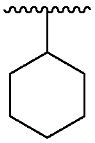, 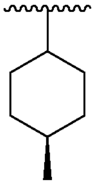, 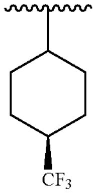,

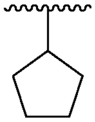, 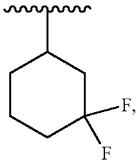 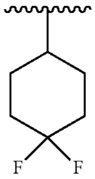, 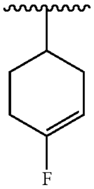,

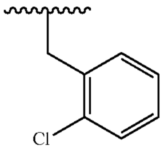, 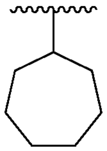, 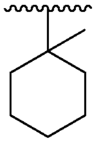,

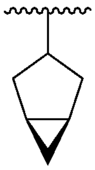, 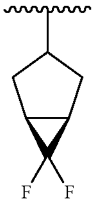, 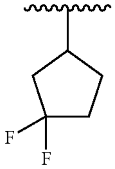,

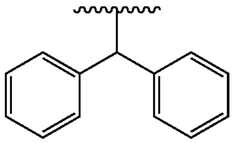 and 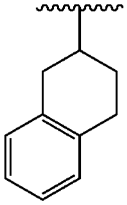.

Embodiment 24. A compound, or a pharmaceutically acceptable salt thereof, according to embodiment 23, wherein $R^9$ is selected from

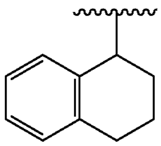, 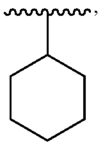, 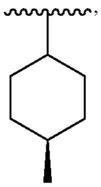, 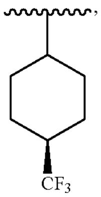,

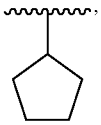, 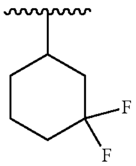, 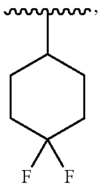, and

-continued

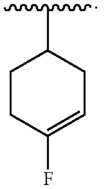

Embodiment 25. A compound, or a pharmaceutically acceptable salt thereof, according to any one of embodiments 22 to 24, wherein the compound is of formula (IB):

(IB)

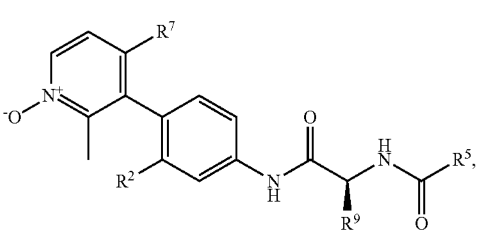

wherein $R^2$, $R^5$, $R^7$ and $R^9$ are as defined in any one of embodiments 22 to 24.

Embodiment 26. A compound, or a pharmaceutically acceptable salt thereof, according to any one of embodiments 1 to 25, wherein $R^5$ is

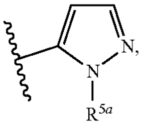

wherein $R^{5a}$ is selected from methyl and ethyl.

Embodiment 27. A compound, or a pharmaceutically acceptable salt thereof, according to any one of embodiments 1 to 25, wherein $R^5$ is

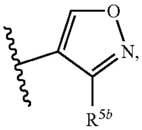

wherein $R^{5b}$ is selected from methyl and ethyl.

Embodiment 28. A compound, or a pharmaceutically acceptable salt thereof, according to any one of embodiments 1 to 25, wherein $R^5$ is

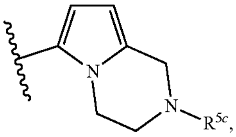

wherein $R^{5c}$ is selected from H, methyl, —$C(O)CH_3$, cyclopropyl, oxetan-3-yl and —$(CH_2)_2OCH_3$.

Embodiment 29. A compound, or a pharmaceutically acceptable salt thereof, according to embodiment 1, wherein the compound is selected from the exemplified compounds herein described.

Embodiment 30. A compound, or a pharmaceutically acceptable salt thereof, according to embodiment 1, wherein the compound is selected from:

2,4-dimethyl-3-(4-(2-(1-methyl-1H-pyrazole-5-carboxamido)-2-(1,2,3,4-tetrahydronaphthalen-1-yl)acetamido) phenyl)pyridine 1-oxide;

4-chloro-3-(4-(2-cyclohexyl-2-(1-methyl-1H-pyrazole-5-carboxamido)acetamido)-2-fluorophenyl)-2-methylpyridine 1-oxide;

2,4-dimethyl-3-(4-(2-(1-methyl-1H-pyrazole-5-carboxamido)-2-(4-methylcyclohexyl)acetamido)phenyl)pyridine 1-oxide;

4-chloro-3-(4-(2-(3-ethylisoxazole-4-carboxamido)-2-(4-(trifluoromethyl)cyclohexyl)acetamido)phenyl)-2-methylpyridine 1-oxide;

3-(4-(2-cyclopentyl-2-(3-ethylisoxazole-4-carboxamido)acetamido)phenyl)-2-methyl-4-(trifluoromethyl)pyridine 1-oxide;

4-chloro-3-(4-(2-(3,3-difluorocyclohexyl)-2-(3-ethylisoxazole-4-carboxamido)acetamido)phenyl)-2-methylpyridine 1-oxide;

3-(4-(2-(1-ethyl-1H-pyrazole-5-carboxamido)-2-(4-(trifluoromethyl)cyclohexyl)acetamido)phenyl)-2,4-dimethylpyridine 1-oxide;

3-(4-(2-(3-ethylisoxazole-4-carboxamido)-2-(4-(trifluoromethyl)cyclohexyl)acetamido)phenyl)-2,4-dimethylpyridine 1-oxide;

3-(4-(2-(3,3-difluorocyclohexyl)-2-(3-methylisoxazole-4-carboxamido)acetamido)phenyl)-2-methyl-4-(trifluoromethyl)pyridine 1-oxide;

3-(4-(2-(3,3-difluorocyclohexyl)-2-(1-ethyl-1H-pyrazole-5-carboxamido)acetamido)phenyl)-2-methyl-4-(trifluoromethyl)pyridine 1-oxide;

3-(4-(2-(4,4-difluorocyclohexyl)-2-(1-ethyl-1H-pyrazole-5-carboxamido)acetamido)phenyl)-2-methyl-4-(trifluoromethyl)pyridine 1-oxide; or 3-(4-(2-(4-fluorocyclohex-3-en-1-yl)-2-(1-methyl-1H-pyrazole-5-carboxamido)acetamido)phenyl)-2,4-dimethylpyridine 1-oxide.

Embodiment 31. A compound, or a pharmaceutically acceptable salt thereof, according to embodiment 1, wherein the compound is selected from:

2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide;

4-chloro-3-(4-((S)-2-cyclohexyl-2-(1-methyl-1H-pyrazole-5-carboxamido)acetamido)-2-fluorophenyl)-2-methylpyridine 1-oxide;

2,4-dimethyl-3-(4-((S)-2-(1-methyl-1H-pyrazole-5-carboxamido)-2-((1r,4S)-4-methylcyclohexyl)acetamido)phenyl)pyridine 1-oxide;

4-chloro-3-(4-((S)-2-(3-ethylisoxazole-4-carboxamido)-2-((1r,4S)-4-(trifluoromethyl)cyclohexyl)acetamido)phenyl)-2-methylpyridine 1-oxide;

(S)-3-(4-(2-cyclopentyl-2-(3-ethylisoxazole-4-carboxamido)acetamido)phenyl)-2-methyl-4-(trifluoromethyl) pyridine 1-oxide;

4-chloro-3-(4-((S)-2-((S)-3,3-difluorocyclohexyl)-2-(3-ethylisoxazole-4-carboxamido)acetamido)phenyl)-2-methylpyridine 1-oxide;

3-(4-((S)-2-(1-ethyl-1H-pyrazole-5-carboxamido)-2-((1r, 4S)-4-(trifluoromethyl)cyclohexyl)acetamido)phenyl)-2, 4-dimethylpyridine 1-oxide;

3-(4-((S)-2-(3-ethylisoxazole-4-carboxamido)-2-((1r,4S)-4-(trifluoromethyl)cyclohexyl)acetamido)phenyl)-2,4-dimethylpyridine 1-oxide;

3-(4-((S)-2-((S)-3,3-difluorocyclohexyl)-2-(3-methylisoxazole-4-carboxamido)acetamido)phenyl)-2-methyl-4-(trifluoromethyl)pyridine 1-oxide;

3-(4-((S)-2-((S)-3,3-difluorocyclohexyl)-2-(1-ethyl-1H-pyrazole-5-carboxamido)acetamido)phenyl)-2-methyl-4-(trifluoromethyl)pyridine 1-oxide;

(S)-3-(4-(2-(4,4-difluorocyclohexyl)-2-(1-ethyl-1H-pyrazole-5-carboxamido)acetamido)phenyl)-2-methyl-4-(trifluoromethyl)pyridine 1-oxide;

3-(4-((2S)-2-(4-fluorocyclohex-3-en-1-yl)-2-(1-methyl-1H-pyrazole-5-carboxamido)acetamido)phenyl)-2,4-dimethylpyridine 1-oxide;

3-(4-((S)-2-((R)-4-fluorocyclohex-3-en-1-yl)-2-(1-methyl-1H-pyrazole-5-carboxamido)acetamido)phenyl)-2,4-dimethylpyridine 1-oxide; or 3-(4-((S)-2-((S)-4-fluorocyclohex-3-en-1-yl)-2-(1-methyl-1H-pyrazole-5-carboxamido)acetamido)phenyl)-2,4-dimethylpyridine 1-oxide.

Embodiment 32. A compound, or a pharmaceutically acceptable salt thereof, wherein the compound is 2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide.

Embodiment 33. A compound, or a pharmaceutically acceptable salt thereof, wherein the compound is 4-chloro-3-(4-((S)-2-cyclohexyl-2-(1-methyl-1H-pyrazole-5-carboxamido)acetamido)-2-fluorophenyl)-2-methylpyridine 1-oxide.

Embodiment 34. A compound, or a pharmaceutically acceptable salt thereof, wherein the compound is 2,4-dimethyl-3-(4-((S)-2-(1-methyl-1H-pyrazole-5-carboxamido)-2-((1r,4S)-4-methylcyclohexyl)acetamido)phenyl)pyridine 1-oxide.

Embodiment 35. A compound, or a pharmaceutically acceptable salt thereof, wherein the compound is 4-chloro-3-(4-((S)-2-(3-ethylisoxazole-4-carboxamido)-2-((1r,4S)-4-(trifluoromethyl)cyclohexyl)acetamido)phenyl)-2-methylpyridine 1-oxide.

Embodiment 36. A compound, or a pharmaceutically acceptable salt thereof, wherein the compound is (S)-3-(4-(2-cyclopentyl-2-(3-ethylisoxazole-4-carboxamido)acetamido)phenyl)-2-methyl-4-(trifluoromethyl)pyridine 1-oxide.

Embodiment 37. A compound, or a pharmaceutically acceptable salt thereof, wherein the compound is 4-chloro-3-(4-((S)-2-((S)-3,3-difluorocyclohexyl)-2-(3-ethylisoxazole-4-carboxamido)acetamido)phenyl)-2-methylpyridine 1-oxide.

Embodiment 38. A compound, or a pharmaceutically acceptable salt thereof, wherein the compound is 3-(4-((S)-2-(1-ethyl-1H-pyrazole-5-carboxamido)-2-((1r,4S)-4-(trifluoromethyl)cyclohexyl)acetamido)phenyl)-2,4-dimethylpyridine 1-oxide.

Embodiment 39. A compound, or a pharmaceutically acceptable salt thereof, wherein the compound is 3-(4-((S)-2-(3-ethylisoxazole-4-carboxamido)-2-((1r,4S)-4-(trifluoromethyl)cyclohexyl)acetamido)phenyl)-2,4-dimethylpyridine 1-oxide.

Embodiment 40. A compound, or a pharmaceutically acceptable salt thereof, wherein the compound is 3-(4-((S)-2-((S)-3,3-difluorocyclohexyl)-2-(3-methylisoxazole-4-carboxamido)acetamido)phenyl)-2-methyl-4-(trifluoromethyl) pyridine 1-oxide.

Embodiment 41. A compound, or a pharmaceutically acceptable salt thereof, wherein the compound is 3-(4-((S)-2-((S)-3,3-difluorocyclohexyl)-2-(1-ethyl-1H-pyrazole-5-carboxamido)acetamido)phenyl)-2-methyl-4-(trifluoromethyl)pyridine 1-oxide.

Embodiment 42. A compound, or a pharmaceutically acceptable salt thereof, wherein the compound is (S)-3-(4-(2-(4,4-difluorocyclohexyl)-2-(1-ethyl-1H-pyrazole-5-carboxamido)acetamido)phenyl)-2-methyl-4-(trifluoromethyl)pyridine 1-oxide.

Embodiment 43. A compound, or a pharmaceutically acceptable salt thereof, wherein the compound is 3-(4-((2S)-2-(4-fluorocyclohex-3-en-1-yl)-2-(1-methyl-1H-pyrazole-5-carboxamido)acetamido)phenyl)-2,4-dimethylpyridine 1-oxide, 3-(4-((S)-2-((R)-4-fluorocyclohex-3-en-1-yl)-2-(1-methyl-1H-pyrazole-5-carboxamido)acetamido)phenyl)-2,4-dimethylpyridine 1-oxide or 3-(4-((S)-2-((S)-4-fluorocyclohex-3-en-1-yl)-2-(1-methyl-1H-pyrazole-5-carboxamido)acetamido)phenyl)-2,4-dimethylpyridine 1-oxide.

Embodiment 44. A pharmaceutical composition comprising a compound, or a pharmaceutically acceptable salt thereof, according to any one of embodiments 1 to 43, and a pharmaceutically acceptable carrier.

Embodiment 45. A combination comprising a compound, or a pharmaceutically acceptable salt thereof, according to any one of embodiments 1 to 43, and one or more therapeutically active agents.

Embodiment 46. A combination comprising a therapeutically effective amount of a compound, or a pharmaceutically acceptable salt thereof, according to embodiment 45, wherein said one or more therapeutically active agents are independently selected from a disease-modifying antirheumatic drug (DMARD); vitamin D derivatives; steroids; retinoids; JAK/TYK inhibitors; salicyclic acid; coal tar; anthralin; a calcineurin inhibitor; a modulator of lymphocyte recirculation; a mTOR inhibitor; an ascomycin having immuno-suppressive properties; immunosuppressive compounds; adhesion molecule inhibitors; a chemotherapeutic agent; UV therapy agent; an anti tumor necrosis factor (TNF) agent; T-cell signal inhibitors; blockers of pro-inflammatory cytokines; chemokines blockers; pyrimidine synthesis inhibitors; antimalarials; lymphocytes interacting compounds; sphingosine-1-phosphate (S1P) inhibitors; non-steroidal anti-inflammatory drugs ("NSAIDs"); an anti-infectious agent; or a acetylsalicylic acid drugs (ASA) including aspirin.

Embodiment 47. A method of modulating IL-17 activity in a subject, wherein the method comprises administering to the subject a therapeutically effective amount of a compound, or a pharmaceutically acceptable salt thereof, according to any one of embodiments 1 to 43.

Embodiment 48. A compound, or a pharmaceutically acceptable salt thereof, according to any one of embodiments 1 to 43, for use as a medicament, in particular for treating, or preventing an IL-17 mediated disease or condition.

Embodiment 49. A compound, or a pharmaceutically acceptable salt thereof, according to any one of embodiments 1 to 43, for use in the treatment, or prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarthropathies including ankylosing spondylitis and non-radiographic axial spondyloarthritis, Reiter syndrome, reactive arthritis, psoriatic arthritis, and enterophathis arthritis, osteoarthritis, tendinopathy, hypersensitivity (including both airways hypersensitivity and dermal hypersensitivity) and allergies, including eczema and dermatitis, as well as asthma; in particular autoimmune diseases such as autoimmune hematological disorders (including e.g. hemolytic anemia, aplastic anemia, pure red cell anemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven Johnson syndrome, idiopathic sprue, autoimmune inflammatory bowel disease (including e.g. ulcerative colitis, Crohn's disease and Irritable Bowel Syndrome), endocrine ophthalmopathy, Grave's disease, sarcoidosis, primary biliary cirrhosis, juvenile diabetes (diabetes mellitus type I), uveitis (anterior and posterior), keratoconjunctivitis sicca and vernal keratoconjunctivitis, Behcet disease, lichen planopilaris, lichen planus, hidradenitis suppurativa, acne, recurrent aphthous stomatitis, and periodontitis, pyoderma gangraenosum, and other neutrophil dermatoses, *Pityriasis rubra* pilaris, bullous pemphigoid and ichthyosis, endometriosis, non-alcoholic steatohepatitis, interstitial lung fibrosis, glomerulonephritis (with and without nephrotic syndrome, e.g. including idiopathic nephrotic syndrome or minimal change nephropathy), tumors, multiple sclerosis, autism, depressiona DNA, Alzheimer's disease, inflammatory disease of skin and cornea, myositis, loosening of bone implants, metabolic disorders, such as atherosclerosis, diabetes, and dislipidemia.

Embodiment 50. A method of treating, or preventing an IL-17 mediated disease or condition selected from autoimmune diseases and of inflammatory conditions, in particular inflammatory conditions with an etiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarthropathies including ankylosing spondylitis and non-radiographic axial spondyloarthritis, Reiter syndrome, reactive arthritis, psoriatic arthritis, and enterophathis arthritis, osteoarthritis, tendinopathy, hypersensitivity (including both airways hypersensitivity and dermal hypersensitivity) and allergies, including eczema and dermatitis, as well as asthma; in particular autoimmune diseases such as autoimmune hematological disorders (including e.g. hemolytic anemia, aplastic anemia, pure red cell anemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven Johnson syndrome, idiopathic sprue, autoimmune inflammatory bowel disease (including e.g. ulcerative colitis, Crohn's disease and Irritable Bowel Syndrome), endocrine ophthalmopathy, Grave's disease, sarcoidosis, primary biliary cirrhosis, juvenile diabetes (diabetes mellitus type I), uveitis (anterior and posterior), keratoconjunctivitis sicca and vernal keratoconjunctivitis, Behcet disease, lichen planopilaris, lichen planus, hidradenitis suppurativa, acne, recurrent aphthous stomatitis, and periodontitis, pyoderma gangraenosum, and other neutrophil dermatoses, *Pityriasis rubra* pilaris, bullous pemphigoid and ichthyosis, endometriosis, non-alcoholic steatohepatitis, interstitial lung fibrosis, glomerulonephritis (with and without nephrotic syndrome, e.g. including idiopathic nephrotic syndrome or minimal change nephropathy), tumors, multiple sclerosis, autism, depressiona DNA, Alzheimer's disease, inflammatory disease of skin and cornea, myositis, loosening of bone implants, metabolic disorders, such as atherosclerosis, diabetes, and dislipidemia, wherein the method comprises administering to the subject a therapeutically effective amount of the compound, or a pharmaceutically acceptable salt thereof, according to any one of embodiments 1 to 43.

Depending on the choice of the starting materials and procedures, the compounds can be present in the form of one of the possible stereoisomers, or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be (E) or (Z) configuration. If the compound contains a disubstituted cycloalkyl, the cycloalkyl substituent may have a cis- or trans-configuration. All tautomeric forms are also intended to be included.

As used herein, the terms "salt" or "salts" refer to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds according to any one of embodiments 1 to 43, in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds according to any one of embodiments 1 to 43, in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the formula (I). Deuterium substituents may be incorporated into the $R^9$ groups of the compounds of the present invention, for example, when $R^9$ is a $C_5$-$C_5$cycloalkyl group as defined herein, e.g. a cyclopentyl, cyclohexyl or cycloheptyl group of the compounds of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, fluorine, and chlorine, such as $^3H$, $^{11}C$, $^{13}C$, $^{14}C$, $^{15}N$, $^{16}O$, $^{17}O$, $^{18}O$, $^{18}F$, $^{35}S$, and $^{36}Cl$. Accordingly, it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutical Composition

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by IL-17, or (ii) associated with IL-17 activity, or (iii) characterized by activity (normal or abnormal) of IL-17; or (2) reduce or inhibit the activity of IL-17; or (3) reduce or inhibit the expression of IL-17. In another non-limiting embodiment, the term "a therapeutically effective amount" refers to the amount of the compound of the present invention that, when administered to a cell, or a tissue, or a non-cellular biological material, or a medium, is effective in at least partially reducing or inhibiting the activity of IL-17; or at least partially reducing or inhibiting the expression of IL-17.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically, or in quality of life from such treatment.

As used herein, the term "a", "an", "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) isomers, stereoisomers, diastereomers, optical isomers (antipodes), racemates, atropisomers or mixtures thereof. For example, the compound of Example 2 herein may exist in substantially the pure form of one of the two atropisomer forms or mixtures of the two forms, thus the name 4-chloro-3-(4-((S)-2-cyclohexyl-2-(1-methyl-1H-pyrazole-5-carboxamido)acetamido)-2-fluorophenyl)-2-methylpyridine 1-oxide used herein includes the pure atropisomer forms (Ra) or (Sa) and mixtures thereof. The two atropisomeric forms are referred to herein as (Ra) or (Sa) forms indicating the stereochemical configuration about the single bond of restricted rotation connecting the substituted phenyl and pyridyl rings.

Any resulting mixtures of stereoisomers can be separated on the basis of the physicochemical differences of the constituents, into the pure or substantially pure geometric or optical isomers, diastereomers, atropisomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic compound may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) using a chiral adsorbent.

Method of Synthesizing the Compounds of the Invention

All methods described herein can be performed in any suitable order unless otherwise indicated herein or otherwise clearly contradicted by context. The use of any and all examples, or exemplary language (e.g. "such as") provided herein is intended merely to better illustrate the invention and does not pose a limitation on the scope of the invention otherwise claimed. The compounds of the present application can be prepared by those skilled in the art of organic synthesis using commercially available starting materials, compounds known in the literature, or from readily prepared intermediates, by employing standard synthetic methods and procedures either known to those skilled in the art, or which will be apparent to the skilled chemist in light of the teachings herein.

The compounds of Formula (I) may be prepared by methods as set forth in the following synthetic reaction schemes. In the schemes described below, it is well understood that protecting groups for sensitive or reactive groups are employed where necessary in accordance with general principles of chemistry. Protecting groups are manipulated according to standard methods of organic synthesis as described for example in Protective Groups in Organic Synthesis, 3rd edition, John Wiley & Sons: New York, 1999 or Protecting Groups, 3rd edition, Thieme, Stuttgart, 2004. Protective groups are removed at a convenient stage of the compound synthesis using methods that are readily apparent to those skilled in the art.

Those skilled in the art will recognize if a stereocentre exists in the compounds disclosed herein. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Compounds of the present disclosure can be synthesized by following the steps outlined in Schemes 1, 2 and 3. Starting materials are either commercially available or made by known procedures in the reported literature or as illustrated.

In the following general methods, $R^2$, $R^3$, $R^4$, $R^5$, $R^6$, $R^7$, $R^8$ and Z are as previously defined in the above embodiments, or limited to designations in the Schemes. PG1 and PG2 are suitable protecting groups. Unless otherwise stated, starting materials are either commercially available or are prepared by known methods.

Scheme 1

Reaction Scheme 1

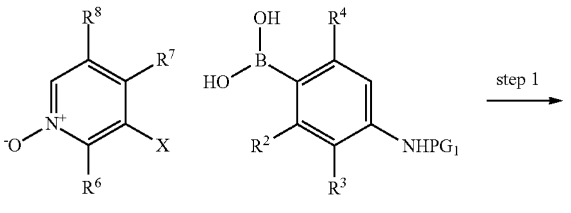

1
X = Br, I

2
PG1 = H, Boc, etc

-continued

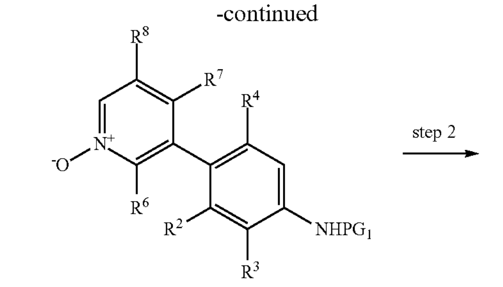

3

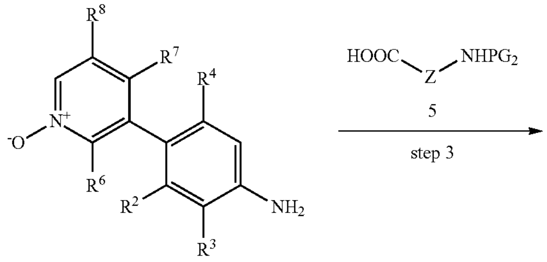

4

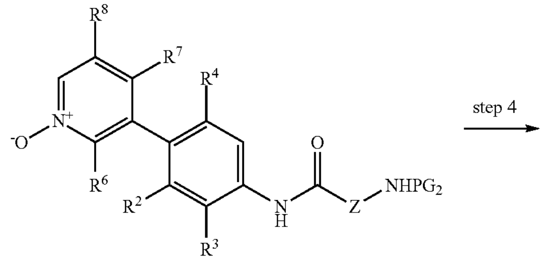

6
PG2 = Boc, Fmoc, etc

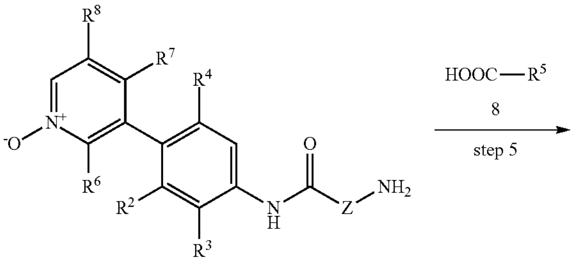

7

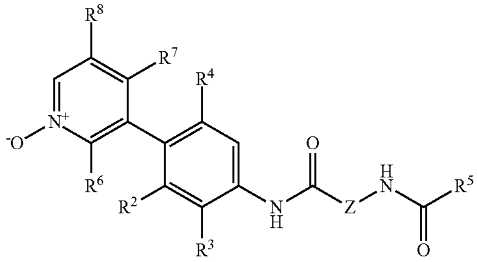

I

Step 1 involves the Suzuki-coupling of compounds 1 and 2 as shown in Scheme 1 in a suitable solvent such as dioxane in the presence of suitable catalysts such as $Pd(dppf)Cl_2$-DCM complex or other Pd-containing catalysts and in the presence of a suitable base, such as aqueous $Na_2CO_3$, at suitable temperatures, such as 100° C.

In step 2 a suitable protecting group PG1, (e.g. PG1=Boc) is removed. This involves reacting 3 with suitable reagent, e.g. HCl or TFA in a suitable solvent, e.g. dioxane at suitable temperatures, such as room temperature. Alternative conditions and protecting groups (e.g. PG1=Fmoc) are described in the literature (e.g. T. W. Green and P. G. M. Wuts (2014) Protective Groups in Organic Synthesis, 5th edition, John Wiley & Sons.

Step 3 involves coupling of 4 with a suitable protected amino acid 5 (e.g. PG2=Boc or Cbz or Fmoc) in a suitable solvent, such as dimethylformamide (DMF), in the presence of a suitable amide coupling reagent, for example @T3P or HATU, and a suitable base, such as DIPEA, at a suitable temperature, such as room temperature.

Step 4 involves removal of the protecting group PG2 from compound 6, by a method similar to that of step 2.

Step 5 involves coupling of 7 with a suitable acid in a suitable solvent, such as dimethylformamide (DMF), in the presence of a suitable amide coupling reagent, for example @T3P or HATU, and a suitable base, such as DIPEA, at a suitable temperature, such as room temperature, leading to compound I.

This synthesis route can also be applied for the synthesis of 4-substituted pyridine-N-oxides.

Scheme 2

Reaction scheme 2

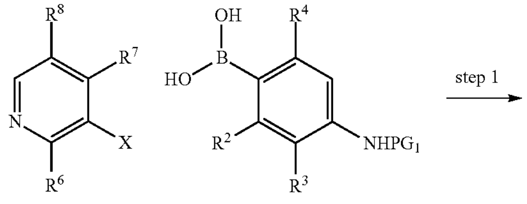

9
X = Br, I

2
PG1 = H, Boc, etc

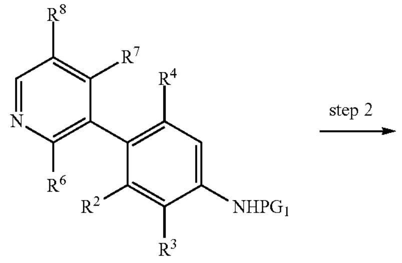

10

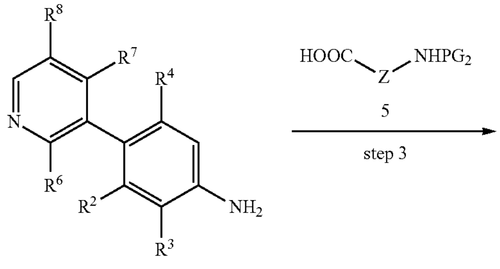

11

-continued

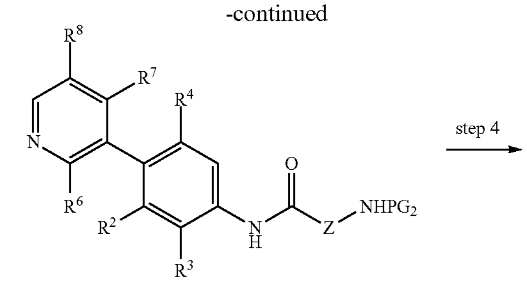

12
PG2 = Boc, Fmoc, etc

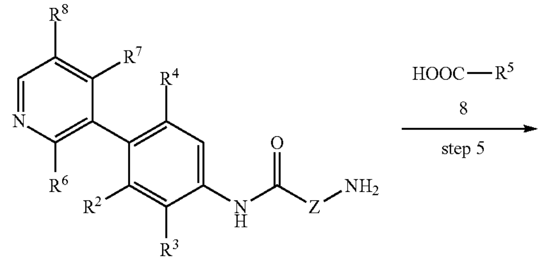

13

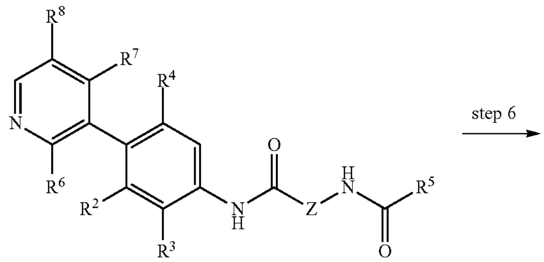

14

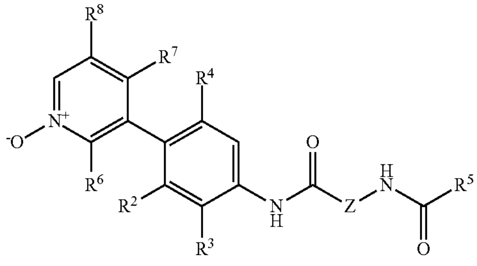

I

Step 1 involves the Suzuki-coupling of compound 2 with a substituted pyridine 9 as shown in Scheme 2, in a suitable solvent such as dioxane in the presence of suitable catalysts such as Pd(dppf)$Cl_2$-DCM complex or other Pd-containing catalysts and in the presence of a suitable base, such as aqueous $Na_2CO_3$, at suitable temperatures, such as 100° C.

In step 2, a suitable protecting group PG1, (e.g. PG1=Boc) is removed. This involves reacting 10 with suitable reagent, e.g. HCl or TFA in a suitable solvent, e.g. dioxane at suitable temperatures, such as room temperature. Alternative conditions and protecting groups (e.g. PG1=Fmoc) are described in the literature (e.g. T. W. Green and P. G. M. Wuts (2014) Protective Groups in Organic Synthesis, 5th edition, John Wiley & Sons.

Step 3 involves coupling of 11 with a suitable protected amino acid 5 (e.g. PG2=Boc or Cbz or Fmoc) in a suitable solvent, such as dimethylformamide (DMF), in the presence of a suitable amide coupling reagent, for example ®T3P or HATU, and a suitable base, such as DIPEA, at a suitable temperature, such as room temperature.

Step 4 involves removal of the protecting group PG2 from compound 12, by a method similar to that of step 2.

Step 5 involves coupling of 13 with a suitable acid 8 in a suitable solvent, such as dimethylformamide (DMF), in the presence of a suitable amide coupling reagent, for example ®T3P or HATU, and a suitable base, such as DIPEA, at a suitable temperature, such as room temperature.

Step 6 involves oxidation of the pyridine 14 to the pyridine-N-oxide with a suitable oxidant (e.g. mCPBA) in a suitable solvent (e.g. DCM), at suitable temperatures, such as RT, leading to compound I.

This synthesis route can also be applied for the synthesis of 4-substituted pyridine-N-oxides.

Scheme 3

Reaction scheme 3

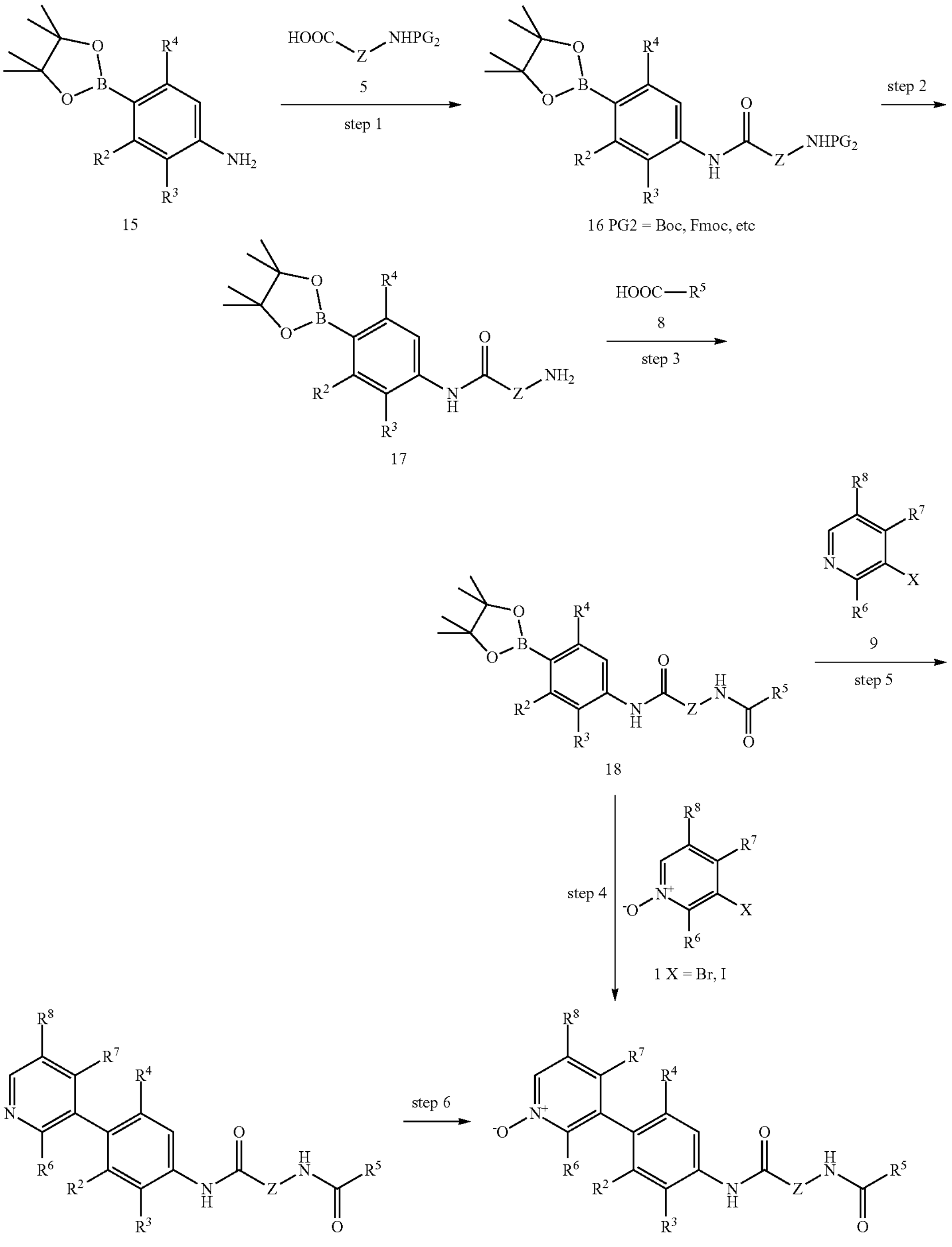

15

16 PG2 = Boc, Fmoc, etc

17

18

1 X = Br, I

19

1

Step 1 involves coupling of a suitable boronic ester 15 with a suitable protected amino acid 5 (e.g. PG2=Boc or Cbz or Fmoc) in a suitable solvent, such as dimethylformamide (DMF), in the presence of a suitable amide coupling reagent, for example ®T3P or HATU, and a suitable base, such as DIPEA, at a suitable temperature, such as room temperature.

In step 2, a suitable protecting group PG1, (e.g. PG1=Boc) is removed. This involves reacting 16 with suitable reagent, e.g. HCl or TFA in a suitable solvent, e.g. dioxane at suitable temperatures, such as room temperature. Alternative conditions and protecting groups (e.g. PG1=Fmoc) are described in the literature (e.g. T. W. Green and P. G. M. Wuts (2014) Protective Groups in Organic Synthesis, 5th edition, John Wiley & Sons.

Step 3 involves coupling of 17 with a suitable acid 8 in a suitable solvent, such as dimethylformamide (DMF), in the presence of a suitable amide coupling reagent, for example @T3P or HATU, and a suitable base, such as DIPEA, at a suitable temperature, such as room temperature.

Step 4 involves Suzuki-coupling of of 18 with a suitable substituted pyridine-N-oxide, in a suitable solvent such as dioxane in the presence of suitable catalysts such as Pd(dppf)$Cl_2$-DCM complex or other Pd-containing catalysts and in the presence of a suitable base, such as aqueous $Na_2CO_3$, at suitable temperatures, such as 100° C., leading to compound I.

Alternatively, compound can be prepared from compound 18 by a 2-step procedure involving a Suzuki coupling of 18 with a suitable substituted pyridine 9 (step 5), followed by N-oxidation of pyridine 14 to the pyridine-N-oxide with a suitable oxidant (e.g. mCPBA) in a suitable solvent (e.g. DCM), at suitable temperatures, such as RT (step 6), leading to compound I.

This synthesis route can also be applied for the synthesis of 4-substituted pyridine-N-oxides.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier.

In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. For topical administration the pharmaceutical compositions of the present invention can be made up, for example, as creams, ointments or gels. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Method of Use of the Invention

The compounds of formulae (I), (IA) or (IB) in free form or in pharmaceutically acceptable salt form, exhibit valuable pharmacological properties, for example IL-17 modulating properties, for example as indicated in in vitro tests as provided in the next sections, and are therefore indicated for therapy or for use as research chemicals, e.g. as tool compounds.

Compounds of the invention may be useful in the treatment, or prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarthropathies including ankylosing spondylitis and non-radiographic axial spondyloarthritis, Reiter syndrome, reactive arthritis, psoriatic arthritis, and enterophathis arthritis, osteoarthritis, tendinopathy, hypersensitivity (including both airways hypersensitivity and dermal hypersensitivity) and allergies, including eczema and dermatitis, as well as asthma; in particular autoimmune diseases such as autoimmune hematological disorders (including e.g. hemolytic anemia, aplastic anemia, pure red cell anemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven Johnson syndrome, idiopathic sprue, autoimmune inflammatory bowel disease (including e.g. ulcerative colitis, Crohn's disease and Irritable Bowel Syndrome), endocrine ophthalmopathy, Grave's disease, sarcoidosis, primary biliary cirrhosis, juvenile diabetes (diabetes mellitus type I), uveitis (anterior and posterior), keratoconjunctivitis sicca and vernal keratoconjunctivitis, Behcet disease, lichen planopilaris, lichen planus, hidradenitis suppurativa, acne, recurrent aphthous stomatitis, and periodontitis, pyoderma gangraenosum, and other neutrophil dermatoses, *Pityriasis rubra* pilaris, bullous pemphigoid and ichthyosis, endometriosis, non-alcoholic steatohepatitis, interstitial lung fibrosis, glomerulonephritis (with and without nephrotic syndrome, e.g. including idiopathic nephrotic syndrome or minimal change nephropathy), tumors, multiple sclerosis, autism, depressiona DNA, Alzheimer's disease, inflammatory disease of skin and cornea, myositis, loosening of bone implants, metabolic disorders, such as atherosclerosis, diabetes, and dislipidemia.

Thus, as a further aspect, the present invention provides the use of a compound of formula (I), (IA) or (IB) (in particular according to any one of embodiments 1 to 43), or a pharmaceutically acceptable salt thereof, in therapy. In a further embodiment, the therapy is treatment of a disease, disorder or condition which may be treated by inhibition of IL-17. In another embodiment, the disease is selected from the afore-mentioned list, suitably from psoriasis, psoriatic arthritis, ankylosing spondylitis and non-radiographic axial spondyloarthritis.

Thus, as a further aspect, the present invention provides a compound of formula (I), (IA) or (IB) (in particular according to any one of embodiments 1 to 43), or a pharmaceutically acceptable salt thereof, for use in therapy. In a further embodiment, the therapy is selected from a disease which may be treated by inhibition of IL-17. In another embodiment, the disease is selected from the afore-mentioned list, suitably from psoriasis, psoriatic arthritis, ankylosing spondylitis and non-radiographic axial spondyloarthritis.

In another aspect, the invention provides a method of treating, or preventing a disease which is treated by inhibiting IL-17 comprising administration of a therapeutically effective amount of a compound of any one of formula (I), (IA) or (IB) (in particular according to any one of embodiments 1 to 43), or a pharmaceutically acceptable salt thereof. In a further embodiment, the disease is selected from the afore-mentioned list, suitably from psoriasis, psoriatic arthritis, ankylosing spondylitis and non-radiographic axial spondyloarthritis.

Thus, as a further aspect, the present invention provides the use of a compound of any one of formula (I), (IA) or (IB) (in particular according to any one of embodiments 1 to 43), or a pharmaceutically acceptable salt thereof, for the manufacture of a medicament. In a further embodiment, the medicament is for treatment, or prevention of a disease, which may be treated by inhibition of IL-17. In another embodiment, the disease is selected from the afore-mentioned list, suitably from psoriasis, psoriatic arthritis, ankylosing spondylitis and non-radiographic axial spondyloarthritis.

In one embodiment of the present invention, there is provided, 2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 4-chloro-3-(4-((S)-2-cyclohexyl-2-(1-methyl-1H-pyrazole-5-carboxamido)acetamido)-2-fluorophenyl)-2-methylpyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 2,4-dimethyl-3-(4-((S)-2-(1-methyl-1H-pyrazole-5-carboxamido)-2-((1r,4S)-4-methylcyclohexyl)acetamido)phenyl)pyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 4-chloro-3-(4-((S)-2-(3-ethylisoxazole-4-carboxamido)-2-((1r,4S)-4-(trifluoromethyl)cyclohexyl)acetamido)phenyl)-2-methylpyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided (S)-3-(4-(2-cyclopentyl-2-(3-ethylisoxazole-4-carboxamido)acetamido)phenyl)-2-methyl-4-(trifluoromethyl)pyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 4-chloro-3-(4-((S)-2-((S)-3,3-difluorocyclohexyl)-2-(3-ethylisoxazole-4-carboxamido)acetamido)phenyl)-2-methylpyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 3-(4-((S)-2-(1-ethyl-1H-pyrazole-5-carboxamido)-2-((1r,4S)-4-(trifluoromethyl)cyclohexyl)acetamido)phenyl)-2,4-dimethylpyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 3-(4-((S)-2-(3-ethylisoxazole-4-carboxamido)-2-((1r,4S)-4-(trifluoromethyl)cyclohexyl)acetamido)phenyl)-2,4-dimethylpyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 3-(4-((S)-2-((S)-3,3-difluorocyclohexyl)-2-(3-methylisoxazole-4-carboxamido)acetamido)phenyl)-2-methyl-4-(trifluoromethyl)pyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 3-(4-((S)-2-((S)-3,3-difluorocyclohexyl)-2-(1-ethyl-1H-pyrazole-5-carboxamido)acetamido)phenyl)-2-methyl-4-(trifluoromethyl)pyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided (S)-3-(4-(2-(4,4-difluorocyclohexyl)-2-(1-ethyl-1H-pyrazole-5-carboxamido)acetamido)phenyl)-2-methyl-4-(trifluoromethyl)pyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

In one embodiment of the present invention, there is provided 3-(4-((2S)-2-(4-fluorocyclohex-3-en-1-yl)-2-(1-methyl-1H-pyrazole-5-carboxamido)acetamido)phenyl)-2,4-dimethylpyridine 1-oxide, 3-(4-((S)-2-((R)-4-fluorocyclohex-3-en-1-yl)-2-(1-methyl-1H-pyrazole-5-carboxamido)acetamido)phenyl)-2,4-dimethylpyridine 1-oxide or 3-(4-((S)-2-((S)-4-fluorocyclohex-3-en-1-yl)-2-(1-methyl-1H-pyrazole-5-carboxamido)acetamido)phenyl)-2,4-dimethylpyridine 1-oxide, or a pharmaceutically acceptable salt thereof, for use in the treatment, or prevention of a disease selected from the afore-mentioned list, suitably from psoriasis, psoriatic arthritis, ankylosing spondylitis and non-radiographic axial spondyloarthritis.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable using in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Combination Product and Combination Therapy of the Invention

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow for the combination partners to have a cooperative, e.g. synergistic effect. The single components may be packaged in a kit or separately. One or both of the components (e.g. powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow for the combination partners to have a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g. tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compounds of the present invention may be administered either simultaneously with, or before, or after, one or more other therapeutic agent. The compounds of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

Thus, in another aspect, the invention provides a combination, in particular a pharmaceutical combination, comprising (e.g. a therapeutically effective amount of) a compound of formula (I), (IA) or (IB) (in particular according to any one of embodiments 1 to 43), or a pharmaceutically acceptable salt thereof, and one or more other therapeutically active agents.

In one embodiment, the invention provides a product comprising a compound of formula (I), (IA) or (IB) (in particular according to any one of embodiments 1 to 43), or a pharmaceutically acceptable salt thereof, and at least one other therapeutic agent as a combined preparation for simultaneous, separate or sequential use in therapy.

In one embodiment, the therapy is the treatment, or prevention of a disease or condition mediated by IL-17. Products provided as a combined preparation include a composition comprising a compound of formula (I), (IA) or (IB), or a pharmaceutically acceptable salt thereof, and the other therapeutic agent(s) together in the same pharmaceutical composition, or a compound of formula (I), (IA) or (IB), or a pharmaceutically acceptable salt thereof, and the other therapeutic agent(s) in separate form, e.g. in the form of a kit.

In one embodiment, the invention provides a pharmaceutical combination comprising a compound of formula (I), (IA) or (IB) (in particular according to any one of embodiments 1 to 43), or a pharmaceutically acceptable salt thereof, and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of formula (I), (IA) or (IB) (in particular according to any one of embodiments 1 to 43), or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I), (IA) or (IB) (in particular according to any one of embodiments 1 to 43), or a pharmaceutically acceptable salt thereof, for treating, or preventing a disease or condition mediated by IL-17, wherein the medicament is prepared for administration with another therapeutic agent. The invention also provides the use of another therapeutic agent for treating, or preventing a disease or condition mediated by IL-17 wherein the medicament is administered with a compound of formula (I), (IA) or (IB) (in particular according to any one of embodiments 1 to 43), or a pharmaceutically acceptable salt thereof.

The invention also provides a compound of formula (I), (IA) or (IB) (in particular according to any one of embodiments 1 to 43), or a pharmaceutically acceptable salt thereof, for use in a method of treating, or preventing a disease or condition mediated by IL-17, wherein the compound of formula (I), (IA) or (IB) (in particular according to any one of embodiments 1 to 43), or a pharmaceutically acceptable salt thereof, is prepared for administration with another therapeutic agent. The invention also provides another therapeutic agent for use in a method of treating, or preventing a disease or condition mediated by IL-17, wherein the other therapeutic agent is prepared for administration with a compound of formula (I), (IA) or (IB) (in particular according to any one of embodiments 1 to 43), or a pharmaceutically acceptable salt thereof. The invention also provides a compound of formula (I), (IA) or (IB) (in particular according to any one of embodiments 1 to 43), or a pharmaceutically acceptable salt thereof, for use in a method of treating, or preventing a disease or condition mediated by IL-17, wherein the compound of formula (I), (IA) or (IB) (in particular according to any one of embodiments 1 to 43), or a pharmaceutically acceptable salt thereof, is administered with another therapeutic agent. The invention also provides another therapeutic agent for use in a method of treating, or preventing a disease or condition mediated by IL-17, wherein the other therapeutic agent is administered with a compound of formula (I), (IA) or (IB) (in particular according to any one of embodiments 1 to 43), or a pharmaceutically acceptable salt thereof.

The invention also provides the use of a compound of any one of formula (I), (IA) or (IB) (in particular according to any one of embodiments 1 to 43), or a pharmaceutically acceptable salt thereof, for treating, or preventing a disease or condition mediated by IL-17, wherein the patient has previously (e.g. within 24 hours) been treated with another therapeutic agent. The invention also provides the use of another therapeutic agent for treating a disease or condition mediated by IL-17, wherein the patient has previously (e.g. within 24 hours) been treated with a compound of formula (I), (IA) or (IB) (in particular according to any one of embodiments 1 to 43), or a pharmaceutically acceptable salt thereof.

In one embodiment, the other therapeutic agent is a therapeutic agent useful in the treatment of a respiratory disorder and/or a therapeutic agent that is useful in the treatment of inflammation and disorders with an inflammatory component (anti-inflammatory drugs).

In one embodiment, the other therapeutic agent useful in the combination therapy is selected from a disease-modifying antirheumatic drug (DMARD); vitamin D derivatives; steroids; retinoids; JAK/TYK inhibitors; salicyclic acid; coal tar; anthralin; a calcineurin inhibitor; a modulator of lymphocyte recirculation; a mTOR inhibitor; an ascomycin having immuno-suppressive properties; immunosuppressive compounds; adhesion molecule inhibitors; a chemotherapeutic agent; UV therapy agent; an anti tumor necrosis factor (TNF) agent; T-cell signal inhibitors; blockers of pro-inflammatory cytokines; chemokines blockers; pyrimidine synthesis inhibitors; antimalarials; lymphocytes interacting compounds; sphingosine-1-phosphate (S1P) inhibitors; non-steroidal anti-inflammatory drugs ("NSAIDs"); an anti-infectious agent; or a acetylsalicylic acid drugs (ASA) including aspirin.

Suitable disease-modifying antirheumatic drugs (DMARDs) for use in the combination include, but are not limited to, gold salts, sulphasalazine, antimalarias, methotrexate, D-penicillamine, azathioprine, mycophenolic acid, cyclosporine A, tacrolimus, sirolimus, minocycline, leflunomide, glococorticoids.

Suitable JAK/TYK inhibitors for use in the combination include, but are not limited to, pan JAK inhibitors or more specific JAK/TYK2 inhibitors such as tofacitinib, baricitinib; JAK inhibitors such as Ruxolitinib.

Suitable calcineurin inhibitors for use in the combination include, but are not limited to, cyclosporin A, FK 506, or FKBP12.

Suitable modulator of lymphocyte recirculation for use in the combination include, but are not limited to, FTY720, or FTY720 analogs.

Suitable mTOR inhibitor for use in the combination include, but are not limited to, rapamycin, 40-O-(2-hydroxyethyl)-rapamycin (everolimus, WO2005/052187), sirolimus, temsirolimus (CC1779), ABT578, AP23573, or TAFA-93.

Suitable ascomycin having immuno-suppressive properties for use in the combination include, but are not limited to ABT-281, ASM981, corticosteroids, cyclophosphamide, azathioprene, methotrexate, leflunomide, mizoribine, mycophenolic acid, mycophenolate mofetil, or 15-deoxyspergualine.

Suitable immunosuppressive compounds for use in the combination include, but are not limited to, a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4lg (for ex. designated ATCC 68629) or a mutant thereof, e.g. LEA29Y; corticosteroids; azathioprin; methotrexate; cyclosporine; retinoids; phosphodiesterase type 4 (PDE4) inhibitors such as apremilast.

Suitable adhesion molecule inhibitors for use in the combination include, but are not limited to, LFA-1 antagonists, ICAM-1 or -3 antagonists, VCAM-4 antagonists, or VLA-4 antagonists.

Suitable chemotherapeutic agent for use in the combination include, but are not limited to, paclitaxel, gemcitabine, cisplatinum, doxorubicin, or 5-fluorouracil.

Suitable UV therapy agent for use in the combination include, but are not limited to, sunlight; or Laser.

Suitable anti-TNF agents for use in the combination include, but are not limited to, monoclonal antibodies to TNF, e.g. infliximab, adalimumab, CDP870; or receptor constructs to TNF-RI or TNF-RII, e.g. Etanercept, PEG-TNF-RI; or TNF-alpha blockers such as adalimumab, infliximab, golimumab.

Suitable T-cell signal inhibitors for use in the combination include, but are not limited to, abatacept, intergrin blockers such as vedolizumab.

Suitable blockers of proinflammatory cytokines for use in the combination include, but are not limited to, IL-1 blockers such as canckinumab; IL-1 trap such as AAL160, ACZ 885; IL-6 blockers; IL-1 receptor blockers such as anakinra; IL-12 inhibitors such as ustekinumab; IL-23 inhibitors such as risankizumab; IL-17 inhibitors such as secukinumab or ixekizumab; or IL17R blockers, such as brodalumab.

Suitable chemokines blockers for use in the combination include, but are not limited to, e.g inhibitors or activators of proteases, e.g. metalloproteases; anti-IL-15 antibodies; anti-IL-6 antibodies such as tocilizumab; or anti-CD20 or anti-CD40 antibodies such as rituximab, iscalimab.

Suitable pyrimidine synthesis inhibitors for use in the combination include, but are not limited to, leflunomide.

Suitable antimalarials for use in the combination include, but are not limited to, chloroquin; or hydroxachloroquine Suitable lymphocytes interacting compounds for use in the combination include, but are not limited to, D-penicillamine.

Suitable sphingosine-1-phosphate (S1P) inhibitors for use in the combination include, but are not limited to, minocycline; or tetracycline.

Suitable NSAIDs for use in the combination include, but are not limited to, Aceclofenac, acemetacin, acetylsalicylic acid, alclofenac, alminoprofen, amfenac, Ampiroxicam, Antolmetinguacil, Anirolac, antrafenine, azapropazone, benorylate, Bermoprofen, bindarit, bromfenac, bucloxic acid, Bucolom, Bufexamac, Bumadizon, butibufen, Butixirat, Carbasalatcalcium, carprofen, choline magnesium trisalicylate, celecoxib, Cinmetacin, Cinnoxicam, clidanac Clobuzarit Deboxamet, dexibuprofen, Dexketoprofen, diclofenac, diflunisal, droxicam, Eltenac, Enfenaminsaure, Etersalat, etodolac, etofenamate, etoricoxib, Feclobuzon, felbinac, fenbufen, fenclofenac, fenoprofen, fentiazac, Fepradinol, Feprazon, Flobufen, floctafenine, flufenamic acid, flufenisal, Flunoxaprofen, flurbiprofen, Flurbiprofenaxetil, Furofenac, Furprofen, Glucametacin, ibufenac, ibuprofen, Indobufen, indomethacin, Indometacinfarnesil, indoprofen, Isoxepac, Isoxicam, ketoprofen, ketorolac, lobenzarit, Lonazolac, lornoxicam, Loxoprofen, lumiracoxib, meclofenamic, Meclofen, mefenamic acid, meloxicam, mesalazine, Miro Profen, Mofezolac, nabumetone, naproxen, niflumic acid, olsalazine, oxaprozin, Oxipinac, oxyphenbutazone, parecoxib, phenylbutazone, Pelubiprofen, Pimeprofen, Pirazolac, Priroxicam, pirprofen, Pranoprofen, Prifelon, Prinomod, Proglumetacin, Proquazon, Protizininsaure, rofecoxib, Romazarit, salicylamide, salicylic acid, Salmi Stein, Salnacedin, salsalate, sulindac, sudoxicam, suprofen, Talniflumate, tenidap, Tenosal, tenoxicam, tepoxalin, tiaprofenic acid, Taramid, Tilnoprofenarbamel, timegadine, Tinoridin, Tiopinac, tolfenamic acid, tolmetin, Ufenamat, valdecoxib, Ximoprofen, zaltoprofen, Zoliprofen and combinations thereof.

Suitable acetylsalicylic acid drugs (ASA) for use in the combination include, but are not limited to, 5-ASA derivatives, such as sulfasalazine.

EXAMPLES

The disclosure is further illustrated by the following examples and synthetic methods, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The compounds of the present invention can be produced by organic synthesis methods known to one of ordinary skill in the art as shown in the following examples. All starting materials, building blocks, reagents, acids, bases, dehydrating agents, solvents, and catalysts utilized to synthesise the compounds of the present invention are either commercially available or can be produced by organic synthesis methods known to one of ordinary skill in the art. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (2014) Protective Groups in Organic Synthesis, 5th edition, John Wiley & Sons). These groups are removed at a convenient stage of the compound synthesis using methods that are readily apparent to those skilled in the art. Unless otherwise noted, reagents and solvents were used as received from commercial suppliers.

The chemical names were generated using ChemDraw Professional v17.1.0.105 from PerkinElmer.

Temperatures are given in degrees Celsius. As used herein, unless specified otherwise, the term "room temperature" or "ambient temperature" means a temperature of from 15° C. to 30° C., such as of from 20° C. to 30° C., such as of from 20° C. to 25° C. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations

Abbreviations used in the following examples and elsewhere herein are:

AC Active control
aq. Aqueous

AcOH Acetic acid
BINAP racemic 2,2'-bis(diphenylphosphino)-1,1'-binaphthyl
BOC tertiary butyloxycarbonyl
BP reaction Gene integration reaction between the attB and the attP sites of a Gateway® Cloning gene vector
br. Broad
Cbz Carboxybenzyl
d doublet
dd doublet of doublets
DAST diethylaminosulfur trifluoride
DCM dichloromethane
DIPEA N,N-diisopropylethylamine
DME 1,4-dimethoxyethane
DMAP 4-Dimethylaminopyridine
DMF N,N-dimethylformamide
DMSO dimethylsulfoxide
EDTA ethylenediamine tetraacetic acid
EtOAc ethyl acetate
EtOH ethanol
eq Equivalent(s)
FRET Fluorescence Resonance energy transfer
GC-MS Gas chromatography and mass spectrometry
h hour(s)
HATU 2-(3H-[1,2,3]triazolo[4,5-b]pyridin-3-yl)-1,1,3,3-tetramethyluronium hexafluorophosphate
HPLC high pressure liquid chromatography
HV high vacuum
Hyflo Celite® Hyflo Super-Cel®, filter aid—$SiO_2$
Hz Hertz
IPA isopropanol
IR Infrared
$IC_{50}$ Half maximal inhibitory concentration
J Coupling constant
L/mL/µL Liter/milliliter/microliter
LC-MS liquid chromatography and mass spectrometry
LDA lithium diisopropylamide
LR reaction Gene recombination reaction between attL and attR sites of a gene vector
M/mM/µM/nM/µM Molar/millimolar/micromolar/nanomolar/picomolar
MeOH methanol
mCPBA meta-chloroperoxybenzoic acid
MS mass spectrometry
m multiplet
mg/µg milligram/microgram
min minutes
mL milliliter
mmol millimol
m/z mass to charge ratio
NC Neutral control
NHDF Normal human dermal fibroblasts
NIS N-iodosuccinimide
NMR nuclear magnetic resonance
n.t. not tested
ON over night
PBS Phosphate buffered saline
PCR Polymerase chain reaction
pDESTRS5a Gateway® Cloning vector
pDON201 Gateway® Cloning entry vector
$Pd(dppf)Cl_2 \cdot DCM$ 1,1'-Bis(diphenylphosphino)ferrocene-palladium(II)dichloride dichloromethane complex
PEI polyethyleneimine
PG Protecting group
ppm parts per million
Prep HPLC Preparatory HPLC
pRS5a Mammalian expression vector
rac racemic
Rt retention time
RT room temperature
Rpm Rotation per minutes
s singlet
sat. saturated
SDS-PAGE Sodium dodecyl sulfate-Polyacrylamide gel electrophoresis
SFC Supercritical fluid chromatography
t triplet
T3P Propylphosphonic anhydride
TBME methyl tert-butyl ether
TFA trifluoroacetic acid
THF tetrahydrofuran
TMS Tetramethylsilane
TNF-α Tumor necrosis factor alpha
TRIS 2-amino-2-hydroxymethyl-1,3-propanediol
Tween 20 Polysorbate 20
XPhos 2-Dicyclohexylphosphino-2',4',6'-triisopropylbiphenyl
XPhos-Pd-G2 Chloro(2-dicyclohexylphosphino-2',4',6'-triisopropyl-1,1'-biphenyl)[2-(2'-amino-1,1'-biphenyl)] palladium(II)

General Conditions:

NMR: Measurements were performed on a Bruker 600 MHz or a Bruker 400 MHz NMR spectrometer using or not tetramethylsilane (TMS) as an internal standard. Chemical shifts (6-values) are reported in ppm downfield from tetramethylsilane (TMS), spectra splitting 5 patterns are designated as singlet (s), doublet (d), doublet of doublets (dd), doublet of triplets (dt), doublet of quartets (dq), triplet (t), triplet of doublets (td), quartet (q), quartet of doublets (qd), quintet (quint), septet (sep), multiplet, unresolved or overlapping signals (m), broad signal (br). Deuterated solvents are given in parentheses and have a chemical shifts of dimethyl sulfoxide (δ 2.50 ppm), methanol (δ 3.31 ppm), chloroform (δ 7.26 ppm), or other solvent as indicated in NMR spectral data.

Column Chromatography was performed on an ISCO CombiFlash Rf 200i system equipped with a Photodiode Array Detector and using ISCO Redisep cartridges. Columns and separation conditions are indicated in brackets in the experimental part.

Supercritical Fluid Chromatography (SFC) purifications and chiral separation were performed on a Waters Preparative SFC-100-MS system equipped with a Waters 2998 Photodiode Array Detector and a Waters MS Single Quadrupole Detector. Columns and separation conditions are indicated in brackets in the experimental part.

Prep-HPLC were performed either on a Gilson prep-HPLC system equipped with a model 322 pump, a model 155 UV-VIS detector and a model 215 liquid handler or on a Waters prep-HPLC system equipped with a UV detector Waters 2487 Dual & Adsorbance Detector and an MS detector Waters MicromassZQ. Columns and separation conditions are indicated in brackets in the experimental part.

Mass Spectrometry was performed with LC-MS, SFC-MS, or GC-MS systems using electrospray, chemical and electron impact ionization methods from a range of instruments of the following configurations: Agilent 1100 HPLC systems with an Agilent 6110 Mass Spectrometer. $[MH]^+$ refers to protonated molecular ion of the chemical species.

MS Methods:

Method 1

Column: Acquity UPLC HSS T3, 1.8 µm, 2.1×50 mm

Column Temperature: 60° C.

Eluents A: water+0.05% FA+3.75 mM AA, B: acetonitrile+0.04% FA
Flow Rate 1.0 mL/min
Gradient from 5 to 98% B in 1.4 min Method 2
Column: Acquity UPLC BEH C18, 1.7 µm, 2.1×50 mm
Column Temperature: 80° C.
Eluents A: water+0.05% FA+3.75 mM AA, B: isopropanol+0.05% FA
Flow Rate 0.6 mL/min
Gradient from 5 to 98% B in 1.7 min Method 3
Column: Acquity UPLC BEH C18, 1.7 µm, 2.1×50 mm
Column Temperature: 80° C.
Eluents A: water+4.76% IPA+0.05% FA+3.75 mM AA, B: isopropanol+0.05% FA
Flow Rate 0.6 mL/min
Gradient from 1 to 98% B in 1.7 min Method 4
Column: Acquity UPLC BEH C18, 1.7 µm, 2.1×50 mm
Column Temperature: 80° C.
Eluents A: water+0.05% FA+3.75 mM AA, B: isopropanol+0.05% FA
Flow Rate 0.4 mL/min
Gradient from 5 to 60% B in 8.4 min, then from 60 to 98% B in 1 min Method 5
Column: CORTECS™ C18, 2.7 µm, 2.1×50 mm
Column Temperature: 80° C.
Eluents A: water+4.76% IPA+0.05% FA+3.75 mM AA, B: isopropanol+0.05% FA
Flow Rate 1.0 mL/min
Gradient from 1 to 50% B in 1.4 min, then from 50 to 98% B in 0.3 min Method 6
Column: XBridge® BEH™ C18 2.5 µm, 2.1×50 mm
Column Temperature: 80° C.
Eluents: A: water+5 mM NH4OH, B: acetonitrile+5 mM NH4OH
Flow Rate 1.0 mL/min
Gradient: from 2 to 98% B in 1.4 min Method 7
Column: CORTECS™ C18, 2.7 µm, 2.1×50 mm
Column Temperature: 80° C.
Eluents A: water+0.05% FA+3.75 mM AA, B: isopropanol+0.05% FA
Flow Rate 1.0 mL/min
Gradient from 1 to 98% B in 1.7 min Method 8
Column: Ascentis™ Express C18, 2.7 µm, 2.1×50 mm
Column Temperature: 80° C.
Eluents A: water+4.76% isopropanol+0.05% FA+3.75 mM AA, B: isopropanol+0.05% FA
Flow Rate 1.0 mL/min
Gradient from 1 to 50% B in 1.7 min, then 50-98% B in 0.3 min Method 9
Column: Acquity UPLC BEH C18 1.7 µm, 2.1×50 mm
Column Temperature: 40° C.
Eluents A: Water+0.1% TFA, B: acetonitrile
Flow Rate 1.0 mL/min
Gradient from 1 to 98% B in 1.4 min Method 10
Column: Ascentis™ Express C18, 2.7 µm, 2.1×50 mm
Column Temperature: 80° C.
Eluents A: water+4.76% isopropanol+0.05% FA+3.75 mM AA, B: isopropanol+0.05% FA
Flow Rate 1.0 mL/min
Gradient from 1 to 50% B in 1.4 min, then 50-98% B in 0.3 min Method 11
Column: CORTECS™ C18+2.7 µm; 2.1×50 mm
Column Temperature: 80.0° C.
Gradient: from 1 to 50% B in 1.4 min; 50 to 98% B in 0.3 min Flow: 1.0 mL/min
Eluent A: water+4.76% isopropanol+0.05% FA+3.75 mM AA
Eluent B: isopropanol+0.05% FA Description:LIMAFA2-002-EXP025-t=2 h Method 12
Column: Ascentis® Express C18 2.7 µm; 2.1×50 mm
Column Temperature: 80° C.
Gradient: from 1 to 50% B in 1.4 min; 50-98% B in 0.30 min Flow: 1.0 mL/min
Eluent A: water+4.76% isopropanol+0.05% FA+3.75 mM AA
Eluent B: isopropanol+0.05% FA Method 13
Column: Waters Xbridge C18 150×4.6 mm, 5µ
Column Temperature: 40° C.
Gradient: 0 min/10% B; 2 min/20% B; 10 min/70% B; 15 min/100% B
Eluent A: 0.05% $NH_4OH$ in water
Eluent B: acetonitrile
Flow: 1 ml/min Method 14
Column: ZORBAX C18 150×4.6 mm 5.0µ
Column Temperature: 40° C.
Gradient: 1 min 5% B; 6 min 100% B; 8 min 100%
Eluent A: 0.01% TFA in water
Eluent B: acetonitrile
Flow: 1.0 ml/min Method 15
Column: AG/CHIRALPAK-IC (250×4.6 mm, 5 micron)
Column Temperature: 25° C.
Eluent A: n-hexane,
Eluent B: ethanol
Flow rate: 1.0 mL/min
Isocratic: 30:70

Method 16
Column: Kinetex, EO, C18 150×4.6 mm 5.0 µm
Column Temperature 40° C.
Gradient: Time/% B: 1.0 min 5% B, then in 5 min to 100% B
Eluent A: 0.01% TFA in water;
Eluent B: acetonitrile
Flow rate: 1.0 mL/min

SYNTHESIS OF THE INTERMEDIATES

Intermediate 1-1: 3-(4-aminophenyl)-2,4-dimethylpyridine 1-oxide

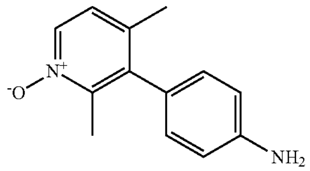

Step 1: 3-bromo-2,4-dimethylpyridine 1-oxide

To a solution of 3-bromo-2,4-dimethylpyridine (80 g, 0.430 mol) in DCM (800 mL) was added m-CPBA (90 g, 0.516 mol, 1.2 eq) at 10~ 15° C. After stirring for 3 hours at the same temperature HPLC analysis indicated complete conversion of the starting material. The mixture was poured into 10% $Na_2SO_3$ aqueous solution, stirred for 5 minutes and the layers were separated. The aqueous phase was extracted with DCM (400 mL). The organic phases were combined and washed with 10% aqueous $Na_2CO_3$. The aqueous phase was re-extracted with DCM (400 mL). The organic phases were combined, washed twice with brine (400 mL), dried ($Na_2SO_4$) and concentrated to yield the title compound (68 g, 78% yield) as an off-white solid. 1H NMR (400 MHz, DMSO) δ 8.22 (d, 1H), 7.30 (d, 1H), 2.57 (s, 3H), 2.34 (s, 3H) ppm.

Step 2: 3-(4-aminophenyl)-2,4-dimethylpyridine 1-oxide

To a solution of 3-bromo-2,4-dimethylpyridine 1-oxide (70 g, 0.346 mol) in dioxane (700 mL) were added 4-(4,4,5,5-tetramethyl-1,3,2-dioxaborolan-2-yl)aniline (91 g, 0.416 mol), $Na_2CO_3$ (110 g, 1.038 mol), water (140 mL) and Pd(dppf)$Cl_2$-DCM complex (12.7 g, 0.017 mol). The reaction mixture was purged with nitrogen, and stirred at 100° C. for 16 hours. HPLC analysis indicated complete conversion of the starting material. The reaction mixture was filtered, the filtrate was concentrated, taken-up with DCM (700 mL) and washed with brine (350 mL). The aqueous phase was extracted with DCM (350 mL×5). The organic phases were combined, dried ($Na_2SO_4$) and concentrated. The crude product was purified by column chromatography on silica (DCM:MeOH 15:1) to yield the title compound (53.4 g, 72% yield) as a light brown solid. 1H NMR (400 MHz, DMSO-d6) δ 8.14 (d, J=6.6 Hz, 1H), 7.17 (d, J=6.6 Hz, 1H), 6.84 (d, J=8.3 Hz, 2H), 6.66 (d, J=8.3 Hz, 2H), 5.26 (s, 2H), 2.11 (s, 3H), 1.99 (s, 3H) ppm.

Intermediate 1-2: 3-(4-aminophenyl)-4-chloro-2-methylpyridine 1-oxide

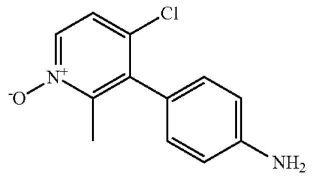

Step 1: 3-iodo-2-methylpyridin-4-ol

To a solution of 2-methylpyridin-4-ol (9.9 g, 88 mmol) in water (100 mL) was added NIS (14.59 g, 61.6 mmol) and the mixture was stirred at RT for 4 hours. The reaction mixture was filtered and the cake was washed with 0.5N HCl (50 mL). Then the filtrate was concentrated in vacuo to remove most of water, the residue was adjusted to pH=3 with sodium hydroxide and suspension was filtered and dried under reduced pressure to yield title compound (7.1 g, 33% yield) as a pinkish solid.

LC-MS: Rt=0.38 min; MS m/z=236.0 $[MH]^+$ (Method 1).

Step 2: 4-chloro-3-iodo-2-methylpyridine

To a solution of 3-iodo-2-methylpyridin-4-ol (6.25 g, 26.1 mmol) in ACN (30 mL) were added slowly $POCl_3$ (18.16 g, 117 mmol) and $P_2O_5$ (154 mg, 1.04 mmol). The reaction mixture was stirred under reflux for 3 hours, then cooled to RT and concentrated to ca. 8 mL. The residue was treated carefully with water (70 mL) with external cooling to keep the internal temperature below 45° C. The precipitate formed was removed by filtration. The pH of the mixture was adjusted to pH=6-7 with sodium hydroxide, the solid was filtered, washed with water and dried on high vacuum to yield title compound (5.6 g, 83% yield) as a beige solid.

LC-MS: Rt=0.99 min; MS m/z=254.0 $[MH]^+$ (Method 1).

Step 3: 4-chloro-3-iodo-2-methylpyridine 1-oxide

To a solution of 4-chloro-3-iodo-2-methylpyridine (10 g, 38.7 mmol) in THF (100 mL) was added m-CPBA (13.43 g, 60 mmol) in 3 portions at 0° C. The reaction mixture was stirred at 0° C. for 10 min, then at RT overnight. The mixture was cooled to 5-10° C., the solid was filtered and washed with MTBE and dried on high vacuum to yield title compound (8.5 g, 81% yield) as a colorless solid.

LC-MS: Rt=0.64 min; MS m/z=269.9 $[MH]^+$ (Method 1).

Step 4: 3-(4-aminophenyl)-4-chloro-2-methylpyridine 1-oxide

To a solution of 4-chloro-3-iodo-2-methylpyridine 1-oxide (8.3 g, 30.5 mmol) in dioxane (150 mL) were added 4-(4,4,5,5-tetramethyl-1,3,2-dioxaborolan-2-yl)aniline (7.10 g, 31.1 mmol), 2M aq. $Na_2CO_3$ (44.2 mL, 88 mmol) and Pd(dppf)$Cl_2$-DCM complex (1.509 g, 1.83 mmol). The reaction mixture was purged with argon and stirred at 100° C. for 3 hours. The reaction mixture was diluted with ethyl acetate and washed with $Na_2CO_3$ 1 M aqueous solution and brine. The organic phase was dried ($Na_2SO_4$) and concentrated. The crude product was purified by column chromatography on silica (ISCO system, 100% EtOAc), followed by recrystallization from TBME:DCM 10:1 to yield the title compound (4.6 g, 62% yield) as a white solid.

LC-MS: Rt=0.56 min; MS m/z=235.1 $[MH]^+$ (Method 1).

1H NMR (400 MHz, DMSO-d6) δ 8.24 (d, J=7.0 Hz, 1H), 7.47 (d, J=7.0 Hz, 1H), 6.9-6.87 (m, 2H), 6.65 (d, 8.3 Hz, 2H), 5.54 (s, 2H), 2.16 (s, 3H) ppm.

Intermediate 1-3: 3-(4-aminophenyl)-2-methyl-4-(trifluoromethyl)pyridine 1-oxide

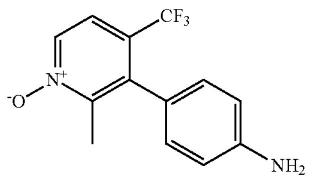

Step 1: 2-chloro-3-iodo-4-(trifluoromethyl)pyridine

To a solution of 2-chloro-4-(trifluoromethyl)pyridine (360 g, 1.98 mol) in THF (3.5 L) was added dropwise at −78° C.

LDA (2M in THF/hexanes, 1.04 L, 2.08 mol). The reaction mixture was stirred at −78° C. for 2 hours, then iodine (538 g, 2.12 mol) was added portionwise and the mixture was stirred at −78° C. for 2 hours under $N_2$ atmosphere. The crude mixture was quenched with a saturated $NH_4Cl$ solution (100 mL) at 0° C. and concentrated. The residue was taken up in water (2 L) and extracted twice with EtOAc (2.5 L). The combined organic phases were washed with brine (1 L), dried ($Na_2SO_4$) and concentrated. The crude product was triturated in petroleum ether and filtered to yield the title compound (300 g, 49% yield) as a yellow solid.

1H NMR (400 MHz, CDCl3) δ 8.49 (d, J=4.8 Hz, 1H), 7.43 (d, J=5.2 Hz, 1H) ppm.

Step 2: tert-butyl (4-(2-chloro-4-(trifluoromethyl) pyridin-3-yl)phenyl)carbamate To a solution of 2-chloro-3-iodo-4-(trifluoromethyl)pyridine (200 g, 650 mmol) in dioxane (2 L) were added tert-butyl (4-(4,4,5,5-tetramethyl-1,3,2-dioxaborolan-2-yl) phenyl)carbamate (169 g, 715 mmol), $Cs_2CO_3$ (445 g, 1.37 mol), water (400 mL) and Pd(dppf)$Cl_2$ DCM complex (26.5 g, 32.5 mmol). The reaction mixture was purged with nitrogen, and stirred at 80° C. for 8 hours. The reaction mixture was filtered through a celite pad. The filtrate was concentrated, taken-up with water (1.5 L) and extracted twice with EtOAc (1.5 L). The combined organic phase was washed with brine (1 L), dried ($Na_2SO_4$) and concentrated. The crude product was triturated with TBME (100 mL) and filtered to yield the title compound (180 g, 74% yield) as a yellow solid. 1H NMR (400 MHz, DMSO-d6) δ 9.56 (s, 1H), 8.69 (d, J=5.2 Hz, 1H), 7.88 (d, J=5.2 Hz, 1H), 7.56 (d, J=8.4 Hz, 2H), 7.18 (d, J=8.4 Hz, 2H), 1.49 (s, 9H) ppm.

Step 3: tert-butyl (4-(2-methyl-4-(trifluoromethyl) pyridin-3-yl)phenyl)carbamate To a solution of tert-butyl (4-(2-chloro-4-(trifluoromethyl)pyridin-3-yl)phenyl)carbamate (170 g, 456 mmol) in dioxane (2 L) were added methylboronic acid (81.9 g, 1.37 mol), Pd(dppf)$Cl_2$-DCM complex (18.6 g, 22.8 mmol) and $K_2CO_3$ (126 g, 912 mmol). The reaction mixture was stirred at 110° C. for 10 hours under $N_2$ atmosphere. Volatiles were evaporated, the residue diluted with water (1 L) and extracted twice with EtOAc (1 L). The combined organic phase were washed with brine (1 L), dried ($Na_2SO_4$) and concentrated. The crude product was purified by column chromatography on silica (petroleum ether/EtOAc 10:1 to 1:1) to yield the title compound (122 g, 76% yield) as a yellow solid. 1H NMR (400 MHz, CDCl3) δ 8.65 (d, J=5.2 Hz, 1H), 7.57-7.39 (m, 3H), 7.12 (d, J=8.4 Hz, 2H), 6.70 (br.s, 1H), 2.32 (s, 3H), 1.54 (s, 9H) ppm.

Step 4: 3-(4-((tert-butoxycarbonyl)amino)phenyl)-2-methyl-4-(trifluoromethyl)pyridine 1-oxide To a solution of tert-butyl (4-(2-methyl-4-(trifluoromethyl)pyridin-3-yl)phenyl)carbamate (120 g, 340 mmol) in DCM (150 mL) was added m-CPBA (91.8 g, 425 mmol) in 3 portions at 0° C. The reaction mixture was stirred at 25° C. for 10 hours. The mixture was quenched with ice water (600 mL) and extracted twice with DCM (1.5 L). The combined organic phase was washed with brine (1.5 L), dried ($Na_2SO_4$) and concentrated. The crude product was triturated in TBME (300 mL) and filtered to yield title compound (83 g, 65% yield) as a yellow solid.

LC-MS: Rt=1.04 min; MS m/z=369.2[MH]$^+$ (Method 5).

Step 5: 3-(4-aminophenyl)-2-methyl-4-(trifluoromethyl)pyridine 1-oxide

To a solution of 3-(4-((tert-butoxycarbonyl)amino)phenyl)-2-methyl-4-(trifluoromethyl)pyridine 1-oxide (80 g, 217 mmol) in EtOAc (500 mL) was added HCl/EtOAc (200 mL) at 0° C. The reaction mixture was stirred at 25° C. for 10 hours. The mixture was quenched with $NaHCO_3$ saturated solution (300 mL), diluted with water (200 mL) and extracted twice with EtOAc (400 mL). The combined organic phase was washed with brine (300 mL), dried ($Na_2SO_4$) and concentrated to yield title compound (55 g, 93% yield) as a yellow solid.

MS: m/z=269.1 [MH]$^+$

1H NMR (400 MHz, $CDCl_3$) δ 8.32 (d, J=7.2 Hz, 1H), 7.44 (d, J=6.8 Hz, 1H), 6.94 (d, J=8.0 Hz, 2H), 6.74 (d, J=8.4 Hz, 2H), 3.87 (br s, 2H), 2.25 (s, 3H) ppm.

Intermediate 1-4: 3-(4-amino-2-fluorophenyl)-4-chloro-2-methylpyridine 1-oxide

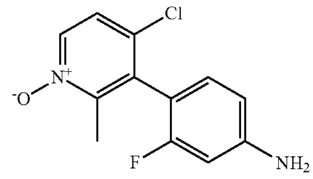

Step 1: Tert-butyl (4-(4-chloro-2-methylpyridin-3-yl)-3-fluorophenyl)carbamate

To a solution of 3-bromo-4-chloro-2-methylpyridine (6.18 g, 30.0 mmol) in toluene (230 mL) were added tert-butyl (3-fluoro-4-(4,4,5,5-tetramethyl-1,3,2-dioxaborolan-2-yl)phenyl)carbamate (10.1 g, 30.0 mmol), CataCXium A Pd G3 (2.181 g, 3.00 mmol) and $K_3PO_4$ 1.5M (59.9 ml, 90 mmol). The reaction mixture was purged with nitrogen, and stirred at 100° C. for 2 hours. The reaction mixture was diluted with EtOAc, washed with a saturated $Na_2CO_3$ solution and water, dried ($Na_2SO_4$) and concentrated. The crude product was purified by column chromatography on silica (cyclohexane/EtOAc 9:1 to 4:1) to yield the title compound (9.04 g, 90% yield) as a yellow foam.

LC-MS: Rt=1.16 min; MS m/z=337.1 [MH]$^+$ (Method 3).

Step 2: 3-(4-((tert-butoxycarbonyl)amino)-2-fluorophenyl)-4-chloro-2-methylpyridine 1-oxide To a solution of tert-butyl (4-(4-chloro-2-methylpyridin-3-yl)-3-fluorophenyl)carbamate (7 g, 20.8 mmol) in DCM (87 mL) was added m-CPBA (6.17 g, 35.75 mmol) in 3 portions at 0° C. The reaction mixture was stirred at RT for 6 hours. The mixture was diluted with DCM, washed with NaOH 1 M and brine, dried ($Na_2SO_4$) and concentrated. The crude product was purified by column chromatography on silica (EtOAc/MeOH 9:1) to yield title compound (5.73 g, 72% yield) as a pale yellow solid.

LC-MS: Rt=1.07 min; MS m/z=353.2 [MH]$^+$ (Method 3).

Step 3: 3-(4-amino-2-fluorophenyl)-4-chloro-2-methylpyridine 1-oxide 3-(4-((tert-butoxycarbonyl)amino)-2-fluorophenyl)-4-chloro-2-methylpyridine 1-oxide (5.73 g, 16.25 mmol) was treated with 4M HCl in dioxane (60.9 ml, 244 mmol) and the mixture was stirred at RT for 20 hours. The reaction mixture was diluted with EtOAc (300 mL) and washed with 1 M NaOH (122 mL) followed by water (2×200 mL). The combined aqueous phases were re-extracted with EtOAc (200 mL). The combined organic phases were dried ($Na_2SO_4$) and concentrated to yield title compound (4.176 g, 95% yield) as a yellow solid.

LC-MS: Rt=0.66 min; MS m/z=253.1 $[MH]^+$ (Method 3).

$^1$H NMR (400 MHz, DMSO-$d_6$) δ 8.30 (d, J=7.0 Hz, 1H), 7.52 (dd, J=7.1, 0.7 Hz, 1H), 6.94 (t, J=8.5 Hz, 1H), 6.51-6.40 (m, 2H), 5.72 (s, 2H), 2.16 (s, 3H) ppm.

Intermediate 1-5: 3-(4-amino-2-fluorophenyl)-2,4-dimethylpyridine 1-oxide

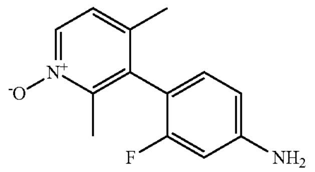

Step 1: Tert-butyl (4-(2,4-dimethylpyridin-3-yl)-3-fluorophenyl)carbamate

A microwave tube was charged with 3-bromo-2,4-dimethylpyridine (2 g, 10.75 mmol), tert-butyl (3-fluoro-4-(4,4,5,5-tetramethyl-1,3,2-dioxaborolan-2-yl)phenyl)carbamate (3.62 g, 10.75 mmol) and Pd(dppf)$Cl_2$·DCM complex (0.878 g, 1.075 mmol) under argon atmosphere. Dioxane (50 mL) was added, followed by 2M $Na_2CO_3$ (10.75 mL, 21.50 mmol). The flask was closed and heated to 130° C. for 30 minutes in a microwave oven. After cooling, the mixture was diluted with EtOAc, washed with a saturated $NaHCO_3$ solution and brine, dried ($Na_2SO_4$) and concentrated. The crude product was purified by column chromatography on silica (0-40% EtOAc in heptane) to yield the title compound (2.48 g, 70% yield) as a colorless oil.

LC-MS: Rt=0.93 min; MS m/z=316.8 [MH]+m/z=315.1 $[M-H]^-$ (Method 3).

Step 2: 3-(4-((tert-butoxycarbonyl)amino)-2-fluorophenyl)-2,4-dimethylpyridine 1-oxide To a solution of tert-butyl (4-(2,4-dimethylpyridin-3-yl)-3-fluorophenyl)carbamate (2.48 g, 7.84 mmol) in THF (40 mL) was added m-CPBA (3.51 g, 15.68 mmol), and the resulting mixture was stirred at RT overnight. The reaction mixture was diluted with EtOAc and quenched with a saturated $NaHCO_3$ solution. Phases were separated and the organic phase was washed with brine, dried ($Na_2SO_4$) and concentrated. The crude product was purified by column chromatography on silica (0-10% MeOH in DCM) to yield the title compound (1.65 g, 62% yield) as white solid.

LC-MS: Rt=0.97 min; MS m/z=333.2 $[MH]^+$ (Method 3).

Step 3: 3-(4-amino-2-fluorophenyl)-2,4-dimethylpyridine 1-oxide 3-(4-((tert-butoxycarbonyl)amino)-2-fluorophenyl)-2,4-dimethylpyridine 1-oxide (1.65 g, 4.96 mmol) was treated with 4M HCl in dioxane (24.82 ml, 99 mmol) and stirred at RT for 3 hours. The reaction mixture was diluted with EtOAc and washed with a saturated $NaHCO_3$ solution. The organic phase was washed with brine, dried ($Na_2SO_4$) and concentrated. The solid was triturated with $Et_2O$ and filtered to yield the title compound (1.02 g, 88% yield) an off-white solid.

LC-MS: Rt=0.62 min; MS m/z=233.1 $[MH]^+$ (Method 3).

1H NMR (400 MHz, DMSO-d6) δ 8.18 (d, J=6.6 Hz, 1H), 7.21 (d, J=6.6 Hz, 1H), 6.87 (t, J=8.5 Hz, 1H), 6.56-6.35 (m, 2H), 5.70 (br. s, 2H), 2.11 (s, 3H), 1.99 (s, 3H) ppm.

Intermediate 1-6: 3-(4-amino-2-fluorophenyl)-2-methyl-4-(trifluoromethyl)pyridine 1-oxide

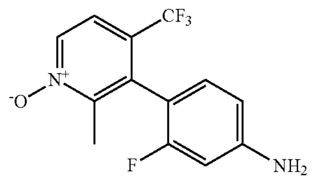

Step 1: 2-chloro-3-iodo-4-(trifluoromethyl)pyridine

To a solution of 2-chloro-4-(trifluoromethyl)pyridine (0.71 mL, 5.40 mmol) in THF (10 mL) was added dropwise at −78° C. LDA 1 M in THF/hexane (5.94 mL, 5.94 mmol). The reaction mixture was stirred at −20° C. for 2 hours, then cooled again down to −78° C., and a solution of iodine (1.64 g, 6.48 mmol) in THF (5 mL) was added. The mixture was stirred overnight at RT. The reaction was quenched with sat. $NH_4Cl$ and extracted twice with EtOAc. The combined organic phase were washed with 10% sodium thiosulfate and brine, dried ($Na_2SO_4$) and concentrated. The crude product was purified by column chromatography on silica (4-12% EtOAc in heptane) to yield the title compound (500 mg, 30% yield) as white solid.

LC-MS: Rt=1.16 min (Method 3).

1H NMR (400 MHz, DMSO-d6) δ 8.63 (d, J=5.0 Hz, 1H), 7.74 (d, J=5.0 Hz, 1H) ppm.

Step 2: Tert-butyl (4-(2-chloro-4-(trifluoromethyl)pyridin-3-yl)-3-fluorophenyl)carbamate To a mixture of tert-butyl (3-fluoro-4-(4,4,5,5-tetramethyl-1,3,2-dioxaborolan-2-yl)phenyl)carbamate (3.62 g, 10.75 mmol), $PdCl_2(PPh_3)_2$ (57 mg, 0.08 mmol) and $Cs_2CO_3$ (1060 mg, 3.25 mmol) was added a solution of 2-chloro-3-iodo-4-(trifluoromethyl)pyridine (500 mg, 1.63 mmol) in dioxane (8 mL) and water (1.7 mL). The reaction mixture was stirred at 80° C. for 3.5 hours, cooled to RT and concentrated. The residue was taken up in EtOAc, washed with water and brine, dried ($Na_2SO_4$) and concentrated. The crude product was purified by column chromatography on silica (0-17% EtOAc in heptane) to yield the title compound (270 mg, 42% yield) as a white foam.

LC-MS: Rt=1.21 min; MS m/z=391.4 $[MH]^+$ (Method 3).

Step 3: Tert-butyl (3-fluoro-4-(2-methyl-4-(trifluoromethyl)pyridin-3-yl)phenyl)carbamate To a solution of tert-butyl (4-(2-chloro-4-(trifluoromethyl)pyridin-3-yl)-3-fluorophenyl)carbamate (255 mg, 0.64 mmol) in dioxane (5 mL) and water (1 mL) was added trimethylboroxine (0.135 mL, 0.96 mmol), Pd(dppf) $Cl_2$·DCM complex (52.2 mg, 0.06 mmol) and $K_2CO_3$ (265 mg, 1.92 mmol). The reaction mixture was stirred overnight at 110° C. After cooling the mixture was concentrated, taken up in EtOAc, washed with water and brine, dried ($Na_2SO_4$) and concentrated. The crude product was purified by column chromatography on silica (7-40% EtOAc in heptane) to yield the title compound (235 mg, 97% yield) as a white foam.

LC-MS: Rt=1.18 min; MS m/z=371.1 $[MH]^+$ (Method 3).

Step 4: 3-(4-((tert-butoxycarbonyl)amino)-2-fluorophenyl)-2-methyl-4-(trifluoromethyl)pyridine 1-oxide To a solution of tert-butyl (3-fluoro-4-(2-methyl-4-(trifluoromethyl)pyridin-3-yl)phenyl)carbamate (230 mg, 0.62 mmol) in DCM (7 mL) was added m-CPBA (182 mg, 1.06 mmol). The reaction mixture was stirred at RT for 3 hours. The crude mixture was diluted with DCM (7 mL), washed with 1 M NaOH and brine, dried ($Na_2SO_4$) and concentrated. The crude product was purified by column chromatography on silica (35-100% EtOAc in heptane) to yield the title compound (192 mg, 80% yield) as a white solid.

LC-MS: Rt=1.08 min; MS m/z=387.1 $[MH]^+$ (Method 3).

Step 5: 3-(4-amino-2-fluorophenyl)-2-methyl-4-(trifluoromethyl)pyridine 1-oxide 3-(4-((tert-butoxycarbonyl)amino)-2-fluorophenyl)-2-methyl-4-(trifluoromethyl)pyridine 1-oxide (187 mg, 0.48 mmol) was treated with 4M HCl in dioxane (5 ml, 20.00 mmol) and stirred at RT for 45 minutes. The mixture was concentrated, diluted with EtOAc, washed twice with sat. $NaHCO_3$ and brine, dried ($Na_2SO_4$) and concentrated. The crude product was purified by column chromatography on silica (40-80% EtOAc in heptane) to yield the title compound (114 mg, 82% yield) as a white solid.

LC-MS: Rt=0.79 min; MS m/z=287.1 $[M+H]^+$ (Method 3).

1H NMR (400 MHz, DMSO-d6) δ 8.47 (d, 1H), 7.69 (d, 1H), 6.90 (t, 1H), 6.50-6.38 (m, 2H), 5.69 (s, 2H), 2.10 (s, 3H) ppm.

19F NMR (376 MHz, DMSO-d6) δ −58.99, −115.29 (t, J=10.1 Hz) ppm.

Intermediate 1-7: 3-(4-amino-3-fluorophenyl)-4-chloro-2-methylpyridine 1-oxide

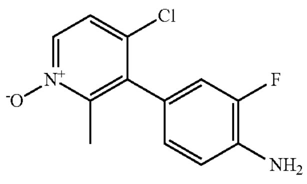

To a solution of 4-chloro-3-iodo-2-methylpyridine 1-oxide (Intermediate 1-2, step 3; 500 mg, 1.8 mmol) in dioxane (8 mL) were added 2-fluoro-4-(4,4,5,5-tetramethyl-1,3,2-dioxaborolan-2-yl)aniline (462 mg, 1.87 mmol), 2M aq. $Na_2CO_3$ (2.97 mL, 5.94 mmol) and Pd(dppf)$Cl_2$. DCM complex (89 mg, 0.108 mmol). The mixture was purged with argon and stirred at 100° C. for 3 hours. After cooling the mixture was diluted with EtOAc and washed with sat. $NaHCO_3$ solution and brine. The organic phase was dried ($Na_2SO_4$) and concentrated. The crude product was purified by column chromatography on silica (25-90% EtOAc in heptane) to yield the title compound (400 mg, 87% yield) as a brown oil.

LC-MS: Rt=0.69 min; MS m/z=253.0 $[MH]^+$ (Method 2).

1H NMR (400 MHz, DMSO-d6) δ 8.27 (d, 1H), 7.50 (dd, 1H), 6.98 (dd, 1H), 6.85 (dd, 1H), 6.78 (dd, 1H), 5.41 (s, 2H), 2.15 (s, 3H) ppm.

Intermediate 1-8: 6'-amino-2,4-dimethyl-[3,3'-bipyridine] 1-oxide

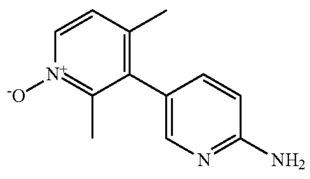

Step 1: 3-bromo-2,4-dimethylpyridine 1-oxide

To a solution of 3-bromo-2,4-dimethylpyridine (1.9 g, 9.8 mmol) in THF (25 mL) was added m-CPBA (3.63 g, 16.18 mmol) in 3 portions at 0° C. The reaction mixture was stirred overnight at RT. Saturated $Na_2CO_3$ solution was added and the mixture extracted with DCM (4 times). The combined organic phases were washed with brine, dried ($Na_2SO_4$) and concentrated to yield the title compound (1.68 g, 84% yield) as a yellow solid which was used in the next step without further purification.

LC-MS: Rt=0.49 min; MS m/z=202.0-204.0 [MH]+(Br pattern) (Method 5).

Step 2: 6'-((tert-butoxycarbonyl)amino)-2,4-dimethyl-[3,3'-bipyridine] 1-oxide

To a solution of 3-bromo-2,4-dimethylpyridine 1-oxide (1.68 g, 8.33 mmol) in dioxane (35 mL) were added tert-butyl (5-(4,4,5,5-tetramethyl-1,3,2-dioxaborolan-2-yl)pyridin-2-yl)carbamate (2.83 g, 8.58 mmol), 2M aq. $Na_2CO_3$ (14.58 mL, 29.2 mmol) and Pd(dppf)$Cl_2$·DCM complex (0.62 g, 0.75 mmol). The reaction mixture was purged with argon and stirred at 100° C. for 6 hours. After cooling 5% aq. $Na_2CO_3$ was added and the mixture was extracted with DCM (4 times). The combined organic phases were dried ($MgSO_4$) and concentrated. The crude product was purified by column chromatography on silica (25-100% EtOAc+10% MeOH in heptane) to yield the title compound (1.5 g, 57% yield) as a brown oil.

LC-MS: Rt=0.82 min; MS m/z=316.2 $[MH]^+$ (Method 5).

Step 3: 6'-amino-2,4-dimethyl-[3,3'-bipyridine] 1-oxide

To a solution of 6'-((tert-butoxycarbonyl)amino)-2,4-dimethyl-[3,3'-bipyridine] 1-oxide (1.45 g, 4.14 mmol) in dioxane (5 mL) was added 4M HCl in Dioxane (15.52 mL, 62.1 mmol) and the reaction mixture was stirred at RT for 3 hours. The mixture was concentrated and the residue was triturated with EtOAc (10 mL). The solid was filtered, washed with EtOAc and dried to yield the title compound (1.1 g, quantitative yield) as a beige solid.

LC-MS: Rt=0.13 min; MS m/z=216.1 $[MH]^+$ (Method 3).

Intermediate 1-9: 6'-amino-4-chloro-2-methyl-[3,3'-bipyridine] 1-oxide

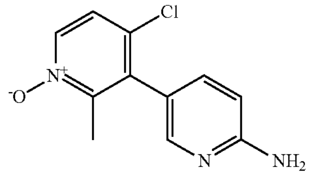

A solution of 4-chloro-3-iodo-2-methylpyridine 1-oxide (Intermediate 1-2, step 3; 1.5 g, 5.51 mmol) and 5-(4,4,5,5-tetramethyl-1,3,2-dioxaborolan-2-yl)pyridin-2-amine in dioxane (20 mL) and 2M aq $Na_2CO_3$ (8.82 mL, 17.6 mmol) was purged with argon. $PdCl_2$(dppf)-DCM adduct (250 mg, 0.30 mmol) was added and the mixture was heated to 100° C. for 2.5 hours. After cooling, the mixture was partitioned between DCM and 5% aq. $NaHCO_3$. The aq. phase was extracted with DCM (5 times), dried ($MgSO_4$), and evaporated. The residue was purified by column chromatography on silica (60 to 100% EtOAc/10% MeOH/1% $NEt_3$ in heptane) to yield the title compound (950 mg, 66% yield) as a brown foam.

1H NMR (400 MHz, DMSO-d6) δ 8.28 (dd, 1H), 7.81 (dd, 1H), 7.52 (dd, 1H), 7.31 (dd, 1H), 6.54 (dd, 1H), 6.22 (s, 2H), 2.19 (s, 3H).

Intermediate 1-10

4-(2-(difluoromethyl)-4-methylpyridin-3-yl)aniline

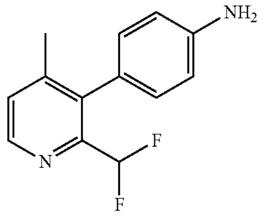 [SMILES: Cc1ccnc(C(F)F)c1-c1ccc(N)cc1]

Step 1: tert-butyl (4-(2-chloro-4-methylpyridin-3-yl)phenyl)carbamate

A solution of 3-bromo-2-chloro-4-methylpyridine (1.50 g, 7.26 mmol), (4-((tert-butoxycarbonyl)amino) phenyl)boronic acid (2.07 g, 8.71 mmol) and $Na_2CO_3$ (2.31 g, 21.79 mmol) in dioxane (100 mL) and $H_2O$ (10 mL) was purged with Ar for 5 min. $PdCl_2$(dppf) (0.53 g, 0.73 mmol) was added, and purging with Ar repeated for 5 min. The mixture was then heated to 100° for 4 h. The resulting mixture was cooled to RT, filtered through a pad of celite, and the pad washed with EtOAc. The filtrates were washed with water, brine, and concentrated under reduced pressure to afford the crude product. Purification by chromatography on silica afforded the title compound (1.15 g, 50%) as a brown solid.

LC-MS: Rt=1.76 min; MS m/z=318.9 $[MH]^+$ (Method 16).

Step 2: tert-butyl (4-(4-methyl-2-vinylpyridin-3-yl)phenyl)carbamate

A solution of tert-butyl (4-(2-chloro-4-methylpyridin-3-yl)phenyl)carbamate (1.15 g, 3.61 mmol), potassium vinyltrifluoroborate (1.93 g, 14.43 mmol) and $Cs_2CO_3$ (3.52 g, 10.82 mmol) in dioxane (100 mL) and $H_2O$ (10 mL) was purged with Ar for 5 min. $PdCl_2$(dppf) (0.26 g, 0.36 mmol) was added, and purging with Ar repeated for 5 min. The mixture was then heated to 100° for 16 h. The resulting mixture was cooled to RT, filtered through a pad of celite, and the pad washed with EtOAc. The filtrates were washed with water, brine, and concentrated under reduced pressure to afford the crude product. Purification by chromatography on silica afforded the title compound (0.80 g, 71%) as a brown solid.

LC-MS: Rt=0.50 min; MS m/z=311.3 $[MH]^+$ (Method 16).

Step 3: tert-butyl (4-(2-formyl-4-methylpyridin-3-yl)phenyl)carbamate

To a solution of tert-butyl (4-(4-methyl-2-vinylpyridin-3-yl)phenyl)carbamate (0.80 g, 2.58 mmol) in dioxane (50 mL) and t-BuOH (25 mL), a solution of $OsO_4$ (0.039 g, 0.154 mmol) in little t-BuOH was added at RT, and the resulting solution stirred for 5 min. A solution of $NaIO_4$ (2.21 g, 10.31 mmol) in $H_2O$ (50 mL) was added, and the mixture stirred at RT for 16 h. The reaction mixture was poured into water and extracted with EtOAc. The organic extract was washed with water and brine, and concentrated under reduced pressure. The crude product was purified by chromatography on silica to afford the title compound (0.40 g, 50%).

Step 4: tert-butyl (4-(2-(difluoromethyl)-4-methylpyridin-3-yl)phenyl)carbamate

A solution of tert-butyl (4-(2-formyl-4-methylpyridin-3-yl)phenyl)carbamate (0.40 g, 1.28 mmol) in DCM (100 mL) was cooled to 0°. DAST (0.62 g, 3.84 mmol) was added, and the resulting mixture stirred at 0° for 2 h. The reaction was quenched with aq. sat. $NaHCO_3$, and then stirred at 0° for 10 min. The resulting mixture was extracted with DCM, and the extract washed with water, brine, and then concentrated under reduced pressure. Purification by chromatography on silica afforded the title compound (0.25 g, 58%).

LC-MS: Rt=1.72 min; MS m/z=335.2 $[MH]^+$ (Method 16).

Step 5: 4-(2-(difluoromethyl)-4-methylpyridin-3-yl)aniline

To a cooled (0° C.) solution of tert-butyl (4-(2-(difluoromethyl)-4-methylpyridin-3-yl)phenyl)carbamate (0.20 g, 0.59 mmol) in dioxane (2 mL), was added 20% HCl in dioxane (8 mL). The resulting mixture was allowed to reach RT and stirred at this temperature for 4 h. The mixture was then poured into ice water and extracted with EtOAc. The extract was washed with sat. aq. $NaHCO_3$ and brine, dried ($Na_2SO_4$) and concentrated under reduced pressure. The residue was purified by repeatedly washing with $Et_2O$ to afford the crude title compound (0.20 g) as a brown solid.

LC-MS: Rt=0.28 min; MS m/z=234.9 $[MH]^+$ (Method 16).

Intermediate 1-11: 4-(4-chloro-2-methylpyridin-3-yl)-3,5-difluoroaniline

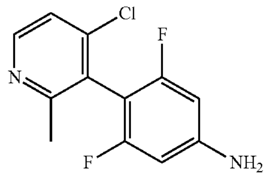 [SMILES: Cc1nccc(Cl)c1-c1c(F)cc(N)cc1F]

Step 1: 3,5-difluoro-4-(4,4,5,5-tetramethyl-1,3,2-dioxaborolan-2-yl)aniline

A mixture of 4-bromo-3,5-difluoroaniline (2.6 g, 12.25 mmol), $PdCl_2$(dppf)-DCM adduct (0.91 mg, 1.10 mmol), bis(pinacolato)diborane (4.71 g, 18.37 mmol) and sodium acetate (2.79 g, 2.75 mmol) in dioxane (30 mL) was purged with argon and then stirred at 100° C. overnight. After cooling the reaction mixture was diluted with EtOAc and washed with a saturated $Na_2CO_3$ solution and brine. The organic phase was dried ($Na_2SO_4$) and evaporated. The residue was purified by column chromatography on silica (elution with 10% to 50% EtOAc in heptane) to yield the title compound (900 mg, 28%) as a brown oil.

LC-MS: Rt=0.94 min; MS m/z=255.1 $[MH]^+$ (Method 1).

Step 2: 4-(4-chloro-2-methylpyridin-3-yl)-3,5-difluoroaniline

A solution of 3-bromo-4-chloro-2-methylpyridine (870 mg, 3.34 mmol), 2M aq. $Na_2CO_3$ (4.5 mL, 9 mmol), 2-dicyclohexylphosphino-2',4',6'-triisopropylbiphenyl (64 mg, 0.134 mmol) in DME (20 mL) was purged with argon. XPhos-Pd-G2 (106 mg, 0.134 mmol) was added and the suspension was again purged with argon. The reaction mixture was heated to 80° C. for 90 min, cooled to RT and diluted with EtOAc. The mixture was washed with saturated $Na_2CO_3$ solution and brine, dried ($Na_2SO_4$) and concentrated. The residue was purified by column chromatography on silica (25% to 80% EtOAc in heptane), to yield the title compound (230 mg, 21%) as a brown solid.

LC-MS: Rt=3.75 min; MS m/z=255.1 $[MH]^+$ (Method 5).

Intermediate 1-12

3-fluoro-4-(2-methylpyridin-3-yl)aniline

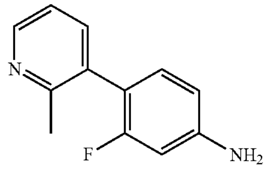

Step 1: Tert-butyl (3-fluoro-4-(2-methylpyridin-3-yl)phenyl)carbamate, Tert-butyl (3-fluoro-4-(2-methylpyridin-3-yl)phenyl)carbamate A solution of 3-bromo-2-methylpyridine (900 mg, 5.23 mmol), tert-butyl (3-fluoro-4-(4,4,5,5-tetramethyl-1,3,2-dioxaborolan-2-yl)phenyl)carbamate (1764 mg, 5.23 mmol) and 2M aq. $Na_2CO_3$ (8.50 mL, 17 mmol) in dioxane (39 mL) was purged with argon. $PdCl_2$(dppf)DCM (302 mg, 0.366 mmol) was added and the mixture heated to 100° C. for 4.5 hours. After cooling to RT the mixture was diluted with EtOAc, washed twice with saturated $NaHCO_3$ solution and brine. The organic phase was dried ($Na_2SO_4$) and evaporated. The residue was purified by column chromatography on silica (0% to 63% EtOAc in heptane) to yield the title compound (2.0 g, quantitative yield) as a yellow foam.

LC-MS: Rt=0.97 min; MS m/z=303 $[M+H]^+$ (Method 1).

Step 2: 3-fluoro-4-(2-methylpyridin-3-yl)aniline tert-Butyl (3-fluoro-4-(2-methylpyridin-3-yl)phenyl)carbamate (2 g, 5.23 mmol) was treated with 4N HCl in dioxane for 5 hours at RT. The mixture was evaporated and dried to yield the title compound (1.33 g, quant.) as an off-white solid which was used in the next steps without further purification.

LC-MS: Rt=0.38 min; MS m/z=203 $[MH]^+$ (Method 1).

Intermediate 1-13

4-(2-chloro-4-(trifluoromethyl)pyridin-3-yl)aniline

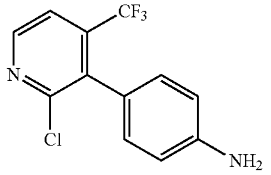 [SMILES: Nc1ccc(-c2c(C(F)(F)F)ccnc2Cl)cc1]

Step 1: 2-chloro-3-iodo-4-(trifluoromethyl)pyridine

To a cooled (−78° C.) solution of 2-chloro-4-(trifluoromethyl)pyridine (10.0 g, 55.1 mmol) in THF (60 mL) was slowly added 2M LDA in hexane (30.3 mL, 60.6 mmol). The mixture stirred at −78° C. for 2 h, then a solution of iodine (16.78 g, 66.1 mmol) in THF (20 mL) was slowly added. The mixture was allowed to warm to 0° C. over 1 h and was then quenched by addition of sat. aq. NH4Cl. The mixture was extracted with EtOAc, the organic layer washed with brine, dried ($Na_2SO_4$) and concentrated under reduced pressure: The residue was purified by column chromatography on silica (elution with a gradient of 0 to 15% EtOAc in hexanes) to yield the title compound (9.20 g, 54%).

TLC: Rf=0.39 (EtOAc/hexane=1:1).

Step 2: tert-butyl (4-(2-chloro-4-(trifluoromethyl)pyridin-3-yl)phenyl)carbamate A solution of 2-chloro-3-iodo-4-(trifluoromethyl)pyridine (step 1; 8.00 g, 26 mmol), (4-((tert-butoxycarbonyl)amino)phenyl)boronic acid (6.79 g, 28.6 mmol) and $Cs_2CO_3$ (16.96 g, 52 mmol) in dioxane/water 10:1 (55 mL) was degassed with Ar. $PdCl_2$(dppf)*DCM (1.06 g, 1.30 mmol) was added and the mixture was stirred a 80° C. for 8 h. The mixture was cooled to rt, diluted with water and extracted with EtOAc. The organic layer was dried ($Na_2SO_4$) and concentrated under reduced pressure. The residue was purified by column chromatography on silica (gradient of 5% to 35% of EtOAc in hexanes to yield the title compound (8.92 g, 93%). 1H NMR (600 MHz, DMSO-d6) δ 8.56 (d, 1H), 7.59 (d, 1H), 7.48 (d, 2H), 7.24 (d, 2H), 6.62 (br. s, 1H), 1.53 (s, 9H) ppm.

Step 3: 4-(2-chloro-4-(trifluoromethyl)pyridin-3-yl) aniline hydrochloride

A solution of tert-butyl (4-(2-chloro-4-(trifluoromethyl) pyridin-3-yl)phenyl)carbamate (400 mg, 1.07 mmol) in 4M HCl in dioxane (4 mL) was stirred under nitrogen atmosphere at 27-30° C. for 3 h. The volatiles were evaporated under reduced pressure to yield the title compound (369 mg, quant.) which was used in the next steps without further purification.

$^1$H NMR (600 MHz, $CDCl_3$) δ 11.0-10.8 (br.s, 2H), 8.64 (d, 1H), 7.75 (d, 2H), 7.63 (d, 1H), 7.36 (d, 2H), 3.70 (s, 3H) ppm.

Intermediate 1-14

3-(4-amino-3-chlorophenyl)-4-chloro-2-methylpyridine 1-oxide

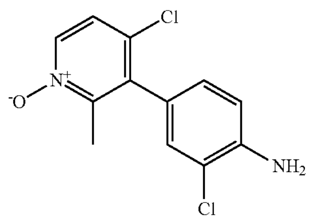

Step 1: 3-bromo-4-chloro-2-methylpyridine 1-oxide

To an ice-cooled solution of 3-bromo-4-chloro-2-methylpyridine (650 mg, 3.02 mmol) in THF (4 mL) was added MCPBA in three portions. After stirring for 10 min at 0-10° C., the reaction mixture was allowed to warm to rt overnight. The mixture was diluted with EtOAc, washed with 10% aqueous $Na_2CO_3$, dried ($Na_2SO_4$) and evaporated. The residue was recrystallized from EtOAc to yield the title compound (380 mg, 55%) as a colorless solid.

LC-MS: Rt=0.62 min; MS m/z=[M+H]$^+$ 224.0 (Method 1).

Step 2: 3-(4-amino-3-chlorophenyl)-4-chloro-2-methylpyridine 1-oxide

To an Ar-purged solution of 3-(4-amino-3-chlorophenyl)-4-chloro-2-methylpyridine 1-oxide (370 mg, 1.65 mmol), 2-chloro-4-(4,4,5,5-tetramethyl-1,3,2-dioxaborolan-2-yl) aniline (439 mg, 1.70 mmol) and 2M aqueous $Na_2CO_3$ (2.7 mL, 5.4 mmol) in dioxane (10 mL) was added $PdCl_2$(dppf)-$CH_2Cl_2$ (81 mg, 0.1 mmol) and the mixture was heated to reflux for 3 hours. After cooling to rt, the mixture was diluted with EtOAc, washed with sat. aqueous $NaHCO_3$ and brine, dried ($Na_2SO_4$) and evaporated. The residue was purified by by column chromatography on silica (ISCO system, column RediSep 40 g, elution w/ elution with 5% to 100% EtOAc in heptane), to yield the title compound (260 mg, 55%) as a brown oil.

LC-MS: Rt=0.71 min; MS m/z=[MH]+269.0 (Method 1).

Intermediate 1-15

4-(2-chloro-4-methylpyridin-3-yl)aniline

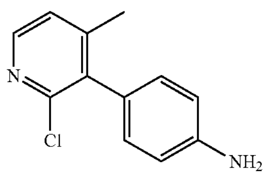

A solution of 2-chloro-3-iodo-4-methylpyridine (5.3 g, 20.5 mmol), 4-aminophenylboronic acid pinacolester (4.8 g, 21.1 mmol) and 2M aq. $Na_2CO_3$ (33.3 mL, 66.6 mmol) in dioxane (80 mL) was purged with argon. $PdCl_2$(dppf)-$CH_2Cl_2$ adduct was added and the reaction mixture was heated to reflux for 3 hours. After cooling the mixture was diluted with EtOAc and washed with sat. $NaHCO_3$ solution and brine. The organic phase was dried ($Na_2SO_4$) and evaporated. The residue was purified by column chromatography on silica (25% to 80% EtOAc in heptane) to yield the title compound (4.0 g, 89% yield) as a brown oil.

LC-MS: Rt=0.81 min; MS m/z=219.1 [M+H]$^+$ (Method 3).

Intermediate 1-16

4-(4-chloro-2-methylpyridin-3-yl)-2,3-difluoroaniline

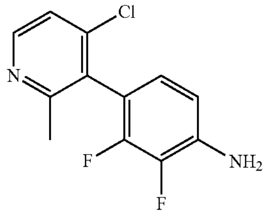 [SMILES: Cc1nccc(Cl)c1-c1ccc(N)c(F)c1F]

Step 1: Tert-butyl (4-(4-chloro-2-methylpyridin-3-yl)-2,3-difluorophenyl)carbamate A mixture of 3-bromo-4-chloro-2-methylpyridine (700 mg, 3.32 mmol), (4-((tert-butoxycarbonyl)amino)-2,3-difluorophenyl)boronic acid (972 mg, 3.49 mmol), $K_2CO_3$ (1.16 g, 8.31 mmol) and 2-dicyclohexylphosphino-2',4',6'-triisopropylbiphenyl (80 mg, 0.166 mmol) in DME (12 mL) and water (3 mL) was purged with argon. XPhos-Pd-G2 (133 mg, 0.166 mmol) was added and the suspension was again purged with argon. The reaction mixture was heated to 65° C. for 70 min, cooled to RT and diluted with EtOAc. The mixture was washed with saturated $Na_2CO_3$ solution and brine, dried ($Na_2SO_4$) and concentrated. The residue was purified by column chromatography on silica (elution with 20% to 70% EtOAc in heptane), to yield the title compound (440 mg, 32%) as a brown oil.

LC-MS: Rt=1.19 min; MS m/z=354.2 [MH]$^+$ (Method 2).

Step 2: 4-(4-chloro-2-methylpyridin-3-yl)-2,3-difluoroaniline

To a solution of tert-butyl (4-(4-chloro-2-methylpyridin-3-yl)-2,3-difluorophenyl)carbamate (Step 1; 460 mg, 1.1 mmol) in DCM (3 mL) was added trifluoroacetic acid (1.2 mL, 15.4 mmol) and the reaction mixture was stirred at RT for 4 hours. The mixture was diluted with EtOAc and washed with 10% aq. $Na_2CO_3$. The aqueous phase was re-extracted with EtOAc, and the combined organic phases were evaporated and dried in vacuo to yield the title compound (300 mg, quant.) as a yellow resin.

LC-MS: Rt=0.71 min; MS m/z=255.1 $[MH]^+$ (Method 2).

Intermediate 1-17

4-(4-chloro-2-methylpyridin-3-yl)-2,5-difluoroaniline

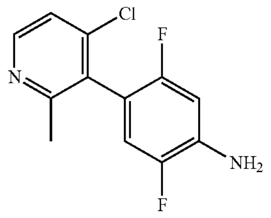 [SMILES: Cc1nccc(Cl)c1-c1cc(F)c(N)cc1F]

A solution of 4-chloro-3-iodo-2-methylpyridine (680 mg, 2.60 mmol), 2,5-difluoro-4-(4,4,5,5-tetramethyl-1,3,2-dioxaborolan-2-yl)aniline (753 mg, 2.86 mmol), $Cs_2CO_3$ (2.14 g, 6.5 mmol) and 2-dicyclohexylphosphino-2',4',6'-triisopropylbiphenyl (38 mg, 0.078 mmol) in DME (12 mL) and water (3 mL) was purged with argon. XPhos-Pd-G2 (62 mg, 0.078 mmol) was added and the suspension was again purged with argon. The reaction mixture was heated to 60° C. for 30 min, cooled to RT and diluted with EtOAc. The mixture was washed with sat. $Na_2CO_3$ and brine, dried ($Na_2SO_4$) and concentrated. The residue was purified by column chromatography on silica (25% to 80% EtOAc in heptane), to yield the title compound (220 mg, 30%) as a brown oil.

LC-MS: Rt=0.92 min; MS m/z=255.1 $[MH]^+$ (Method 2).

Intermediate 1-18

4-(3,5-dimethylpyridin-4-yl)aniline

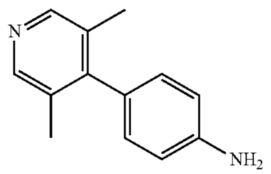

To a solution of 2 g 4-bromo-3,5-dimethylpyridine (2 g, 9 mmol) and $PdCl_2$(dppf)-$CH_2Cl_2$ (734 mg, 0.9 mmol) in dioxane (90 mL) was added 4-aminophenylboronic acid pinacolester (2.56 g, 11.7 mmol) and 2M aq. $Na_2CO_3$ (18 mL, 36 mmol) under an atmosphere of Ar. The reaction mixture was heated to 100° C. overnight. After cooling to RT, the mixture was diluted with EtOAc and washed with sat. $NaHCO_3$, water and brine. The org. phase was dried ($Na_2SO_4$) and evaporated. The residue was purified by column chromatography on silica (elution with 5% to 100% EtOAc in heptane), to yield the title compound (1.56 g, 88%) as a yellow oil which crystallized on standing.

LC-MS: Rt=0.38 min; MS m/z=199.2 $[MH]^+$ (Method 1).

Intermediate 1-19

4-(2,4-dimethylpyridin-3-yl)aniline

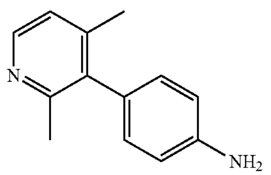

The title compound was prepared by Suzuki-coupling of 3-bromo-2,4-dimethylpyridine with 4-Aminophenylboronic acid pinacolester using a method similar to that used in the synthesis of Intermediate 1-18.

LC-MS: Rt=0.38 min; MS m/z=199.3 $[MH]^+$ (Method 1).

Intermediate 1-20

4-(4-chloro-2-methylpyridin-3-yl)-3-fluoroaniline

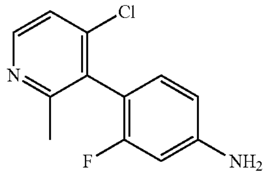 [SMILES: Cc1nccc(Cl)c1-c1ccc(N)cc1F]

tert-Butyl (4-(4-chloro-2-methylpyridin-3-yl)-3-fluorophenyl)carbamate (Intermediate 1-2, step 1; 6.3 g, 18.71 mmol) was treated with 4M HCl in dioxane (30 mL) for 3.5 h at rt, followed by filtration of the resulting solid and drying in vacuo to yield the title compound (5.83 g, 100%) as a yellow solid.

LC-MS: Rt=0.85 min; MS m/z=237 and 239 $[MH]^+$ (Method 3).

Intermediate 1-21

4-(2,4-dimethylpyridin-3-yl)-3-fluoroaniline

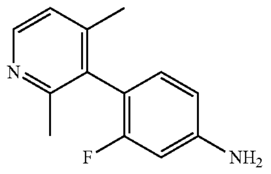 [SMILES: Cc1ccnc(C)c1-c1ccc(N)cc1F]

tert-butyl (4-(2,4-dimethylpyridin-3-yl)-3-fluorophenyl) carbamate (Intermediate 1-5, step 1; 957 mg, 3.0 mmol) was treated with excess 4M HCl in dioxane for 3.5 h at rt, followed by evaporation and drying in vacuo to yield the title compound (832 mg, 100%) as a colorless solid.

LC-MS: Rt=0.38 min; MS m/z=217.1 $[MH]^+$ (Method 2).

Intermediate 1-22

4-(4-chloropyridin-3-yl)-3-fluoroaniline

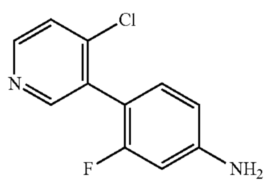 [SMILES: Nc1ccc(-c2cnccc2Cl)c(F)c1]

The title compound was prepared by Suzuki-coupling of 3-bromo-4-chloropyridine with 4-(Boc-amino)-2-fluorobenzene boronic acid pinacolester, followed by Boc-cleavage using a method similar to that used in the synthesis of Intermediate 1-16.

LC-MS: Rt=0.85 min; MS m/z=223.2 $[MH]^+$ (Method 2).

Synthesis of Intermediates 2-1 to 2-12

Intermediate 2-1

(S)-2-((tert-butoxycarbonyl)amino)-2-((S)-1,2,3,4-tetrahydronaphthalen-1-yl)acetic acid

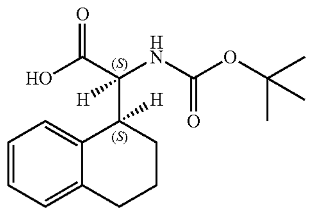

To a cooled (0° C.) mixture of 2-(1,2,3,4-tetrahydronaphthalen-1-yl)glycine (2 g, 9.74 mmol) in a mixture of dioxane (30 mL) and 1 M aq. NaOH (15 mL) was added di-tert.-butyl-dicarbonate (3.4 g, 14.6 mmol). After stirring for 5 h at RT, the mixture was partitioned between EtOAc and aq. 10% $KHSO_4$. The organic layer was washed with water and brine, dried ($Na_2SO_4$) and evaporated. The residue was triturated with DCM/methanol 1:1, the resulting solid was filtered and dried in vacuo. The mother liquor was purified by column chromatography on silica (column: RediSep 40 g; elution with 5 to 70% EtOAc in heptane). Pure fractions were evaporated and combined with the filtered material to yield a stereoisomeric mixture of the title compound (2.37 g, 76%) as a colorless solid. The separation of the individual stereoisomers was achieved by chiral SFC (column: ChiralPak AY, 300×50 mm I.D., 10 μm; 25% ethanol, flow: 100 mL/min.

Analytical chiral SFC (ChiralPak AY, 150×4.6 mm I.D., 3 μm, 5-40% ethanol+0.05% DEA; flow=2.5 mL/min, T=35° C.):

Peak 1: Rt=2.41 min: 873 mg

Peak 2: Rt=2.99 min: 130 mg

Peak 3: Rt=3.29 min: 1040 mg

Peak 4: Rt=4.71 min: 78 mg

LC-MS: Rt=5.05 min; MS m/z=304.2 $[M-H]^+$ (Method 2).

The stereochemistry of the eluted compound of peak 3 (designated intermediate 2-1) was determined as (S,S) by X-ray crystallography.

Intermediate 2-2: (S)-2-((tert-butoxycarbonyl)amino)-2-((1r,4S)-4-methylcyclohexyl)acetic acid

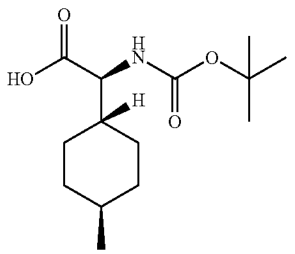 [SMILES: CC(C)(C)OC(=O)N[C@H](C(=O)O)[C@H]1CC[C@H](C)CC1]

Step 1: ((1r,4r)-4-methylcyclohexyl)methanol

To a cooled (0° C.) mixture of $LiAlH_4$ (18.7 g, 492 mmol) in THF (400 mL) was added dropwise a solution of (1r,4r)-4-methylcyclohexane-1-carboxylic acid (70.0 g, 492 mmol) dissolved in THF (90 mL) was added. The reaction mixture was stirred for 1.5 h at −5-5° C. under nitrogen and then warmed to rt. TLC (PE:EtOAc=3:1, Rf=0.50) indicated complete conversion of the starting material. Water (500 mL) and 10% NaOH (500 mL) were added. After stirring for 3 h at rt the mixture was filtered and the organic layer was concentrated to yield the title compound (55.0 g, 87%) as a yellow liquid which was used in the next step without further purification.

Step 2: (1r,4r)-4-methylcyclohexane-1-carbaldehyde

To a solution of ((1r,4r)-4-methylcyclohexyl)methanol (Step 1; 55.0 g, 428 mmol) in DMSO (100 mL) and DCM (300 mL) was added DIPEA (123.2 ml, 1.29 mol). The mixture was cooled to 0° C. before Py·SO3 (136 g, 857 mmol) was slowly added. After the addition was complete, the reaction mixture was stirred at rt for 16 h. TLC (PE:EtOAc=3:1, Rf=0.88) indicated complete conversion of the starting material. The reaction mixture was washed with aq. sat. citric acid (3×1.0 L) and brine (500 ml). The combined organic layers were dried ($Na_2SO_4$) and concentrated to yield the title compound. (54 g) which was used in the next step without further purification.

Step 3: (S)—N-((E)-((1r,4S)-4-methylcyclohexyl)methylene)benzenesulfinamide

To a solution of (1r,4r)-4-methylcyclohexane-1-carbaldehyde (Step 2; 54.0 g, 427 mmol) in DCM (300 mL) was added (S)-(+)-p-toluenesulfineamide (66.4 g, 427 mmol) and $Ti(OEt)_4$ (292 g, 1.28 mol). After stirring for 3 h at 40° C. TLC (PE:EtOAc=3:1, Rf=0.24) indicated complete conversion of the starting material. The mixture was cooled to 0° C. Water (500 mL) was added and the resulting thick paste was filtered through a celite pad and washed with DCM (500 mL). The organic layers were washed with brine, dried ($Na_2SO_4$) and concentrated. The residue was crystallized with petroleum ether to yield the title compound as a colorless solid. (84 g, 75%).

Step 4: ((S)—N—((S)-cyano((1r,4S)-4-methylcyclohexyl)methyl)benzenesulfinamide

To a cooled (−65° C.) solution of $Et_2AlCN$ (1 M in THF, 478 mL) in THF (200 mL) was added i-PrOH (50 mL) followed by a precooled (−65° C.) solution of (S)—N-((E)-((1r,4S)-4-methylcyclohexyl)methylene)benzenesulfinamide (Step 3; 84.0 g, 319 mmol) in THF (400 mL). The reaction mixture was stirred for 3 h at −65° C. TLC (PE:EtOAc=3:1, $R_f$=0.33) indicated complete conversion of the starting material. The mixture was warmed to 0° C. before aq. $NH_4Cl$ (200 mL) was added. After stirring for 30 min the mixture was filtered through a pad of Celite, washed with water and EtOAc. The organic layer was washed with water and brine, dried ($Na_2SO_4$) and concentrated. The residue was purified by column chromatography on silica (eluent: petroleum ether/EtOAc 50:1 to 10:1) to yield the title compound as a colorless solid (23 g, 25%).

Step 5: (S)-cyano((1r,4S)-4-methylcyclohexyl)methanaminium chloride

A solution of ((S)—N—((S)-cyano((1r,4S)-4-methylcyclohexyl)methyl)benzenesulfinamide (Step 4; 23.0 g, 79.1 mmol) in HCl/MeOH (4M, 19.8 mL) was stirred at RT for 30 min. TLC (PE:EtOAc=1:1, Rf=0.0) indicated complete consumption of the starting material. The mixture was concentrated to yield the title compound (16 g, 85%) as a colorless solid.

$^1H$ NMR (400 MHz, DMSO) δ 8.34 (s, 3H), 4.52 (s, 1H), 1.98-1.70 (m, 5H), 1.14-1.14 (m, 3H), 1.09-1.06 (m, 1H), 0.90-0.85 (m, 5H) ppm.

Step 6: (S)-carboxy((1r,4S)-4-methylcyclohexyl)methanaminium chloride

A solution of (S)-cyano((1r,4S)-4-methylcyclohexyl)methanaminium chloride (Step 5; 16.0 g, 85.7 mmol) in 6M HCl (160 mL) and AcOH (16 mL, 279 mmol) was stirred for 2 h at 125° C. Then 12M HCl (74.6 mL) was added and the reaction mixture was stirred for another 6 h. The reaction mixture was cooled to RT and filtered of to yield the title compound (15g) as a colorless solid which was used in the next step without further purification.

$^1H$ NMR (400 MHz, DMSO) δ 8.47 (s, 3H), 3.66 (s, 1H), 1.71-1.60 (m, 5H), 1.28-1.12 (m, 3H), 0.88-0.83 (m, 5H).

Step 7: (S)-2-((tert-butoxycarbonyl)amino)-2-((1r,4S)-4-methylcyclohexyl)acetic acid To a cooled (10° C.) solution of (S)-carboxy((1r,4S)-4-methylcyclohexyl)methanaminium chloride (Step 6; 15.0 g, 72.2 mmol) in dioxane (150 mL) was added a solution of $Na_2CO_3$ (22.9 g, 216 mmol) in H2O (300 mL). The mixture was cooled to 0° C. before $(Boc)_2O$ (20.4 g, 93.8 mmol) was added. After stirring for 16 h at rt the reaction mixture was neutralized to pH=5 with 1 M HCl and extracted with EtOAc. The organic layers were washed with brine, dried ($Na_2SO_4$) and concentrated. The residue was trituated with n-heptane (100 ml) and filtered of to yield the title compound (10.5 g, 100%) as a colorless solid.

$^1H$ NMR (400 MHz, CDCl3) δ 12.42 (s, 1H), 6.92-6.59 (m, 1H), 3.79-3.64 (m, 1H), 1.67-1.55 (m, 5H), 1.39 (s, 9H), 1.12-1.08 (m, 1H), 1.08-1.05 (m, 2H), 0.87-0.81 (m, 5H) ppm.

Intermediate 2-3: (S)-2-((tert-butoxycarbonyl)amino)-2-((1r,4S)-4-(trifluoromethyl)cyclohexyl)acetic acid

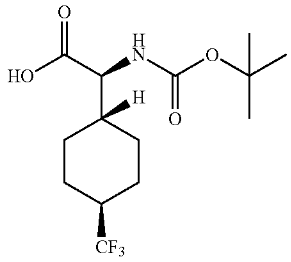 [SMILES: CC(C)(C)OC(=O)N[C@H](C(=O)O)[C@H]1CC[C@H](C(F)(F)F)CC1]

Step 1: ((1r,4r)-4-(trifluoromethyl)cyclohexyl)methanol

To a cooled (0° C.) solution of (1r,4r)-4-(trifluoromethyl)cyclohexane-1-carboxylic acid (20.7 g, 106 mmol) in THF (300 mL) was added dropwise a solution of $LiAlH_4$ (1 M in THF, 79 mL, 79 mmol) within 20 min. After the addition was complete, the mixture was stirred at RT for 1.5 h, followed by addition of another batch of $LiAlH_4$ (2M in $Et_2O$, 10.55 mL, 21.10 mmol). After stirring at reflux overnight, the mixture was cooled to 0° C., and water (20 mL) was added carefully. Once the evolution of gas has ceased, $Na_2SO_4$ (160 g) were added and the mixture was vigorously stirred for 20 min. The precipitate was filtered off and washed with ethyl acetate. The combined filtrate was washed with water and evaporated to yield the title compound (12.45 g, 65%) as a colorless oil.

1H NMR (400 MHz, DMSO-d6) δ 4.44 (t, 1H), 3.21 (dd, 2H), 2.23-2.08 (m, 1H), 1.88-1.78 (m, 4H), 1.39-1.28 (m, 1H), 1.27-1.16 (m, 2H), 0.99-0.88 (m, 2H) ppm.

Step 2: (1r,4r)-4-(trifluoromethyl)cyclohexane-1-carbaldehyde

To a mixture of pyridine-sulfur trioxide complex (21.75 g, 137 mmol) and pyridine (11.05 ml, 137 mmol) was added DMSO (15 mL) at RT and the mixture was stirred for 10 min to afford a white suspension. This suspension was slowly added to a cooled (−10° C.) solution of ((1r,4r)-4-(trifluoromethyl)cyclohexyl)methanol (12.45 g, 68.3 mmol) and DIPEA (59.7 mL, 342 mmol) in DCM (95 mL) and DMSO (15 mL) over 10 min. The reaction mixture was stirred at −10° C. to 0° C. for 1 h, then at 0° C. for 2 h followed by stirring overnight at RT. The mixture was diluted with DCM (250 mL) and extracted with 2×200 mL of 10% citric acid, followed by 200 mL of brine. The combined aqueous layers were re-extracted with DCM, the organic layers were combined, dried ($MgSO_4$) and evaporated to yield the title compound (13.89 g, quant.) as a purple oil, which was used in the next step without further purification.

1H NMR (400 MHz, DMSO-d6) δ 9.57 (s, 1H), 2.36-2.17 (m, 2H), 2.03-1.92 (m, 4H), 1.16-1.18 (m, 4H) ppm.

Step 3: (S)-4-methyl-N-((E)-((1r,4S)-4-(trifluoromethyl)cyclohexyl)methylene) benzenesulfinamide To a solution of (1r,4r)-4-(trifluoromethyl)cyclohexane-1-carbaldehyde (4 g, 22.20 mmol) and (S)-(+)-p-toluenesulfinamide (3.45 g, 22.20 mmol) in DCM (120 mL) was added titanium(IV)ethoxide (13.92 mL, 68.8 mmol). After heating to reflux for 2 h followed by stirring at RT for 16 h the mixture was partitioned between water and EtOAc. The resulting thick suspension was filtered through a bed of hyflo and rinsed with EtOAc. The layers were separated, the water layer was extracted with EtOAc. The combined organic layers were dried ($MgSO_4$) and evaporated. The residue was purified by column chromatography on silica (Redisep 120 g, elution with 5 to 40% EtOAc in cyclohexane) to yield the title compound (3.99 g, 57%) as a pale yellow oil which solidified on standing.

$^1$H NMR (400 MHz, DMSO) δ 8.08 (d, 1H), 7.52 (d, 2H), 7.38 (d, 2H), 2.49-2.44 (m, 1H), 2.30-2.21 (m, 1H), 1.99-1.87 (m, 4H), 1.37-1.22 (m, 4H) ppm.

Step 4: (S)—N-(cyano((1r,4S)-4-(trifluoromethyl) cyclohexyl)methyl)-4-methyl benzenesulfinamide To a cooled (−78° C.) solution of diethylaluminium cyanide (1M in toluene, 18.83 mL, 18.83 mmol) in THF (70 mL) was added anhydrous 2-propanol (0.97 mL, 12.56 mmol). The mixture was stirred at −78° C. for 60 minutes, then slowly added to a cooled (−78° C.) solution of (S)-4-methyl-N-((E)-((1r,4S)-4-(trifluoromethyl)cyclohexyl) methylene)benzenesulfinamide (3.985 g, 12.56 mmol) in THF (90 mL). Stirring was continued at −78° C. for 20 min, then the mixture was allowed to warm to room temperature and was stirred overnight. The mixture was cooled in an ice bath, then sat. aq. $NH_4Cl$ was carefully added. After stirring for 1 h the mixture was filtered through Celite, the pad was washed with water and EtOAc. The aqueous layer was extracted with EtOAc and the combined organic layers were washed with water and evaporated. The residue was purified by column chromatography on silica (column: RediSep 80 g, 5-30% EtOAc in cyclohexane) to yield the title compound (4.23 g, 98%) as a colorless solid.

LC-MS: Rt=1.11 min; MS m/z=345.3 $[MH]^+$ (Method 2).

Step 5: (S)-2-amino-2-((1r,4S)-4-(trifluoromethyl) cyclohexyl)acetonitrile

To a solution of (R)—N—((S)-cyano((1r,4S)-4-(trifluoromethyl)cyclohexyl)methyl)-4-methylbenzenesulfinamide (4.22 g, 12.25 mmol) in methanol (70 mL) was added 4M HCl in dioxane (64.6 mL, 259 mmol) at RT within 5 min. After stirring at RT for 2 h the solvents were evaporated and the residue was triturated under sonication with diethyl ether. The formed precipitate was filtered and dried in vacuo to yield the title compound (2.96 g, quant.) as a colorless solid which was used in the next step without further purification.

$^1$H NMR (400 MHz, DMSO) δ 9.21 (br. s, 3H), 4.56 (d, 1H), 2.36-2.32 (m, 1H), 2.02-1.89 (m, 5H), 1.31-1.11 (m, 4H) ppm.

Step 6: (S)-2-amino-2-((1r,4S)-4-(trifluoromethyl) cyclohexyl)acetic acid

A solution of (S)-2-amino-2-((1r,4S)-4-(trifluoromethyl) cyclohexyl)acetonitrile (2.963 g, 14.37 mmol) in a mixture of AcOH (10.33 mL, 180 mmol) and HCl conc. (56.4 mL, 687 mmol) was heated to reflux. More HCl conc. (16.75 ml, 204 mmol each) was added after 2 and 4 h of heating. After a total of 5 h at reflux the mixture was cooled to RT. The precipitate was filtered, washed with diethyl ether and dried in vacuo to yield the title compound (2.55 g) as a colorless solid. A second crop (331 mg) could be isolated by evaporating the filtrate, followed by tituration of the residue with cold water under sonication, filtration, and drying the solid in vacuo to give a combined yield of 2.88 g (89%).

$^1$H NMR (400 MHz, DMSO) δ 13.83 (br. s, 1H), 8.38 (br. s, 3H), 3.78 (s, 1H), 2.27-2.12 (m, 1H), 1.98-1.69 (m, 5H), 1.40-1.10 (m, 4H) ppm.

Step 7: (S)-2-((tert-butoxycarbonyl)amino)-2-((1r, 4S)-4-(trifluoromethyl)cyclohexyl)acetic acid To a suspension of (S)-2-amino-2-((1r,4S)-4-(trifluoromethyl)cyclohexyl)acetic acid (2.88 mg, 12.8 mmol) in water (31 mL) was added solid $Na_2CO_3$ (5.84 g, 55.1 mmol) followed by dropwise addition of a solution of $Boc_2O$ (4.2 g, 19.2 mmol) in dioxane (46.5 mL). After stirring at RT overnight, the main amount of solvents were evaporated. The resulting suspension was cooled in an ice bath and acidified to pH=1 with 1 N HCl. The mixture was extracted with EtOAc, the aqueous layer was extracted twice with EtOAc. The combined organic layers were evaporated and the residue was triturated with heptanes, filtered and dried in vacuo to yield the title compound (3.00 g, 72%) as a colorless solid.

1H NMR (400 MHz, DMSO) δ 12.5 (br. s, 1H), 6.97 (d, 1H), 3.79 (m, 1H), 2.22-2.08 (br. m, 1H), 1.91-1.83 (m, 2H), 1.74-1.63 (m, 3H), 1.38 (s, 9H), 1.24-1.12 (m, 4H) ppm.

Intermediate 2-4

(S)-2-((((9H-fluoren-9-yl)methoxy)carbonyl)amino)-2-((S)-3,3-difluorocyclohexyl)acetic acid

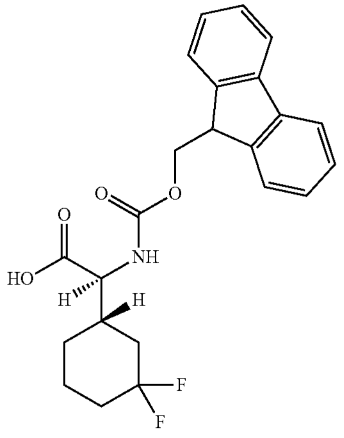 [SMILES: O=C(N[C@H](C(=O)O)[C@H]1CCCC(F)(F)C1)OCC1c2ccccc2-c2ccccc21]

Step 1: Tert-butyl (S)-2-((diphenylmethylene) amino)-2-((S)-3-oxocyclohexyl)acetate To a solution of diphenylmethylene-glycine t-butyl ester (5.0 g, 16.93 mmol) in DCM (340 mL) was added O(9)-allyl-N-9-anthracenylmethylcinchonidinium bromide (1.14 g, 1.64 mmol), followed by cesium hydroxide monohydrate (29.6 g, 169 mmol). The mixture was cooled to −75° C., before a solution of cyclohex-2-en-1-one (5.50 mL, 54.2 mmol) in DCM (10 mL) was added dropwise over 15 min. After stirring at −75° C. for 30 min and for further 6 h at −60° C., the mixture was filtered through Celite. The filtrate was washed with water and brine, the organic. phase was dried ($Na_2SO_4$) and evaporated. The residue was purified by column chromatography on silica (ISCO system; eluent: 3-15% EtOAc in heptane; column: RediSep 220 g) to yield the title compound (6.07 g, 92%) as a purple solid.

LC-MS: Rt=1.37 min; MS m/z=392.3 [MH] (Method 5).

Step 2: Tert-butyl (S)-2-((S)-3,3-difluorocyclohexyl)-2-((diphenylmethylene)amino)acetate To tert-butyl (S)-2-((diphenylmethylene)amino)-2-((S)-3-oxocyclohexyl)acetate (6.0 g, 15.33 mmol) was added DAST (20.49 ml, 155 mmol). After stirring at 60° C. to RT for 2.5 h the mixture was cooled in an ice bath and diluted with DCM (250 mL). 1 M $Na_2CO_3$ (190 mL) was added dropwise over a period of 2 h, followed by solid $Na_2CO_3$ (20 g) and stirring was continued for 30 min at 0° C. The organic layer was separated and the aqueous layer was extracted with DCM. The combined organic layers were dried ($Na_2SO_4$) and evaporated. The residue was purified by column chromatography on silica (column: RediSep 220 g; eluent: 0-10% EtOAc in heptane) to yield the title compound (4.02 g, 63%) as a yellow oil.

LC-MS: Rt=1.63 min; MS m/z=414.3 $[MH]^+$ (Method 5).

Step 3: Tert-butyl (S)-2-((((9H-fluoren-9-yl)methoxy)carbonyl)amino)-2-((S)-3,3-difluorocyclohexyl)acetate To a solution of tert-butyl (S)-2-((S)-3,3-difluorocyclohexyl)-2-((diphenylmethylene)amino)acetate (4.02 g, 9.72 mmol) in THF (100 mL) was added 15% aq. citric acid solution (62 mL) and the mixture was stirred at 40° C. for 1.5 h. The mixture was cooled to RT, and $NaHCO_3$ (6.53 g, 78 mmol) followed by (9H-fluoren-9-yl)methyl carbonochloridate (5.03 g, 19.44 mmol) was added. After stirring at RT for 18 h the mixture was diluted with EtOAc and was washed with water and brine. The organic layer was dried ($Na_2SO_4$) and evaporated. The residue was purified by column chromatography on silica (column: RediSep 220 g; eluent: 0-20% EtOAc in heptane) to yield the title compound (3.73 g, 81%) as a colorless foam.

HPLC: Rt=1.57 min (Method 5).

Step 5: (S)-2-((((9H-fluoren-9-yl)methoxy)carbonyl)amino)-2-((S)-3,3-difluorocyclohexyl)acetic acid To a solution of tert-butyl (S)-2-((((9H-fluoren-9-yl)methoxy)carbonyl)amino)-2-((S)-3,3-difluorocyclohexyl)acetate (3.73 g, 7.91 mmol) in DCM (80 mL) was added TFA (18.3 mL, 237 mmol). After stirring the mixture at RT for 8 h the mixture was evaporated and the residue was purified by column chromatography on silica (column: RediSep 120 g; eluent: 5-75% EtOAc in heptane) to yield the title compound (3.06 g, 93%) as a white foam.

LC-MS: Rt=1.24 min; MS m/z=416.3 $[MH]^+$ (Method 5).

Intermediate 2-5

(S)-2-((tert-butoxycarbonyl)amino)-2-(4,4-difluorocyclohexyl)acetic acid

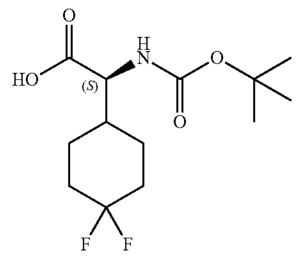

Step 1: Methyl (S)-2-amino-2-(4-hydroxyphenyl)acetate

HCl gas was slowly bubbled though a solution of (S)-2-amino-2-(4-hydroxyphenyl)acetic acid (20 g, 120 mmol) in MeOH (250 mL) at 50° C. for 2.5 h. After cooling, the volatiles were evaporated and the residue was dried in vacuo to yield the title compound as a brown solid (26.5 g, quant.) which was used in the next step without further purification.

LC-MS: Rt=0.24 min; MS m/z=182.2 $[MH]^+$ (Method 3).

Step 2: Methyl (S)-2-((tert-butoxycarbonyl)amino)-2-(4-hydroxyphenyl)acetate

To a suspension of methyl (S)-2-amino-2-(4-hydroxyphenyl)acetate (Step 1; 26.5 g, 122 mmol) and DIPEA (63.8 mL, 365 mmol) in THF (80 mL) was added $Boc_2O$ (26.6 g, 122 mmol). After stirring at RT for 17 h the solvent was evaporated, the residue was dissolved in EtOAc and washed with aq. $NH_4Cl$ and water. The organic layer was dried ($Na_2SO_4$) and evaporated to yield the title compound as a brown solid (33.89 g, 95%) which was used in the next step without further purification.

LC-MS: Rt=0.88 min; MS m/z=282.3 $[MH]^+$ (Method 3).

Step 3: Methyl (2S)-2-((tert-butoxycarbonyl)amino)-2-(4-hydroxycyclohexyl)acetate In a hydrogenation shaker, a mixture of methyl (S)-2-((tert-butoxycarbonyl)amino)-2-(4-hydroxyphenyl)acetate (Step 2; 33 g, 117 mmol) and rhodium-platinum oxide (Nishimura catalyst, 3.3 g, 117 mmol) in MeOH (1320 mL) was shaken under an atmosphere of 1 bar hydrogen overnight. The mixture was filtered through a 5 μm PTFE membrane filter and the filtrate was evaporated to yield the title compound (33 g, 93%) as a yellow oil.

LC-MS: Rt=0.89 min; MS m/z=288.2 $[MH]^+$ (Method 3).

Step 4: Methyl (S)-2-((tert-butoxycarbonyl)amino)-2-(4-oxocyclohexyl)acetate

To a solution of methyl (S)-2-((tert-butoxycarbonyl)amino)-2-(4-hydroxycyclohexyl)acetate (Step 3; 23.0 g, 80 mmol) in DCM (500 mL) was added portionwise Dess-Martin iodinane (50.9 g, 120 mmol) over a period of 4 h. After the addition was complete, the mixture was stirred for 1 h at RT, then the solvent was evaporated, the residue was taken up in EtOAc and washed with sat. aq. $NaHCO_3$ solution and water. The aqueous layers were re-extracted with EtOAc and the combined organic layers were evaporated. The residue was purified by column chromatography on silica (column: RediSep 330 g; eluent: 5-50% EtOAc in cyclohexane) to yield the title compound (20.22 g, 84%) as a yellow oil.

1H NMR (400 MHz, DMSO-d6) δ 7.31 (d, 1H), 4.06-3.97 (m, 1H), 3.64 (s, 3H), 2.45-2.26 (m, 2H), 2.23-2.10 (m, 3H), 1.88-1.82 (br. m, 2H), 1.61-1.34 (m, 2H), 1.38 (s, 9H) ppm.

Step 5: Methyl (S)-2-((tert-butoxycarbonyl)amino)-2-(4,4-difluorocyclohexyl)acetate and methyl (S)-2-((tert-butoxycarbonyl)amino)-2-((R)-4-fluorocyclohex-3-en-1-yl)acetate

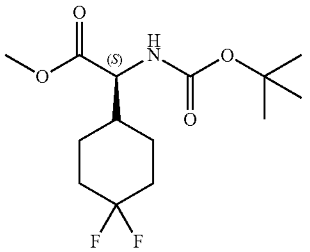

and

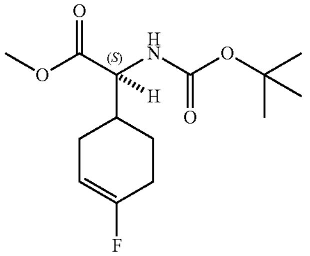

To a cooled (0° C.) solution of methyl (S)-2-((tert-butoxycarbonyl)amino)-2-(4-oxocyclohexyl)acetate (Step 4; 20.22 g, 70.9 mmol) in DCM (200 mL) was added dropwise a 50% solution of DAST (56.2 mL, 425 mmol) in THF (56 mL) during 75 min. After stirring for 30 min at 0° C. and overnight at RT the reaction mixture was diluted with DCM and extracted with aq. $NaHCO_3$ solution. The aqueous layer was re-extracted twice with DCM, the combined organic layers were washed with water and evaporated in vacuo. The residue was purified by column chromatography on silica (column: RediSep 330 g; eluent: 5 to 50% EtOAc in cyclohexane) to yield two fractions:

P1: 7.5 g (34%) methyl (S)-2-((tert-butoxycarbonyl)amino)-2-(4,4-difluorocyclohexyl)acetate as pale yellow oil.

LC-MS: Rt=1.09 min; MS m/z=308.8 $[MH]^+$ (Method 2)

1H NMR (400 MHz, DMSO-d6) δ 7.30 (d, 1H), 4.10-3.91 (m, 1H), 3.63 (s, 3H), 2.08-1.91 (m, 2H), 1.91-1.58 (m, 4H), 1.38 (s, 9H), 1.36-1.11 (m, 3H) ppm.

P2: 4.6 g (23%) methyl (S)-2-((tert-butoxycarbonyl)amino)-2-((R)-4-fluorocyclohex-3-en-1-yl)acetate as pale yellow solid LC-MS: Rt=1.11 min; MS m/z=288.2 $[MH]^+$ (Method 2)

1H NMR (400 MHz, DMSO-d6) δ 7.31 (d, 1H), 5.16 (d, 1H), 4.02-3.91 (m, 1H), 3.64 (s, 3H), 2.29-2.05 (m, 2H), 2.04-1.64 (m, 4H), 1.38 (s, 9H) 1.36-1.31 (m, 2H) ppm.

Step 6: (S)-2-((tert-butoxycarbonyl)amino)-2-(4,4-difluorocyclohexyl)acetic acid To a solution of methyl (S)-2-((tert-butoxycarbonyl)amino)-2-(4,4-difluorocyclohexyl)acetate (Step 5-P1; 708 mg, 2.304 mmol) in MeOH (5 mL) was added 4M aq. NaOH (1.15 mL, 4.61 mmol). After stirring the mixture at 50° C. for 1 h, 2M HCl (4.61 mL) was added. The mixture was diluted with water (50 mL) and was extracted twice with EtOAc. The combined organic layers were evaporated to yield the title compound (643 mg, 85%) as a colorless solid.

LC-MS: Rt=0.90 min; MS m/z=292.2 $[M-H]^+$ (Method 3).

Intermediate 2-6

(2S)-2-((tert-butoxycarbonyl)amino)-2-(4-fluorocyclohex-3-en-1-yl)acetic acid

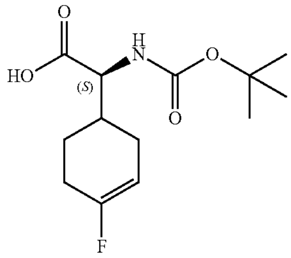

The title compound was prepared from Intermediate 2-5, step 5 P2 by a procedure similar to Intermediate 2-5 step 6 to yield the title compound as a yellow solid (2.62 g, 102%).

LC-MS: Rt=0.94 min; MS m/z [M−H]+=272.2 (Method 3).

Intermediate 2-7

2-((tert-butoxycarbonyl)amino)-2-((1R,3s,5S)-6,6-difluorobicyclo[3.1.0]hexan-3-yl)acetic acid

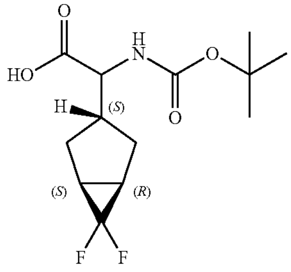

Step 1: cyclopent-3-en-1-yl benzoate

To a cooled (0° C.) solution of cyclopent-3-en-1-ol (10.0 g, 118.8 mmol) in DCM (200 mL) was added $NEt_3$ (19.77 mL, 142.6 mmol) and the resulting solution was stirred for 15 min. Benzoyl chloride (16.57 mL, 142.6 mmol) was slowly added, and the resulting mixture was stirred at RT for 15 h. Water was added, and the mixture was extracted with DCM. The organic layer was washed with brine, dried ($Na_2SO_4$) and concentrated under reduced pressure. The residue was purified by chromatography on silica to afford 18.21 g (76%) of the title compound.

1H NMR (400 MHz, $CDCl_3$) δ 8.03 (d, 2H), 7.54 (t, 1H), 7.42 (t, 2H), 5.77 (s, 1H), 5.62 (m, 1H), 2.85 (dd, 2H), 2.60-2.51 (m, 2H).

Step 2: 6,6-difluorobicyclo[3.1.0]hexan-3-yl benzoate

A solution of cyclopent-3-en-1-yl benzoate (Step 1; 3.0 g, 15.95 mmol), trifluoromethyl)trimethylsilane (4.54 g, 63.80 mmol) and sodium iodide (5.26 g, 35.09 mmol) in THF (24 mL) was heated to 150° C. in a microwave reactor for 40 min. Another portion of trifluoromethyl)trimethylsilane (4.54 g, 63.80 mmol) was added and heating continued for another 40 min. Water was added, and the mixture extracted with DCM. The organic phase was washed with brine, dried ($Na_2SO_4$) and concentrated under reduced pressure. The residue was purified by chromatography on silica to afford 1.50 g (79%) of the title compound.

1H NMR (300 MHz, $CDCl_3$) δ 8.06-7.97 (m, 2H), 7.55 (t, 1H), 7.43 (t, 2H), 5.55 (m, 1H), 2.63 (m, 2H), 2.11-1.92 (m, 4H).

Step 3: (1R,3r,5S)-6,6-difluorobicyclo[3.1.0]hexan-3-yl 4-methylbenzenesulfonate A solution of 6,6-difluorobicyclo[3.1.0]hexan-3-yl benzoate (Step 2; 3.0 g, 12.60 mmol) and KOH (0.71 g in 7.1 mL water, 12.6 mmol) in MeOH (15 mL) was stirred at RT for 6 h. Extractive aqueous work-up with EtOAc provided the crude intermediate alcohol, which was dissolved in DCM (25 mL). p-Toluenesulfonyl chloride (4.80 g, 25.2 mmol) and pyridine (3.99 g, 50.4 mmol) were added, and the mixture stirred at RT for 16 h. Water was added, and the mixture was extracted with DCM. The organic layer was washed with brine, dried ($Na_2SO_4$) and concentrated under reduced pressure. The residue was purified by chromatography on silica to afford 1.80 g (38%) of the title compound. 1H NMR (300 MHz, $CDCl_3$) δ 7.77 (d, 2H), 7.34 (d, 2H), 5.11-4.97 (m, 1H), 2.45 (s, 3H), 2.43-2.29 (m, 2H), 1.98-1.82 (m, 4H).

Step 4: Ethyl 2-((1R,3s,5S)-6,6-difluorobicyclo[3.1.0]hexan-3-yl)-2-((diphenylmethylene)amino) acetate To a solution of (1R,3r,5S)-6,6-difluorobicyclo[3.1.0]hexan-3-yl 4-methylbenzenesulfonate (Step 3; 1.80 g, 6.25 mmol) in toluene (20 mL) were added N-(diphenylmethylene)glycine ethyl ester (2.17 g, 8.12 mmol) followed by 1M LiHMDS in THF (9.99 mL, 9.99 mmol), and the mixture heated to 100° in a microwave reactor for 5 h. After cooling the mixture was diluted with DCM and washed with water. The organic layer was separated, dried ($Na_2SO_4$) and concentrated under reduced pressure. The residue was purified by chromatography on silica to afford 1.65 g (69%) of the title compound.

LC-MS: Rt=2.04 min; MS m/z=384.3 $[MH]^+$ (Method 16).

Step 5: Ethyl 2-amino-2-((1R,3s,5S)-6,6-difluorobicyclo[3.1.0]hexan-3-yl)

To a solution of ethyl 2-((1R,3s,5S)-6,6-difluorobicyclo[3.1.0]hexan-3-yl)-2-((diphenylmethylene)amino)acetate (Step 4; 1.65 g, 4.30 mmol) in THF (8.25 mL), 2.0 N aq. HCl (8.25 mL, 4.12 mmol) was added and the resulting solution stirred at RT for 3 h. The mixture was diluted with water and extracted with EtOAc. The organic extract was discarded. The aqeuous layer was basified with sat. aq. $NaHCO_3$ and extracted with EtOAc. The organic layer was washed with brine, dried ($Na_2SO_4$) and concentrated under reduced pressure to afford the crude title compound (0.74 g) which was used for the next step without purification.

LC-MS: Rt=0.11 min; MS m/z=220.2 $[MH]^+$ (Method 16).

Step 6: Ethyl 2-((tert-butoxycarbonyl)amino)-2-((1R,3s,5S)-6,6-difluorobicyclo[3.1.0]hexan-3-yl) acetate To a solution of ethyl 2-amino-2-((1R,3s,5S)-6,6-difluorobicyclo[3.1.0]hexan-3-yl)acetate (Step 5; 0.74 g, 3.37 mmol) in DCM (10 mL), $Boc_2O$ (1.06 g, 4.86 mmol) and $Et_3N$ (2.36 mL, 16.88 mmol) were added and the resulting mixture stirred at RT for 16 h. The solution was diluted with DCM and washed with water and brine. The organic layer was dried ($Na_2SO_4$) and evaporated under reduced pressure to afford the crude product (0.95 g, 88%) which was used for the next step without purification.

LC-MS: Rt=1.76 min; MS m/z=264.3 $[MH]^+$ (Method 16).

Step 7: 2-((tert-butoxycarbonyl)amino)-2-((1R,3s,5S)-6,6-difluorobicyclo[3.1.0]hexan-3-yl)acetic acid To a solution of ethyl 2-((tert-butoxycarbonyl)amino)-2-((1R,3s,5S)-6,6-difluorobicyclo[3.1.0]hexan-3-yl)acetate (Step 6; 0.95 g, 2.98 mmol) in THF (10 mL) and EtOH (10 mL), a solution of LiOH monohydrate (0.62 g, 14.88) in $H_2O$ (10 mL) was added, and the resulting solution stirred at RT for 16 h. All volatiles were evaporated under reduced pressure, and the residue treated with 1.0 N aq. HCl at 0°. The resulting mixture was extracted with MeOH/DCM 1:9, the organic extract was washed with water and brine, and dried over $Na_2SO_4$. Evaporation under reduced pressure afforded the crude title compound (0.75 g) which was used for the next step without further purification.

Intermediate 2-8

(2S)-2-((((9H-fluoren-9-yl)methoxy)carbonyl)amino)-2-(3,3-difluorocyclopentyl)acetic acid

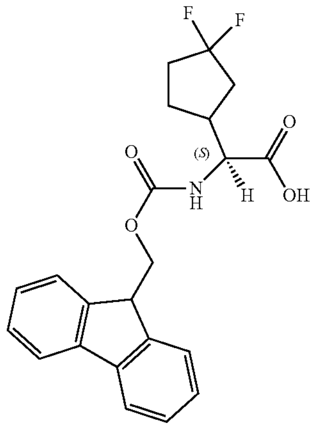

Step 1: Tert-butyl (2S)-2-((diphenylmethylene)amino)-2-(3-oxocyclopentyl)acetate Tetrakis(acetonitrile)copper(I) hexafluorophosphate (25.2 mg, 0.068 mmol) and (S)-1-(diphenylphosphino)-2-[(S)-4- isopropyloxazolin-2-yl]ferrocene (32.6 mg, 0.068 mmol) were added to a dried, argon flushed reaction vessel. THF (8 mL) was then added and the mixture was stirred for 30 minutes at rt. The resulting solution was then cooled to −78° C. and a solution of N—(N,N-diphenylmethyleneglycine-tert.butylester (2000 mg, 6.77 mmol) and 2-cyclopenten-1one (0.624 mL, 7.45 mmol) in THF (10 mL) was added. After 25 min, a solution of DBU (10.21 μl, 0.068 mmol) in THF (2 mL) was added. The yellow solution was stirred for 100 h while warming up to RT. The reaction mixture was dissolved in of EtOAc (70 mL) and extracted with water, and brine. The aqueous layers were re-extracted with EtOAc. The combined organic layers were evaporated and the residue was purified by column chromatography on silica (column: RediSep 40 g; eluent: 0-20% EtOAc in heptane) to yield the title compound (707 mg, 24%) as a yellow solid.

LC-MS: Rt=1.30 min; MS m/z=378.3 $[M-H]^+$ (Method 3).

Step 2: Tert-butyl (2S)-2-(3,3-difluorocyclopentyl)-2-((diphenylmethylene)amino)acetate The title compound was prepared from tert-butyl (2S)-2-((diphenylmethylene)amino)-2-(3-oxocyclopentyl)acetate (Step 1; 700 mg, 1.854 mmol) by a procedure similar to that used for Intermediate 2-5, step 5, to to yield the title compound as a yellow oil (370 mg, 42%).

LC-MS: Rt=1.60 min; MS m/z=400.2 $[MH]^+$ (Method 3).

Step 3: Tert-butyl (2S)-2-((((9H-fluoren-9-yl)methoxy)carbonyl)amino)-2-(3,3-difluorocyclopentyl) acetate To a solution of tert-butyl (2S)-2-(3,3-difluorocyclopentyl)-2-((diphenylmethylene)amino)acetate (Step 2; 368 mg, 0.921 mmol) in THF (9 mL) was added 15% citric acid in $H_2O$ (5.36 mL, 4.61 mmol). After stirring the reaction mixture at 45° C. for 20 h, $NaHCO_3$ (619 mg, 7.37 mmol) and Fmoc-Cl (481 mg, 1.842 mmol) were added and the reaction mixture was stirred at RT for 5 h. The mixture was diluted with EtOAc and extracted with sat aq. $NaHCO_3$ solution, followed by brine. The aqueous layers were re-extracted with EtOAc and the combined organic layers were evaporated. The residue was purified by column chromatography RP-18 (column: RediSep 86 g silicagel RP-18; eluent: water/acetonitrile 95:5 to 0:100) to yield the title compound 390 mg, 86%) as a yellow solid.

(LC-MS: Rt=1.47 min; MS m/z=402.3 $[M-H]^+$ (Method 3).

Step 4: (2S)-2-((((9H-fluoren-9-yl)methoxy)carbonyl)amino)-2-(3,3-difluorocyclopentyl)acetic acid To a solution of tert-butyl (2S)-2-((((9H-fluoren-9-yl)methoxy)carbonyl)amino)-2-(3,3-difluorocyclopentyl)acetate (Step 3; 380 mg, 0.831 mmol) in DCM (1 mL) was added TFA (128 μl, 1.661 mmol). After stirring at RT for 3 h the volatiles were evaporated and the residue was treated with again with TFA (2 mL) at RT for 1 h. The volatiles were evaporated and the residue was dried in vacuoto to yield the title compound (361 mg, 104%) as a green sticky oil.

LC-MS: Rt=1.17 min; MS m/z=402.3 $[M-H]^+$ (Method 3).

Intermediate 2-9

Methyl (2S)-2-((tert-butoxycarbonyl)amino)-2-(4-fluorocyclohexyl)acetate, Methyl (S)-2-((tert-butoxycarbonyl)amino)-2-cyclohexylacetate

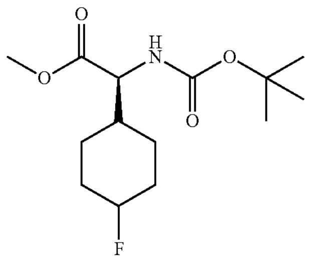 [SMILES: COC(=O)[C@@H](NC(=O)OC(C)(C)C)C1CCC(F)CC1]

To a solution of methyl (S)-2-((tert-butoxycarbonyl)amino)-2-((R)-4-fluorocyclohex-3-en-1-yl)acetate (Intermediate 2-5, step 5-P2; 1.0 g, 3.48 mmol) in EtOH (40 mL), was added a spatula of activated carbon and 3 spatulas of silica gel. The mixture was stirred for 10 min, filtered, washed with EtOH and evaporated. The residue was dissolved in EtOH (60 mL), the solution was purged with Ar and Pd/C (0.370 g, 0.348 mmol) was added followed by purging the mixture with hydrogen. The reaction mixture was stirred under $H_2$ atmosphere for 50 min followed by filtration and evaporation to yield the title compound (855 mg, 85%) which was used in the next steps without further purification.

LC-MS: Rt=1.02 min; MS m/z=290.2 $[M+H]^+$ (Method 3).

Intermediate 2-10

2-((tert-butoxycarbonyl)amino)-2-(1-methylcyclohexyl)acetic acid

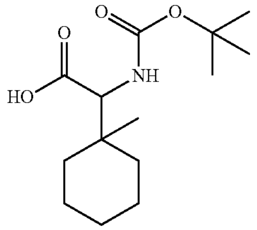 [SMILES: CC(C)(C)OC(=O)NC(C(=O)O)C1(C)CCCCC1]

To a suspension of 2-amino-2-(1-methylcyclohexyl)acetic acid hydrochloride (500 mg, 2.407 mmol) in THF (12 mL) was added $BOC_2O$ (0.615 mL, 2.65 mmol) followed by Et3N (0.434 mL, 3.13 mmol) and a spatula tip of DMAP. After stirring at RT overnight the reaction mixture was partitioned between aq. $NaHCO_3$ and EtOAc. The organic layer was discarded, the aqueous layer was acidified with citric acid (5%) and extracted with twice with EtOAc. The combined organic layers were dried ($Na_2SO_4$) and concentrated to yield the title compound (61 mg, 9%) as an off-white foam.

LC-MS: Rt=1.06 min; MS m/z=270.1 $[M-H]^+$ (Method 2).

Intermediate 2-11

2-(((benzyloxy)carbonyl)amino)-2-(3,3-difluorocycloheptyl)acetic acid

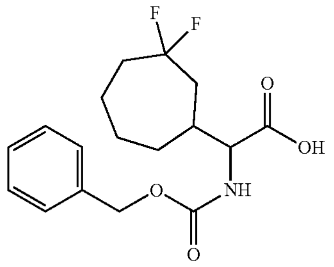 [SMILES: O=C(NC(C(=O)O)C1CCCCC(F)(F)C1)OCc1ccccc1]

Step 1: Tert-butyl 2-((diphenylmethylene)amino)-2-(3-oxocycloheptyl)acetate

To a solution of cyclohept-2-en-1-one (2.081 mL, 14.93 mmol) and diphenylmethylene-glycine tert-butyl ester (3 g, 9.95 mmol) in THF (40 mL) was added DBU (0.450 mL, 2.99 mmol). After stirring at 60° C. for 12 h, the mixture was cooled to −78° C. and 1 M KHMDS in THF (9.65 mL, 9.65 mmol) was added. After stirring at −78° C. for 4 h, the reaction was quenched at −78° C. with sat. aq. $NH_4Cl$ and warmed to RT. The mixture was extracted three times with EtOAc, the combined organic layers were dried ($MgSO_4$) and evaporated. The residue was purified by column chromatography (columns: RediSep 120 g and RediSep 80 g; eluents: 10-100% DCM in cyclohexane, then 10-100% EtOAc in cyclohexane) to yield the title compound as a yellow oil (2.18 g, 51%).

LC-MS: Rt=1.41 min; MS m/z=406.4 $[MH]^+$ (Method 1).

Step 2: Tert-butyl 2-(3,3-difluorocycloheptyl)-2-((diphenylmethylene)amino)acetate tert-Butyl 2-((diphenylmethylene)amino)-2-(3-oxocycloheptyl)acetate (Step 1; 901 mg, 2.111 mmol) was treated with neat DAST (5 ml, 37.8 mmol) at 60° C. for 2 h. The mixture was added dropwise to a mixture of ice and solid $NaHCO_3$ and was extracted twice with DCM. The combined organic layers were dried ($MgSO_4$) and evaporated. The residue was purified by column chromatography on silica (column: RediSep 120 g; eluent: 0 to 100% EtOAc in cyclohexane to yield the title compound as a pale yellow oil (543 mg, 51%).

LC-MS: Rt=1.52 min; MS m/z=428.4 $[MH]^+$ (Method 1).

Step 3: Tert-butyl 2-(((benzyloxy)carbonyl)amino)-2-(3,3-difluorocycloheptyl)acetate To a solution of tert-butyl 2-(3,3-difluorocycloheptyl)-2-((diphenylmethylene)amino)acetate (Step 2; 543 mg, 1.143 mmol) in THF (15 mL) was added 15% aq. citric acid (6.65 mL, 5.72 mmol). After stirring at 40° C. for 2 h, the mixture was cooled to RT and $NaHCO_3$ (776 mg, 9.14 mmol) followed by benzyl chloroformate (0.326 mL, 2.286 mmol) were added. After stirring at RT for 12 h the mixture was diluted with EtOAc and washed with sat.$NaHCO_3$ and brine.

The organic layer was dried ($MgSO_4$) and evaporated. The residue was purified by column chromatography (column: RediSep 120 g; eluent: 3 to 15% TBME in cyclohexane) to yield the title compound (397 mg, 87%) as a colourless oil.

LC-MS: Rt=1.34 min; MS m/z=398 $[MH]^+$ (Method 1).

Step 4: 2-(((benzyloxy)carbonyl)amino)-2-(3,3-difluorocycloheptyl)acetic acid

To a solution of tert-butyl 2-(((benzyloxy)carbonyl)amino)-2-(3,3-difluorocycloheptyl) (Step 3; 490 mg, 1.233 mmol) in DCM (7 mL) was added TFA (6 mL, 26.0 mmol). After stirring at RT for 2 h the volatiles were evaporated and the residue was dried in vacuo to yield the title compound (524 mg, 100%) which was used in the next steps without further purification.

LC-MS: Rt=0.97 min; MS m/z=342.3 $[MH]^+$ (Method 1).

Synthesis of Intermediates 3-1 to 3-60

Intermediate 3-1

3-(4-((S)-2-amino-2-((S)-1,2,3,4-tetrahydronaphthalen-1-yl)acetamido)phenyl)-2,4-dimethylpyridine 1-oxide

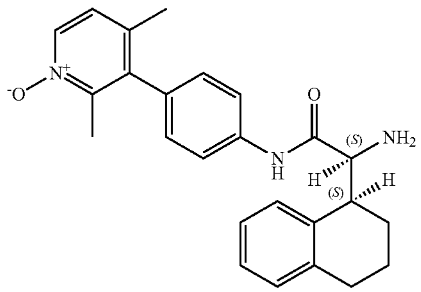

Step 1: 3-(4-((S)-2-((tert-butoxycarbonyl)amino)-2-((S)-1,2,3,4-tetrahydronaphthalen-1-yl)acetamido)phenyl)-2,4-dimethylpyridine 1-oxide To a solution of 3-(4-aminophenyl)-2,4-dimethylpyridine 1-oxide (Intermediate 1-1; 1.26 g, 5.89 mmol) in DMF (30 mL) were sequentially added (S)-2-((tert-butoxycarbonyl)amino)-2-((S)-1,2,3,4-tetrahydronaphthalen-1-yl)acetic acid (Intermediate 2-1, compound of peak 3; 1.50 g, 4.91 mmol), HATU (2.24 g, 5.89 mmol) and $Et_3N$ (2.04 mL, 14.74 mmol). The mixture was stirred at RT for 18 h, then diluted with EtOAc and washed with sat. aq. $NaHCO_3$, water, and brine. The organic phase was dried ($Na_2SO_4$) and all volatiles were evaporated under reduced pressure. The residue was purified by column chromatography on silica (eluent: 0% to 25% TBME in MeOH) to yield the title compound (1.97 g, 80%) as a slightly yellow solid.

LC-MS: Rt=1.08 min; MS m/z=502.3 $[MH]^+$ (Method 12).

Step 2: 3-(4-((S)-2-amino-2-((S)-1,2,3,4-tetrahydronaphthalen-1-yl)acetamido)phenyl)-2,4-dimethylpyridine 1-oxide To a solution of 3-(4-((S)-2-((tert-butoxycarbonyl)amino)-2-((S)-1,2,3,4-tetrahydronaphthalen-1-yl)acetamido)phenyl)-2,4-dimethylpyridine 1-oxide (1.97 g, 3.93 mmol) in dioxane (40 mL), was added dropwise 4M HCl in dioxane (40 mL) and the solution stirred for 18 h at RT. All volatiles were removed under reduced pressure. The residue was diluted with 1 M aq. $Na_2CO_3$ and extracted three times with DCM/isopropanol 4:1. The combined organic phases were dried ($Na_2SO_4$) and concentrated. The residue was purified by column chromatography on silica (0% to 10% TBME in MeOH) to yield the title compound (1.47 g, 91%) as a white foam.

LC-MS: Rt=0.62 min; MS m/z=402.2 [MH]*(Method 12).

Intermediate 3-2

3-(4-((S)-2-amino-2-cyclohexylacetamido)-2-fluoro-phenyl)-4-chloro-2-methylpyridine 1-oxide

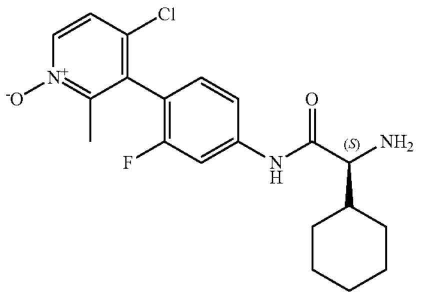

Step-3-(4-((S-2-(tertbutoxycaronyl)amino)-2-cyclo-hexylacetamido)-2-fluorophenyl)-4-chloro-2-methylpyridine 1-oxide To a solution of (S)-2-((tert-butoxycarbonyl)amino)-2-cyclohexylacetic acid (3.56 g, 6.79 mmol), 3-(4-amino-2-fluorophenyl)-4-chloro-2-methylpyridine 1-oxide (Intermediate 1-4; 1.75 g, 6.79 mmol) and DIPEA (4.43 g, 33.9 mmol) in DMF (50 mL) was added HATU (5.74 g, 14.93 mmol) and the mixture was stirred for 18 h at RT. A second portion of (S)-2-((tert-butoxycarbonyl)amino)-2-cyclohexylacetic acid (0.5 g, 0.95 mmol) and HATU (0.6 g, 1.56 mmol) was added, and stirring continued for 48 h. The reaction mixture was diluted with EtOAc and washed with aq. citric acid solution, sat. aq. $Na_2CO_3$ and brine. The organic phase was dried ($Na_2SO_4$) and evaporated. The residue was purified by column chromatography on silica (column: RediSep 220 g; eluent: 70 to 100% EtOAc in heptane/EtOAc, then 10% MeOH in EtOAc) to yield the title compound (1.85 g, 49.9%) as a brown foam.

LC-MS: Rt=1.14 min; MS m/z=492.3 $[MH]^+$ (Method 2).

Step 2: 3-(4-((S)-2-amino-2-cyclohexylacetamido)-2-fluorophenyl)-4-chloro-2-methylpyridine 1-oxide To a solution of 3-(4-((S)-2-((tert-butoxycarbonyl)amino)-2-cyclohexylacetamido)-2-fluorophenyl)-4-chloro-2-methylpyridine 1-oxide (Step 1; 1.80 g, 3.11 mmol) in DCM (10 mL), was added dropwise TFA (2.42 mL, 31.1 mmol). After stirring at RT for 14 h, the reaction mixture was diluted with EtOAc and washed with 10% aq. $Na_2CO_3$. The $Na_2CO_3$ layer was re-extracted with EtOAc, and the combined layers were concentrated under reduced pressure, resulting in the crude title compound (1.11 g, 80% yield, 88% pure by LC-MS) as a yellow resin that was used for the next step without further purification.

LC-MS: Rt=0.71 min and 0.72 min, 1.1 mixture of atropisomers; MS m/z=492.3 $[MH]^+$ (Method 2).

Intermediate 3-3

3-(4-((S)-2-amino-2-((1r,4S)-4-methylcyclohexyl) acetamido)phenyl)-2,4-dimethylpyridine 1-oxide

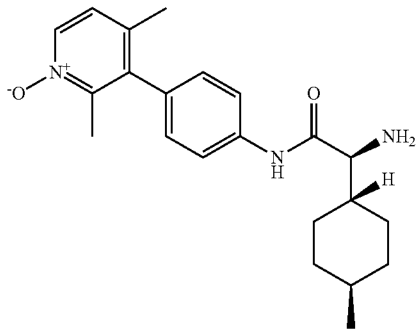

Step 1: 3-(4-((S)-2-((tert-butoxycarbonyl)amino)-2-((1r,4S)-4-methylcyclohexyl)acetamido)phenyl)-2,4-dimethylpyridine 1-oxide A solution of (S)-2-((tert-butoxycarbonyl)amino)-2-((1r,4S)-4-methylcyclohexyl)acetic acid (Intermediate 2-2; 160 mg, 0.590 mmol), 2,4,6-collidine (0.314 ml, 2.359 mmol) and HATU (247 mg, 0.649 mmol) in DMF (2 mL) was stirred at RT for 10 min. To the resulting colourless solution, 3-(4-aminophenyl)-2,4-dimethylpyridine 1-oxide (Intermediate 1-1; 126 mg, 0.590 mmol) was added at RT in one portion, and this mixture stirred at RT for 72 h. The resulting solution was diluted with sat. aq. $NaHCO_3$ and extracted twice with EtOAc. The combined organic extracts were washed with brine, dried ($Na_2SO_4$), and all volatiles evaporated under reduced pressure. Purification by preparative RP HPLC ($H_2O$/ACN+0.1% TFA) and lyophilization afforded the title compound (156 mg, 55.4%) as a white solid.

LC-MS: Rt=1.18 min; MS m/z=468.3 $[MH]^+$ (Method 1).

Step 2: 3-(4-((S)-2-amino-2-((1r,4S)-4-methylcyclohexyl)acetamido)phenyl)-2,4-dimethylpyridine 1-oxide 3-(4-((S)-2-((tert-butoxycarbonyl)amino)-2-((1r,4S)-4-methylcyclohexyl)acetamido)-phenyl)-2,4-dimethylpyridine 1-oxide (Step 1; 140 mg, 0.299 mmol) was treated with 4M HCl in dioxane (2 mL). After stirring at RT for 1 h the mixture was concentrated under reduced pressure and dried in HV to yield the title compound (127 mg, 100%) as a white solid, which was used for the next step without further purification.

LC-MS: Rt=0.79 min; MS m/z=468.2 $[MH]^+$ (Method 1).

Intermediate 3-4

3-(4-((S)-2-amino-2-((1r,4S)-4-(trifluoromethyl)cyclohexyl)acetamido)phenyl)-4-chloro-2-methylpyridine 1-oxide

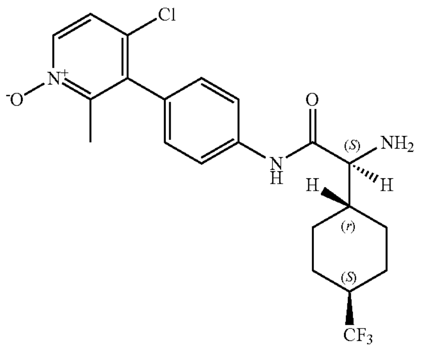

Step 1: 3-(4-((S)-2-((tert-butoxycarbonyl)amino)-2-((1r,4S)-4-(trifluoromethyl)cyclohexyl)acetamido)phenyl)-4-chloro-2-methylpyridine 1-oxide To a solution of 3-(4-aminophenyl)-4-chloro-2-methylpyridine 1-oxide (Intermediate 1-2; 600 mg, 2.43 mmol) in acetonitrile/DMF 1:1 (5 mL) were sequentially added (S)-2-((tert-butoxycarbonyl)amino)-2-((1r,4S)-4-(trifluoromethyl)-cyclohexyl)acetic acid (Intermediate 2-3; 1.04 g, 3.04 mmol), $Et_3N$ (745 mg, 7.29 mmol) and HATU (1.31 g, 3.40 mmol). The resulting mixture was stirred at RT for 18 h, then diluted with EtOAc and washed with sat. aq. $NaHCO_3$, water and brine. The organic layer was dried ($Na_2SO_4$) and evaporated under reduced pressure. The residue was purified by column chromatography on silica (column: RediSep 40 g; eluent: 70-100% (EtOAc+5% MeOH) in heptane) to yield the title compound (1.30 g, 97%).

LC-MS: Rt=1.39 min; MS m/z=542.3 $[MH]^+$ (Method 5).

Step 2: 3-(4-((S)-2-amino-2-((1r,4S)-4-(trifluoromethyl)cyclohexyl)acetamido)phenyl)-4-chloro-2-methylpyridine 1-oxide To a solution of 3-(4-((S)-2-((tert-butoxycarbonyl)amino)-2-((1r,4S)-4-(trifluoromethyl)cyclohexyl)-acetamido)phenyl)-4-chloro-2-methylpyridine 1-oxide (1.25 g, 1.96 mmol)) in dioxane (10 mL) was slowly added 4M HCl in dioxane (7.35 mL, 29.4 mmol). After stirring at RT for 14 h the mixture was diluted with 10% aq. $Na_2CO_3$ and extracted twice with EtOAc. The combined organic extracts were dried ($MgSO_4$) and concentrated under reduced pressure. The residue was recrystallized from TBME to yield the title compound (630 mg, 72%) as yellow crystals.

LC-MS: Rt=0.67 min; MS m/z=442.2 $[MH]^+$ (Method 5).

Intermediate 3-5

(S)-3-(4-(2-amino-2-cyclopentylacetamido)phenyl)-2-methyl-4-(trifluoromethyl)pyridine 1-oxide

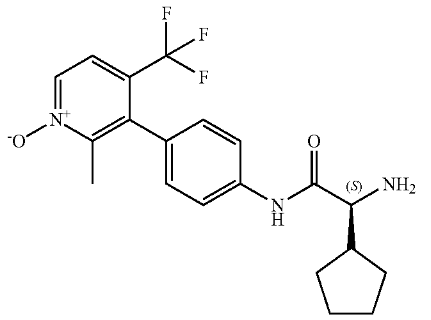

Step 1: (S)-3-(4-(2-((tert-butoxycarbonyl)amino)-2-cyclopentylacetamido)phenyl)-2-methyl-4-(trifluoromethyl)pyridine 1-oxide To a solution of 3-(4-aminophenyl)-2-methyl-4-(trifluoromethyl)pyridine 1-oxide (Intermediate 1-3; 6.2 g, 23.11 mmol) in DMF (70 mL), were sequentially added Boc-L-cyclopentylglycine (8.15 g, 33.5 mmol), 2,4,6-collidine (10.16 mL, 76 mmol) and HATU (17.58 g, 46.2 mmol), and the solution stirred at RT for 18 h. The mixture was concentrated in vacuo, and the residue dissolved in EtOAc. Sat. aq. $Na_2CO_3$ solution was added and the mixture was extracted three times with EtOAc. The combined organic layers were washed with brine, dried and concentrated under reduced pressure. Purification of this crude material by column chromatography on silica afforded 12.13 g (98%) of the title compound as a foam.

LC-MS: Rt=1.19 min; MS m/z 494.4 [MH]*=(Method 5).

Step 2: (S)-3-(4-(2-amino-2-cyclopentylacetamido)phenyl)-2-methyl-4-(trifluoromethyl)pyridine 1-oxide To a solution of (S)-3-(4-(2-((tert-butoxycarbonyl)amino)-2-cyclopentylacetamido)phenyl)-2-methyl-4-(trifluoromethyl)pyridine 1-oxide (Step 1; 12.13 g, 22.61 mmol) in dioxane (40 mL), was slowly added 4M HCl in dioxane (67.8 mL, 271 mmol). After stirring for 1.5 h at RT the mixture was concentrated and dried in vacuo to afford the title compound (11.19 g, 100%) as hydrochloride salt, which was used for the next step without further purification.

LC-MS: Rt=0.52 min; MS m/z=394.3 [MH]*(Method 5).

Intermediate 3-6

3-(4-((S)-2-amino-2-((S)-3,3-difluorocyclohexyl) acetamido)phenyl)-4-chloro-2-methylpyridine 1-oxide

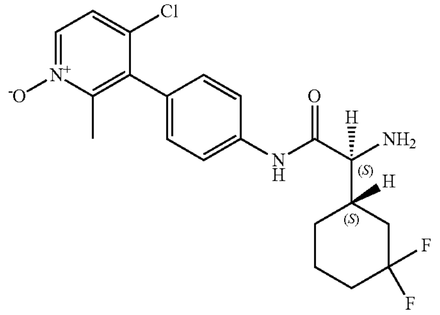

Step 1: 3-(4-((S)-2-((((9H-fluoren-9-yl)methoxy) carbonyl)amino)-2-((S)-3,3-difluorocyclohexyl) acetamido)phenyl)-4-chloro-2-methylpyridine 1-oxide To a solution of 3-(4-aminophenyl)-4-chloro-2-methylpyridine 1-oxide (Intermediate 1-2; 750 mg, 3.20 mmol) in acetonitrile (40 mL) were added (S)-2-((((9H-fluoren-9-yl) methoxy)carbonyl)amino)-2-((S)-3,3-difluorocyclohexyl)-acetic acid (Intermediate 2-4; 1328 mg, 3.20 mmol) and DIPEA (1.675 mL, 9.59 mmol) followed by dropwise addition of $T_3P$ (50% in EtOAc, 3.80 mL, 6.39 mmol). After stirring at RT for 18 h the mixture was diluted with EtOAc, and sat. aq. $NaHCO_3$ was added. The aqueous layer was extracted with EtOAc, and the combined organic layers were washed with water and brine, dried ($Na_2SO_4$), and concentrated in vacuo. The residue was purified by column chromatography on silica to yield the title compound (1.44 g, 68.4%) as a colorless solid.

LC-MS: Rt=1.31 min; MS m/z=632.3 [MH]1 (Method 5).

Step 2: 3-(4-((S)-2-amino-2-((S)-3,3-difluorocyclohexyl)acetamido)phenyl)-4-chloro-2-methylpyridine 1-oxide To a solution of 3-(4-((S)-2-((((9H-fluoren-9-yl)methoxy) carbonyl)amino)-2-((S)-3,3-difluorocyclohexyl)acetamido) phenyl)-4-chloro-2-methylpyridine 1-oxide (Step 1; 1.44 g, 2.278 mmol) in DMF (30 mL) was added piperidine (0.564 mL, 5.70 mmol), and the solution stirred at RT for 2 h. The mixture was concentrated in vacuo, and the residue purified by column chromatography on silica, affording the title compound (850 mg 86%).

LC-MS: Rt=0.46 min; MS m/z=410.4 $[MH]^+$ (Method 5).

Intermediate 3-7

3-(4-((S)-2-amino-2-((1r,4S)-4-(trifluoromethyl) cyclohexyl)acetamido)phenyl)-2,4-dimethylpyridine 1-oxide

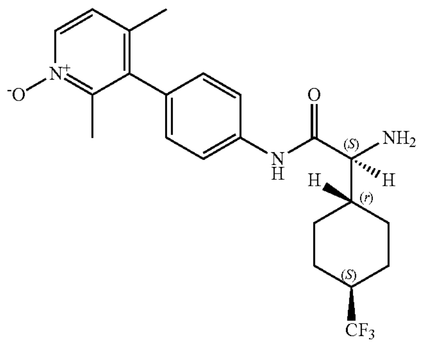

Step 1: 3-(4-((S)-2-((tert-butoxycarbonyl)amino)-2-((1r,4S)-4-(trifluoromethyl) cyclohexyl)acetamido) phenyl)-2,4-dimethylpyridine 1-oxide To a stirred solution of 3-(4-aminophenyl)-2,4-dimethylpyridine 1-oxide (Intermediate 1-1; 220 mg, 0.924 mmol) in acetonitrile/DMF 1:1 (3 mL), were added (S)-2-((tert-butoxycarbonyl)amino)-2-((1r,4S)-4-(trifluoromethyl)-cyclohexyl)acetic acid (411 mg, 1.20 mmol), $Et_3N$ (0.45 mL, 3.23 mmol) and HATU (497 mg, 1.29 mmol) at RT. After stirring RT for 18 h the mixture was partitioned between EtOAc and sat. aq. $NaHCO_3$. The organic layer washed with water and brine, dried ($Na_2SO_4$) and evaporated. Crystallization of the residue from TBME/acetonitrile 1:5 afforded the title compound (190 mg, 33.5%) as colorless crystals.

LC-MS: Rt=1.23 min; MS m/z=522.2 $[MH]^+$ (Method 5).

Step 2: 3-(4-((S)-2-amino-2-((1r,4S)-4-(trifluoromethyl)cyclohexyl)acetamido)phenyl)-2,4-dimethylpyridine 1-oxide To a solution of 3-(4-((S)-2-((tert-butoxycarbonyl) amino)-2-((1r,4S)-4-(trifluoromethyl)cyclohexyl)-acetamido)phenyl)-2,4-dimethylpyridine 1-oxide (Step 1; 950 mg, 1.80 mmol) in DCM (10 mL) was added dropwise TFA (1.68 mL). The resulting solution was stirred at RT for 14 h and was then charged on a cation exchange column (Agilent BondElut SCX). The resin was extensively washed with MeOH, then a 2M solution of $NH_3$ in MeOH was passed through the column to release the product. Evaporation afforded the title compound (750 mg, 90% pure by LC-MS, 89% yield) as a yellow resin that was used for the next step without further purification.

LC-MS: Rt=0.58 min; MS m/z=421.2 $[MH]^+$ (Method 5).

Intermediate 3-8

3-(4-((S)-2-amino-2-((S)-3,3-difluorocyclohexyl)acetamido)phenyl)-2-methyl-4-(trifluoromethyl)pyridine 1-oxide

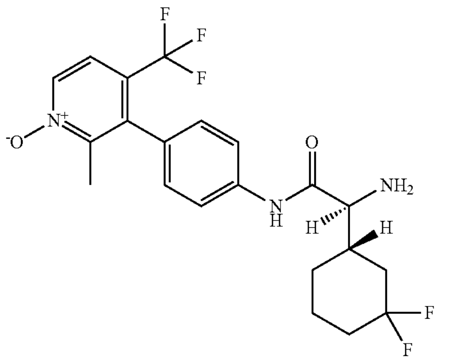

Step 1: 3-(4-((S)-2-((((9H-fluoren-9-yl)methoxy)carbonyl)amino)-2-((S)-3,3-difluorocyclohexyl)acetamido)phenyl)-2-methyl-4-(trifluoromethyl)pyridine 1-oxide To a solution of 3-(4-aminophenyl)-2-methyl-4-(trifluoromethyl)pyridine 1-oxide (Intermediate 1-3; 835 mg, 3.1 mmol) in acetonitrile (35 mL) were sequentially added (S)-2-((((9H-fluoren-9-yl)methoxy)carbonyl)amino)-2-((S)-3,3-difluorocyclohexyl)acetic acid (Intermediate 2-4; 1.25 g, 3.01 mmol), DIEA (1.20 g, 9.30 mmol) and $T_3P$ (50 wt. % in EtOAc, 3.69 mL, 6.20 mmol) at RT. The resulting solution was stirred at RT for 18 h. A second portion of DIEA (1.7 mL) and $T_3P$ (2 mL) was added and stirring was continued for another 24 h. The resulting mixture was diluted with EtOAc and washed with sat. aq. $Na_2CO_3$, water and brine, dried ($Na_2SO_4$), and evaporated to yield the title compound (3.12 g) as a yellow foam, which was used for the next step without further purification.

LC-MS: Rt=6.64 min; MS m/z=666.3 [MH]1 (Method 4).

Step 2: 3-(4-((S)-2-amino-2-((S)-3,3-difluorocyclohexyl)acetamido)phenyl)-2-methyl-4-(trifluoromethyl)pyridine 1-oxide To a cooled (0°) solution of 3-(4-((S)-2-((((9H-fluoren-9-yl)methoxy)carbonyl)amino)-2-((S)-3,3-difluorocyclohexyl)acetamido)phenyl)-2-methyl-4-(trifluoromethyl)pyridine 1-oxide (Step 1; 2.06 g, 3.1 mmol) in DMF (15 mL) was added dropwise piperidine (0.78 mL, 7.75 mmol) and stirring was continued at 0° for 2 h. All volatiles were removed under reduced pressure to afford a brown solid which was purified by chromatography on silica (0% to 100% TBME in MeOH) to yield the title compound (1.3 g, 90%) as a yellow foam.

LC-MS: Rt=2.60 min; MS m/z=444.3 $[MH]^+$ (Method 4).

Intermediate 3-9

(S)-3-(4-(2-amino-2-(4,4-difluorocyclohexyl)acetamido)phenyl)-2-methyl-4-(trifluoromethyl)pyridine 1-oxide

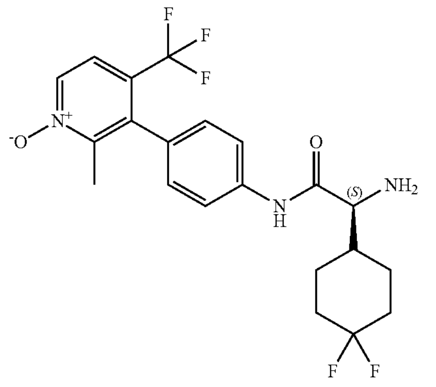

Step 1: (S)-3-(4-(2-((tert-butoxycarbonyl)amino)-2-(4,4-difluorocyclohexyl)acetamido)phenyl)-2-methyl-4-(trifluoromethyl)pyridine 1-oxide To a solution of 3-(4-aminophenyl)-2-methyl-4-(trifluoromethyl)pyridine 1-oxide (Intermediate 1-3; 275 mg, 1.023 mmol) in DMF (6 mL) were sequentially added (S)-2-((tert-butoxycarbonyl)amino)-2-(4,4-difluorocyclohexyl)-acetic acid (Intermediate 2-5; 300 mg, 1.023 mmol), HATU (467 mg, 1.227 mmol) and $Et_3N$ (0.71 mL, 5.11 mmol) at RT. After stirring at RT for 18 h the mixture was diluted with EtOAc and washed with sat. aq. $NaHCO_3$, water, and brine. The organic phase was dried ($Na_2SO_4$) and evaporated. The residue was purified by column chromatography on silica to yield the title compound (337 mg, 57%) as a yellow foam.

LC-MS: Rt=5.59 min; MS m/z=544.2 [MH]1 (Method 4).

Step 2: (S)-3-(4-(2-amino-2-(4,4-difluorocyclohexyl)acetamido)phenyl)-2-methyl-4-(trifluoromethyl)pyridine 1-oxide To a stirred solution of (S)-3-(4-(2-((tert-butoxycarbonyl)amino)-2-(4,4-difluorocyclohexyl)-acetamido)-phenyl)-2-methyl-4-(trifluoromethyl)pyridine 1-oxide (Step 1; 300 mg, 0.552 mmol) in dioxane (5.5 mL) was added dropwise 4M HCl in dioxane (5.5 mL, 22.08 mmol) at RT. Stirring was continued at RT for 18 h. The resulting solution was then evaporated to dryness under reduced pressure, the residue diluted with 1 M aq. $Na_2CO_3$ (30 mL), and extracted with DCM/IPA 4:1 (3x30 mL). The combined organic phases were dried ($Na_2SO_4$) and concentrated. The residue was purified by column chromatography on silica (column: RediSep 24 g; eluent: 5 to 100% EtOAc in Heptane, then 0 to 2% MeOH in EtOAc) to yield the title compound (209 mg, 81%) as a yellow foam.

LC-MS: Rt=2.51 min; MS m/z=444.2 $[MH]^+$ (Method 4).

Intermediate 3-10

3-(4-((2S)-2-amino-2-(4-fluorocyclohex-3-en-1-yl) acetamido)phenyl)-2,4-dimethylpyridine 1-oxide

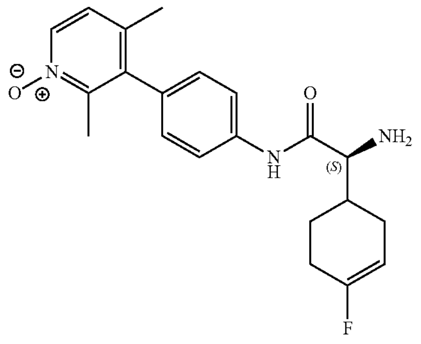

Step 1: 3-(4-((2S)-2-((tert-butoxycarbonyl)amino)-2-(4-fluorocyclohex-3-en-1-yl)acetamido)phenyl)-2,4-dimethylpyridine 1-oxide To a solution of (2S)-2-((tert-butoxycarbonyl)amino)-2-(4-fluorocyclohex-3-en-1-yl)acetic acid (Intermediate 2-6; 200 mg, 0.732 mmol), 3-(4-aminophenyl)-2,4-dimethylpyridine 1-oxide (Intermediate 1-1; 172 mg, 0.805 mmol) and 2,4,6-collidine (0.292 mL, 2.195 mmol) in DMF (4 mL), was added HATU (306 mg, 0.805 mmol). After stirring at RT for 16 h the mixture was concentrated under reduced pressure. The residue was dissolved in ACN/MeOH 9:1 (6 mL) and heated to reflux for 2 min. Cooling to RT and storage for 15 min led to an off-white precipitate, which was filtered, washed with acetonitrile (3×2 mL) and dried to afford the title compound (291 mg, 83%) as an off-white solid.

LC-MS: Rt=1.09 min; MS m/z=[MH]+470.3 (Method 5).

Step 2: 3-(4-((2S)-2-amino-2-(4-fluorocyclohex-3-en-1-yl)acetamido)phenyl)-2,4-dimethylpyridine 1-oxide To a suspension of 3-(4-((2S)-2-((tert-butoxycarbonyl) amino)-2-(4-fluorocyclohex-3-en-1-yl)acetamido)phenyl)-2,4-dimethylpyridine 1-oxide (Step 1; 290.8 mg, 0.619 mmol) in dioxane (3 mL) was added 4M HCl in dioxane (3.10 mL, 12.39 mmol). After stirring at RT for 3 h the mixture was concentrated under reduced pressure. The residue was purified by preparative HPLC (water/ACN+0.1% TFA) to yield the title compound (132 mg, 57.7%) as a colorless solid.

LC-MS: Rt=0.50 min; MS m/z=370.3 $[MH]^+$ (Method 5).

The diastereomers were separated by chiral HPLC (column: Chiralpak IG 206×30 mm 5 μm, eluent: DCM/MeOH/n-Heptane 30:25:30+0.1% DEA):

Peak 1: Rt=5.60 min: 72.9 mg white solid, ee=99.5%.

Peak 2: Rt=8.40 min: 57.6 mg white solid, ee=99.5%.

Intermediate 3-11

3-(4-((S)-2-amino-2-((S)-3,3-difluorocyclohexyl) acetamido)phenyl)-2,4-dimethylpyridine 1-oxide

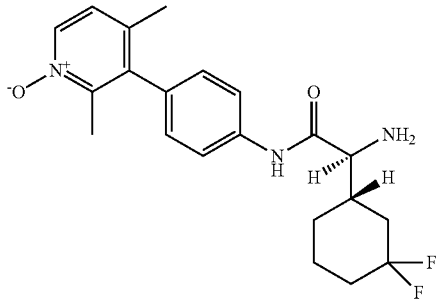

The title compound was prepared by a procedure similar to Intermediate 3-6, using intermediate 1-1 and intermediate 2-4, to yield the title compound as an off-white foam (515 mg, 36%). LC-MS: Rt=1.93 min; MS m/z=390.4 $[MH]^+$ (Method 4).

Intermediate 3-12

3-(4-(2-amino-2-(4,4-difluorocyclohexyl)acetamido) phenyl)-2,4-dimethylpyridine 1-

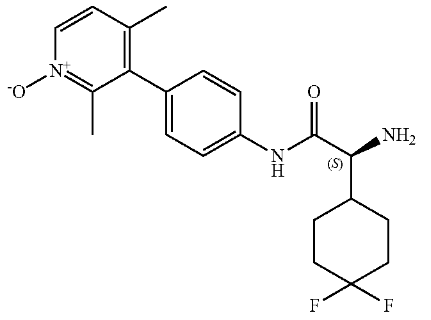

The title compound was prepared by a procedure similar to Intermediate 3-1, using intermediate 1-1 and intermediate 2-5, to yield the title compound (175 mg, 39%).

LC-MS: Rt=0.54 min; MS m/z=390.2 $[MH]^+$ (Method 1).

Intermediate 3-13

(S)-3-(4-(2-amino-2-cyclopentylacetamido)phenyl)-2,4-dimethylpyridine 1-oxide

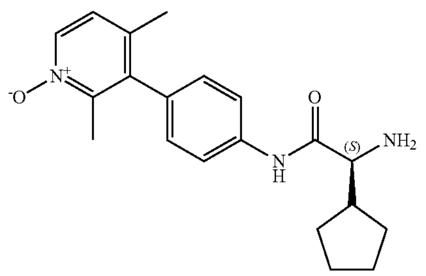

The title compound was prepared by a procedure similar to Intermediate 3-1, using intermediate 1-1 and commercial (S)-2-((tert-butoxycarbonyl)amino)-2-cyclopentylacetic acid, to yield the title compound (2.9 g, 61%) as off-white crystals.

LC-MS: Rt=0.40 min; MS m/z=340.2 $[MH]^+$ (Method 11).

Intermediate 3-14

(S)-3-(4-(2-amino-3-(2-chlorophenyl)propanamido)phenyl)-2,4-dimethylpyridine 1-

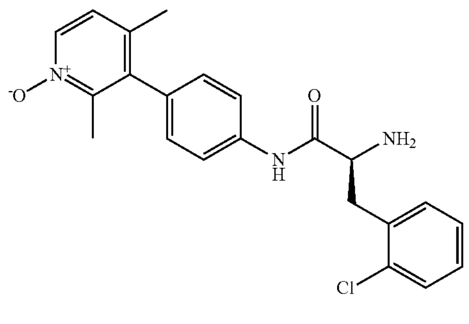

The title compound was prepared by a procedure similar to Intermediate 3-1, using intermediate 1-1 and commercial (S)-2-((tert-butoxycarbonyl)amino)-3-(2-chlorophenyl)propanoic acid, to yield the title compound (661 mg, 69%) as a white foam.

LC-MS: Rt=0.41 min; MS m/z=396.4 $[MH]^+$ (Method 12).

Intermediate 3-15

(S)-3-(4-(2-amino-2-cyclohexylacetamido)phenyl)-2,4-dimethylpyridine 1-oxide

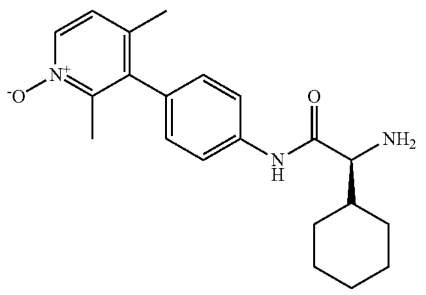

The title compound was prepared by a procedure similar to Intermediate 3-1, using intermediate 1-1 and commercial (S)-2-((tert-butoxycarbonyl)amino)-2-cyclohexylacetic acid, to yield the title compound (1008 mg, 57%) as a white foam.

LC-MS: Rt=2.05 min; MS m/z=354.3 $[MH]^+$ (Method 4).

Intermediate 3-16

(S)-3-(4-(2-amino-2-cycloheptylacetamido)phenyl)-2,4-dimethylpyridine 1-oxide

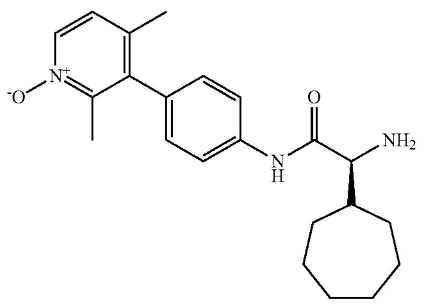

The title compound was prepared by a procedure similar to Intermediate 3-1, using intermediate 1-1 and commercial (S)-2-((tert-butoxycarbonyl)amino)-2-cycloheptylacetic acid, to yield the title compound (5.98 g, 77%) as an off-white foam.

LC-MS: Rt=2.40 min; MS m/z=368.3 $[MH]^+$ (Method 4).

Intermediate 3-17

3-(4-(2-amino-2-(1-methylcyclohexyl)acetamido)phenyl)-2,4-dimethylpyridine 1-oxide

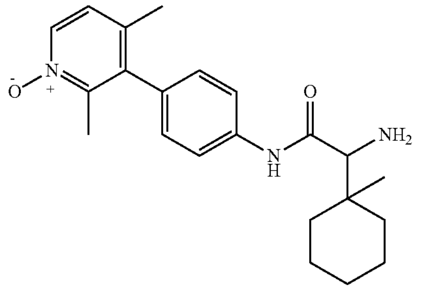

The title compound was prepared by a procedure similar to Intermediate 3-1, using intermediate 1-1 and intermediate 2-10, to yield the title compound (74 mg, 75%) as a white solid.

LC-MS: Rt=0.61 min; MS m/z=368.3 $[MH]^+$ (Method 11).

Intermediate 3-18

(S)-6'-(2-amino-2-cycloheptylacetamido)-2,4-dimethyl-[3,3'-bipyridine] 1-oxide

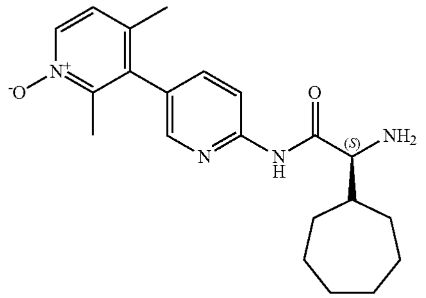

The title compound was prepared by a procedure similar to Intermediate 3-1, using intermediate 1-8 and commercial (S)-2-((tert-butoxycarbonyl)amino)-2-cycloheptylacetic acid, to yield the title compound (400 mg, 43%) as a yellow resin.

LC-MS: Rt=0.45 min; MS m/z=392.2 $[MH]^+$ (Method 3).

Intermediate 3-19

(S)-6'-(2-amino-2-cyclopentylacetamido)-2,4-dimethyl-[3,3'-bipyridine] 1-oxide

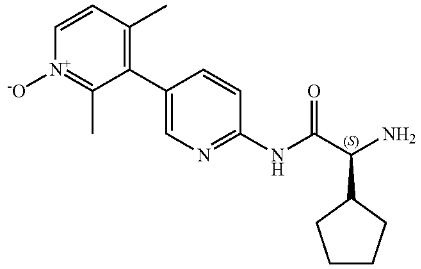

The title compound was prepared by a procedure similar to Intermediate 3-1, using intermediate 1-8 and commercial (S)-2-((tert-butoxycarbonyl)amino)-2-cyclopentylacetic acid, to yield the title compound (490 mg, 46%) as off-white crystals.

LC-MS: Rt=0.33 min; MS m/z=341.2 $[MH]^+$ (Method 5).

Intermediate 3-20

(S)-3-(4-(2-amino-2-cyclohexylacetamido)phenyl)-4-chloro-2-methylpyridine 1-oxide

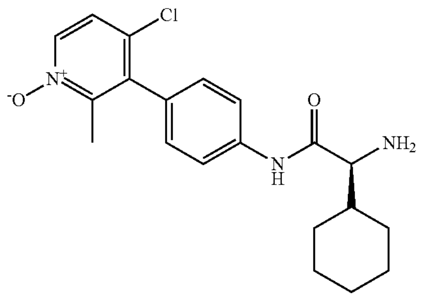

The title compound was prepared by a procedure similar to Intermediate 3-6, using intermediate 1-2 and commercial (S)-2-((tert-butoxycarbonyl)amino)-2-cyclohexylacetic acid, to yield the title compound (1.31 g, 62%) as a white foam.

LC-MS: Rt=2.31 min; MS m/z=374.2 $[MH]^+$ (Method 4).

Intermediate 3-21

3-(4-((S)-2-amino-2-((1r,4S)-4-methylcyclohexyl) acetamido)phenyl)-4-chloro-2-methylpyridine 1-oxide

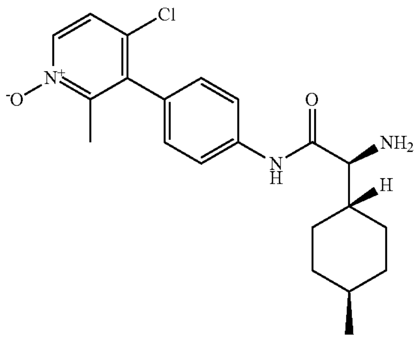

The title compound was prepared by a procedure similar to Intermediate 3-6, using intermediate 1-2 and intermediate 2-2, to yield the title compound (122 mg, 50%) as a white solid.

LC-MS: Rt=0.79 min; MS m/z=401.2 $[MH]^+$ (Method 1).

Intermediate 3-22

(S)-3-(4-(2-amino-2-cycloheptylacetamido)phenyl)-4-chloro-2-methylpyridine 1-oxide

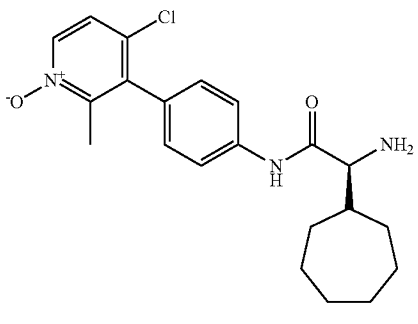

The title compound was prepared by a procedure similar to Intermediate 3-6, using intermediate 1-2 and commercial (S)-2-((tert-butoxycarbonyl)amino)-2-cycloheptylacetic acid, to yield the title compound (347 mg, 44%) as a white solid.

LC-MS: Rt=2.71 min; MS m/z=388.4 $[MH]^+$ (Method 11).

Intermediate 3-23

(S)-3-(4-(2-amino-2-(4,4-difluorocyclohexyl)acetamido)phenyl)-4-chloro-2-methylpyridine 1-oxide

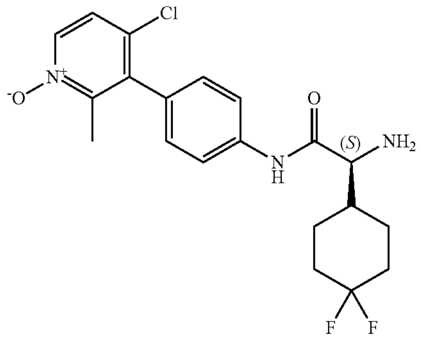

The title compound was prepared by a procedure similar to Intermediate 3-6, using intermediate 1-2 and intermediate 2-5, to yield the title compound (84 mg, 31%) as a yellow foam.

LC-MS: Rt=2.17 min; MS m/z=410.1 $[MH]^+$ (Method 4).

Intermediate 3-24

(S)-3-(4-(2-amino-2-(4,4-difluorocyclohexyl)acetamido)phenyl)-4-chloro-2-methylpyridine 1-oxide

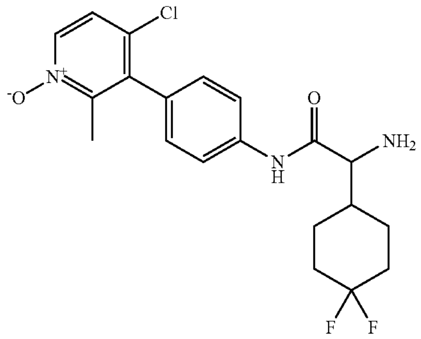

The title compound was prepared by a procedure similar to Intermediate 3-6, using intermediate 1-2 and commercial Boc-(4,4-difluorocyclohexyl)-acetic acid, to yield the title compound (660 mg, 80%) as a yellow foam.

LC-MS: Rt=2.17 min; MS m/z=410.1 $[MH]^+$ (Method 4).

Intermediate 3-25

3-(4-(2-amino-2-(bicyclo[3.1.0]hexan-3-yl)acetamido)phenyl)-4-chloro-2-methylpyridine 1-oxide

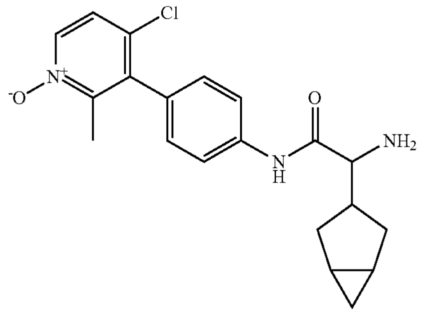

The title compound was prepared by a procedure similar to Intermediate 3-6, using intermediate 1-2 and commercial 2-(bicyclo[3.1.0]hexan-3-yl)-2-((tert-butoxycarbonyl)amino)acetic acid, to yield the title compound (787 mg, 49%) as a yellow foam.

LC-MS: Rt=2.17 min; MS m/z=372.2 $[MH]^+$ (Method 4).

Intermediate 3-26

3-(4-(2-amino-2-((1R,3s,5S)-6,6-difluorobicyclo[3.1.0]hexan-3-yl)acetamido)phenyl)-4-chloro-2-methylpyridine-1-oxide hydrochloride

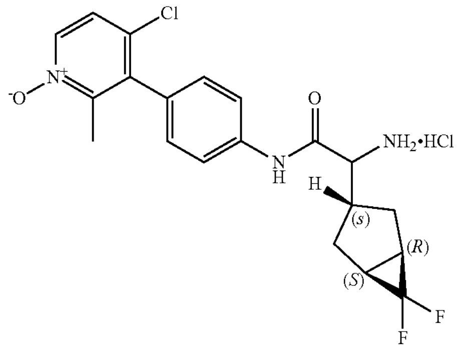

The title compound was prepared by a procedure similar to Intermediate 3-1, using intermediate 1-2 and intermediate 2-7, to yield the title compound (0.20 g, 68%).

LC-MS: MS m/z=516.3 $[MH]^+$ (Method 16).

Intermediate 3-27

3-(4-((2S)-2-amino-2-(4-fluorocyclohex-3-en-1-yl)acetamido)phenyl)-4-chloro-2-methylpyridine 1-oxide

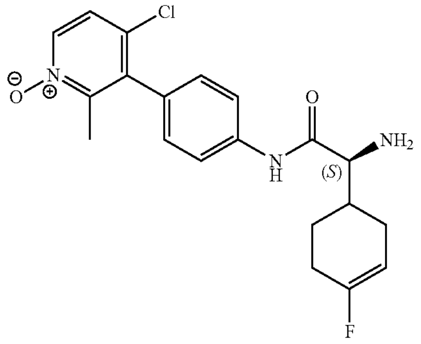

The title compound was prepared by a procedure similar to Intermediate 3-6, using intermediate 1-2 and intermediate 2-6, to yield the title compound (287 mg, 72%) as an off-white solid. LC-MS: Rt=0.47 min; MS m/z=390.1 $[MH]^+$ (Method 5).

Intermediate 3-28

3-(4-((S)-2-amino-2-((1r,4S)-4-methylcyclohexyl)acetamido)-2-fluorophenyl)-4-chloro-2-methylpyridine 1-oxide

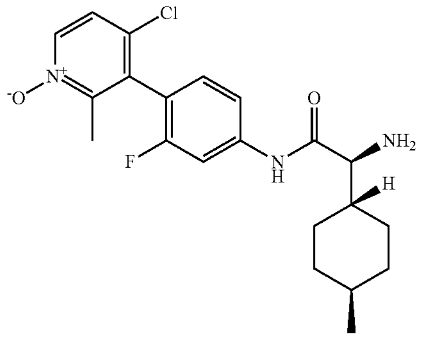

The title compound was prepared by a procedure similar to Intermediate 3-2, using intermediate 1-4 and intermediate 2-2, to yield the title compound (57 mg, 14%) as a white solid.

LC-MS: Rt=0.80 min; MS m/z=406.2 $[MH]^+$ (Method 1).

Intermediate 3-29

3-(4-(2-amino-2-(bicyclo[3.1.0]hexan-3-yl)acetamido)-2-fluorophenyl)-4-chloro-2-methylpyridine 1-oxide

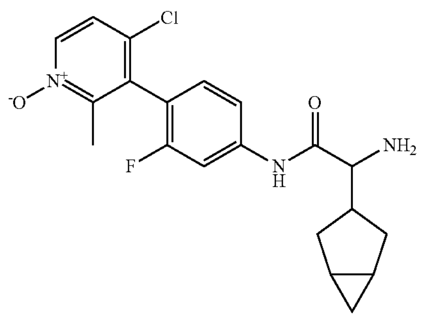

The title compound was prepared by a procedure similar to Intermediate 3-2, using intermediate 1-4 and commercial 2-(bicyclo[3.1.0]hexan-3-yl)-2-((tert-butoxycarbonyl)amino)acetic acid, to yield the title compound (210 mg, 50.4%) as a white solid.

LC-MS: Rt=2.33 and 2.44 min, 1:1 mixture of atropisomers; MS m/z=390.1 $[MH]^+$ (Method 4).

Intermediate 3-30

3-(4-((S)-2-amino-2-cycloheptylacetamido)-2-fluorophenyl)-4-chloro-2-methylpyridine 1-oxide

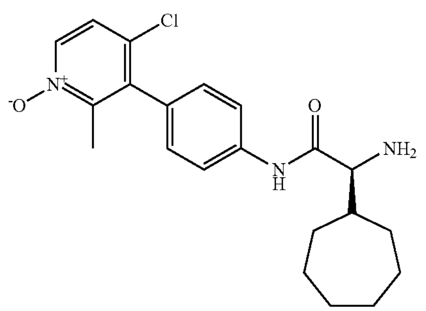

The title compound was prepared by a procedure similar to Intermediate 3-2, using intermediate 1-4 and commercial (S)-2-((tert-butoxycarbonyl)amino)-2-cycloheptylacetic acid, to yield the title compound (64 mg, 35%) as an orange foam.

LC-MS: Rt=2.88 and 3.01 min, 1:1 mixture of atropisomers; MS m/z=406.1 $[MH]^+$ (Method 4).

Intermediate 3-31

2-amino-N-(4-(4-chloro-2-methylpyridin-3-yl)-3-fluorophenyl)-2-(4,4-difluorocyclohexyl)acetamide

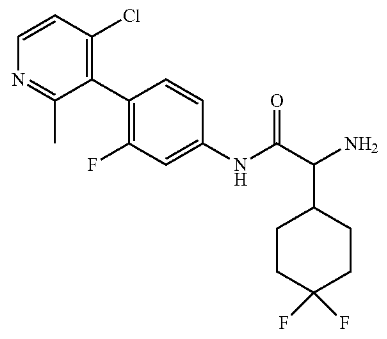 [SMILES: Cc1nccc(Cl)c1-c1ccc(NC(=O)C(N)C2CCC(F)(F)CC2)cc1F]

The title compound was prepared by a procedure similar to Intermediate 3-2, using intermediate 1-11 and commercial tert-butoxycarbonylamino-(4,4-difluoro-cyclohexyl)-acetic acid, to yield the title compound as a colorless solid.

LC-MS: Rt=0.81 min; MS m/z=412 and 414 $[MH]^+$ (Method 2).

Intermediate 3-32

(S)-3-(4-(2-amino-2-cyclohexylacetamido)-3-fluorophenyl)-4-chloro-2-methylpyridine 1-oxide

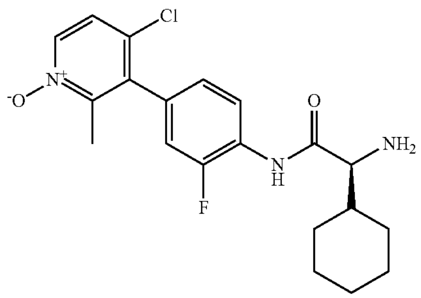

The title compound was prepared by a procedure similar to Intermediate 3-6, using intermediate 1-7 and commercial (S)-2-((tert-butoxycarbonyl)amino)-2-cyclohexylacetic acid, to yield the title compound (21 mg, 10%) as a yellow resin.

LC-MS: Rt=0.60; MS m/z=392.3 $[MH]^+$ (Method 11).

Intermediate 3-33

(S)-6'-(2-amino-2-cyclohexylacetamido)-4-chloro-2-methyl-[3,3'-bipyridine] 1-oxide

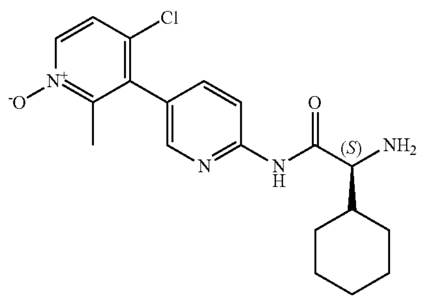

The title compound was prepared by a procedure similar to Intermediate 3-6, using intermediate 1-9 and commercial (S)-2-((tert-butoxycarbonyl)amino)-2-cyclohexylacetic acid, to yield the title compound (200 mg, 20%) as a yellow resin.

LC-MS: Rt=0.68; MS m/z=375.1 $[MH]^+$ (Method 2).

Intermediate 3-34

(S)-3-(4-(2-amino-2-cyclohexylacetamido)-2,6-difluorophenyl)-4-chloro-2-methylpyridine 1-oxide

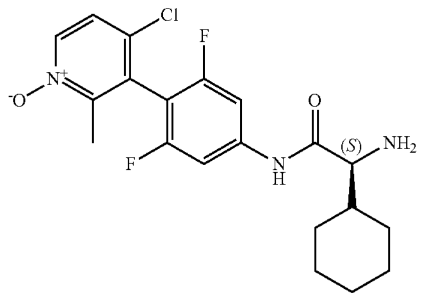

The title compound was prepared by a procedure similar to Intermediate 3-6, using intermediate 1-11 and commercial (S)-2-((tert-butoxycarbonyl)amino)-2-cyclohexylacetic acid, to yield the title compound (75 mg, 17%) as a yellow resin.

LC-MS: Rt=0.74 min; MS m/z=236.1 $[MH]^+$ (Method 12).

Intermediate 3-35

3-(4-((S)-2-amino-2-cyclohexylacetamido)-2,3-difluorophenyl)-4-chloro-2-methylpyridine 1-oxide

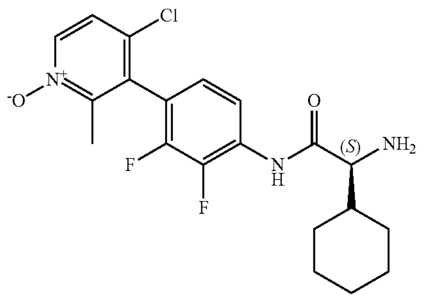

The title compound was prepared by a procedure similar to Intermediate 3-6, using intermediate 1-16 and commercial (S)-2-((tert-butoxycarbonyl)amino)-2-cyclohexylacetic acid, to yield the title compound (190 mg, 39%) as yellow resin.

LC-MS: Rt=0.74 and 0.75 min, 1:1 mixture of atropisomers; MS m/z=410.1 $[MH]^+$ (Method 2).

Intermediate 3-36

3-(4-((S)-2-amino-2-cyclohexylacetamido)-2,5-difluorophenyl)-4-chloro-2-methylpyridine 1-oxide

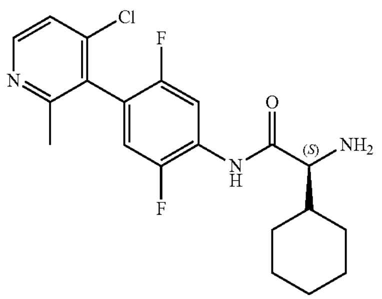

Step 1: tert-butyl ((1S)-2-((4-(4-chloro-2-methylpyridin-3-yl)-2,5-difluorophenyl)amino)-1-cyclohexyl-2-oxoethyl)carbamate

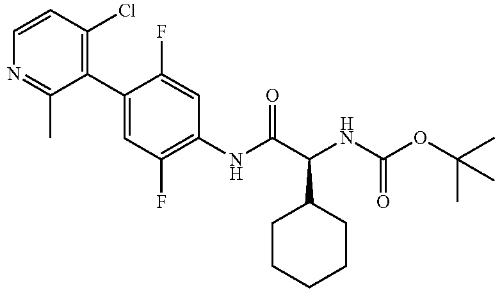 [SMILES: Cc1nccc(Cl)c1-c1cc(F)c(NC(=O)[C@@H](NC(=O)OC(C)(C)C)C2CCCCC2)cc1F]

To a cooled (−30° C.) solution of 4-(4-chloro-2-methylpyridin-3-yl)-2,5-difluoroaniline (Intermediate 1-17; 170 mg, 0.66 mmol), pyridine (950 mg, 11.9 mmol) and Boc-L-cyclohexylglycine (221 mg, 0.83 mmol) in DCM (0.8 mL) was added $POCl_3$ (169 mg, 1.09 mmol) with the temperature maintained between −20 and −30° C. The mixture was stirred at this temperature for 12 min and was then poured into ice-water. The mixture was extracted with DCM, the organic layer was washed with 0.5N HCl, 10% $Na_2CO_3$ and with brine, dried ($Na_2SO_4$) and evaporated. The residue was purified by column chromatography on silica (column: RediSep 40 g; eluent: 40 to 100% EtOAc+5% MeOH in heptane) to yield the title compound (160 mg, 46%4) as a brown oil.

LC-MS: Rt=1.29 min, MS m/z=494.2 $[MH]^+$ (Method 2).

Step 2: 3-(4-((S)-2-((tert-butoxycarbonyl)amino)-2-cyclohexylacetamido)-2,5-difluorophenyl)-4-chloro-2-methylpyridine 1-oxide

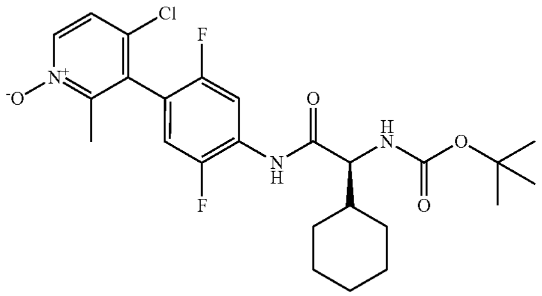

The title compound was prepared by treatment of tert-butyl ((1S)-2-((4-(4-chloro-2-methylpyridin-3-yl)-2,5-difluorophenyl)amino)-1-cyclohexyl-2-oxoethyl)carbamate (Step 1; 150 mg, 0.27 mmol) with mCPBA (98 mg, 0.44 mmol) following the procedure describe for Intermediate 1-1, step 1 to yield the title compound (115 mg, 70%) as a yellow resin.

LC-MS: Rt=1.18 min, MS m/z=509.2 $[MH]^+$ (Method 2).

Step 3: 3-(4-((S)-2-amino-2-cyclohexylacetamido)-2,5-difluorophenyl)-4-chloro-2-methylpyridine 1-oxide

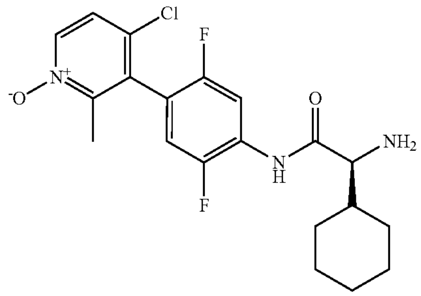

The title compound was prepared by treatment of 3-(4-((S)-2-((tert-butoxycarbonyl)amino)-2-cyclohexylacetamido)-2,5-difluorophenyl)-4-chloro-2-methylpyridine 1-oxide (Step 2; 110 mg, 0.183 mmol) with TFA (98 mg, 0.44 mmol) following the procedure describe for Intermediate 3-2, step 2 to yield the title compound (80 mg, 64%) as a yellow solid.

LC-MS: Rt=0.62 and 0.72 min (1:1 mixture of atropisomers), MS m/z=410.1 $[MH]^+$ (Method 2).

Intermediate 3-37

3-(4-((S)-2-amino-2-((1R,3s,5S)-bicyclo[3.1.0]hexan-3-yl)acetamido)phenyl)-2-methyl-4-(trifluoromethyl)pyridine 1-oxide

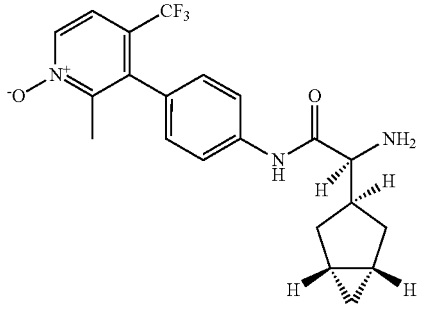

The title compound was prepared by a procedure similar to Intermediate 3-6, using intermediate 1-3 and (S)-2-((1R,3s,5S)-bicyclo[3.1.0]hexan-3-yl)-2-((tert-butoxycarbonyl)amino)acetic acid (prepared according to WO2014/65791 A1), to yield the title compound as a brown solid.

TLC (DCM/MeOH=95:5) Rf=0.22; MS m/z=406.3 [MH]+

Intermediate 3-38

3-(4-((2S)-2-amino-2-(4-fluorocyclohex-3-en-1-yl)acetamido)phenyl)-2-methyl-4-(trifluoromethyl)pyridine 1-oxide

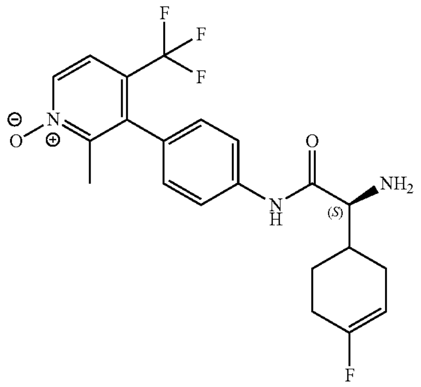

The title compound was prepare by a procedure similar to Intermediate 3-5, using intermediate 1-3 and intermediate 2-6, to yield the crude title compound (326 mg, 67%) as a yellow solid.

LC-MS: Rt=0.61; MS m/z=424.3 $[MH]^+$ (Method 4).

Intermediate 3-39

3-(4-((S)-2-amino-2-cyclohexylacetamido)-2-fluorophenyl)-2-methyl-4-(trifluoromethyl)pyridine 1-oxide

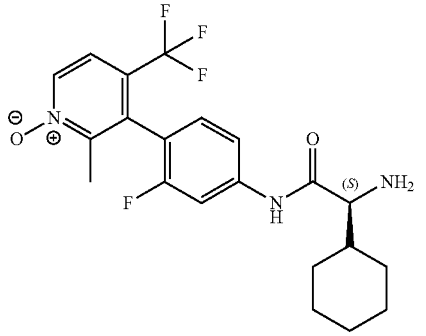

The title compound was prepared by a procedure similar to Intermediate 3-5, using intermediate 1-6 and commercial (S)-2-((tert-butoxycarbonyl)amino)-2-cyclohexylacetic acid.

LC-MS: Rt=0.79 and 0.81 min, 1:1 mixture of atropisomers; MS m/z=426.2 $[MH]^+$ (Method 1).

Intermediate 3-40

(S)-3-(4-(2-amino-2-cyclohexylacetamido)phenyl)-2-methyl-4-(trifluoromethyl)pyridine 1-oxide

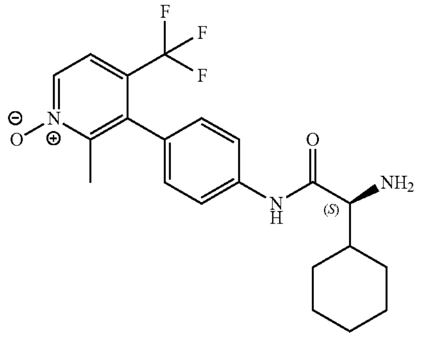

The title compound was prepared by a procedure similar to Intermediate 3-5, using intermediate 1-3 and commercial (S)-2-((tert-butoxycarbonyl)amino)-2-cyclohexylacetic acid as an off-white amorphous solid.

LC-MS: Rt=0.71; MS m/z 408.4 $[MH]^+$ (Method 4).

Intermediate 3-41

(S)-3-(4-(2-amino-2-cyclohexylacetamido)-2-fluorophenyl)-2-methylpyridine 1-oxide

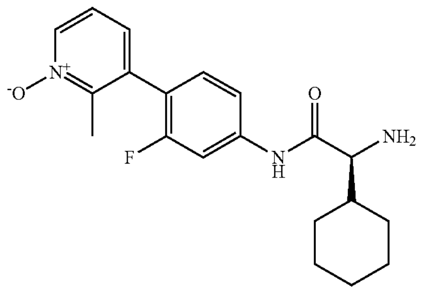

The title compound was prepared by a procedure similar to Intermediate 3-1, using intermediate 1-12 and commercial (S)-2-((tert-butoxycarbonyl)amino)-2-cyclohexylacetic acid as a yellow solid.

LC-MS: Rt=0.64; MS m/z=358.3 $[MH]^+$ (Method 2).

Intermediate 3-42

(S)-3-(4-(2-amino-2-cyclohexylacetamido)phenyl)-2-(difluoromethyl)-4-methylpyridine 1-oxide

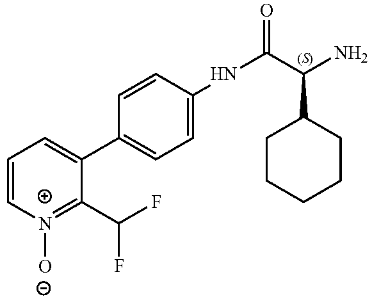

Step 1: tert-butyl (S)-(1-cyclohexyl-2-((4-(2-(difluoromethyl)-4-methylpyridin-3-yl)phenyl)amino)-2-oxoethyl)carbamate To a solution of 4-(2-(difluoromethyl)-4-methylpyridin-3-yl)aniline (intermediate 1-10, 0.20 g, 0.85 mmol), (S)-2-((tert-butoxycarbonyl)amino)-2-cyclohexylacetic acid (0.26 g, 1.02 mmol) and HATU (0.65 g, 1.71 mmol) in DMF (10 mL) was added DIEA (0.44 g, 3.41 mmol) and the mixture stirred at RT for 16 h. The reaction mixture was poured into ice water and extracted with EtOAc. The extracts were washed with sat. aq. $NaHCO_3$ and brine, and dried over $Na_2SO_4$. Concentration under reduced pressure afforded the crude product, which was purified by column chromatography on silica to yield the title compound (0.20 g, 44%) as a brown solid.

LC-MS: Rt=1.86 min; MS m/z=474.1 $[M+H]^+$ (Method 16).

Step 2: (S)-3-(4-(2-((tert-butoxycarbonyl)amino)-2-cyclohexylacetamido)phenyl)-2-(difluoromethyl)-4-methylpyridine 1-oxide To a solution of tert-butyl (S)-(1-cyclohexyl-2-((4-(2-(difluoromethyl)-4-methylpyridin-3-yl)phenyl)amino)-2-oxoethyl)carbamate (Step 1; 0.20 g, 0.42 mmol) in $CHCl_3$ (15 mL), mCPBA (0.22 g, 1.27 mmol) was added and the resulting mixture stirred at RT for 4 h. The reaction mixture was poured into aq. sat. $NaHCO_3$ and extracted with $CHCl_3$. The extract was washed with water and brine, and concentrated under reduced pressure to afford the crude product. Purification by chromatography on silica afforded the title compound (0.17 g, 82%) as a white solid.

LC-MS: Rt=1.66 min; MS m/z=490.3 $[MH]^+$ (Method 16).

Step 3: (S)-3-(4-(2-amino-2-cyclohexylacetamido)phenyl)-2-(difluoromethyl)-4-methylpyridine 1-oxide To a cooled (0° C.) solution of (S)-3-(4-(2-((tert-butoxycarbonyl)amino)-2-cyclohexylacetamido)phenyl)-2-(difluoromethyl)-4-methylpyridine 1-oxide (Step 2; 0.17 g, 0.35 mmol) in dioxane (2 mL) was added 20% HCl in dioxane (8 mL). The resulting mixture was allowed to reach RT and stirred at this temperature for 4 h. The mixture was then poured into ice water and extracted with EtOAc. The extract was washed with sat. aq. $NaHCO_3$ and brine, dried ($Na_2SO_4$) and concentrated under reduced pressure. The residue was purified by repeatedly washing with $Et_2O$ to afford the crude title compound (0.17 g) as a brown solid.

LC-MS: Rt=0.12 min; MS m/z=390.5 $[MH]^+$ (Method 16).

Intermediate 3-43

(2S)-2-amino-N-(4-(2,4-dimethylpyridin-3-yl)-3-fluorophenyl)-2-((1r,4S)-4-methylcyclohexyl)acetamide

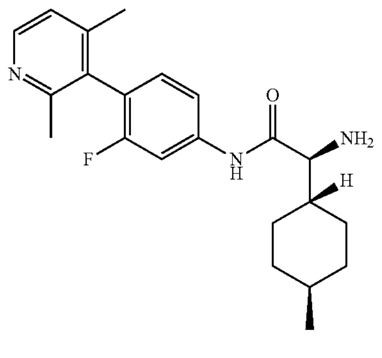 [SMILES: Cc1ccnc(C)c1-c1ccc(NC(=O)[C@@H](N)[C@H]2CC[C@H](C)CC2)cc1F]

Step 1: 4-(2,4-dimethylpyridin-3-yl)-3-fluoroaniline

To a solution of 3-bromo-2,4-dimethylpyridine (500 mg, 2.69 mmol) in dioxane (10 mL) and water (5 mL), 4-amino-2-fluorophenylboronic acid pinacol ester (637 mg, 2.69 mmol), XPhos Pd G2 (106 mg, 0.134 mmol), TBAB (26.0 mg, 0.081 mmol) and $K_3PO_4$ (1711 mg, 8.06 mmol) was added. The vial was purged with argon for 5 min at RT, then the mixture was stirred at 70° for 2.5 h and for 16 h at RT. The reaction mixture was poured into EtOAc and washed with sat. aq. $Na_2CO_3$ and water. The aqueous layers were extracted with EtOAc, the organic phases were combined and evaporated. The residue was purified by column chromatography on silica (column: RediSep 80 g; eluent: 10 to 100% EtOAc in cyclohexane) to yield the title compound (532 mg, 92%) as a yellow oil.

LC-MS: Rt=0.39 min; MS m/z=217.1 $[MH]^+$ (Method 2).

Step 2: Tert-butyl ((1S)-2-((4-(2,4-dimethylpyridin-3-yl)-3-fluorophenyl)amino)-1-((1r,4S)-4-methylcyclohexyl)-2-oxoethyl)carbamate A solution of (S)-2-((tert-butoxycarbonyl)amino)-2-((1r,4S)-4-methylcyclohexyl)acetic acid (Step 1; 180 mg, 0.663 mmol), 2,4,6-trimethylpyridine (0.353 ml, 2.65 mmol) and HATU (277 mg, 0.730 mmol) in DMF (2 mL) was stirred at RT for 10 min. To the resulting colorless solution, 4-(2,4-dimethylpyridin-3-yl)-3-fluoroaniline (143 mg, 0.663 mmol) was added at RT in one portion, and the mixture stirred at RT for 72 h. The mixture was diluted with aq. sat. $NaHCO_3$ and extracted twice with $Et_2O$. The extracts were washed with brine, dried ($Na_2SO_4$) and evaporated. Purification by preparative HPLC afforded the title compound (237 mg, 75%) as a white solid.

LC-MS: Rt=1.19 min; MS m/z=470.2 $[MH]^+$ (Method 1).

Step 3: (2S)-2-amino-N-(4-(2,4-dimethylpyridin-3-yl)-3-fluorophenyl)-2-((1r,4S)-4-methylcyclohexyl)acetamide A solution of tert-butyl ((1S)-2-((4-(2,4-dimethylpyridin-3-yl)-3-fluorophenyl)amino)-1-((1r,4S)-4-methylcyclohexyl)-2-oxoethyl)carbamate (Step 2; 200 mg, 0.426 mmol) in 4M HCl in dioxane (4 mL) was stirred at RT for 1 h, resulting in a white suspension. Evaporation of all volatiles under reduced pressure afforded the title compound (170 mg, 96%) as a colorless solid that was used for the next steps without further purification.

LC-MS: Rt=0.79 min; MS m/z=401.1 $[MH]^+$ (Method 1).

Intermediate 3-44

(S)-2-amino-N-(2-chloro-4-(4-chloro-2-methylpyridin-3-yl)phenyl)-2-cyclohexylacetamide

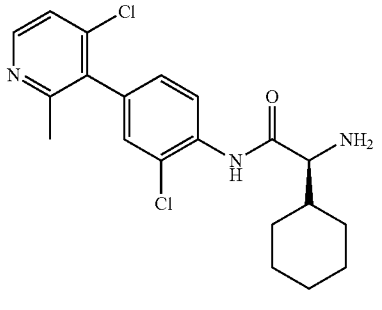 [SMILES: Cc1nccc(Cl)c1-c1ccc(NC(=O)[C@@H](N)C2CCCCC2)c(Cl)c1]

The title compound was prepared by a procedure similar to Intermediate 3-43, using intermediate 1-14 and commercial (S)-2-((tert-butoxycarbonyl)amino)-2-cyclohexylacetic acid, to yield the title compound as a yellow resin.

LC-MS: Rt=0.79 min; MS m/z=392.2 $[MH]^+$ (Method 11).

Intermediate 3-45

(2S)-2-amino-2-(3,3-difluorocyclopentyl)-N-(4-(2,4-dimethylpyridin-3-yl)phenyl)acetamide

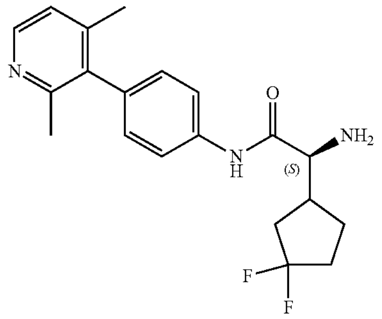

The title compound was prepared by a procedure similar to Intermediate 3-6, using intermediate 1-19 and intermediate 2-8 to yield the title compound as an off-white amorphous solid.

LC-MS: Rt=0.21 min; MS m/z=360.3 $[MH]^+$ (Method 11).

Intermediate 3-46

(2S)-2-amino-2-(4,4-difluorocyclohexyl)-N-(4-(2,4-dimethylpyridin-3-yl)-3-fluorophenyl)acetamide

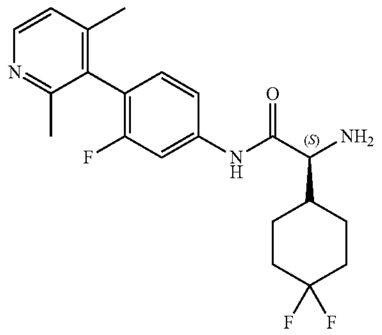

The title compound was prepared by a procedure similar to Intermediate 3-43, using intermediate 1-21, and Intermediate 2-5 to yield the title compound as a yellow foam.

LC-MS: Rt=0.61 and 0.63 min, 1:1 mixture of atropisomers; MS m/z=392.3 $[MH]^+$ (Method 2).

Intermediate 3-47

(S)-2-amino-N-(4-(2-chloro-4-methylpyridin-3-yl)phenyl)-2-cyclohexylacetamide

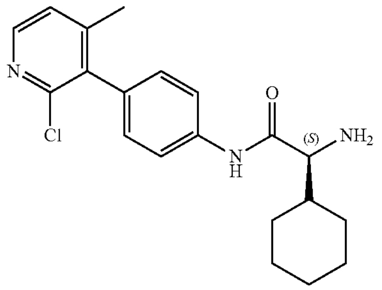

The title compound was prepared by a procedure similar to intermediate 3-43, using intermediate 1-15 and commercial (S)-2-((tert-butoxycarbonyl)amino)-2-cyclohexylacetic acid, to yield the title compound as a yellow resin.

LC-MS: Rt=0.84 min; MS m/z=358.3 $[MH]^+$ (Method 2).

Intermediate 3-48

(2S)-2-amino-N-(4-(4-chloro-2-methylpyridin-3-yl)-3-fluorophenyl)-2-cyclohexylacetamide

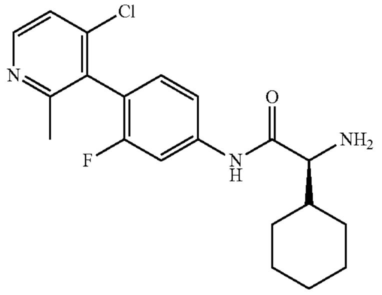 [SMILES: Cc1nccc(Cl)c1-c1ccc(NC(=O)[C@@H](N)C2CCCCC2)cc1F]

The title compound was prepared by a procedure similar to intermediate 3-43, using intermediate 1-20 and commercial (S)-2-((tert-butoxycarbonyl)amino)-2-cyclohexylacetic acid, to yield the title compound as an off-white foam.

LC-MS: Rt=3.52 and 3.61 min, 1:1 mixture of atropisomers; MS m/z=376.3 $[MH]^+$ (Method 4).

Intermediate 3-49

(2S)-2-amino-N-(4-(2,4-dimethylpyridin-3-yl)-3-fluorophenyl)-2-((1r,4S)-4-(trifluoromethyl)cyclohexyl)acetamide

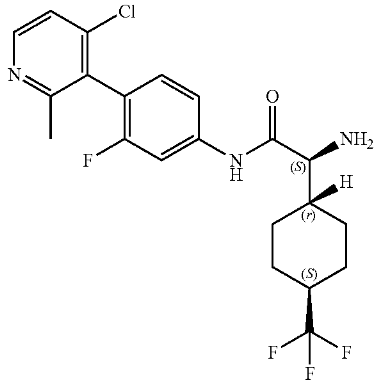

The title compound was prepared by a procedure similar to Intermediate 3-43, using Intermediate 1-21 and intermediate 2-3, to yield the title compound as a colorless solid.

LC-MS: Rt=0.76 and 0.77 min, 1:1 mixture of atropisomers; MS m/z=424.2 $[MH]^+$ (Method 2).

Intermediate 3-50

(S)-2-amino-N-(4-(5-chloro-2-methylpyridin-3-yl)-3-fluorophenyl)-2-cyclohexylacetamide

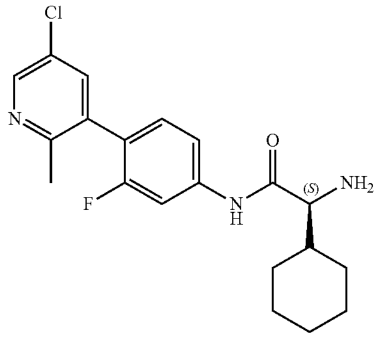

The title compound was prepared by a procedure similar to intermediate 3-43, using 3-bromo-5-chloro-2-methylpyridine and commercial (S)-2-((tert-butoxycarbonyl)amino)-2-cyclohexylacetic acid, to yield the title compound as an off-white solid.

LC-MS: Rt=0.89 min; MS m/z=376.3 $[MH]^+$ (Method 1).

Intermediate 3-51

(S)-2-amino-2-cyclohexyl-N-(4-(3,5-dimethylpyridin-4-yl)phenyl)acetamide

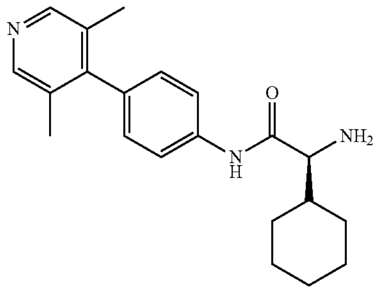 [SMILES: Cc1cncc(C)c1-c1ccc(NC(=O)[C@@H](N)C2CCCCC2)cc1]

The title compound was prepared by a procedure similar to Intermediate 3-43, using intermediate 1-18 and commercial (S)-2-((tert-butoxycarbonyl)amino)-2-cyclohexylacetic acid, to yield the title compound as a colorless solid.

LC-MS: Rt=1.97 min; MS m/z=338.2 $[M+H]^+$ (Method 4).

Intermediate 3-52

(S)-2-amino-2-cycloheptyl-N-(4-(3,5-dimethylpyridin-4-yl)phenyl)acetamide

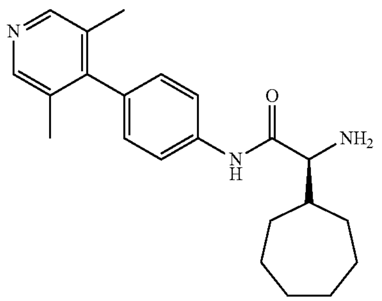 [SMILES: Cc1cncc(C)c1-c1ccc(NC(=O)[C@@H](N)C2CCCCCC2)cc1]

The title compound was prepared by a procedure similar to Intermediate 3-43, using intermediate 1-18 and commercial (S)-2-((tert-butoxycarbonyl)amino)-2-cycloheptylacetic acid, to yield the title compound as a colorless solid.

LC-MS: Rt=2.33 min; MS m/z=352.3 $[MH]^+$ (Method 4).

Intermediate 3-53

(S)-2-amino-N-(4-(3,5-dimethylpyridin-4-yl)phenyl)-2-((S)-1,2,3,4-tetrahydronaphthalen-2-yl)acetamide

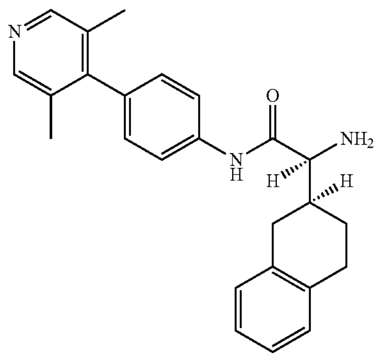 [SMILES: Cc1cncc(C)c1-c1ccc(NC(=O)[C@@H](N)[C@H]2CCc3ccccc3C2)cc1]

The title compound was prepared by a procedure similar to Intermediate 3-43, using Intermediate 1-18 and Intermediate 2-12, to yield the title compound as a yellow solid.

LC-MS: Rt=0.51 min; MS m/z=386.2 $[MH]^+$ (Method 1).

Intermediate 3-54

(S)-3-(4-(2-amino-3,3-diphenylpropanamido)phenyl)-2,4-dimethylpyridine 1-oxide

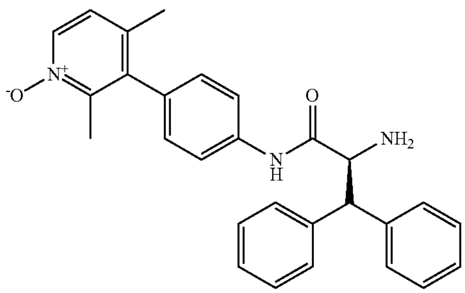

The title compound was prepared by a procedure similar to Intermediate 3-1, using intermediate 1-1 and commercial (S)-2-((tert-butoxycarbonyl)amino)-3,3-diphenylpropanoic acid, to yield the title compound as an off-white solid.

LC-MS: Rt=2.80 min; MS m/z=438.2 $[MH]^+$ (Method 4).

Intermediate 3-55

(S)-3-(4-(2-amino-3,3-diphenylpropanamido)phenyl)-4-chloro-2-methylpyridine 1-oxide

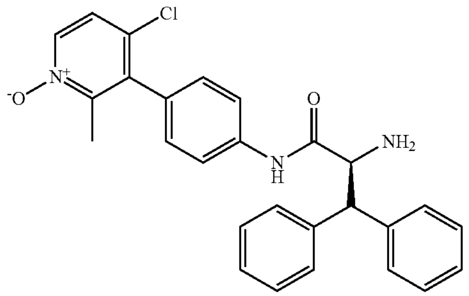

The title compound was prepared by a procedure similar to Intermediate 3-1, using intermediate 1-2 and commercial (S)-2-((tert-butoxycarbonyl)amino)-3,3-diphenylpropanoic acid, to yield the title compound as an off-white solid.

LC-MS: Rt=3.06 min; MS m/z=458.4 $[MH]^+$ (Method 4).

Intermediate 3-56

2-amino-N-(4-(4-chloro-2-methylpyridin-3-yl)-3-fluorophenyl)-2-(3,3-difluorocyclohexyl)acetamide

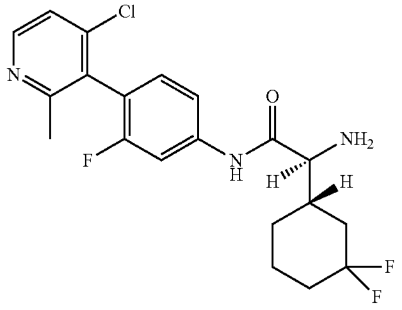 [SMILES: Cc1nccc(Cl)c1-c1ccc(NC(=O)[C@@H](N)[C@H]2CCCC(F)(F)C2)cc1F]

The title compound was prepared by a procedure similar to Intermediate 3-6, using Intermediate 1-4 and Intermediate 2-4, to yield the title compound as an off-white foam LC-MS: Rt=0.86 min; MS: m/z=412.1 $[MH]^+$ (Method 2).

Intermediate 3-57

(2S)-2-amino-2-cyclohexyl-N-(4-(2,4-dimethylpyridin-3-yl)-3-fluorophenyl)acetamide

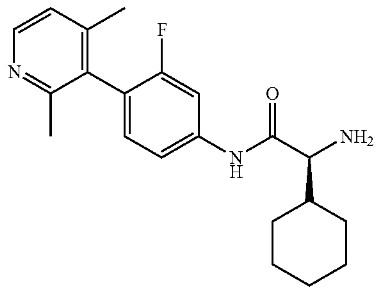 [SMILES: Cc1ccnc(C)c1-c1ccc(NC(=O)[C@@H](N)C2CCCCC2)cc1F]

The title compound was prepared by a procedure similar to Intermediate 3-43, using Intermediate 1-21 and commercial (S)-2-((tert-butoxycarbonyl)amino)-2-cyclohexylacetic acid, to yield the title compound as a colorless solid.

LC-MS: Rt=0.57 and 0.58 min (1:1 mixture of atropisomers); MS: m/z=356.2 $[MH]^+$ (Method 1).

Intermediate 3-58

(S)-3-(4-(2-amino-2-cyclohexylacetamido)phenyl)-2-chloro-4-(trifluoromethyl)pyridine 1-oxide

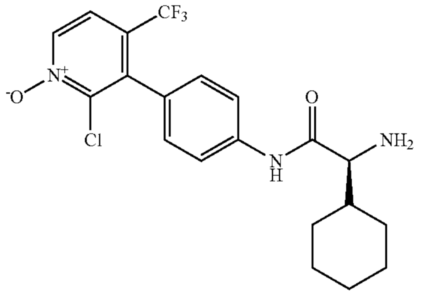

The title compound was prepared by a procedure similar to Intermediate 3-1, using intermediate 1-13 and commercial (S)-2-((tert-butoxycarbonyl)amino)-2-cyclohexylacetic acid, to yield the title compound as an off-white solid.

TLC (EtOAc/hexane=1:1) Rf=0.04; MS: m/z=428.3 [MH]+.

Intermediate 3-59

(S)-3-(4-(2-amino-3-phenylpropanamido)phenyl)-2,4-dimethylpyridine 1-oxide

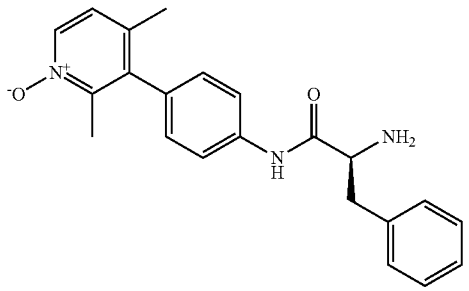

The title compound was prepared by a procedure similar to Intermediate 3-1, using intermediate 1-2 and commercial Boc-(L)-phenylalanine, to yield the title compound as an off-white solid.

LC-MS: Rt=1.02 min; MS m/z=462.3 $[MH]^+$ (Method 2).

Intermediate 3-60

(S)-3-(4-(2-amino-3-(2-fluorophenyl)propanamido)phenyl)-2,4-dimethylpyridine 1-oxide

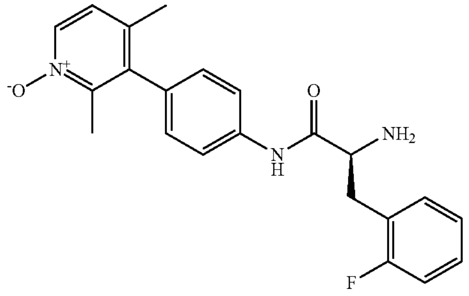

The title compound was prepared by a procedure similar to Intermediate 3-6, using Intermediate 1-2 and commercial Fmoc-2-fluoro-L-phenylalanine, to yield the title compound as an off-white foam.

LC-MS: Rt=1.71 min; MS m/z [MH]+=380.2 (Method 4).

Intermediate 3-61

(S)-2-amino-N-(4-(4-chloropyridin-3-yl)-3-fluorophenyl)-2-cyclohexylacetamide

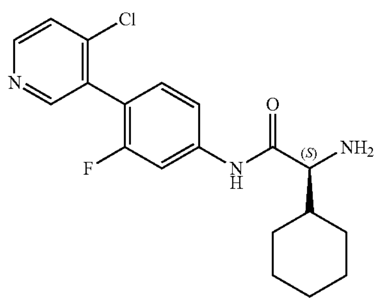

The title compound was prepared by a procedure similar to Intermediate 3-43, using Intermediate 1-22 and commercial (S)-2-((tert-butoxycarbonyl)amino)-2-cyclohexylacetic acid, to yield the title compound as a colorless solid.

LC-MS: Rt=0.88 min; MS: m/z=362.3 $[MH]^+$ (Method 3).

Intermediate 4-1

1-(2-methoxy-2-oxoethyl)-1H-pyrazole-5-carboxylic acid

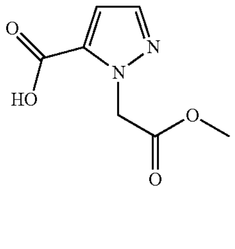

A solution of t-butyl 1-(2-methoxy-2-oxoethyl)-1H-pyrazole-5-carboxylate (200 mg, 0.832 mmol) in DCM (500 μl) was treated with TFA (96 μl, 1.249 mmol). The mixture was stirred at RT for 1 h, then additional 200 μl of TFA were added, followed by stirring at RT overnight. The mixture was evaporated. The crude products of two similar experiments were combined and purified by column chromatography on RP-18 (ISCO system; eluent: water/acetonitrile 95:5 to 0:100; column: RediSep 43 g silicagel RP-18) to yield the title compound (287 mg, 94%) as a colorless oil. 1H NMR (400 MHz, DMSO-d6) δ 13.46 (s, 1H), 7.59 (d, 1H), 6.88 (d, 1H), 5.32 (s, 2H), 3.67 (s, 3H).

Intermediate 4-2

(S)—N-(1-cyclohexyl-2-oxo-2-((4-(4,4,5,5-tetramethyl-1,3,2-dioxaborolan-2-yl)phenyl)amino)ethyl)-1-methyl-1H-pyrazole-5-carboxamide

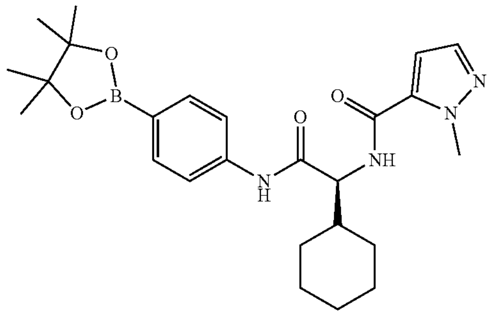 [SMILES: Cn1nccc1C(=O)N[C@H](C(=O)Nc1ccc(B2OC(C)(C)C(C)(C)O2)cc1)C1CCCCC1]

Step 1: Tert-butyl (S)-(1-cyclohexyl-2-oxo-2-((4-(4,4,5,5-tetramethyl-1,3,2-dioxaborolan-2-yl)phenyl)amino)ethyl)carbamate To a solution of Boc-(L)-cyclohexylglycine (6.0 g, 23.32 mmol) in DMF (120 mL) was added 4-(4,4,5,5-tetramethyl-1,3,2-dioxaborolan-2-yl)aniline (5.62 g, 25.6 mmol) followed by $NEt_3$ (9.70 mL, 69.9 mmol) and HATU (10.64 g, 28.0 mmol). After stirring the mixture at RT for 16 h at RT the solvent was evaporated and the residue was partitioned between EtOAc and sat. aq. $Na_2CO_3$. The organic layer was washed with brine, the combined aqeuous layers were re-extracted with EtOAc and the combined organic layers were evaporated. The residue was purified by column chromatography on silica (600 g silica, elution with 20% EtOAc in cyclohexane) to yield the title compound (10.81 g, 96%) as an off-white solid.

LC-MS: Rt=1.35 min; MS: m/z=459.4 $[MH]^+$ (Method 3).

Step 2: (S)-2-amino-2-cyclohexyl-N-(4-(4,4,5,5-tetramethyl-1,3,2-dioxaborolan-2-yl)phenyl)acetamide To a cooled (0° C.) solution of tert-butyl (S)-(1-cyclohexyl-2-oxo-2-((4-(4,4,5,5-tetramethyl-1,3,2-dioxaborolan-2-yl)phenyl)amino)ethyl)carbamate (Step 1; 10.8 g, 23.56 mmol) in 1,4-dioxane (10 mL) was added 4M HCl in dioxane (88 mL, 353 mmol). After stirring the mixture at RT for 2 h PLC-MS indicated the complete consumption of the starting material. The volatiles were evaporated and the residue was dried in HV to yield the title compound (8.64 g, 93%) as an off-white solid which was used in the next step without further purification.

LC-MS: Rt=0.99 min; MS: m/z=359.4 $[MH]^+$ (Method 3).

Step 3: (S)—N-(1-cyclohexyl-2-oxo-2-((4-(4,4,5,5-tetramethyl-1,3,2-dioxaborolan-2-yl)phenyl)amino)ethyl)-1-methyl-1H-pyrazole-5-carboxamide To a solution of (S)-2-amino-2-cyclohexyl-N-(4-(4,4,5,5-tetramethyl-1,3,2-dioxaborolan-2-yl)phenyl)acetamide (Step 2; 8.64 g, 21.89 mmol) and 2,4,6-collidine (11.66 mL, 88 mmol) in DMF (30 mL) was added 1-methyl-1H-pyrazole-5-carboxylic acid (4.14 g, 32.8 mmol), followed by HATU (16.64 g, 43.8 mmol) was added. After stirring the reaction mixture for 2 h at RT HPLC-MS indicated the complete consumption of the starting material. The mixture was diluted with EtOAc and washed with 0.5M $Na_2CO_3$ solution and with brine. The combined aqueous layers were re-extracted with EtOAc. The combined organic layers were dried ($MgSO_4$) and evaporated. The residue was suspended in DCM (100 mL) and stirred for 20 min. Pentane (50 mL) was added dropwise and stirring was continued for 20 min at RT. The mixture was filtered through a 5 μm PTFE membrane filter, the filter cake was washed with DCM/pentane 1:1 (3×20 mL) and dried in vacuo to yield the title compound (7.81 g, 77%) as a colorless solid.

LC-MS: Rt=1.29 min; MS: m/z=467.4 $[MH]^+$ (Method 3).

Intermediate 4-3

3-bromo-5-(((tert-butyldimethylsilyl)oxy)methyl)-2-methylpyridine

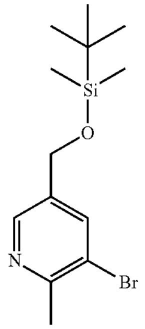

To a solution of (5-bromo-6-methylpyridin-3-yl)methanol (US 2016/0222028 A1, 850 mg, 4.21 mmol) and imidazole (573 mg, 8.41 mmol) in DCM (30 mL) was added TBDMSCl (951 mg, 6.31 mmol). After stirring the mixture at RT overnight the volatiles were evaporated and the residue was partitioned between EtOAc and sat. $Na_2CO_3$. The organic layer was washed with brine, the combined aqueous layers were re-extracted with EtOAc and the combined organic layers were evaporated. The residue was purified by column chromatography on silica (column: Redisep 80 g; elution with 0-40% EtOAc in cyclohexane) to yield the title compound (792 mg; 60%) as a yellow oil.

LC-MS: Rt=1.44 min; MS m/z=318.1 $[MH]^+$ (Method 3).

Example 1

2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide

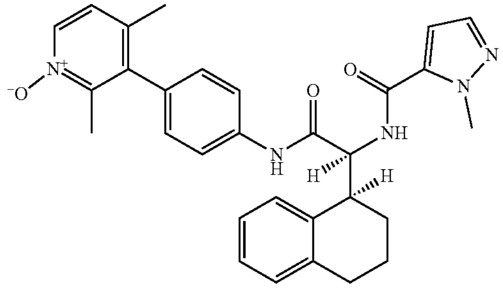

To a solution of 3-(4-((S)-2-amino-2-((S)-1,2,3,4-tetrahydronaphthalen-1-yl)acetamido)phenyl)-2,4-dimethylpyridine 1-oxide (Intermediate 3-1; 1.10 g, 2.46 mmol) in DMF (15 mL) were added 1-methyl-1H-pyrazole-5-carboxylic acid (530 mg, 4.2 mmol) followed by HATU (1.9 g, 4.93 mmol), and finally triethylamine (1.7 mL, 12.3 mmol). After stirring at RT overnight, the reaction mixture was diluted with EtOAc (200 mL) and extracted with sat. aq. $NaHCO_3$, water (twice) and with brine. The organic phase was dried ($Na_2SO_4$) and evaporated. The residue was purified by column chromatography on silica (column: RediSep 80 g; eluent:TBME/MeOH 100:0 to 0:100) to yield a pale yellow solid which was triturated with DCM/MeOH 4:1 at 0° C., followed by filtering and washing the solid with cold iso-pentane to yield the title compound (771 mg, 62%) as a colorless solid.

LC-MS: Rt=4.48 min; MS: m/z=510 $[MH]^+$ (Method 4)

1H NMR (400 MHz, DMSO-d6) δ 10.57 (s, 1H), 8.95 (d, 1H), 8.20 (d, 1H), 7.83 (d, 2H), 7.46 (d, 1H), 7.40 (d, 1H), 7.28-7.16 (m, 3H), 7.11-7.05 (m, 3H), 7.05-6.94 (m, 1H), 4.82 (dd, 1H), 3.90 (s, 3H), 3.38-3.34 (m, 1H), 2.93-2.71 (m, 2H), 2.23-2-12 (br. m, 1H), 2.09 (s, 3H), 1.97 (s, 3H), 1.85-1.65 (m, 3H) ppm.

The absolute stereochemical configuration was confirmed as (S,S) by X-ray crystallography.

Example 2

4-chloro-3-(4-((S)-2-cyclohexyl-2-(1-methyl-1H-pyrazole-5-carboxamido)acetamido)-2-fluorophenyl)-2-methylpyridine 1-oxide

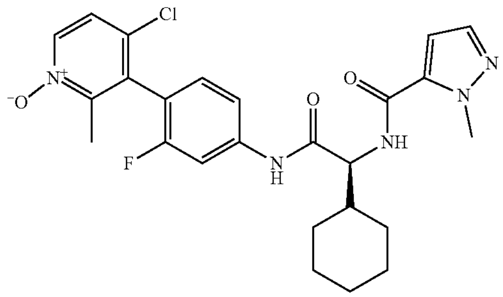

To a solution of 3-(4-((S)-2-amino-2-cyclohexylacetamido)-2-fluorophenyl)-4-chloro-2-methylpyridine 1-oxide (Intermediate 3-2; 2.10 g, 5.36 mmol) in DMF (30 mL) were added 1-methyl-1H-pyrazole-5-carboxylic acid (1.01 g, 8.04 mmol) followed by HATU (3.46 g, 9.11 mmol), and finally triethylamine (3.71 mL, 26.8 mmol). After stirring at RT for 2 h, the reaction mixture was diluted with EtOAc (150 mL) and extracted with sat. aq. $NaHCO_3$, water (twice) and with brine. The organic phase was dried ($Na_2SO_4$) and evaporated. The residue was purified by column chromatography on silica (column: RediSep 120 g; eluent:TBME/MeOH 100:0 to 0:100) to yield an off-white foam, which was triturated with acetonitrile, filtered, washed with MTBE and dried on HV to yield the title compound (1.95 g, 72%) as a colorless solid (mixture of atropisomers).

LC-MS: Rt=4.68 and 4.75 min (double peak, ratio 1:1, due to atropisomers); MS: m/z=500 and 502 $[MH]^+$ (Method 4).

1H NMR (400 MHz, DMSO-d6) δ 10.63 (s, 1H), 8.57 (d, 1H), 8.36 (d, 1H), 7.81 (m, 1H), 7.59 (d, 1H), 7.55-7.42 (m, 2H), 7.34 (dd, 1H), 7.07 (d, 1H), 4.40 (t, 1H), 4.03 (s, 3H), 2.15 (s, 3H), 1.98-1.81 (br. m, 2H), 1.78-1.69 (br. m, 2H), 1.67-1.57 (br. m, 2H), 1.32-0.89 (m, 5H) ppm.

The absolute stereochemical configuration at the chiral carbon atom was confirmed as (S) by X-ray crystallography.

Example 2a and Example 2b

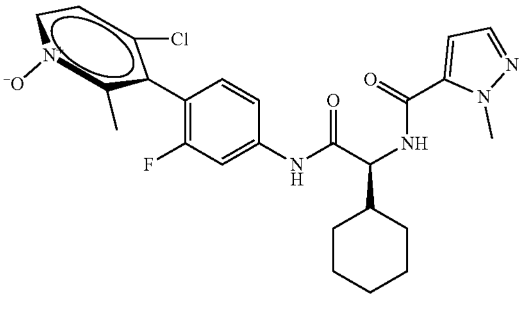

or (Ra, S atropisomer)

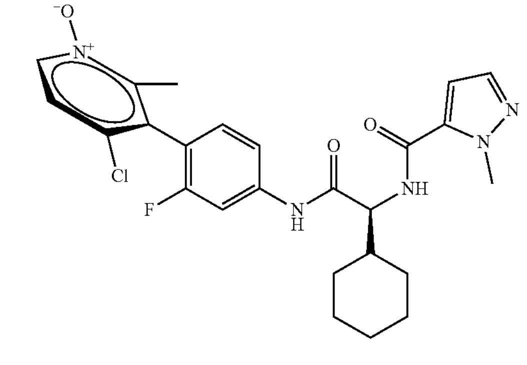

(Sa, S atropisomer)

250 mg of the mixture of atropisomers obtained from Example 2 was separated by chiral prep. HPLC (Gilson Trilution system, eluent: n-heptane:DCM:MeOH=60:30:10 (v:v:v); Column: Chiralpak IG, 250×30 mm 5 μm) to afford the individual atropisomers.

Analytical chiral HPLC (Column: Chiralpak IG, 250×4.6 mm, 5 μm; solvent:n-heptane:DCM MeOH=60:30:10 (v:v:v)+0.1% DEA; flow=2.5 mL/min, T=35° C.):

Example 2a (single atropisomer absolute stereoconfiguration at bond of rotation not determined, Ra,S or Sa,S)=Peak 1: Rt=8.66 min.

Example 2b (single atropisomer absolute stereoconfiguration at bond of rotation not determined, Ra,S or Sa,S)=Peak 2: Rt=12.43 min.

The individual atropisomers were found to interconvert on standing.

Example 3

2,4-dimethyl-3-(4-((S)-2-(1-methyl-1H-pyrazole-5-carboxamido)-2-((1r,4S)-4-methylcyclohexyl)acetamido)phenyl)pyridine 1-oxide

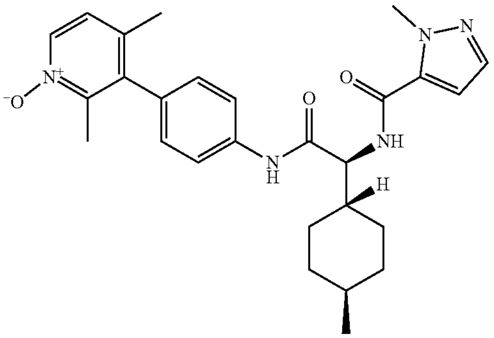

To a solution of 1-methyl-1H-pyrazole-5-carboxylic acid (29.7 mg, 0.235 mmol), 2,4,6-collidine (0.125 ml, 0.941 mmol) in DMF (2 mL) was added HATU (98 mg, 0.259 mmol) and the resulting solution was stirred for 10 min. 3-(4-((S)-2-amino-2-((1r,4S)-4-methylcyclohexyl)acetamido)phenyl)-2,4-dimethylpyridine 1-oxide (Intermediate 3-3, 100 mg, 0.235 mmol) was added at RT in one portion, and stirring was continued at RT for 2 h. The reaction mixture was partitioned between aq. 10% $NaHCO_3$ and EtOAc, the organic layer was washed with brine, dried ($Na_2SO_4$) and evaporated. The residue was purified by prep HPLC (column: Sunfire 30×100 mm; gradient of acetonitrile/water+0.1% TFA) to yield the title compound (72 mg, 63%) as a colorless solid.

LC-MS: Rt=1.02 min; MS: m/z=476 $[MH]^+$ (Method 3).

1H NMR (400 MHz, DMSO-d6) δ 10.36 (s, 1H), 8.54 (d, 1H), 8.19 (d, 1H), 7.77 (d, 2H), 7.46 (d, 1H), 7.26-7.14 (m, 3H), 7.07 (d, 1H), 4.40 (t, 1H), 4.03 (s, 3H), 2.08 (s, 3H), 1.96 (s, 3H), 1.94-1.80 (m, 2H), 1.76-1.59 (m, 3H), 1.36-1.14 (m, 2H), 1.14-1.00 (m, 1H), 0.96-0.81 (m, 5H) ppm.

Example 4

4-chloro-3-(4-((S)-2-(3-ethylisoxazole-4-carboxamido)-2-((1r,4S)-4-(trifluoromethyl)cyclohexyl)acetamido)phenyl)-2-methylpyridine 1-oxide

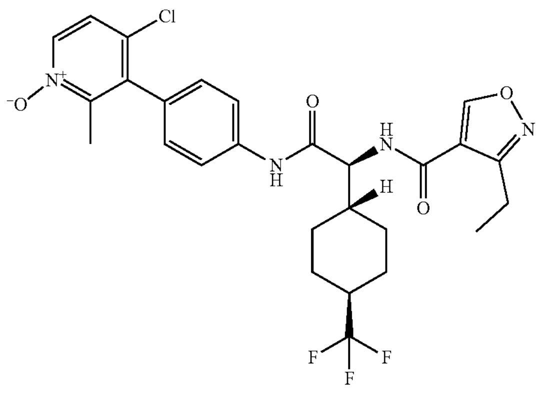

To a solution of 3-(4-((S)-2-amino-2-((1r,4S)-4-(trifluoromethyl)cyclohexyl)acetamido)phenyl)-4-chloro-2-methylpyridine 1-oxide (Intermediate 3-4; 473 mg, 1.070 mmol), 3-ethyl-4-isoxazolecarboxylic acid (166 mg, 1.177 mmol) and 2,4,6-collidine (0.214 ml, 1.606 mmol) in DMF (10 mL) was added HATU (611 mg, 1.61 mmol). After stirring the reaction mixture for 1 h at RT, the solvent was evaporated and residue was partitioned between EtOAc and sat. aq. $Na_2CO_3$. The organic layer was washed with brine and the combined aqueous layers were re-extracted with EtOAc. The combined organic layers were dried ($Na_2SO_4$) and evaporated. The residue was purified by column chromatography on RP-18 (column: RediSep 43 g; eluent: water/acetonitrile 95:5 to 0:100) to yield the title compound (428 mg, 69%) as an off-white solid.

LC-MS: Rt=1.13 min; MS: m/z=565 and 567 $[MH]^+$ (Method 5).

1H NMR (400 MHz, DMSO-d6) δ 10.43 (s, 1H), 9.42 (s, 1H), 8.56 (d, 1H), 8.31 (d, 1H), 7.77 (m, 2H), 7.54 (d, 1H), 7.24 (d, 2H), 4.48 (dd, 1H), 2.85 (q, 2H), 2.13 (s, 3H), 2.01-1.71 (m, 5H), 1.36-1.15 (m, 5H), 1.16 (t, 3H) ppm.

Example 5

(S)-3-(4-(2-cyclopentyl-2-(3-ethylisoxazole-4-carboxamido)acetamido)phenyl)-2-methyl-4-(trifluoromethyl)pyridine 1-oxide

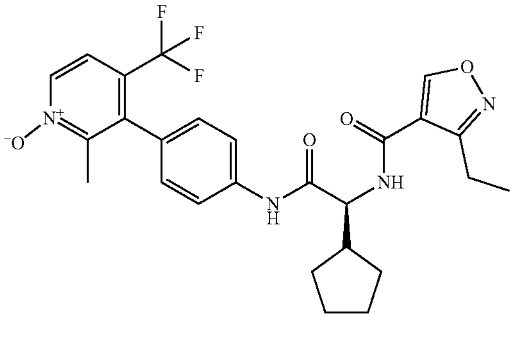

To a solution of (S)-3-(4-(2-amino-2-cyclopentylacetamido)phenyl)-2-methyl-4-(trifluoromethyl)pyridine 1-oxide (Intermediate 3-5, 5 g, 10.1 mmol) in DMF (40 mL) were added 3-ethylisoxazole-4-carboxylic acid (2.13 g, 15.1 mmol) and triethylamine (7.33 mL, 52.9 mmol), followed by HATU (6.51 g, 17.1 mmol) and the reaction mixture was stirred overnight at RT. Most of the DMF was removed in vacuo, the residue was taken up in EtOAc and washed with half-saturated brine, dried ($Na_2SO_4$), and concentrated in vacuo. The residue was purified by column chromatography on silica (column: RediSep 330 g; eluent:cyclohexane/EtOAc+5% MeOH 50:50 to 10:90) to yield an off-white foam (5.19 g) which was crystallized from TBME/EtOAc/MeOH (80/15/5, 6 mL) to yield the title compound (3.54 g, 66%) as colorless crystals, mp 149-151° C.

LC-MS: Rt=1.06 min; MS: m/z=517.3 $[MH]^+$ (Method 5).

1H NMR (400 MHz, DMSO-d6) δ 10.44 (s, 1H), 9.41 (s, 1H), 8.67 (d, 1H), 8.48 (d, 1H), 7.75 (d, 2H), 7.70 (d, 1H), 7.24 (d, 2H), 4.43 (t, 1H), 2.85 (q, 2H), 2.32 (q, 1H), 2.05 (s, 3H), 1.90-1.21 (m, 8H), 1.17 (t, 3H) ppm.

The absolute stereochemical configuration was confirmed as (S) by X-ray crystallography.

Example 6

4-chloro-3-(4-((S)-2-((S)-3,3-difluorocyclohexyl)-2-(3-ethylisoxazole-4-carboxamido)acetamido)phenyl)-2-methylpyridine 1-oxide

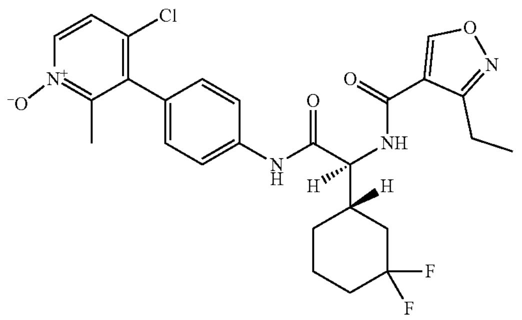

To a solution of 3-(4-((S)-2-amino-2-((S)-3,3-difluorocyclohexyl)acetamido)phenyl)-4-chloro-2-methylpyridine 1-oxide (Intermediate 3-6, 840 mg, 2.05 mmol) in DMF (11 mL) were added 3-ethylisoxazole-4-carboxylic acid (434 mg, 3.1 mmol), HATU (1325 mg, 3.5 mmol) and triethylamine (1.420 mL, 10.25 mmol). After stirring at RT overnight the reaction mixture was partitioned between EtOAc and aq. $NaHCO_3$. The aqueous layer was extracted with EtOAc, the combined organic layers were washed with brine, dried via phase separator and evaporated. The residue was purified by column chromatography on silica (column: RediSep 80 g; eluent: EtOAc/MeOH 100:0 to 70:30) to yield a colorless solid. This material was stirred in water, filtered and dried to yield the title compound (1.02 g, 91%) as colorless crystals, mp 247-250° C.

LC-MS: Rt=0.96 min; MS: m/z=533 and 535 $[MH]^+$ (Method 5).

1H NMR (400 MHz, DMSO-d6) δ 10.47 (s, 1H) 9.44 (s, 1H) 8.62 (d, 1H) 8.31 (d, 1H) 7.71-7.87 (m, 2H) 7.54 (d, 1H) 7.26 (d, 2H) 4.63 (t, 1H) 2.85 (q, 2H) 1.57-2.25 (m, 10H) 1.11-1.53 (m, 5H) ppm.

Example 7

3-(4-((S)-2-(1-ethyl-1H-pyrazole-5-carboxamido)-2-((1r,4S)-4-(trifluoromethyl)cyclohexyl)acetamido)phenyl)-2,4-dimethylpyridine 1-oxide

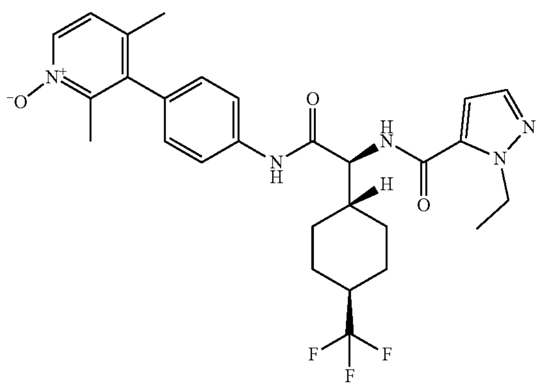

To a solution of 3-(4-((S)-2-amino-2-((1r,4S)-4-(trifluoromethyl)cyclohexyl)acetamido)phenyl)-2,4-dimethylpyridine 1-oxide (Intermediate 3-7; 350 mg, 0.83 mmol), 1-ethylpyrazole-5-carboxylic acid (128 mg, 0.91 mmol) and 2,4,6-collidine (0.332 ml, 2.5 mmol) in DMF (10 mL) was added HATU (474 mg, 1.246 mmol). After stirring the reaction mixture for 1 h at RT, the solvent was evaporated and residue was partitioned between EtOAc and sat. aq. $Na_2CO_3$. The organic layer was washed with brine and the combined aqueous layers were re-extracted with EtOAc. The combined organic layers were dried ($Na_2SO_4$) and evaporated. The residue was purified by column chromatography on RP-18 (column: RediSep 43 g; eluent: water/acetonitrile 95:5 to 0:100) to yield the title compound (330 mg, 73%) as an off-white solid.

LC-MS: Rt=1.03 min; MS: m/z=544.4 $[MH]^+$ (Method 5).

1H NMR (400 MHz, DMSO-d6) δ 10.39 (s, 1H), 8.56 (d, 1H), 8.19 (d, 1H), 7.81-7.72 (m, 2H), 7.49 (d, 1H), 7.28-7.14 (m, 3H), 7.03 (d, 1H), 4.52-4.39 (m, 3H), 3.52 (dd, 1H), 2.08 (s, 3H), 1.97 (s, 3H), 2.01-1.83 (m, 5H), 1.75 (d, 1H), 1.36-1.19 (m, 5H), 1.22-1.08 (m, 1H) ppm Example 8

3-(4-((S)-2-(3-ethylisoxazole-4-carboxamido)-2-((1r,4S)-4-(trifluoromethyl)cyclohexyl)acetamido)phenyl)-2,4-dimethylpyridine 1-oxide

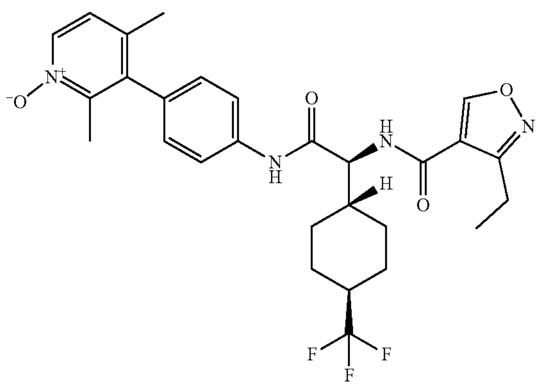

To a solution of 3-(4-((S)-2-amino-2-((1r,4S)-4-(trifluoromethyl)cyclohexyl)acetamido)phenyl)-2,4-dimethylpyridine 1-oxide (Intermediate 3-7; 350 mg, 0.83 mmol), 3-ethyl-4-isoxazolecarboxylic acid (117 mg, 0.83 mmol) and 2,4,6-collidine (0.332 ml, 2.5 mmol) in DMF (10 mL) was added HATU (474 mg, 1.246 mmol). After stirring the reaction mixture for 1 h at RT, the solvent was evaporated and residue was partitioned between EtOAc and sat. aq. $Na_2CO_3$. The organic layer was washed with brine and the combined aqueous layers were re-extracted with EtOAc. The combined organic layers were dried ($Na_2SO_4$) and evaporated. The residue was purified by column chromatography on RP-18 (column: RediSep 43 g; eluent: water/acetonitrile 95:5 to 0:100) to yield the title compound (355 mg, 78%) as a colorless solid.

LC-MS: Rt=1.06 min; MS: m/z=545.4 $[MH]^+$ (Method 5).

1H NMR (400 MHz, DMSO-d6) δ 10.41 (s, 1H), 9.42 (s, 1H), 8.57 (d, 1H), 8.20 (d, 1H), 7.76 (d, 2H), 7.22 (d, 1H), 7.18 (d, 2H), 4.47 (dd, 1H), 2.84 (q, 2H), 2.33-2.20 (br. m, 1H), 2.08 (s, 3H), 1.96 (s, 3H), 1.95-1.72 (br. m, 5H), 1.35-1.22 (m, 4H), 1.18 (t, 3H) ppm.

Example 9

3-(4-((S)-2-((S)-3,3-difluorocyclohexyl)-2-(3-methylisoxazole-4-carboxamido)acetamido)phenyl)-2-methyl-4-(trifluoromethyl)pyridine 1-oxide

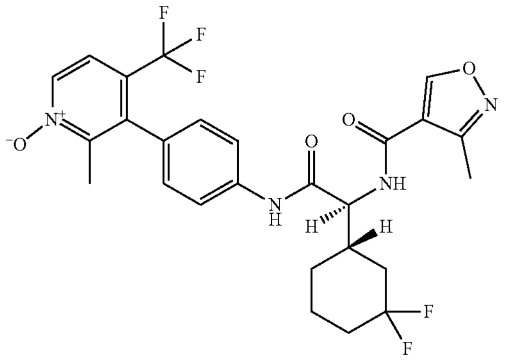

To a solution of 3-(4-((S)-2-amino-2-((S)-3,3-difluorocyclohexyl)acetamido)phenyl)-2-methyl-4-(trifluoromethyl) pyridine 1-oxide (Intermediate 3-8; 400 mg, 0.90 mmol) and 3-methylisoxazole-4-carboxylic acid (172 mg, 1.35 mmol) in DMF (9 mL) were added HATU (583 mg, 1.53 mmol), followed by triethylamine (0.625 mL, 4.5 mmol). After stirring at RT overnight, the reaction mixture was partitioned between EtOAc and sat. aq. $NaHCO_3$. The organic layer was washed with water and brine, the organic layer was dried ($Na_2SO_4$) and evaporated. The residue was purified by column chromatography on silica (column: RediSep 80 g; eluent: TBME/MeOH 100:0 to 75:25) to yield the title compound (429 mg, 86%) as an off-white solid.

LC-MS: Rt=4.62 min; MS: m/z=553.2 $[MH]^+$ (Method 4).

1H NMR (400 MHz, DMSO-d6) δ 10.47 (s, 1H), 9.47 (s, 1H), 8.60 (d, 1H), 8.48 (d, 1H), 7.83-7.64 (m, 3H), 7.25 (d, 2H), 4.63 (dd, 1H), 2.38 (s, 3H), 2.24-2.11 (br. m, 2H), 2.05 (s, 3H), 2.03-1.92 (br. m, 1H), 1.89-1.60 (br. m, 4H), 1.53-1.35 (br. m, 1H), 1.30-1.19 (br. m, 1H) ppm.

Example 10

3-(4-((S)-2-((S)-3,3-difluorocyclohexyl)-2-(1-ethyl-1H-pyrazole-5-carboxamido)acetamido)phenyl)-2-methyl-4-(trifluoromethyl)pyridine 1-oxide

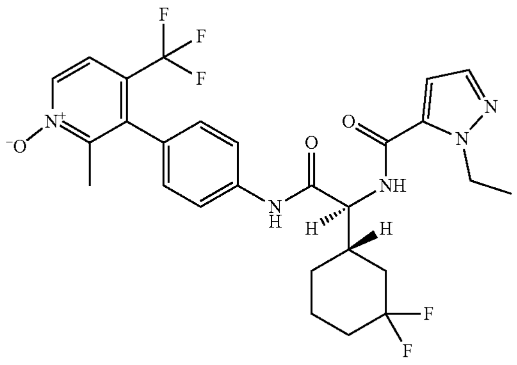

To a solution of 3-(4-((S)-2-amino-2-((S)-3,3-difluorocyclohexyl)acetamido)phenyl)-2-methyl-4-(trifluoromethyl) pyridine 1-oxide (Intermediate 3-8; 400 mg, 0.90 mmol) and 1-ethyl-1H-pyrazole-5-carboxylic acid (190 mg, 1.35 mmol) in DMF (9 mL) were added HATU (583 mg, 1.53 mmol), followed by triethylamine (0.625 mL, 4.5 mmol). After stirring at RT overnight, the reaction mixture was partitioned between EtOAc and sat. aq. $NaHCO_3$. The organic layer was washed with water and brine, the organic layer was dried ($Na_2SO_4$) and evaporated. The residue was purified by column chromatography on silica (column: RediSep 80 g; eluent: TBME/MeOH 100:0 to 78:22) to yield the title compound (424 mg, 81%) as an off-white solid.

LC-MS: Rt=4.86 min; MS: m/z=566.3 $[MH]^+$ (Method 4).

1H NMR (400 MHz, DMSO-d6) δ 10.45 (s, 1H), 8.65 (d, 1H), 8.48 (d, 1H) 7.75 (m, 2H), 7.70 (d, 1H), 7.49 (d, 1H), 7.25 (d, 2H), 7.06 (d, 1H), 4.61 (dd, 1H), 4.48 (q, 2H), 2.30-2.19 (br. m, 1H), 2.18-2.09 (br. m, 1H), 2.04 (s, 3H), 2.04-1.95 (br. m, 1H), 1.89-1.62 (br. m, 4H), 1.48-1.36 (br. m, 1H), 1.29 (t, 3H), 1.26-1.20 (br. m, 1H) ppm.

Example 11

(S)-3-(4-(2-(4,4-difluorocyclohexyl)-2-(1-ethyl-1H-pyrazole-5-carboxamido)acetamido)phenyl)-2-methyl-4-(trifluoromethyl)pyridine 1-oxide

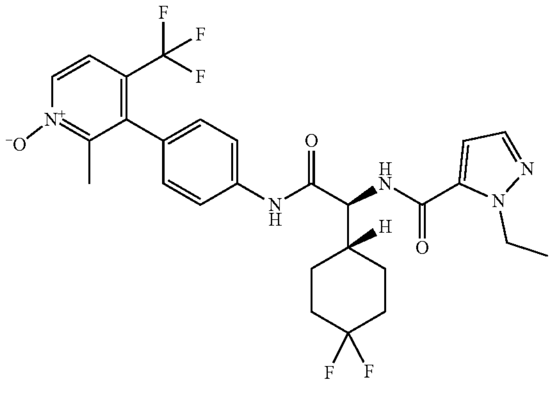

To a solution of (S)-3-(4-(2-amino-2-(4,4-difluorocyclohexyl)acetamido)phenyl)-2-methyl-4-(trifluoromethyl)pyridine 1-oxide (Intermediate 3-9; 546 mg, 1.14 mmol), 1-ethyl-1H-pyrazole-4-carboxylic acid (159 mg, 1.14 mmol) and 2,4,6-trimethylpyridine (0.455 ml, 3.41 mmol) in DMF (10 mL) was added HATU (649 mg, 1.71 mmol). After stirring the reaction mixture for 16 h at RT, the solvent was evaporated and residue was partitioned between EtOAc and sat. aq. $Na_2CO_3$. The organic layer was washed with brine and the combined aqueous layers were re-extracted with EtOAc. The combined organic layers were dried ($Na_2SO_4$) and evaporated. The residue was purified by prep. HPLC on RP-18 (column: Xbridge 50×100 mm, flow 100 mL/min; eluent: water+0.1% TFA/acetonitrile 80:20 to 50:50,) to yield the title compound (309 mg, 48%) as an off-white solid.

LC-MS: Rt=1.01 min; MS: m/z=566.3 $[MH]^+$ (Method 5).

1H NMR (400 MHz, DMSO-d6) δ ppm 10.50 (s, 1H), 8.73 (br. m, 1H), 8.48 (d, 1H), 7.81-7.64 (m, 3H), 7.49 (d, 1H), 7.25 (d, 2H), 7.03 (d, 1H), 4.60-4.39 (m, 3H), 2.18-2.00 (br. m, 3H), 2.05 (s, 3H), 1.99-1.69 (br. m, 4H) 1.52-1.32 (br. m, 2H), 1.28 (t, 3H) ppm.

Example 12

3-(4-((2S)-2-(4-fluorocyclohex-3-en-1-yl)-2-(1-methyl-1H-pyrazole-5-carboxamido)acetamido)phenyl)-2,4-dimethylpyridine 1-oxide

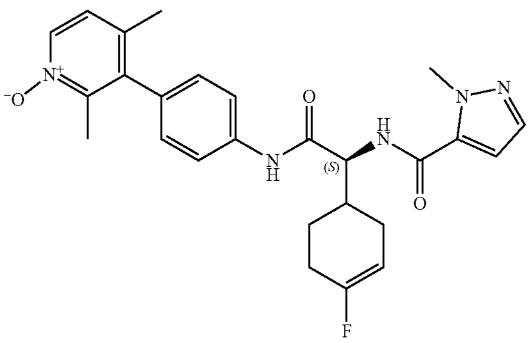

To a solution of 3-(4-((2S)-2-amino-2-(4-fluorocyclohex-3-en-1-yl)acetamido)phenyl)-2,4-dimethylpyridine 1-oxide (Intermediate 3-10; 707 mg, 1.742 mmol), 1-methyl-1H-pyrazole-5-carboxylic acid (242 mg, 1.916 mmol) and 2,4,6-collidine (0.928 ml, 6.97 mmol) in DMF (10 mL) was added HATU (993 mg, 2.61 mmol). After stirring the reaction mixture for 16 h at RT, the solvent was evaporated and residue was partitioned between EtOAc and sat. aq. $Na_2CO_3$. The organic layer was washed with brine and the combined aqueous layers were re-extracted with EtOAc. The combined organic layers were dried ($Na_2SO_4$) and evaporated. The residue was purified by prep. HPLC on RP-18 (column: Waters SunFire 30×100 mm, flow 40 mL/min; eluent: water+0.1% TFA/acetonitrile+0.1% TFA 95:5 to 0:100) to yield the title compound (542 mg, 65%) as an off-white solid.

LC-MS: Rt=0.84 min; MS: m/z=478.3 $[MH]^+$ (Method 5).

1H NMR (400 MHz, DMSO-d6) δ 10.49 (d, 1H), 8.71 (dd, 1H), 8.21 (d, 1H), 7.83-7.74 (m, 2H), 7.47 (t, 1H), 7.24 (d, 1H), 7.18 (d, 2H), 7.09 (d, 1H), 5.23 (d, 1H), 4.54 (m, 1H), 4.04 (s, 3H), 2.30-2.15 (m, 4H), 2.09 (s, 3H), 2.06-2.00 (br. m, 1H), 1.97 (s, 3H), 1.94-1.74 (br. m, 1H), 1.64-1.41 (m, 1H) ppm.

Examples 12a and 12b

3-(4-((S)-2-((R)-4-fluorocyclohex-3-en-1-yl)-2-(1-methyl-1H-pyrazole-5-carboxamido)acetamido)phenyl)-2,4-dimethylpyridine 1-oxide or 3-(4-((S)-2-((S)-4-fluorocyclohex-3-en-1-yl)-2-(1-methyl-1H-pyrazole-5-carboxamido)acetamido)phenyl)-2,4-dimethylpyridine 1-oxide

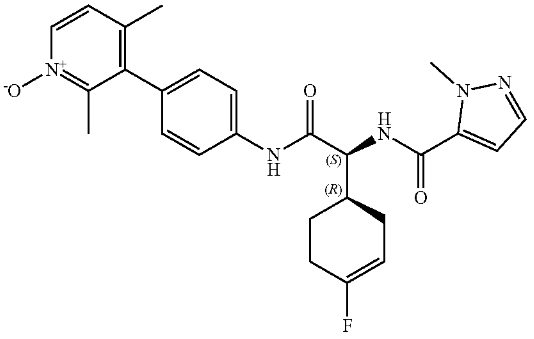

or

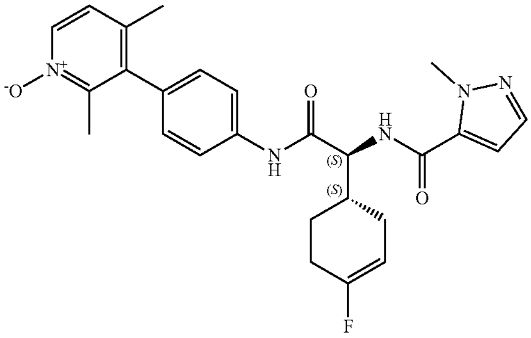

The product from Example 12 was separated into two pure diastereomers by chiral prep. HPLC (Gilson Trilution system, eluent: n-heptane:DCM:MeOH=30:30:10 (v:v:v)+0.05% DEA; Column: 250×30 mm 5 μm Chiralpak ID; flow=20 mL/min).

Analytical chiral HPLC (Column: Chiralpak ID, 250×4.6 mm, 5 μm; solvent:n-heptane:DCM:MeOH=60:30:10 (v:v:v)+0.1% DEA; flow=2.5 mL/min, T=35° C.):

Example 12a (S,R or S,S)=Peak 1: Rt=11.1 min.

Example 12b (S,R or S,S)=Peak 2: Rt=13.66 min.

Example 13

4-chloro-3-(4-(2-(4,4-difluorocyclohexyl)-2-(1-ethyl-1H-pyrazole-5-carboxamido)acetamido)phenyl)-2-methylpyridine 1-oxide

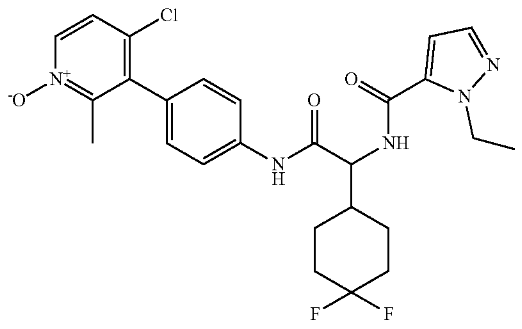

The title compound was prepared from Intermediate 3-24 and 1-ethyl-1H-pyrazole-5-carboxylic acid by a procedure similar to that of Example 1.

LC-MS: Rt=0.96 min; MS: m/z=532 and 534 $[MH]^+$ (Method 2).

1H NMR (400 MHz, DMSO-d6) δ 10.46 (s, 1H), 8.68 (d, 1H), 8.31 (d, 1H), 7.77 (m, 2H), 7.54 (d, 1H), 7.49 (d, 1H), 7.26 (d, 2H), 7.03 (d, 1H), 4.61-4.38 (m, 3H), 2.13 (s, 3H), 2.10-1.60 (br. m, 7H), 1.57-1.30 (m, 2H), 1.28 (t, 3H) ppm.

Example 13a (S)-4-chloro-3-(4-(2-(4,4-difluorocyclohexyl)-2-(1-ethyl-1H-pyrazole-5-carboxamido)acetamido)phenyl)-2-methylpyridine 1-oxide and

Example 13b (R)-4-chloro-3-(4-(2-(4,4-difluorocyclohexyl)-2-(1-ethyl-1H-pyrazole-5-carboxamido)acetamido)phenyl)-2-methylpyridine 1-oxide 13a

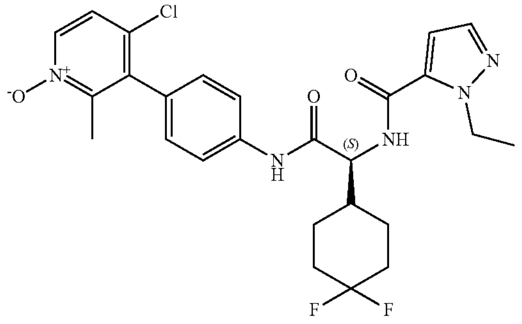

13b

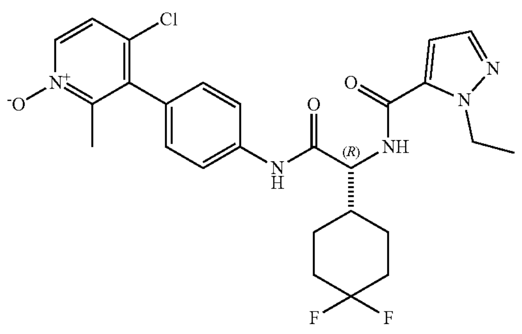

280 mg of the racemic mixture obtained from Example 13 were separated by chiral SFC (column: Chiralpak IC 250×30 mm ID; 5 μm, 10 μm; 45% IPA+0.1% $NH_3$, flow: 80 mL/min).

Analytical chiral SFC (ChiralPak IC, 100×4.6 mm I.D., 5 μm, 45% IPA+0.1% $NH_3$), Example 13a=Peak 1: Rt=2.14 min: 128 mg; 99% ee Example 13b=Peak 2: Rt=3.26 min: 125 mg; 99% ee The faster eluting compound was assigned as the (S)-enantiomer based on the higher potency observed with the TR-FRET assay.

The following Examples were prepared by amide bond formation of Intermediate 3-x and the corresponding carboxylic acids (prepared as Intermediates 4-x or commercially available) by procedures similar to that of Examples 1-13.

| Example | Structure/Name | Intermediate 3-x | Intermediate 4-x | LC-MS (Method) | 1H NMR |
|---|---|---|---|---|---|
| 14 | 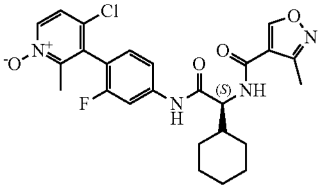 4-chloro-3-(4-((S)-2-cyclohexyl-2-(3-methylisoxazole-4-carboxamido)acetamido)-2-fluorophenyl)-2-methylpyridine 1-oxide | 3-2 | 3-methylisoxazole-4-carboxylic acid | Rt = 1.02 min; MS: m/z = 501.2 $[MH]^+$ (Method 3) | 1H NMR (500 MHz, DMSO-d6, 120° C.) δ 10.12 (s, 1H), 9.33 (s, 1H), 8.29 (d, 1H), 7.95 (d, 1H), 7.79 - 7.71 (m, 1H), 7.57 - 7.52 (m, 1H), 7.49 (d, 1H), 7.29 (t, 1H), 4.54 (t, 1H), 2.41 (s, 3H), 2.20 (s, 3H), 2.01 - 1.63 (m, 6H), 1.36 - 1.10 (m, 5H) ppm. |
| 15 | 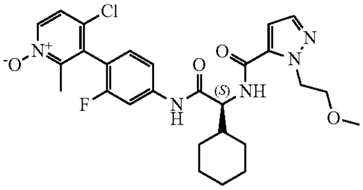 4-chloro-3-(4-((S)-2-cyclohexyl-2-(1-(2-methoxyethyl)-1H-pyrazole-5-carboxamido)acetamido)-2-fluorophenyl)-2-methylpyridine 1-oxide | 3-2 | 1-(2-methoxy ethyl)-1H-pyrazole-5-carboxylic acid | Rt = 0.99 and 1.01 min (atropisomers); MS: m/z= 544 and 546 $[MH]^+$ (Method 8) | 1H NMR (400 MHz, DMSO-d6) δ 10.62 (s, 1H), 8.59 (d, 1H), 8.36 (d, 1H), 7.81 (m, 1H), 7.59 (d, 1H), 7.54 - 7.45 (m, 2H), 7.34 (t, 1H), 6.99 (d, 1H), 4.63 (t, 2H), 4.40 (t, 1H), 3.63 (t, 2H), 3.16 (s, 3H), 2.15 (s, 3H), 2.01 - 1.79 (m, 2H), 1.72 (s, 2H), 1.62 (s, 2H), 1.31 - 0.96 (m, 5H) ppm |
| 16 | 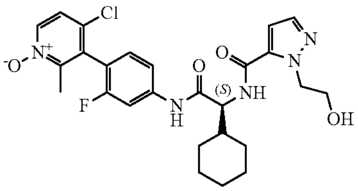 4-chloro-3-(4-((S)-2-cyclohexyl-2-(1-(2-methoxyethyl)-1H-pyrazole-5-carboxamido)acetamido)-2-fluorophenyl)-2-methylpyridine 1-oxide | 3-2 | 1-(2-hydroxyethyl)-1H-pyrazole-5-carbolyxlic acid | RT = 0.92 and 1.01 min (atropisomers); MS: m/z = 544 and 546 $[MH]^+$ (Method 8) | 1H NMR (400 MHz, DMSO-d6) δ 10.61 (s, 1H), 8.62 (d, 1H), 8.36 (d, 1H), 7.81 (m, 1H), 7.59 (d, 1H), 7.47 - 7.53 (m, 2H), 7.34 (m, 1H), 6.99 (d, 1H), 4.88 (t, 2H), 4.51 (m, 2H), 4.41 (t, 1H), 3.69 (m, 2H), 2.15 (s, 3H), 1.52 - 1.99 (m, 6H), 0.94 - 1.33 (m, 5H) ppm. |
| 17 | 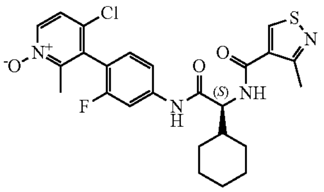 4-chloro-3-(4-((S)-2-cyclohexyl-2-(3-methylisothiazole-4-carboxamido)acetamido)-2-fluorophenyl)-2-methylpyridine 1-oxide | 3-2 | 3-methylis othiazole-4-carboxylic acid | Rt = 1.04 min; MS: m/z = 517 and 519 $[MH]^+$ (Method 2) | 1H NMR (400 MHz, DMSO-d6) δ 10.62 (s, 1H), 9.51 (s, 1H), 8.59 (d, 1H), 8.36 (d, 1H), 7.82 (m, 1H), 7.59 (d, 1H), 7.51 (m, 1H), 7.34 (m, 1H), 4.41 (dd, 1H), 2.54 (s, 3H), 2.15 (2s, 3H), 1.90 - 1.62 (m, 5H), 1.26 - 1.01 (m, 6H) ppm. |

-continued

| Example | Structure/Name | Intermediate 3-x | Intermediate 4-x | LC-MS (Method) | 1H NMR |
|---|---|---|---|---|---|
| 18 | 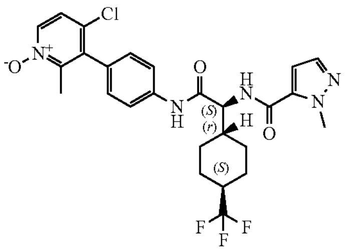 4-chloro-2-methyl-3-(4-((S)-2-(1-methyl-1H-pyrazole-5-carboxamido)-2-((1r,4S)-4-(trifluoromethyl)cyclohexyl) acetamido)phenyl)pyridine 1-oxide | 3-4 | 1-methyl-H-pyrazole-5-carboxylic acid | Rt = 1.03 min; MS: m/z = 550 and 552 $[MH]^+$ (Method 3) | 1H NMR (400 MHz, DMSO-d6) δ 10.45 (s, 1H), 8.58 (br. s, 1H), 8.31 (d, 1H), 7.78 (m, 2H), 7.54 (d, 1H), 7.47 (d, 1H), 7.25 (d, 2H), 7.07 (d, 1H), 4.44 (br. m, 1H), 4.04 (s, 3H), 2.29 - 2.22 (m, 1H), 2.13 (s, 3H), 1.97 - 1.74 (m, 5H), 1.21 (m, 4H) ppm. |
| 19 | 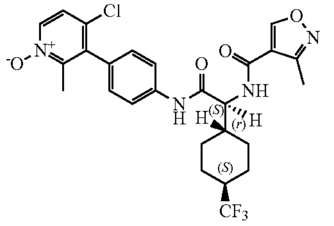 4-chloro-2-methyl-3-(4-((S)-2-(3-methylisoxazole-4-carboxamido)-2-((1r,4S)-4-(trifluoromethyl)cyclohexyl) acetamido)phenyl)pyridine 1-oxide | 3-4 | 3-methylisoxazole-4-carboxylic acid | Rt = 1.06 min; MS: m/z = 551 and 553 $[MH]^+$ (Method 5) | 1H NMR (400 MHz, DMSO-d6) δ 10.45 (s, 1H), 9.44 (d, 1H), 8.56 (d, 1H), 8.31 (d, 1H), 7.77 (m, 2H), 7.54 (m, 1H), 7.25 (d, 2H), 4.47 (dd, 1H), 2.38 (s, 3H), 2.30 - 2.20 (br. m, 1H), 2.13 (s, 3H), 2.00 - 1.88 (br. m, 3H), 1.86 - 1.73 (br. m, 2H), 1.75 (d, 1H), 1.30 - 1.12 (m, 3H). |
| 20 | 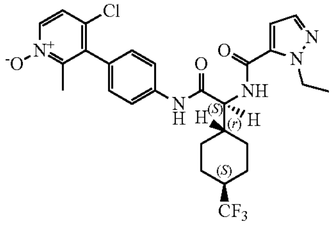 4-chloro-3-(4-((S)-2-(1-ethyl-1H-pyrazole-5-carboxamido)-2-((1r,4S)-4-(trifluoromethyl)cyclohexyl) acetamido)phenyl)-2-methylpyridine 1-oxi | 3-4 | 3-ethylisoxazole-4-carboxylic acid | Rt = 1.14 min; MS: m/z = 564 and 566 $[MH]^+$ (Method 5) | 1H NMR (400 MHz, DMSO-d6) δ 10.51 (s, 1H), 8.67 (d, 1H), 8.31 (d, 1H), 7.79 (m, 2H), 7.54 (d, 1H), 7.48 (d, 1H), 7.25 (d, 2H), 7.04 (d, 1H), 4.46 (q, 2H), 4.42 (dd, 1H), 2.33 - 2.19 (br. m, 1H), 2.13 (s, 3H), 2.01 - 1.87 (br. m, 4H), 1.78 - 1.71 (br. m, 1H), , 1.28 (t, 3H), 1.24 - 1.09 (m, 4H). |
| 21 | 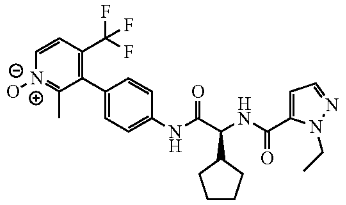 [SMILES: CCn1nccc1C(=O)N[C@H](C(=O)Nc1ccc(-c2c(C(F)(F)F)cc[n+]([O-])c2C)cc1)C1CCCC1] (S)-3-(4-(2-cyclopentyl-2-(1-ethyl-1H-pyrazole-5-carboxamido)acetamido) phenyl)-2-methyl-4-(trifluoromethyl)pyridine 1-oxide | 3-5 | 3-ethylisoxazole-4-carboxylic acid | Rt = 1.51 min; MS: m/z = 516.3 $[MH]^+$ (Method 16) | 1H NMR (400 MHz, $CDCl_3$) δ 8.39 - 8.29 (m, 2H), 7.70 - 7.61 (m, 2H), 7.50 - 7.44 (m, 2H), 7.15 (d, 2H), 6.64 (d, 1H), 6.59 (d, 1H), 4.59 (m, 2H), 4.49 (dd, 1H), 2.53 (m, 1H), 2.21 (s, 3H), 2.02 - 1.82 (br. m, 2H), 1.77 - 1.62 (br. m, 4H), 1.43 (q, 3H), 1.42 - 1.37 (br, m, 1H), 1.33 - 1.21 (br. m, 1H). |

-continued

| Example | Structure/Name | Intermediate 3-x | Intermediate 4-x | LC-MS (Method) | 1H NMR |
| --- | --- | --- | --- | --- | --- |
| 22 | 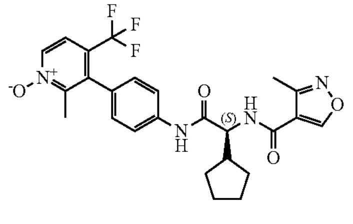 (S)-3-(4-(2-cyclopentyl-2-(3-methylisoxazole-4-carboxamido)acetamido) phenyl)-2-methyl-4-(trifluoromethyl)pyridine 1-oxide | 3-5 | 3-methylisoxazole-4-carboxylic acid | Rt = 1.48 min; MS: m/z = 503.3 $[MH]^+$ (Method 16) | $^1$H NMR (400 MHz, DMSO-d6) δ 10.43 (s, 1H), 9.43 (s, 1H), 8.64 (d, 1H), 8.48 (d, 1H), 7.80 – 7.65 (m, 3H), 7.24 (d, 2H), 4.43 (dd, 1H), 2.38 (s, 3H), 2.32 (m, 1H), 2.05 (s, 3H), 1.90 – 1.80 (br. m, 1H), 1.70 – 1.29 (br. m, 7H). |
| 23 | 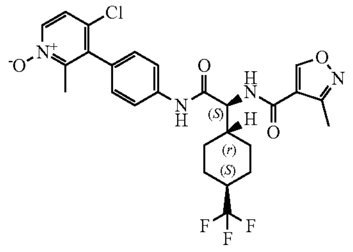 2,4-dimethyl-3-(4-((S)-2-(3-methylisoxazole-4-carboxamido)-2-((1r,4S)-4-(trifluoromethyl)cyclohexyl) acetamido)phenyl)pyridine 1-oxide | 3-7 | 3-methyl-4-isoxazole carboxylic acid | Rt = 1.00 min; MS: m/z = 531.3 $[MH]^+$ (Method 5) | 1H NMR (400 MHz, DMSO-d6) δ 10.42 (s, 1H), 9.45 (s, 1H), 8.58 (d, 1H), 8.19 (d, 1H), 7.76 (d, 2H), 7.22 (d, 1H), 7.17 (d, 2H), 4.47 (dd, 1H), 2.38 (s, 3H), 2.34 – 2.15 (m, 1H), 2.08 (s, 3H), 1.92 (s, 3H), 1.94 – 1.70 (m, 5H), 1.34 – 1.11 (m, 4H) ppm. |
| 24 | 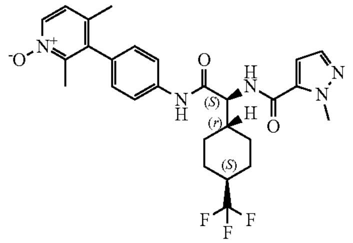 2,4-dimethyl-3-(4-((S)-2-(1-methyl-1H-pyrazole-5-carboxamido)-2-((1r,4S)-4-(trifluoromethyl)cyclohexyl) acetamido)phenyl)pyridine 1-oxide | 3-7 | 1-methyl-H-pyrazole-5-carboxylic acid | Rt = 1.01 min; MS: m/z = 530.2 $[MH]^+$ (Method 2) | 1H NMR (400 MHz, DMSO-d6) δ 10.41 (s, 1H), 8.57 (d, 1H), 8.19 (d, 1H), 7.77 (d, 2H), 7.47 (d, 1H), 7.26 – 7.14 (m, 3H), 7.07 (d, 1H), 4.44 (dd, 1H), 4.04 (s, 3H), 2.26 (br. m, 1H), 2.08 (s, 3H), 1.98 (s, 3H), 1.92 (s, 3H), 1.92-1.81 (m, 1H), 1.75 (m, 1H), 1.36 – 1.07 (m, 4H) ppm. |
| 25 | 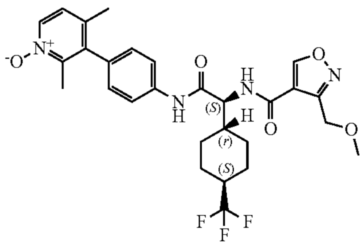 3-(4-((S)-2-(3-(methoxymethyl)isoxazole-4-carboxamido)-2-((1r,4S)-4-(trifluoromethyl)cyclohexyl) acetamido)phenyl)-2,4-dimethylpyridine 1-oxide | | 3-(methoxy methyl)-4-isoxazole carboxylic acid | Rt = 1.03 min; MS: m/z = 561.3 $[MH]^+$ (Method 5) | 1H NMR (400 MHz, DMSO-d6) δ 10.45 (s, 1H), 9.50 (s, 1H), 8.61 (d, 1H), 8.24 (d, 1H), 7.74 (d, 2H), 7.26 (d, 1H), 7.19 (d, 2H), 4.72 (s, 2H), 4.56 (dd, 1H), 3.36 (s, 3H), 2.26 (s, 1H), 2.35 – 2.20 (m, 1H), 2.09 (s, 3H), 1.97 (s, 3H), 2.00 – 1.72 (m, 5H), 1.33 – 1.11 (m, 4H) ppm. |

-continued

| Example | Structure/Name | Intermediate 3-x | Intermediate 4-x | LC-MS (Method) | 1H NMR |
|---|---|---|---|---|---|
| 26 | 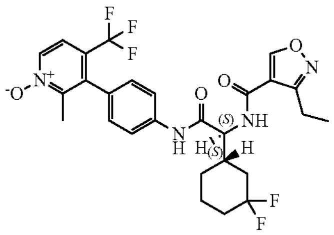 3-(4-((S)-2-((S)-3,3-difluorocyclohexyl)-2-(3-ethylisoxazole-4-carboxamido)acetamido)phenyl)-2-methyl-4-(trifluoromethyl)pyridine 1-oxide | 3-8 | 3-ethylisoxazole-4-carboxylic acid | Rt = 4.98 min; MS: m/z = 567.3 $[MH]^+$ (Method 4) | 1H NMR (400 MHz, DMSO-d6) δ 10.46 (s, 1H) 9.44 (s, 1H) 8.61 (d, 1H) 8.48 (d, 1H) 7.75 (m, 2H), 7.70 (d, 1H) 7.25 (d, 2H), 4.63 (dd, 1H), 2.85 (q, 2H), 2.24 – 2.10 (br. m, 2H), 2.05, (s, 3H), 2.05 – 1.95 (br. m, 1H), 1.90 – 1.58 (br. m, 4H), 1.41 (m, 1H), 1.30 – 1.21 (m, 1H), 1.18 (t, 3H) ppm. |
| 27 | 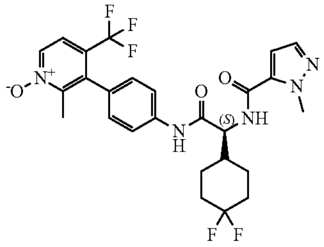 (S)-3-(4-(2-(4,4-difluorocyclohexyl)-2-(1-methyl-1H-pyrazole-5-carboxamido)acetamido)phenyl)-2-methyl-4-(trifluoromethyl)pyridine 1-oxide | 3-9 | 1-methyl-1H-pyrazole-5-carboxylic acid | Rt = 4.55 min; MS: m/z = 552.3 $[MH]^+$ (Method 4) | 1H NMR (400 MHz, DMSO-d6) δ 10.45 (s, 1H), 8.67 (d, 1H), 8.48 (d, 1H), 7.75 (m, 2H), 7.69 (d, 1H), 7.47 (d, 1H), 7.25 (d, 2H), 7.07 (d, 1H), 4.52 (dd, 1H), 4.04 (s, 3H), 2.15 – 2.00 (br. m, 3H), 2.05 (s, 3H), 1.98 – 1.69 (br. m, 4H), 1.53 – 1.30 (br. m, 2H). |
| 28 | 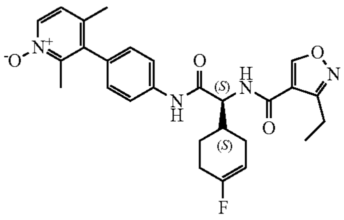 3-(4-((S)-2-(3-ethylisoxazole-4-carboxamido)-2-((S)-4-fluorocyclohex-3-en-1-yl)acetamido)phenyl)-2,4-dimethylpyridine 1-oxide | 3-10 | 3-ethyl-4-isoxazole carboxylic acid | Rt = 0.95 min; MS: m/z = 493.3 $[MH]^+$ (Method 5) | 1H NMR (400 MHz, DMSO-d6) δ 10.47 (d, 1H), 9.43 (d, 1H), 8.68 (d, 1H), 8.20 (d, 1H), 7.77 (d, 2H), 7.22 (d, 1H), 7.18 (d, 1H), 5.22 (br. m, 1H), 4.56 (dd, 1H), 2.85 (q, 2H), 2.24 (br. m, 3H), 2.15 – 2.05 (br. m, 1H), 2.08 (s, 3H), 2.01 – 1.90 (br. m, 1H), 1.97 (s, 3H), 1.87 – 1.76 (br. m, 1H), 1.65 – 1.53 (m, 1H), 1.29 – 1.16 (br. m, 1H), 1.18 (t, 3H) ppm. |

-continued

| Example | Structure/Name | Intermediate 3-x | Intermediate 4-x | LC-MS (Method) | 1H NMR |
|---|---|---|---|---|---|
| 29 | 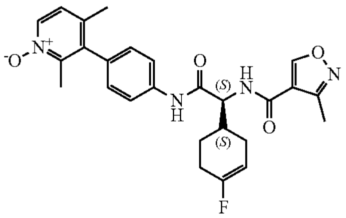 3-(4-((S)-2-((S)-4-fluorocyclohex-3-en-1-yl)-2-(3-methylisoxazole-4-carboxamido)acetamido) phenyl)-2,4-dimethylpyridine 1-oxide | 3-10 | 3-methyl-isoxazole carboxylic acid | Rt = 0.85 min; MS: m/z = 479.3 $[MH]^+$ (Method 5) | 1H NMR (400 MHz, DMSO-d6) δ 10.48 (d, 1H), 9.46 (s, 1H), 8.67 (dd, 1H), 8.20 (d, 1H), 7.77 (dd, 2H), 7.22 (d, 1H), 7.19 (d, 2H), 5.22 (br. d, 1H), 4.56 (m, 1H), 2.38 (s, 3H), 2.23 (br. m, 3H), 2.14 – 1.94 (br. m, 2H), 2.08 (s, 3H), 1.96 (s, 3H), 1.86 – 1.76 (br. m, 1H), 1.63 – 1.43 (br. m, 1H) ppm. |
| 30 | 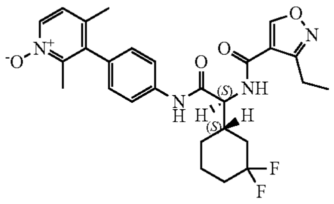 3-(4-((S)-2-((S)-3,3-difluorocyclohexyl)-2-(3-ethylisoxazole-4-carboxamido)acetamido) phenyl)-2,4-dimethylpyridine 1-oxide | 3-11 | 3-ethylisoxazole-4-carboxylic acid | Rt = 4.29 min; MS: m/z = 513.3 $[MH]^+$ (Method 4) | 1H NMR (400 MHz, DMSO-d6) δ 10.43 (s, 1H), 9.44 (s, 1H), 8.61 (d, 1H), 8.19 (d, 1H), 7.76 (d, 2H), 7.23 (d, 1H), 7.19 (d, 2H), 4.63 (dd, 1H), 2.85 (q, 2H), 2.15 (br. m, 2H), 2.08 (s, 3H), 2.05 – 1.95 (m, 1H), 1.97 (s, 3H), 1.88 – 1.60 (m, 4H), 1.48 – 1.35 (m, 1H), 1.30 – 1.19 (m, 1H), 1.18 (t, 3H) ppm. |
| 31 | 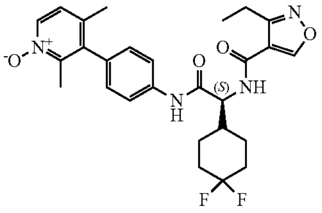 (S)-3-(4-(2-(4,4-difluorocyclohexyl)-2-(3-ethylisoxazole-4-carboxamido)acetamido) phenyl)-2,4-dimethylpyridine 1-oxide | 3-12 | 3-ethyl-4-isoxazole carboxylic acid | Rt = 0.97 min; MS: m/z = 513.5 $[MH]^+$ (Method 2) | 1H NMR (400 MHz, DMSO-d6) δ 10.45 (s, 1H), 9.42 (s, 1H), 8.67 (d, 1H), 8.20 (d, 1H), 7.76 (d, 2H), 7.22 (d, 1H), 7.19 (d, 2H), 4.54 (dd, 1H), 2.89 – 2.82 (m, 2H), 2.15 – 1.70 (br. m, 7H), 2.08 (s, 3H), 1.96 (s, 3H), 1.51 – 1.32 (br. m, 2H), 1.18 (t, 3H) ppm. |
| 32 | 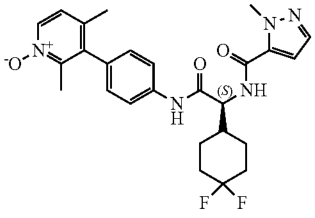 (S)-3-(4-(2-(4,4-difluorocyclohexyl)-2-(1-methyl-1H-pyrazole-5-carboxamido)acetamido) phenyl)-2,4-dimethylpyridine 1-oxide | 3-12 | 1-methyl-[1H]pyrazole-5-carboxylic acid | Rt = 0.87 min; MS: m/z = 498.3 $[MH]^+$ (Method 2) | 1H NMR (400 MHz, DMSO-d6) δ 10.45 (s, 1H), 8.68 (d, 1H), 8.20 (d, 1H), 7.77 (d, 2H), 7.47 (d, 1H), 7.22 (d, 1H), 7.16 (d, 2H), 7.07 (d, 1H), 4.51 (dd, 1H), 4.04 (s, 3H), 2.15 – 2.00 (br. m, 3H), 2.08 (s, 3H), 1.96 (s, 3H), 1.96 – 1.65 (m, 4H), 1.52 – 1.30 (br. m, 2H) ppm. |

-continued

| Example | Structure/Name | Intermediate 3-x | Intermediate 4-x | LC-MS (Method) | 1H NMR |
|---|---|---|---|---|---|
| 33 | 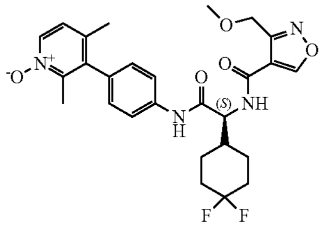 (S)-3-(4-(2-(4,4-difluorocyclohexyl)-2-(3-(methoxymethyl)isoxazole-4-carboxamido)acetamido) phenyl)-2,4-dimethylpyridine 1-oxide | 3-12 | 3-methoxy methyl) isooxazole-4-caboxylic acid | Rt = 0.88 min; MS: m/z = 529.3 $[MH]^+$ (Method 2) | 1H NMR (400 MHz, DMSO-d6) δ 10.48 (s, 1H), 9.50 (s, 1H), 8.67 (d, 1H), 8.26 (d, 1H), 7.76 (d, 2H), 7.28 (d, 1H), 7.23 (d, 2H), 4.71 (s, 2H), 4.62 (dd, 1H), 3.36 (s, 3H), 2.10 (s, 3H), 2.09 - 2.06 (br. m, 2H), 1.99 (s, 3H), 2.09 - 1.70 (m, 5H), 1.50 - 1.31 (br.m, 2H) ppm. |
| 34 | 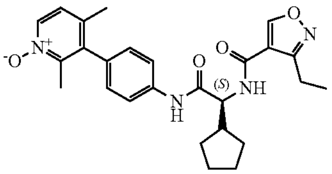 (S)-3-(4-(2-cyclopentyl-2-(3-ethylisoxazole-4-carboxamido)acetamido) phenyl)-2,4-dimethylpyridine 1-oxide | 3-13 | 3-ethylisoxazole-4-carboxylic acid | Rt = 0.95 min; MS: m/z = 463,3 $[MH]^+$ (Method 5) | 1H NMR (400 MHz, DMSO-d6) δ 10.43 (s, 1H), 9.45 (s, 1H), 8.71 (d, 1H), 8.19 (d, 1H), 7.78 (d, 2H), 7.22 (d, 1H), 7.17 (d, 2H), 4.43 (dd, 1H), 2.84 (q, 2H), 2.08 (s, 3H), 1.96 (s, 3H), 1.87 - 1.79 (br. m, 1H), 1.69 - 1.29 (br. m, 8H), 1.17 (t, 3H) ppm. |
| 35 | 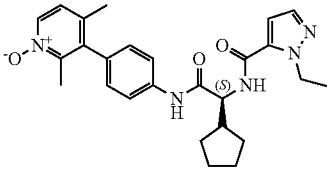 (S)-3-(4-(2-cyclopentyl-2-(1-ethyl-1H-pyrazole-5-carboxamido)acetamido) phenyl)-2,4-dimethylpyridine 1-oxide | 3-13 | 1-ethyl-1H-pyrazole-5-carboxylic acid | Rt = 0.92 min; MS: m/z = 462,3 $[MH]^+$ (Method 5) | 1H NMR (400 MHz, DMSO-d6) δ 10.52 (s, 1H), 8.78 (d, 1H), 8.19 (d, 1H), 7.79 (d, 2H), 7.48 (d, 1H), 7.22 (d, 1H), 7.17 (d, 2H),7.08 (d, 1H), 4.47 (q, 2H), 4.40 (dd, 1H), 2.08 (s, 3H), 1.96 (s, 3H), 1.88 - 1.77 (br. m, 1H), 1.69 - 1.25 (br. m, 8H), 1.28 (t, 3H) ppm. |
| 36 | 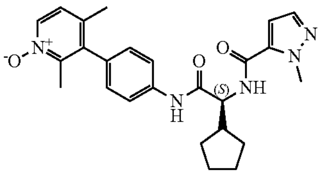 (S)-3-(4-(2-cyclopentyl-2-(1-methyl-1H-pyrazole-5-carboxamido)acetamido) phenyl)-2,4-dimethylpyridine 1-oxide | 3-13 | 1-methyl-1H-pyrazole-5-carboxylic acid | Rt = 0.81 min; MS: m/z = 448.5 $[MH]^+$ (Method 10) | 1H NMR (400 MHz, DMSO-d6) δ 10.36 (s, 1H), 8.64 (d, 1H), 8.19 (d, 1H), 7.76 (d, 2H), 7.46 (d, 1H), 7.22 (d, 1H), 7.17 (d, 2H), 7.05 (d, 1H), 4.42 (dd, 1H), 4.04 (s, 3H), 2.39 (br. m, 1H), 2.08 (s, 3H), 1.97 (s, 3H), 1.90 - 1.82 (br. m, 1H), 1.71 -1.27(m, 7H) ppm. |

-continued

| Example | Structure/Name | Intermediate 3-x | Intermediate 4-x | LC-MS (Method) | 1H NMR |
|---|---|---|---|---|---|
| 37 | 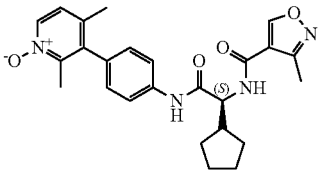 (S)-3-(4-(2-cyclopentyl-2-(3-methylisoxazole-4-carboxamido)acetamido) phenyl)-2,4-dimethylpyridine 1-oxide | 3-13 | 3-methylisoxazole-4-carboxylic acid | Rt = 0.87 min; MS: m/z = 449.3 $[MH]^+$ (Method 5) | 1H NMR (400 MHz, DMSO-d6) δ 10.38 (s, 1H), 9.42 (s, 1H), 8.61 (d, 1H), 8.19 (d, 1H), 7.76 (d, 2H), 7.22 (d, 1H), 7.18 (d, 2H), 4.43 (dd, 1H), 2.38 (s, 3H), 2.32 (m, 1H), 2.08 (s, 3H), 1.97 (s, 3H), 1.87 - 1.78 (br. m, 1H), 1.69 - 1.29 (br. m, 7H) ppm. |
| 38 | 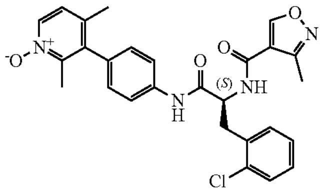 (S)-3-(4-(3-(2-chlorophenyl)-2-(3-methylisoxazole-4-carboxamido)propanamido )phenyl)-2,4-dimethylpyridine 1-oxide | 3-14 | 3-methylisoxazole-4-carboxylic acid | Rt = 4.13 min; MS: m/z = 505 and 507 $[MH]^+$ (Method 4) | 1H NMR (400 MHz, DMSO-d6) δ 10.31 (s, 1H), 9.35 (s, 1H), 8.79 (d, 1H), 8.19 (d, 1H) 7.74 (d, 2H), 7.43 (m, 2H), 7.27 - 7.21 (m, 3H), 7.17 (d, 2H), 4.97 (m, 1H), 3.34 - 3.28 (m, 1H, partially covered by water peak), 3.15 (m, 1H), 2.31 (s, 3H), 2.08 (s, 3H), 1.96 (s, 3H) ppm. |
| 39 | 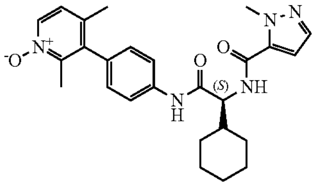 (S)-3-(4-(2-cyclohexyl-2-(1-methyl-1H-pyrazole-5-carboxamido)acetamido)phenyl)-2,4-dimethylpyridine 1-oxide | 3-15 | 1-methyl-1H-pyrazole-5-carboxylic acid | Rt = 0.90 min; MS: m/z = 462.5 $[MH]^+$ (Method 12) | 1H NMR (400 MHz, DMSO-d6) δ 10.39 (s, 1H), 8.55 (d, 1H), 8.19 (d, 1H), 7.78 (m, 2H), 7.46 (d, 1H), 7.22 (d, 1H), 7.17 (d, 2H), 7.07 (d, 1H), 4.42 (dd, 1H), 4.04 (s, 3H), 2.08 (s, 3H), 1.96 (s, 3H), 1.92 - 1.84 (br. m, 2H), 1.73 (br. m, 2H), 1.63 (br. m, 2H), 1.30 - 0.98 (m, 5H) ppm. |
| 40 | 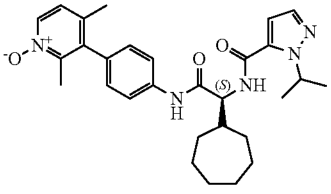 (S)-3-(4-(2-cycloheptyl-2-(1-isopropyl-1H-pyrazole-5-carboxamido)acetamido) phenyl)-2,4-dimethylpyridine 1-oxide | 3-16 | 1-isopropyl-1H-pyrazole-5-carboxylic acid | Rt = 5.60 min; MS: m/z = 504.3 $[MH]^+$ (Method 4) | 1H NMR (400 MHz, DMSO-d6) δ 10.35 (s, 1H), 8.51 (d, 1H), 8.19 (d, 1H), 7.77 (d, 2H), 7.49 (d, 1H), 7.22 (d, 1H), 7.18 (d, 2H), 6.95 (d, 1H), 5.39 (quin, 1H), 4.49 (dd, 1H), 2.16 - 2.09 (br. m, 1H), 2.08 (s, 3H), 1.97 (s, 3H), 1.83 - 1.23 (br. m, 12H), 1.36 (dd, 6H) ppm. |

-continued

| Example | Structure/Name | Intermediate 3-x | Intermediate 4-x | LC-MS (Method) | 1H NMR |
|---|---|---|---|---|---|
| 41 | 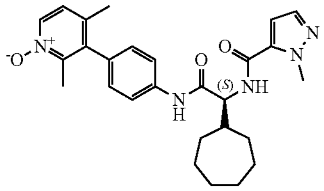 (S)-3-(4-(2-cycloheptyl-2-(1-methyl-1H-pyrazole-5-carboxamido)acetamido) phenyl)-2,4-dimethylpyridine 1-oxide | 3-16 | 1-methyl-1H-pyrazole-5-carboxylic acid | Rt = 4.75 min; MS: m/z = 476.3 $[MH]^+$ (Method 4) | 1H NMR (400 MHz, DMSO-d6) δ 10.37 (s, 1H), 8.53 (d, 1H), 8.19 (d, 1H), 7.77 (d, 2H), 7.46 (d, 1H), 7.22 (d, 1H), 7.18 (d, 2H), 7.07 (d, 1H), 4.50 (dt, 1H), 4.04 (s, 3H), 2.17 - 2.09 (br. m, 1H), 2.08 (s, 3H), 1.96 (s, 3H), 1.27 - 1.86 (br. m, 12H) ppm. |
| 42 | 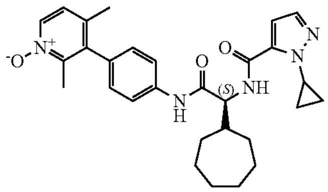 (S)-3-(4-(2-cycloheptyl-2-(1-cyclopropyl-1H-pyrazole-5-carboxamido)acetamido) phenyl)-2,4-dimethylpyridine 1-oxide | 3-16 | 1-cyclopropyl-1H-pyrazole-5-carboxylic acid | Rt = 4.98 min; MS: m/z = 502.3 $[MH]^+$ (Method 4) | 1H NMR (400 MHz, DMSO-d6) δ 10.38 (s, 1H), 8.54 (d, 1H), 8.19 (d, 1H), 7.77 (d, 2H), 7.41 (d, 1H), 7.22 (d, 1H), 7.18 (d, 2H), 6.96 (d, 1H), 4.52 (dd, 1H), 4.42 (m, 1H), 2.16 - 2.10 (br. m, 1H), 2.08 (s, 3H), 1.97 (s, 3H), 1.82 - 1.61 (br. m, 4H), 1.58 - 1.34 (br. m, 8H), 1.11 - 1.02 (m, 2H), 0.96 - 0.88 (m, 2H) ppm. |
| 43 | 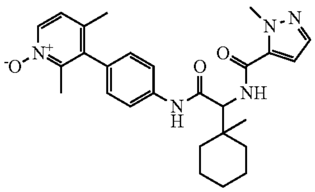 2,4-dimethyl-3-(4-(2-(1-methyl-1H-pyrazole-5-carboxamido)-2-(1-methylcyclohexyl)acetamido) phenyl)pyridine 1-oxide | 3-17 | 1-methyl-1H-pyrazole-5-carboxylic acid | Rt = 0.93 min; MS: m/z = 476.4 $[MH]^+$ (Method 2) | 1H NMR (400 MHz, DMSO-d6) δ 10.38 (s, 1H), 8.27 (d, 1H), 8.15 (d, 1H), 7.78 (m, 2H), 7.46 (d, 1H), 7.26 (d, 1H), 7.19 (d, 2H), 7.11 (d, 1H), 4.72 (d, 1H), 4.03 (s, 3H), 2.11 (s, 3H), 1.99 (s, 3H), 1.62 - 1.14 (br. m, 10 H), 1.10 (s, 3H) ppm. |
| 44 | 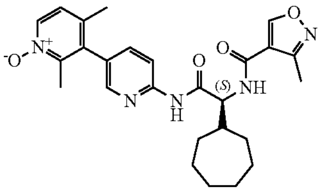 (S)-6'-(2-cycloheptyl-2-(3-methylisoxazole-4-carboxamido)acetamido)-2,4-dimethyl-[3,3'-bipyridine] 1-oxide | 3-18 | 3-methylisoxazole-4-carboxylic acid | Rt = 0.93 min; MS: m/z = 478.3 $[MH]^+$ (Method 10) | 1H NMR (400 MHz, DMSO-d6) δ 10.84 (s, 1H), 9.44 (s, 1H), 8.43 (d, 1H), 8.27 - 8.16 (m, 3H), 7.72 (dd, 1H), 7.26 (d, 1H), 4.67 (m, 1H), 2.37 (s, 3H), 2.11 (d, 3H), 2.09- 2.02 (br. m, 1H), 2.00 (d, 3H), 1.77 - 1.33 (m, 11H), 1.16 - 1.07 (br. m, 1H) ppm. |

-continued

| Example | Structure/Name | Intermediate 3-x | Intermediate 4-x | LC-MS (Method) | 1H NMR |
|---|---|---|---|---|---|
| 45 | 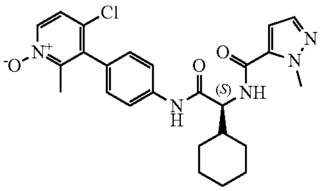 (S)-4-chloro-3-(4-(2-cyclohexyl-2-(1-methyl-1H-pyrazole-5-carboxamido)acetamid) phenyl)-2-methylpyridine 1-oxide | 3-20 | 1-methyl-1H-pyrazole-5-carboxylic acid | Rt = 4.28 min; MS: m/z = 482 and 484 $[MH]^+$ (Method 4) | 1H NMR (400 MHz, DMSO-d6) δ 10.46 (s, 1H), 8.59 (d, 1H), 8.31 (d, 1H), 7.82 - 7.75 (m, 2H), 7.54 (d, 1H), 7.46 (d, 1H), 7.25 (d, 2H), 7.08 (d, 1H), 4.41 (dd, 1H), 4.03 (s, 3H), 2.13 (s, 3H), 1.93 - 1.81 (br.m, 2H), 1.79 - 1.57 (br.m, 4H), 1.27 - 0.99 (br.m, 5H) ppm. |
| 46 | 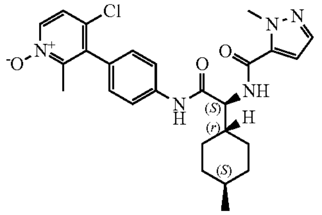 4-chloro-2-methyl-3-(4-((S)-2-(1-methyl-1H-pyrazole-5-carboxamido)-2-((1r,4S)-4-methylcyclohexyl)acetamido) phenyl)pyridine 1-oxide | 3-21 | 1-methyl-1H-pyrazole-5-carboxylic acid | Rt = 1.07 min; MS: m/z = 496 and 498 $[MH]^+$ (Method 5) | 1H NMR (400 MHz, DMSO-d6) δ 10.41 (s, 1H), 8.55 (d, 1H), 8.31 (d, 1H), 7.77 (m, 2H), 7.54 (d, 1H), 7.46 (d, 1H), 7.25 (d, 2H), 7.07 (d, 1H), 4.39 (dd, 1H), 4.03 (s, 3H), 2.13 (s, 3H), 1.92 - 1.78 (m, 2H), 1.75 - 1.66 (br. m, 2H), 1.65 - 1.57 (br. m, 1H), 1.37 - 1.19 (m, 2H), 1.11 - 0.99 (br. m, 1H), 0.94 - 0.80 (m, 5H) ppm. |
| 47 | 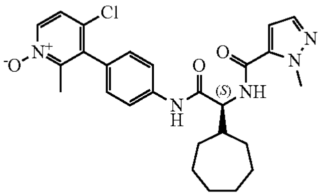 (S)-4-chloro-3-(4-(2-cycloheptyl-2-(1-methyl-1H-pyrazole-5-carboxamido)acetamido) phenyl)-2-methylpyridine 1-oxide | 3-22 | 1-methyl-1H-pyrazole-5-carboxylic acid | Rt = 4.41 min; MS: m/z = 496 and 498 $[MH]^+$ (Method 4) | 1H NMR (400 MHz, DMSO-d6) δ 10.42 (s, 1H), 8.55 (d, 1H), 8.31 (d, 1H), 7.78 (m, 2H), 7.54 (d, 1H), 7.46 (s, 1H), 7.25 (d, 2H), 7.07 (s, 1H), 4.50 (dd, 1H), 4.04 (s, 3H), 2.19 - 2.07 (m, 1H), 2.13 (s, 3H), 1.26 (m, 12H) ppm. |
| 48 | 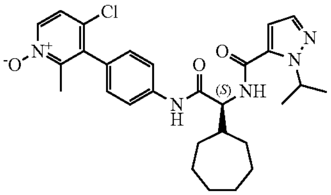 (S)-4-chloro-3-(4-(2-cycloheptyl-2-(1-isopropyl-1H-pyrazole-5-carboxamido)acetamido) phenyl)-2-methylpyridine 1-oxide | 3-22 | 1-isopropyl-1H-pyrazole-5-carboxylic acid | Rt = 5.33 min; MS: m/z 524 and 526 $[MH]^+$ (Method 4) | 1H NMR (400 MHz, DMSO-d6) δ 10.40 (s, 1H), 8.53 (d, 1H), 8.31 (d, 1H), 7.77 (m, 2H), 7,54 (d, 1H), 7.49 (s, 1H), 7.25 (d, 2H), 6.95 (s, 1H), 5.39 (sep, 1H), 4.48 (dd, 1H), 2.18 - 2.08 (m, 1H), 2.13 (s, 3H), 1.84 - 1.31 (m, 12H), 1.36 (m, 6H) ppm. |

-continued

| Example | Structure/Name | Intermediate 3-x | Intermediate 4-x | LC-MS (Method) | 1H NMR |
|---|---|---|---|---|---|
| 49 | 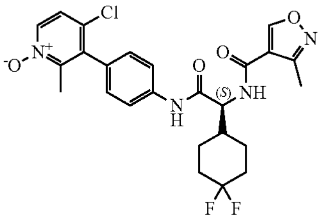 (S)-4-chloro-3-(4-(2-(4,4-difluorocyclohexyl)-2-(3-methylisoxazole-4-carboxamido)acetamido) phenyl)-2-methylpyridine 1-oxide | 3-23 | 3-methylis oxazole-4-carboxylic acid | Rt = 4.00 min; MS: m/z = 519 and 521 $[MH]^+$ (Method 4) | 1H NMR (400 MHz, DMSO-d6) δ 10.46 (s, 1H), 9.44 (s, 1H), 8.62 (d, 1H), 8.32 (d, 1H), 7.78 (m, 2H), 7.54 (d, 1H), 7.26 (d, 2H), 4.55 (dd, 1H), 2.38 (s, 3H), 2.13 (s, 3H), 2.12 - 1.68 (m, 7H), 1.24 - 1.57 (m, 2H) ppm. |
| 50 | 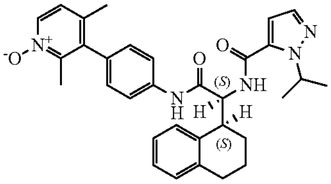 3-(4-((S)-2-(1-isopropyl-1H-pyrazole-5-carboxamido)-2-((S)-1,2,3,4-tetrahydronaphthalen-1-yl)acetamido)phenyl)-2,4-dimethylpyridine 1-oxide | 3-1 | 1-isopropyl-1H-pyrazole-5-carboxylic | Rt = 5.07 min; MS: m/z = 538.5 $[MH]^+$ (Method 4) | 1H NMR (400 MHz, DMSO-d6) δ 10.54 (s, 1H), 8.92 (d, 1H), 8.20 (d, 1H), 7.82 (d, 2H), 7.49 (d, 1H), 7.38 (d, 1H), 7.29 - 7.15 (m, 3H), 7.08 (d, 2H), 7.02 6.89 (m, 2H), 5.17 (sep, 1H), 4.81 (t, 1H), 3.40 - 3.25 (m, ca 1H, partly covered by water sign -al), 2.97 - 2.64 (m, 2H), 2.27 - 2.09 (m, 1H), 2.09 (s, 3H), 1.98 (s, 3H), 1.65 - 1.86 (m, 3H), 1.28 (t, 6H) ppm. |
| 51 | 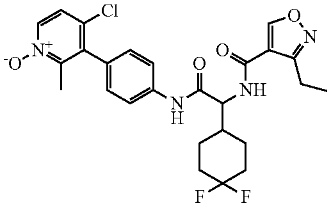 4-chloro-3-(4-(2-(4,4-difluorocyclohexyl)-2-(3-ethylisoxazole-4-carboxamido)acetamido) phenyl)-2-methylpyridine 1-oxide | 3-24 | 3-ethylisoxazole-4-carboxylic acid | Rt = 0.98 min; MS: m/z = 533 and 535 $[MH]^+$ (Method 5) | 1H NMR (400 MHz, DMSO-d6) δ 10.48 (s, 1H), 9.42 (d, 1H), 8.66 (d, 1H), 8.32 (dd, 1H), 7.77 (m, 2H), 7.54 (d, 1H), 7.27 (d, 2H), 4.54 (dd, 1H), 2.85 (q, 2H), 2.14 (s, 3H), 2.10 - 1.69 (m, 7H), 1.51 - 1.30 (m, 2H), 1.17 (t, 3H) ppm. |
| 52 | 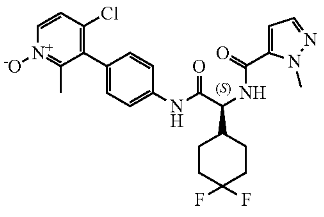 (S)-4-chloro-3-(4-(2-(4,4-difluorocyclohexyl)-2-(1-methyl-1H-pyrazole-5-carboxamido)acetamido) phenyl)-2-methylpyridine 1-oxide | 3-23 | 1-methyl-1H-pyrazole-5-carboxylic acid | Rt = 0.84 min; MS: m/z = 518 and 520 $[MH]^+$ (Method 1) | 1H NMR (400 MHz, DMSO-d6) δ 10.47 (s, 1H), 8.67 (d, 1H), 8.32 (d, 1H), 7.78 (m, 2H), 7.54 (d, 1H), 7.47 (d, 1H), 7.26 (d, 2H), 7.07 (d, 1H), 4.51 (dd, 1H), 4.04 (s, 3H), 2.13 (s, 3H), 2.11 - 1.67 (br. m, 6H), 1.54 - 1.27 (m, 3H). |

-continued

| Example | Structure/Name | Intermediate 3-x | Intermediate 4-x | LC-MS (Method) | 1H NMR |
|---|---|---|---|---|---|
| 53 | 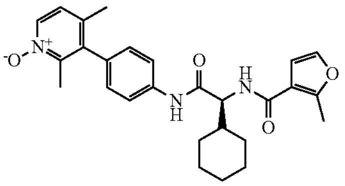 (S)-3-(4-(2-cyclohexyl-2-(2-methylfuran-3-carboxamido)acetamido)phenyl)-2,4-dimethylpyridine 1-oxide | 3-15 | 2-methylfuran-3-carboxylic acid | Rt = 1.05 min; MS: m/z = 462.5 $[MH]^+$ (Method 5) | 1H NMR (400 MHz, DMSO-d6) δ 10.34 (s, 1H), 8.19 (d, 1H), 8.00 (d, 1H), 7.77 (d, 2H), 7.52 (d, 1H), 7.21 (d, 1H), 7.16 (d, 2H), 7.06 (d, 1H), 4.41 (dd, 1H), 2.50 (Furan-$CH_3$, covered by water signal), 2.08 (s, 3H), 1.96 (s, 3H), 1.92 – 1.82 (br. m, 2H), 1.76 – 1.68 (br. m, 2H), 1.65 – 1.59 (br.m, 2H), 1.24 – 0.98 (br. m, 5H) ppm. |
| 54a | 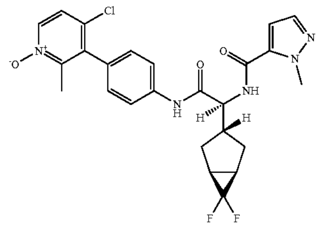 4-chloro-3-(4-((S)-2-((1R,3s,5S)-6,6-difluorobicyclo[3.1.0]hexan-3-yl)-2-(1-methyl-1H-pyrazole-5-carboxamido)acetamido) phenyl)-2-methylpyridine 1-oxide | 3-26 | 1-methyl-1H-pyrazole-5-carboxylic acid | Rt = 10.15 min; MS: m/z = 516.2 and 518 $[MH]^+$ (Method 13) | $^1$H NMR (300 MHz, DMSO-d6) δ 10.45 (s, 1H), 8.76 (d, 1H), 8.32 (d, 1H), 7.83 – 7.69 (br. m, 2H), 7.55 (d, 1H), 7.47 (d, 1H), 7.26 (d, 2H), 7.07 (d, 1H), 4.45 (dd, 1H), 4.04 (s, 3H), 2.27 – 2.05 (br. m, 4H), 2.13 (s, 3H), 2.05 – 1.76 (m, 3H). |
| 54b | 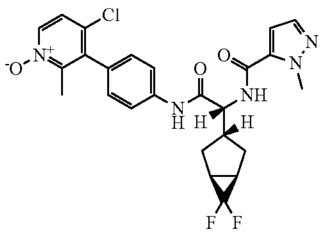 4-chloro-3-(4-((R)-2-((1R,3s,5S)-6,6-difluorobicyclo[3.1.0]hexan-3-yl)-2-(1-methyl-1H-pyrazole-5-carboxamido)acetamido) phenyl)-2-methylpyridine 1-oxide | 3-26 | 1-methyl-1H-pyrazole-5-carboxylic acid | Rt = 10.15 min; MS: m/z = 516.2 and 518 $[MH]^+$ (Method 13) | $^1$H NMR (300 MHz, DMSO-d6) δ 10.45 (s, 1H), 8.76 (d, 1H), 8.32 (d, 1H), 7.83 – 7.69 (m, 2H), 7.55 (d, 1H), 7.47 (d, 1H), 7.26 (d, 2H), 7.07 (d, 1H), 4.45 (dd, 1H), 4.04 (s, 3H), 2.27 – 2.09 (br. m, 4H), 2.13 (s, 3H), 2.05 – 1.76 (m, 3H). |
| 55 | 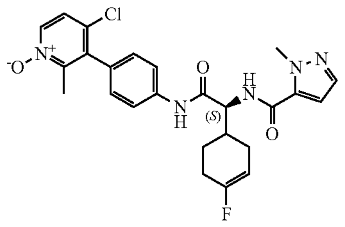 4-chloro-3-(4-((2S)-2-(4-fluorocyclohex-3-en-1-yl)-2-(1-methyl-1H-pyrazole-5-carboxamido)acetamido) phenyl)-2-methylpyridine 1-oxide | 3-27 | 1-methyl-1H-pyrazole-5-carboxylic acid | Rt = 0.89 min; MS: m/z = 498 and 500 $[MH]^+$ (Method 5) | 1H NMR (400 MHz, DMSO-d6) δ 10.53 (s, 1H), 8.70 (d, 1H), 8.31 (d, 1H), 7.79 (m, 2H), 7.54 (d, 1H), 7.47 (d, 1H), 7.26 (d, 2H), 7.09 (d, 1H), 5.22 (br. m, 1H), 4.56 (dd, 1H), 4.04 (s, 3H), 2.31 – 2.16 (br. m, 4H), 2.13 (s, 3H), 2.00 – 1.88 (br. m, 1H), 1.86 – 1.77 (br. m, 1H), 1.63 – 1.53 (br. m, 1H) ppm. |

-continued

| Example | Structure/Name | Intermediate 3-x | Intermediate 4-x | LC-MS (Method) | 1H NMR |
|---|---|---|---|---|---|
| 56 | 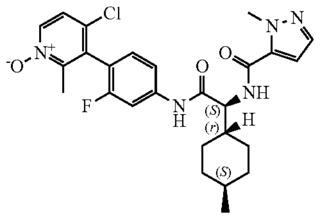 4-chloro-3-(2-fluoro-4-((S)-2-(1-methyl-1H-pyrazole-5-carboxamido)-2-((1r,4S)-4-methylcyclohexyl)acetamido)phenyl)-2-methylpyridine 1-oxide | 3-28 | 1-methyl-1H-pyrazole-5-carboxylic acid | LC-MS: Rt = 1.08 min; MS: m/z = 514 and 516 $[MH]^+$ (Method 1) | 1H NMR (400 MHz, DMSO-d6) δ 10.63 (s, 1H), 8.59 (d, 1H), 8.36 (d, 1H), 7.81 (m, 1H), 7.59 (d, 1H), 7.54 – 7.44 (m, 2H), 7.34 (m, 1H), 7.07 (d, 1H), 4.37 (dd, 1H), 4.03 (s, 3H), 2.15 (s, 3H), 1.94 – 1.78 (br. m, 2H), 1.77 – 1.66 (br. m, 2H), 1.65 – 1.57 (br. m, 1H), 1.38 – 1.16 (br. m, 2H), 1.12 – 0.98 (m, 1H), 0.96 – 0.79 (m, 5H) ppm. |
| 57 | 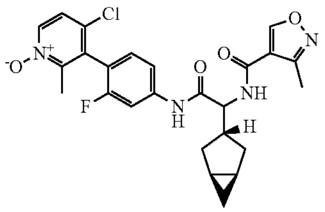 3-(4-(2-((1R,3s,5S)-bicyclo[3.1.0]hexan-3-yl)-2-(3-methylisoxazole-4-carboxamido)acetamido)-2-fluorophenyl)-4-chloro-2-methylpyridine 1-oxide | 3-29 | 3-methylisoxazole-4-carboxylic acid | LC-MS: Rt = 6.34 min; MS: m/z = 499.2 $[MH]^+$ (Method 16) | $^1$H NMR (300 MHz, Methanol-d4) δ 10.40 (s, 1H), 9.12 (s, 1H), 8.46 (d, 1H), 8.39 (d, 1H), 7.78 (d, 1H), 7.61 (d, 1H), 7.47 (d, 1H), 7.27 (dd, 1H), 4.41 (m, 1H), 2.43 (s, 3H), 2.33 (s, 3H), 2.20 – 1.98 (m, 2H), 1.88 – 1.57 (m, 3H), 1.33 (br. m, 2H), 0.41 – 0.22 (m, 2H). |
| 58 | 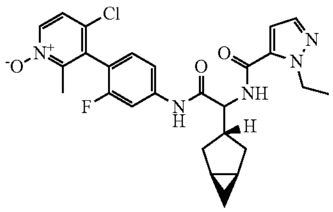 3-(4-(2-((1R,3s,5S)-bicyclo[3.1.0]hexan-3-yl)-2-(1-ethyl-1H-pyrazole-5-carboxamido)acetamido)-2-fluorophenyl)-4-chloro-2-methylpyridine 1-oxide | 3-29 | 1-ethyl-1H-pyrazole-5-carboxylic acid | LC-MS: Rt = 6.44 min; MS: m/z = 512.2 $[MH]^+$ (Method 16) | $^1$H NMR (300 MHz, Methanol-d4) δ 10.40 (s, 1H, exchangeable), 8.39 (d, 1H), 7.79 (m, 1H), 7.61 (d, 1H), 7.47 (m, 2H), 7.28 (dd, 1H), 6.86 (d, 1H), 4.56 – 4.39 (m, 3H),2.33 (s, 3H), 2.19 – 2.01 (br. m, 2H), 1.89 – 1.54 (m, 3H), 1.44 – 1.25 (m, 5H), 0.40 – 0.25 (m, 2H). |
| 59 | 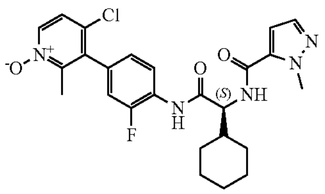 (S)-4-chloro-3-(4-(2-cyclohexyl-2-(1-methyl-1H-pyrazole-5-carboxamido)acetamido)-3-fluorophenyl)-2-methylpyridine 1-oxide | 3-32 | 1-methyl-1H-pyrazole-5-carboxylic acid | Rt = 0.93 min; MS: m/z = 500 and 502 $[MH]^+$ (Method 1) | 1H NMR (400 MHz, DMSO-d6) δ 10.12 (s, 1H), 8.50 (d, 1H), 8.34 (d, 1H), 8.02 (td, 1H), 7.56 (dd, 1H), 7.46 (d, 1H), 7.33 (dd, 1H), 7.11 (dd, 1H), 7.05 (d, 1H), 4.59 (m, 1H), 4.04 (s, 3H), 2.14 (s, 3H), 1.93 – 1.81 (br. m, 2H), 1.77 – 1.60 (br. m, 4H), 1.27 – 1.02 (br. m, 5H) ppm |

-continued

| Example | Structure/Name | Intermediate 3-x | Intermediate 4-x | LC-MS (Method) | 1H NMR |
|---|---|---|---|---|---|
| 60 | 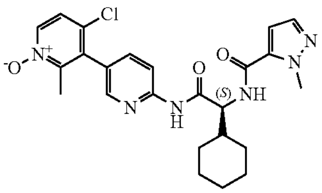 (S)-4-chloro-6'-(2-cyclohexyl-2-(1-methyl-1H-pyrazole-5-carboxamido)acetamido)-2-methyl-[3,3'-bipyridine] 1-oxide | 3-33 | 1-methyl-1H-pyrazole-5-carboxylic acid | Rt = 0.84 min; MS: m/z = 483 and 485 [MH]$^+$ (Method 2) | 1H NMR (400 MHz, DMSO-d6) δ 10.85 (d, 1H), 8.49 (d, 1H), 8.36 (d, 1H), 8.31 (d, 1H), 8.22 (d, 1H), 7.79 (dd, 1H), 7.58 (d, 1H), 7.47 (d, 1H), 7.05 (d, 1H), 4.56 (dd, 1H), 4.02 (s, 3H), 2.16 (s, 3H), 1.95 - 1.79 (br. m, 2H), 1.73 (br. m, 2H), 1.62 (br. m, 2H), 1.28 - 1.02 (m, 5H) ppm. |
| 61 | 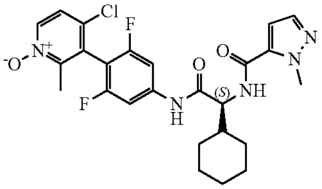 (S)-4-chloro-3-(4-(2-cyclohexyl-2-(1-methyl-1H-pyrazole-5-carboxamido)acetamido)-2,6-difluorophenyl)-2-methylpyridine 1-oxide | 3-34 | 1-methyl-1H-pyrazole-5-carboxylic acid | Rt = 1.05 min; MS: m/z = 518 and 520 [MH]$^+$ (Method 2) | 1H NMR (400 MHz, DMSO-d6) δ 10.83 (s, 1H), 8.61 (d, 1H), 8.42 (d, 1H), 7.65 (dd, 1H), 7.57 (m, 2H), 7.47 (d, 1H), 7.07 (d, 1H), 4.36 (dd, 1H), 4.03 (s, 3H), 2.19 (s, 3H), 1.96 - 1.62 (m, 6H), 1.21 - 0.97 (m, 5H) ppm. |
| 62 | 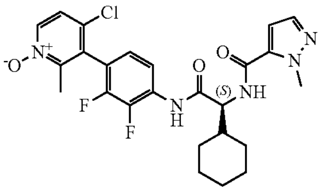 4-chloro-3-(4-((S)-2-cyclohexyl-2-(1-methyl-1H-pyrazole-5-carboxamido)acetamido)-2,3-difluorophenyl)-2-methylpyridine 1-oxide | 3-35 | 1-methyl-1H-pyrazole-5-carboxylic acid | Rt = 1.01 and 1.02 min (1:1 mixture of atropisomers); MS: m/z = 518 and 520 [MH]$^+$ (Method 2) | 1H NMR (500 MHz, DMSO-d6, faster eluting atropisomer) δ 10.37(s, 1H), 8.54 (d, 1H), 8.40 (d, 1H), 7.84 (t, 1H), 7.62 (d, 1H), 7.47 (d, 1H), 7.24 - 7.17 (m, 1H), 7.05 (d, 1H), 4.59 (dd, 1H), 4.04 (s, 3H), 2.18 (s, 3H), 1.95 - 1.81 (br. m, 2H), 1.74 (br. m, 2H), 1.65 (br. m, 2H), 1.26 - 1.05 (br. m, 5H) ppm. |
| 63 | 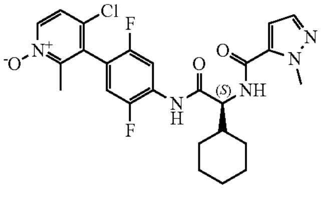 4-chloro-3-(4-((S)-2-cyclohexyl-2-(1-methyl-1H-pyrazole-5-carboxamido)acetamido)-2,5-difluorophenyl)-2-methylpyridine 1-oxide | 3-36 | 1-methyl-1H-pyrazole-5-carboxylic acid | Rt = 1.00 and 1.02 min (1:1 mixture of atropisomers); MS: m/z = 518 and 520 [MH]$^+$ (Method 2) | 1H NMR (400 MHz, DMSO-d6, faster eluting atropisomer) δ 10.34 (s, 1H), 8.53 (d, 1H), 8.39 (d, 1H), 8.08 (dd, 1H), 7.61 (d, 1H), 7.53 - 7.48 (m, 1H), 7.47 (d, 1H), 7.05 (d, 1H), 4.63 (dd, 1H), 4.03 (s, 3H), 2.17 (s, 3H), 1.97 - 1.80 (m, 2H), 1.80 - 1.70 (m, 2H), 1.63 (m, 2H), 1.34 - 0.93 (m, 5H) ppm. |

-continued

| Example | Structure/Name | Intermediate 3-x | Intermediate 4-x | LC-MS (Method) | 1H NMR |
|---|---|---|---|---|---|
| 64 | 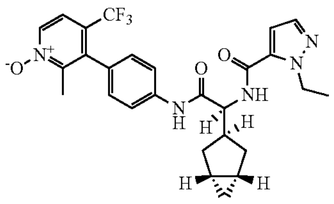 3-(4-((S)-2-((1R,3s,5S)-bicyclo[3.1.0]hexan-3-yl)-2-(1-ethyl-1H-pyrazole-5-carboxamido)acetamido) phenyl)-2-methyl-4-(trifluoromethyl)pyridine 1-oxide | 3-37 | 1-ethyl-1H-pyrazole-5-carboxylic acid | LC-MS: Rt = 1.38 min; MS: m/z = 528 $[MH]^+$ (Method 15) | 1H NMR (300 MHz, Chloroform-d) δ 8.35 (d, 1H), 8.26 (s, 1H), 7.65 (d, 2H), 7.47 (d, 2H), 7.16 (d, 2H), 6.68 - 6.54 (m, 2H), 4.59 (q, 2H), 4.49 (dd, 1H), 2.21 (s, 4H), 2.01 (ddd, 2H), 1.44 (t, 3H), 1.32 (dd, 4H), 0.86 (d, 2H). |
| 65 | 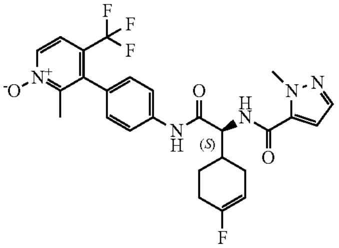 3-(4-((2S)-2-(4-fluorocyclohex-3-en-1-yl)-2-(1-methyl-1H-pyrazole-5-carboxamido)acetamido) phenyl)-2-methyl-4-(trifluoromethyl)pyridine 1-oxide | 3-38 | 1-methyl-1H-pyrazole-5-carboxylic acid | Rt = 0.97 min; MS: m/z = 532 [MH]+ (Method 9) | 1H NMR (400 MHz, DMSO-d6) δ 10.51 (d, 1H), 8.69 (dd, 1H), 8.48 (d, 1H), 7.83 - 7.75 (m, 2H), 7.70 (d, 1H), 7.47 (m, 1H), 7.25 (d, 2H), 7.09 (d, 1H), 5.23 (br. d, 1H), 4.54 (dt, 1H), 4.04 (s, 3H), 2.61 (br. s, 1H), 2.30 - 2.09 (m, 3H), 2.05 (s, 3H), 2.00 - 1.80 (br. m, 2H), 1.64 - 1.46 (br. m, 1H) ppm. |
| 66 | 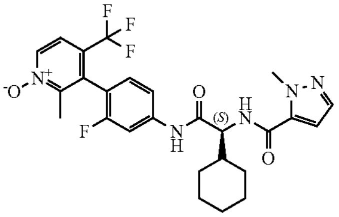 3-(4-((S)-2-cyclohexyl-2-(1-methyl-1H-pyrazole-5-carboxamido)acetamido)-2-fluorophenyl)-2-methyl-4-(trifluoromethyl)pyridine 1-oxide | 3-39 | 1-methyl-1H-pyrazole-5-carboxylic acid | Rt = 1.10 min; MS: m/z = 534 $[MH]^+$ (Method 3) | 1H NMR (400 MHz, DMSO-d6) δ 10.66 (s, 1H), 8.60 (d, 1H), 8.54 (d, 1H), 7.79 (dd, 1H), 7.76 (d, 1H), 7.50 (dd, 1H), 7.46 (d, 1H), 7.32 (t, 1H), 7.07 (d, 1H), 4.40 (dd, 1H), 4.03 (s, 3H), 2.08 (s, 3H), 1.99 - 1.56 (m, 6H), 1.24 - 1.01 (br. m, 5H). |
| 67 | 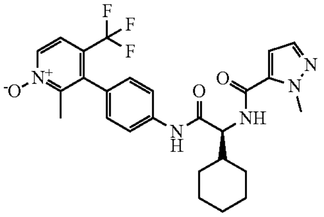 (S)-3-(4-(2-cyclohexyl-2-(1-methyl-1H-pyrazole-5-carboxamido)acetamido) phenyl)-2-methyl-4-(trifluoromethyl)pyridine 1-oxide | 3-47 | 1-methyl-1H-pyrazole-5-carboxylic acid | Rt = 1.52 min; MS: m/z = 516 $[MH]^+$ (Method 7) | 1H NMR(400 MHz, DMSO-d6) δ 10.42 (s, 1H), 8.55 (d, 1H), 8.48 (d, 1H), 7.75 (m, 2H), 7.70 (d, 1H), 7.46 (d, 1H), 7.24 (d, 2H), 7.07 (d, 1H), 4.42 (dd, 1H), 4.04 (s, 3H), 2.05 (s, 3H), 1.88 (br. m, 2H), 1.79 - 1.69 (br. m, 2H), 1.67 - 1.58 (br. m, 2H), 1.52 - 0.99 (br. m, 5H) ppm. |

-continued

| Example | Structure/Name | Intermediate 3-x | Intermediate 4-x | LC-MS (Method) | 1H NMR |
|---|---|---|---|---|---|
| 68 | 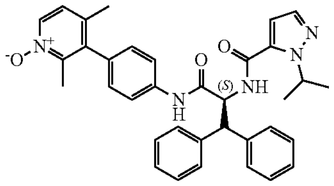 (S)-3-(4-(2-(1-isopropyl-1H-pyrazole-5-carboxamido)-3,3-diphenylpropanamido) phenyl)-2,4-dimethylpyridine 1-oxide | 3-54 | 1-isopropyl-1H-pyrazole-5-carboxylic acid | Rt = 4.96 min; MS: m/z = 574 $[MH]^+$ (method 8). | 1H NMR (400 MHz, DMSO-d6) δ ppm 10.39 (s, 1H), 8.91 (d, 1H), 8.18 (d, 1H), 7.55 (d, 2H), 7.48 - 7.42 (m, 4H), 7.39 (d, 1H), 7.29 - 7.19 (m, 5H), 7.16 - 7.08 (m, 4H), 6.60 (d, 1H), 5.65 (dd, 1H), 5.12 (sep, 1H), 4.63 (d, 1H), 2.03 (s, 3H), 1.92 (s, 3H), 1.29 (d, 3H), 1.21 (d, 3H) ppm. |
| 69 | 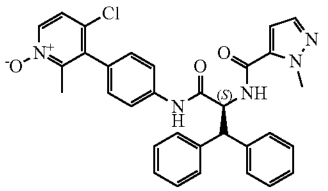 (S)-4-chloro-2-methyl-3-(4-(2-(1-methyl-1H-pyrazole-5-carboxamido)-3,3-diphenylpropanamido) phenyl)pyridine 1-oxide | 3-55 | 1-methyl-1H-pyrazole-5-carboxylic acid | Rt = 4.55 min; MS: m/z = 566, 568 $[MH]^+$ (method 8) | 1H NMR (400 MHz, DMSO-d6) δ ppm 10.45 (s, 1H), 8.91 (d, 1H), 8.29 (d, 1H), 7.55 (d, 2H), 7.52 - 7.47 (m, 3H), 7.43 (d, 2H), 7.37 (d, 1H), 7.29 - 7.22 (m, 4H), 7.18 - 7.09 (m, 4H), 6.77 (d, 1H), 5.65 (dd, 1H), 4.65 (d, 1H), 2.50 (s, 3H), 2.08 (s, 3H) ppm. |
| 70 | 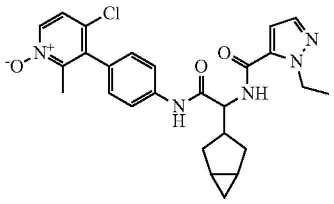 3-(4-(2-(bicyclo[3.1.0]hexan-3-yl)-2-(1-ethyl-1H-pyrazole-5-carboxamido)acetamido) phenyl)-4-chloro-2-methylpyridine 1-oxide | 3-25 | 1-ethyl-1H-pyrazole-5-carboxylic acid | Rt = 1.05 min; MS: m/z = 494, 496 $[MH]^+$ (method 3) | 1H NMR (400 MHz, DMSO-d6) 8 ppm 10.35 (s, 1H), 8.58 (d, 1H), 8.31 (d. 1H). 7.78 (m, 2H), 7.54 (d, 1H), 7.48 (d, 1H), 7.25 (d, 2H), 7.00 (d, 1H), 4.46 (q, 2H). 4.39 (dd, 1H), 2.19 - 1.97 (m, 2H), 2.13 (s, 3H), 1.78 - 1.64 (m, 2H), 1.56 - 1.48 (m, 1H), 1.20 - 1.38 (m, 5H), 0.34 - 0.28 (m, 1H), 0.21 - 0.17 (m, 1H) |
| 71 | 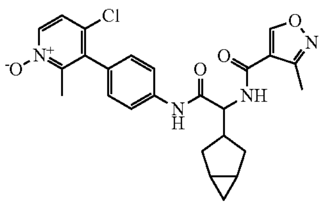 3-(4-(2-(bicyclo[3.1.0]hexan-3-yl)-2-(3-methylisoxazole-4-carboxamido)acetamido) phenyl)-4-chloro-2-methylpyridine 1-oxide | 3-25 | 3-methylisoxazole-4-carboxylic acid | Rt = 4.27 min; MS: m/z = 481, 483 $[MH]^+$ (method 4) | 1H NMR (400 MHz, DMSO-d6) δ 10.35 (s, 1H), 9.41 (s, 1H), 8.53 (d, 1H), 8.32 (d, 1H), 7.86 - 7.66 (m, 2H), 7.54 (d, 1H), 7.25 (d, 2H) 4.43 (dd, 1H), 2.37 (s, 3H), 2.13 (s, 3H), 2.10 - 1.91 (m, 2H), 1.77 - 1.65 (m, 2H), 1.58 - 1.52 (m, 1H), 1.27 (br m, 2H), 0.35 - 0.28 (m, 1H), 0.21 - 0.16 (m, 1H) ppm |

-continued

| Example | Structure/Name | Intermediate 3-x | Intermediate 4-x | LC-MS (Method) | 1H NMR |
|---|---|---|---|---|---|
| 72 | 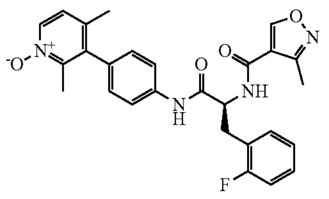 (S)-3-(4-(3-(2-fluorophenyl)-2-(3-methylisoxazole-4-carboxamido)propanamido)phenyl)-2,4-dimethylpyridine 1-oxide | 3-60 | 3-methylisoxazole-4-carboxylic acid | Rt = 0.85 min; MS: m/z = 489.3 $[MH]^+$ (method 3) | 1H NMR (400 MHz, DMSO-d6) δ 10.34 (s, 1H), 9.34 (s, 1H), 8.76 (d, 1H), 8.20 (d, 1H), 7.72 (m, 2H), 7.39 (m, 1H), 7.29 – 7.09 (m, 6H), 4.94 (dt, 1H), 3.23 (m, 1H), 3.06 (m, 1H), 2.31 (s, 3H), 2.08 (s, 3H), 1.96 (s, 3H) ppm. |
| 73 | 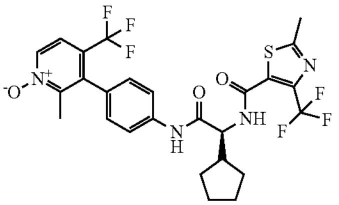 (S)-3-(4-(2-cyclopentyl-2-(2-methyl-4-(trifluoromethyl)thiazole-5-carboxamido)acetamido)phenyl)-2-methyl-4-(trifluoromethyl)pyridine 1-oxide | 3-5 | 2-methyl-4-(trifluoro methyl) thiazole-5-carboxylic acid | Rt = 1.09 min; MS: m/z = 587.2 $[MH]^+$ (method 5) | 1H NMR (400 MHz, DMSO-d6) δ 10.43 (s, 1H), 9.29 (d, 1H), 8.48 (d, 1H), 7.78 – 7.67 (m, 3H), 7.25 (d, 2H), 4.45 (dd, 1H), 2.73 (s, 3H), 2.29 (m, 1H), 2.06 (s, 3H), 1.83 – 1.74 (br. m, 1H), 1.69 – 1.57 (br. m, 3H), 1.57 – 1.28 (br. m, 4H) ppm. |
| 74 | 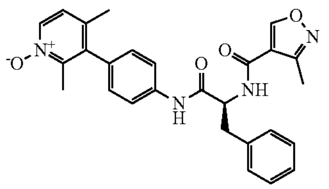 (S)-2,4-dimethyl-3-(4-(2-(3-methylisoxazole-4-carboxamido)-3-phenylpropanamido)phenyl) pyridine 1-oxide | 3-59 | 3-methylisoxazole-4-carboxylic acid | Rt = 0.83 min; MS: m/z = 471.4 $[MH]^+$ (method 3) | 1H NMR (400 MHz, DMSO-d6) δ 10.40 (s, 1H), 9.34 (s, 1H), 8.75 (d, 1H), 8.20 (d, 1H), 7.74 (m, 2H), 7.38 (d, 2H), 7.29 (t, 2H), 7.20 (m, 4H), 4.86 (m, 1H), 3.17 (dd, 1H), 3.00 (dd, 1H), 2.29 (s, 3H), 2.09 (s, 3H), 1.97 (s, 3H) ppm. |
| 75 | 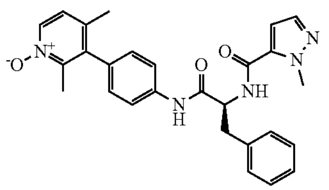 (S)-2,4-dimethyl-3-(4-(2-(1-methyl-1H-pyrazole-5-carboxamido)-3-phenylpropanamido)phenyl) pyridine 1-oxide | 3-59 | 1-methyl-1H-pyrazole-5-carboxylic acid | Rt = 0.82 min; MS: m/z = 470.3 $[MH]^+$ (method 3) | 1H NMR (400 MHz, DMSO-d6) δ 10.41 (s, 1H), 8.79 (d, 1H), 8.20 (d, 1H), 7.76 (d, 2H), 7.45 (d, 1H), 7.41 (d, 2H), 7.29 (t, 2H), 7.21 (m, 4H), 6.96 (d, 1H), 4.86 (m, 1H), 3.18 (dd, 1H), 3.08 (dd, 1H), 2.50 (s, 3H), 2.09 (s, 3H), 1.97 (s, 3H) ppm. |

Example 76

4-chloro-3-(4-((S)-2-cyclohexyl-2-(1-(2-methoxy-2-oxoethyl)-1H-pyrazole-5-carboxamido)acetamido)-2-fluorophenyl)-2-methylpyridine 1-oxide

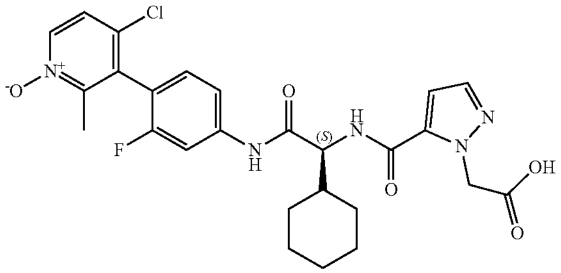

To a solution of 3-(4-((S)-2-amino-2-cyclohexylacetamido)-2-fluorophenyl)-4-chloro-2-methylpyridine 1-oxide (Intermediate 3-2, 61 mg, 0.142 mmol), 1-(2-methoxy-2-oxoethyl)-1H-pyrazole-5-carboxylic acid (Intermediate 4-1, 28.8 mg, 0.157 mmol) and 2,4,6-collidine (0.057 ml, 0.427 mmol) in DMF (5 mL) was added 4-(4,6-dimethoxy-1,3,5-triazin-2-yl)-4-methyl-morpholinium chloride (50.0 mg, 0.171 mmol) and the reaction mixture was stirred for 80 h at RT. The solvent was evaporated, the residue was taken up in EtOAc (50 mL) and extracted with sat $Na_2CO_3$ followed by water. The combined aqueous layers were re-extracted with EtOAc. LC-MS analysis of the aqueous layer indicated that the initially formed methyl ester was saponified under the extraction conditions to the desired acid. The aqueous layer was evaporated to a volume of ca 5 mL and then acidified to pH 4 by addition of 1 M HCl and evaporated again. The residue was taken up in acetonitrile/MeOH 1:1 (4 mL), filtered, and the filtrate was purified by column chromatography on RP-18 (column: RediSep RP-18, 26 g; eluent: water/acetonitrile 95:5 to 0:100,) to yield the title compound (44 mg, 55%) as a colorless solid.

LC-MS: Rt=0.87 and 0.88 min (1:1 mixture of atropisomers); MS: m/z=544 and 546 [MH]+(Method 5).

1H NMR (400 MHz, DMSO-d6) δ 10.62 (s, 1H), 9.82 (br. s, 1H), 8.36 (d, 1H), 7.87 (m, 1H), 7.58 (m, 2H), 7.40 (br. s, 1H), 7.31 (m, 1H), 6.80 (br. s, 1H), 4.97-4.74 (br. m, 2H), 4.38 (m, 1H), 2.15 (s, 3H), 1.95-1.84 (br. m, 1H), 1.80-1.66 (br. m, 3H), 1.64-1.55 (br. m, 2H), 1.25-1.07 (br. m, 5H) ppm.

Example 77

4-chloro-3-(4-((S)-2-cyclohexyl-2-(1-(2-(dimethylamino)ethyl)-1H-pyrazole-5-carboxamido)acetamido)-2-fluorophenyl)-2-methylpyridine 1-oxide

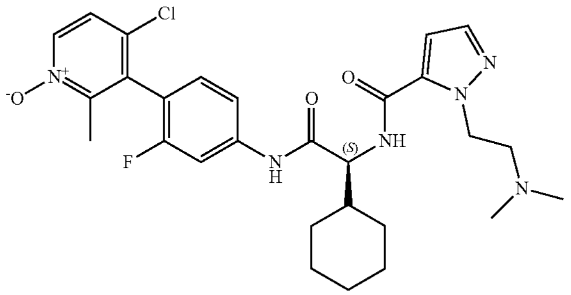

Step 1: 4-chloro-3-(4-((S)-2-cyclohexyl-2-(1-(2-oxoethyl)-1H-pyrazole-5-carboxamido)acetamido)-2-fluorophenyl)-2-methylpyridine 1-oxide To a cooled (0° C.) solution of 100 mg 4-chloro-3-(4-((S)-2-cyclohexyl-2-(1-(2-hydroxyethyl)-1H-pyrazole-5-carboxamido)acetamido)-2-fluorophenyl)-2-methylpyridine 1-oxide (Example 17; 100 mg, 0.19 mmol) in DCM (1.9 mL) was added portionwise Dess-Martin periodinane (160 mg, 0.38 mmol). After stirring at 0° C. for 30 min and 2.5 h at RT the reaction mixture was diluted with EtOAc and washed with 1 M NaOH solution, water and brine washed. The organic phase was dried ($Na_2SO_4$) and evaporated to yield the title compound (98 mg, 98%) as a yellow oil which was used in the next step without further purification.

LC-MS: Rt=0.93 and 0.94 min (atropisomers); MS: m/z=528 and 530 $[MH]^+$ (Method 3).

Step 2: 4-chloro-3-(4-((S)-2-cyclohexyl-2-(1-(2-(dimethylamino)ethyl)-1H-pyrazole-5-carboxamido)acetamido)-2-fluorophenyl)-2-methylpyridine 1-oxide To a solution of 4-chloro-3-(4-((S)-2-cyclohexyl-2-(1-(2-oxoethyl)-1H-pyrazole-5-carboxamido)acetamido)-2-fluorophenyl)-2-methylpyridine 1-oxide (Step 1; 90 mg, 0.17 mmol) in methanol (1.7 mL) was added a 2M solution of dimethylamine in methanol (0.51 mL, 1.02 mmol).

After stirring the mixture for 10 min at RT, $NaBH_3CN$ (54 mg, 0.85 mmol) and acetic acid (0.02 mL, 0.34 mmol) were added and the reaction mixture was stirred at RT overnight. The mixture was diluted with EtOAc and washed with sat. aq. $NaHCO_3$, water and brine. The organic layer was dried ($Na_2SO_4$) and evaporated. Purification of the residue by SFC (column: 250×30 Waters Torrus 2-PIC 130 A 5 μm; gradient: 15-24% MeOH in 7 min) provided the title compound (33 mg, 33%) as a yellow oil.

LC-MS: Rt=0.70 and 0.72 min (atropisomers); MS: m/z=557 and 559 $[MH]^+$ (Method 10)

1H NMR (400 MHz, DMSO-d6) δ 10.68 (s, 1H), 8.75 (d, 1H), 8.37 (d, 1H), 7.82 (m, 1H), 7.44-7.64 (m, 3H), 7.34 (m, 1H), 7.11 (d, 1H), 4.69 (br. m, 2H), 4.42 (dd, 1H), 3.03 (br. s, 2H), 2.39-2.47 (br. s, 6H), 2.15 (s, 3H), 1.52-2.01 (m, 6H), 0.95-1.32 (m, 5H) ppm.

Example 78

3-(4-((S)-2-(3-(hydroxymethyl)isoxazole-4-carboxamido)-2-((1r,4S)-4-(trifluoromethyl)cyclohexyl)acetamido)phenyl)-2,4-dimethylpyridine 1-oxide

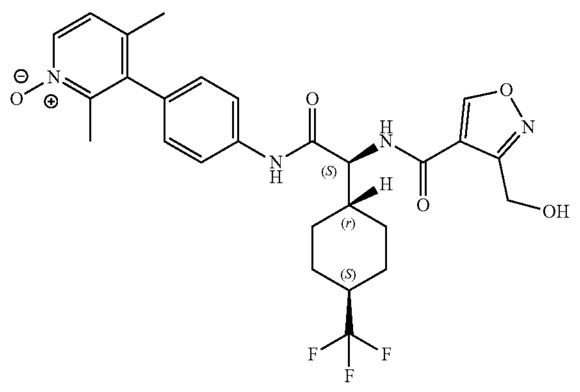

To a cooled (−78° C.) solution of 3-(4-((S)-2-(3-(methoxymethyl)isoxazole-4-carboxamido)-2-((1r,4S)-4-(trifluoromethyl)cyclohexyl)acetamido)phenyl)-2,4-dimethylpyridine 1-oxide (Example 31, 110 mg, 0.196 mmol) in DCM (10 mL) was added dropwise a 1 M solution of $BBr_3$ in DCM (0.59 mL, 0.59 mmol). The mixture was stirred at −78° C. for 1 h, then at 0° C. for 1 h, then at RT for 4 h. The reaction mixture was then diluted with EtOAc, extracted with sat. aq. $NaHCO_3$ and water, dried ($Na_2SO_4$) and evaporated. The residue was purified by prep. HPLC on RP-18 (column: Waters SunFire 30×100 mm; eluent: water+0.1% TFA/acetonitrile+0.1% TFA 95:5 to 0:100; flow 15 mL/min) to yield the title compound (63 mg, 57%) as a colorless solid.

LC-MS: Rt=0.91 min; MS: m/z=547.3 $[MH]^+$ (Method 5).

1H NMR (400 MHz, DMSO-d6) δ 10.43 (s, 1H), 9.46 (s, 1H), 8.94 (d, 1H), 8.20 (d, 1H), 7.75 (d, 2H), 7.22 (d, 1H), 7.18 (d, 2H), 6.11 (dd, 1H), 4.74 (d, 2H), 4.55 (t, 1H), 2.34-2.20 (br. m, 1H), 2.08 (s, 3H), 1.96 (s, 3H), 2.00-1.73 (m, 5H), 1.36-1.12 (m, 4H) ppm.

Example 79

(S)-3-(4-(2-(3-(aminomethyl)isoxazole-4-carboxamido)-2-cyclohexylacetamido)phenyl)-2,4-dimethylpyridine 1-oxide

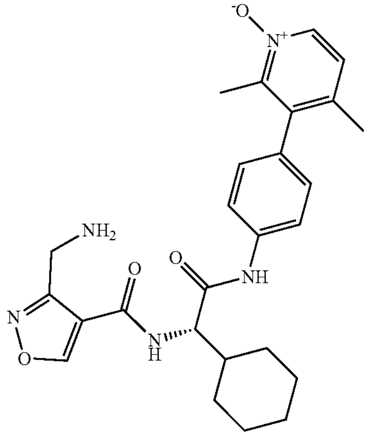

Step 1: (S)-3-(4-(2-(3-(((tert-butoxycarbonyl)amino)methyl)isoxazole-4-carboxamido)-2-cyclohexylacetamido)phenyl)-2,4-dimethylpyridine 1-oxide The title compound was prepared from Intermediate 3-15 and 3-(((tert-butoxycarbonyl)amino)methyl)isoxazole-4-carboxylic acid by a procedure similar to that of Example 1.

LC-MS: Rt=1.04 min; MS: m/z=578.5 $[MH]^+$ (Method 2).

Step 2: (S)-3-(4-(2-(3-(aminomethyl)isoxazole-4-carboxamido)-2-cyclohexylacetamido)phenyl)-2,4-dimethylpyridine 1-oxide (S)-3-(4-(2-(3-(((tert-butoxycarbonyl)amino)methyl)isoxazole-4-carboxamido)-2-cyclohexylacetamido)phenyl)-2,4-dimethylpyridine 1-oxide (Step 1, 250 mg, 0.433 mmol) was treated with 4N HCl in dioxane (4 mL). A small amount of methanol was added to obtain a clear solution. After stirring at RT for 1 h the mixture was evaporated and the residue was partitioned between sat. aq. $NaHCO_3$ and EtOAc. The aqueous layer was extracted with EtOAc, the combined organic layers were washed with brine, dried ($Na_2SO_4$) and evaporated to yield the title compound (273 mg, 100%) as an off-white solid. For biological testing, a part of this material was further purified by SFC (column: 250×30 Princeton PPU 100 A 5 um; elution with 15-24% MeOH in 7 min).

LC-MS: Rt=0.71 min; MS: m/z=578.5 $[MH]^+$ (Method 12).

1H NMR (400 MHz, DMSO-d6) δ 10.42 (s, 1H), 9.72 (s, 1H), 8.92 (d, 1H), 8.30 (br. m, 2H), 8.20 (d, 1H), 7.83-7.70 (m, 2H), 7.23 (d, 1H), 7.18 (d, 2H), 4.47 (dd, 1H), 4.35 (s, 2H), 2.08 (s, 3H), 1.96 (s, 3H), 1.90-1.80 (br. m, 2H), 1.78-1.69 (br. m, 2H), 1.67-1.60 (br. m, 2H), 1.25-1.04 (br. m, 5H) ppm.

Example 80

(S)-3-(4-(2-cyclohexyl-2-(3-((dimethylamino)methyl)isoxazole-4-carboxamido)acetamido)phenyl)-2,4-dimethylpyridine 1-oxide

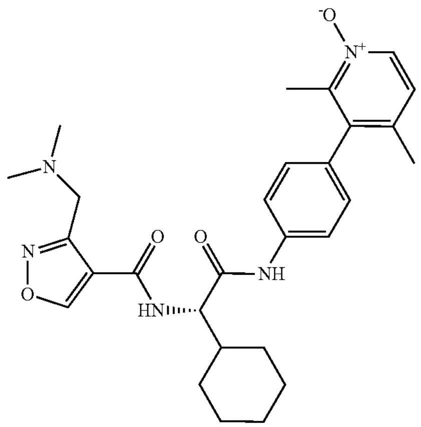

To a stirred solution of (S)-3-(4-(2-(3-(aminomethyl)isoxazole-4-carboxamido)-2-cyclohexylacetamido)phenyl)-2,4-dimethylpyridine 1-oxide (Example 62; 200 mg, 0.419 mmol) in MeOH (4 mL) was added 37% aqueous formaldehyde (0.187 ml, 2.51 mmol). After 10 min $NaBH_3CN$ (132 mg, 2.1 mmol) and acetic acid (0.048 ml, 0.84 mmol) were added and stirring was continued at RT for 80 min. The mixture was partitioned between EtOAc and sat. $NaHCO_3$, the aqueous layer was extracted twice with EtOAc, the combined organic layers were washed with water and brine, dried ($Na_2SO_4$) and evaporated. The residue was purified by prep. HPLC (column: Sunfire 30×100 mm, gradient: 5-90% ACN in water+0.1% TFA) to yield the title compound 69 mg, 32%) as a colorless solid.

LC-MS: Rt=0.78 min; MS: m/z=506.5 $[MH]^+$ (Method 2).

1H NMR (400 MHz, DMSO-d6) δ 10.72 (d, 1H), 10.38 (s, 1H), 9.40 (s, 1H), 8.19 (d, 1H), 7.74 (d, 2H), 7.23 (d, 1H), 7.16 (d, 2H), 4.58 (dd, 1H), 3.73 (s, 2H), 2.29 (s, 6H), 2.08 (s, 3H), 1.96 (s, 3H), 1.80-1.54 (m, 6H), 1.36-0.96 (m, 5H) ppm.

Example 81

(S)-3-(4-(2-cyclohexyl-2-(1-methyl-1H-pyrazole-5-carboxamido)acetamido)phenyl)-4-methylpyridine 1-oxide

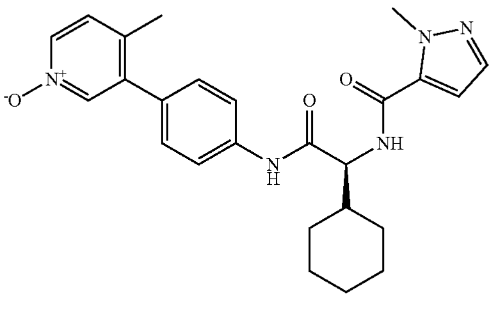

Step 1: Tert-butyl (S)-(1-cyclohexyl-2-((4-iodophenyl)amino)-2-oxoethyl)carbamate To a solution of Boc-(L)-cyclohexyl glycine (3.0 g, 11.66 mmol) and 2,4,6-collidine (6.21 ml, 46.6 mmol) in DMF (20 mL) was added HATU (4.88 g, 12.82 mmol). After stirring this mixture for 10 min at RT p-iodoaniline (2.55 g, 11.66 mmol) was added and stirring was continued at RT overnight. The reaction mixture was partitioned between aq. $NaHCO_3$ and EtOAc, the aqueous layer was extracted with EtOAc. The combined organic layers were washed with brine, dried ($Na_2SO_4$) and evaporated. The residue was purified by column chromatography on silica (column: RediSep 80 g; solvent: 10-20% EtOAc in cyclohexane) to yield the title compound (4.42 g, 78%) as a colorless solid.

LC-MS: Rt 1.35 min; MS: m/z=459 $[MH]^+$ (Method 1).

Step 2: (S)-2-amino-2-cyclohexyl-N-(4-iodophenyl)acetamide

Tert-butyl (S)-(1-cyclohexyl-2-((4-iodophenyl)amino)-2-oxoethyl)carbamate (Step 1; 4.42 g, 9.64 mmol) was treated with 4N HCl in dioxane (1 mL). After stirring at RT for 30 min HPLC analysis indicated the complete consumption of the starting material. The mixture was evaporated and dried in HV to yield the title compound (3.94 g, 100%) as an off-white solid which was used in the next step without further purification.

LC-MS: Rt 0.79 min; MS: m/z=358 $[MH]^+$ (Method 1).

Step 3: (S)—N-(1-cyclohexyl-2-((4-iodophenyl)amino)-2-oxoethyl)-1-methyl-1H-pyrazole-5-carboxamide To a solution of 1-methyl-1H-pyrazole-5-carboxylic acid (0.620 g, 4.92 mmol) and 2,4,6-collidine (2.62 ml, 19.66 mmol) in DMF (20 ml) was added HATU (2.056 g, 5.41 mmol). After stirring this mixture for 10 min at RT, (S)-2-amino-2-cyclohexyl-N-(4-iodophenyl)acetamide (Step 2; 2 g, 4.92 mmol) was added at rt in one portion, and stirring was continued at RT for 1 h. The reaction mixture was partitioned between aq. $NaHCO_3$ and EtOAc, the aqueous layer was extracted with EtOAc. The combined organic layers were washed with brine, dried ($Na_2SO_4$) and evaporated. The residue was purified by column chromatography on silica (column: RediSep 80 g; solvent: 0-65% EtOAc in cyclohexane) to yield the title compound (2.06 g, 86%) as an off-white solid.

LC-MS: Rt 1.19 min; MS: m/z=467 $[MH]^+$ (Method 1).

Step 4: (S)—N-(1-cyclohexyl-2-((4-(4-methylpyridin-3-yl)phenyl)amino)-2-oxoethyl)-1-methyl-1H-pyrazole-5-carboxamide A MW-Vial was charged 3-bromo-4-methylpyridine (100 mg, 0.581 mmol), XPhos Pd G2 (45.7 mg, 0.058 mmol), diboronic acid (78 mg, 0.872 mmol), potassium acetate (171 mg, 1.744 mmol) and XPhos (55.4 mg, 0.116 mmol) in ethanol (7 mL). Ethylene glycol (0.097 mL, 1.744 mmol) was added, and mixture was purged with nitrogen for 5 min, followed by stirring for 90 min at 90° C. After cooling to RT, 1 M aq. $K_3PO_4$ (1.75 mL) and a solution of (S)—N-(1-cyclohexyl-2-((4-iodophenyl)amino)-2-oxoethyl)-1-methyl-1H-pyrazole-5-carboxamide (Step 3; 271 mg, 0.581 mmol) in EtOH (2 mL) were added and the mixture was stirred at 90° C. for 2 h. After cooling, the mixture was diluted with EtOAc (50 mL) and filtered through Celite. The filtrate was washed with 1 M $Na_2CO_3$ solution and water. The aqueous phases were re-extracted with EtOAc and the combined organic layers were evaporated. The residue was purified by prep HPLC (column: Waters SunFire 30×100 mm; C18; 5 μm; Flow 40 ml/min solvents:water+0.1% TFA/acetonitrile+0.1% TFA), to yield the title compound (196 mg, 78%) as a colorless solid.

LC-MS: Rt 0.97 min; MS: m/z=432.3 $[MH]^+$ (Method 2).

Step 5: (S)-3-(4-(2-cyclohexyl-2-(1-methyl-1H-pyrazole-5-carboxamido)acetamido)phenyl)-4-methylpyridine 1-oxide To a solution of (S)—N-(1-cyclohexyl-2-((4-(4-methylpyridin-3-yl)phenyl)amino)-2-oxoethyl)-1-methyl-1H-pyrazole-5-carboxamide (Step 4; 153 mg, 0.355 mmol) in DCM (5 mL) was added mCPBA (73.4 mg, 0.425 mmol) 4 portions over 1 h. After stirring the mixture at RT for 1 h HPLC indicated complete conversion of the starting material. The mixture was diluted with EtOAc and extracted with sat. aq. $Na_2CO_3$ solution, followed by water. The aqueous layers were re-extracted with EtOAc and the combined organic layers were evaporated to yield the title compound (93 mg, 59%) as a colorless solid.

LC-MS: Rt 0.93 min; MS: m/z=448.4 $[MH]^+$ (Method 2).

1H NMR (400 MHz, DMSO-d6) δ 10.40 (s, 1H), 8.55 (d, 1H), 8.10 (d, 1H), 8.04 (d, 1H), 7.75 (d, 2H), 7.46 (d, 1H), 7.37 (d, 2H), 7.33 (d, 1H), 7.07 (d, 1H), 4.41 (dd, 1H), 4.03 (s, 3H), 2.20 (s, 3H), 1.93-1.81 (br. m, 2H), 1.76-1.68 (br. m, 2H), 1.65-1.57 (br. m, 2H), 1.24-0.98 (m, 5H) ppm.

Example 82

(S)-3-(4-(2-cyclohexyl-2-(1-isopropyl-1H-pyrazole-5-carboxamido)acetamido)-2-fluorophenyl)-2-methylpyridine 1-oxide

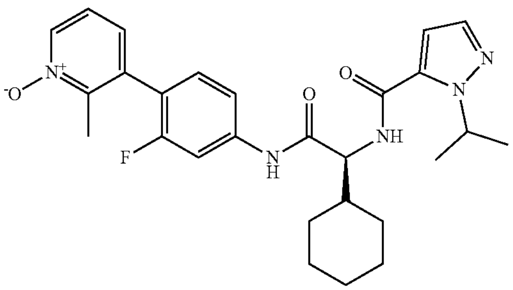

Step 1: (S)—N-(1-cyclohexyl-2-((3-fluoro-4-(2-methylpyridin-3-yl)phenyl)amino)-2-oxoethyl)-1-isopropyl-1H-pyrazole-5-carboxamide The title compound (100 mg, 46%) was prepared from Intermediate 3-41 (250 mg, 0.44 mmol) and 1-isopropyl-1H-pyrazole-5-carboxylic acid (68 mg, 0.44 mmol) by a procedure similar to that of Example 1.

LC-MS: Rt 1.11 min; MS: m/z=478.2 $[MH]^+$ (Method 2).

Step 2: (S)-3-(4-(2-cyclohexyl-2-(1-isopropyl-1H-pyrazole-5-carboxamido)acetamido)-2-fluorophenyl)-2-methylpyridine 1-oxide To a solution of (S)—N-(1-cyclohexyl-2-((3-fluoro-4-(2-methylpyridin-3-yl)phenyl)amino)-2-oxoethyl)-1-isopropyl-1H-pyrazole-5-carboxamide (Step 1, 80 mg, 0.168 mmol) in THF (1.1 mL). was added mCPBA (75 mg, 0.33 mmol). After stirring for 4 h at RT, the reaction mixture was partitioned between EtOAc and sat aq. $NaHCO_3$. The organic layer was washed with brine, dried ($Na_2SO_4$) and evaporated. The residue was purified by prep. HPLC on RP-18 (column: Waters SunFire 30×100 mm; flow 15 mL/min; eluent: water+0.1% TFA/acetonitrile+0.1% TFA 95:5 to 0:100) to yield the title compound (63 mg, 75%) as a colorless solid.

LC-MS: Rt=1.04 min; MS: m/z=494.2 $[MH]^+$ (Method 2).

1H NMR (400 MHz, DMSO-d6) δ 10.60 (d, 1H), 8.56 (d, 1H), 8.34 (d, 1H), 7.78 (dd, 1H), 7.56-7.46 (m, 2H), 7.38 (m, 2H), 7.21 (d, 1H), 6.96 (d, 1H), 5.39 (hep, 1H), 4.38 (dd, 1H), 2.21 (s, 3H), 1.95-1.54 (br. m, 6H), 1.37 (d, 3H), 1.35 (d, 3H), 1.25-1.04 (br. m, 5H) ppm.

The following Examples were prepared by amide bond formation of Intermediate 3-x and the corresponding carboxylic acids (prepared as Intermediates 4-x or commercially available) followed by oxidation of the pyridine by procedures similar to that of Example 82.

| Example | Structure/Name | Intermediate 3-x | Intermediate 4-x | LC-MS (Method) | 1H NMR |
|---|---|---|---|---|---|
| 83 | 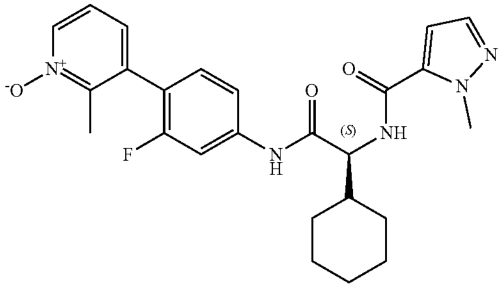 | 3-41 | 1-methyl-1H-pyrazole-5-carboxylic acid | Rt = 5.07 min; MS: m/z = 538.5 $[MH]^+$ (Method 4) | 1H NMR (400 MHz, DMSO-d6 ) δ 10.61 (s, 1H), 8.58 (d, 1H), 8.34 (dd, 1H), 7.78 (dd, 1H), 7.54-7.45 (m, 2H), 7.37 (m, 2H), 7.21 (dd, 1H), 7.07 (d, 1H), 4.40 (dd, 1H), 4.03 (s, 3H), 2.20 (s, 3H), 1.87 (br. m, 2H), 1.72 (br. m, 2H), |

-continued

| Example | Structure/Name | Intermediate 3-x | Intermediate 4-x | LC-MS (Method) | 1H NMR |
|---|---|---|---|---|---|
| | (S)-3-(4-(2-cyclohexyl-2-(1-methyl-1H-pyrazole-5-carboxamido)acetamido)-2-fluorophenyl)-2-methylpyridine 1-oxide | | | | 1.61 (br. m, 2H), 1.25-1.04 (br. m, 5H) ppm. |
| 84 | 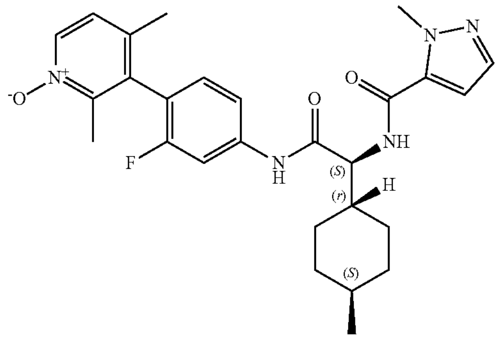 3-(2-fluoro-4-((S)-2-(1-methyl-1H-pyrazole-5-carboxamido)-2-((1r,4S)-4-methylcyclohexyl)acetamido) phenyl)-2,4-dimethylpyridine 1-oxide | 3-43 | 1-methyl-1H-pyrazole-5-carboxylic acid | Rt = 1.04 min; MS: m/z = 494 $[MH]^+$ (Method 3) | 1H NMR (400 MHz, DMSO-d6) δ 10.67 (s, 1H), 8.66 (d, 1H), 8.24 (d, 1H), 7.81 (d, 1H), 7.51 (d, 1H), 7.46 (d, 1H), 7.35-7.21 (m, 2H), 7.08 (d, 1H), 4.37 (dd, 1H), 4.03 (s, 3H), 2.10 (s, 3H), 1.98 (s, 3H), 1.93-1.77 (br. m, 2H), 1.75-1.66 (br. m, 2H), 1.65-1.56 (br. m, 1H), 1.37-1.14 (br. m, 2H), 1.11-0.98 (m, 1H), 0.87 (m, 5H) ppm. |
| 85 | 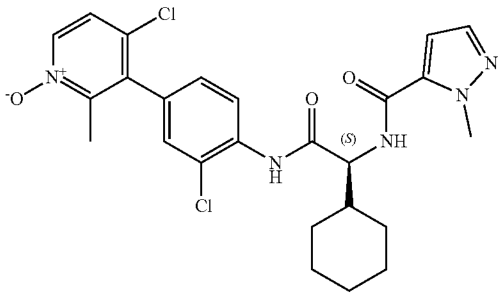 (S)-4-chloro-3-(3-chloro-4-(2-cyclohexyl-2-(1-methyl-1H-pyrazole-5-carboxamido)acetamido)phenyl)-2-methylpyridine 1-oxide | 3-44 | 1-methyl-1H-pyrazole-5-carboxylic acid | Rt = 0.98 min; MS: m/z = 516.2 $[MH]^+$ (Method 1) | 1H NMR (400 MHz, DMSO-d6) δ 9.80 (br. s, 1H), 8.53 (d, 1H), 8.34 (d, 1H), 7.90 (d, 1H), 7.54 (m, 2H), 7.47 (s, 1H), 7.28 (d, 1H), 7.04 (s, 1H), 4.59 (dd, 1H), 4.05 (s, 3H), 2.13 (s, 3H), 2.01-1.61 (br. m, 9H), 1.28-1.11 (br. m, 2H) ppm. |
| 86 | 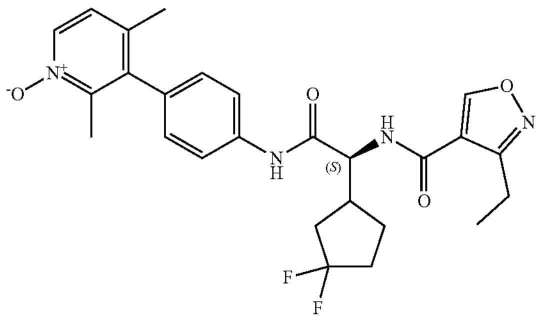 | 3-45 | 3-ethyliso-xazole-4-carboxylic acid | Rt = 0.87 min; MS: m/z = 499.3 $[MH]^+$ (Method 5) | 1H NMR (400 MHz, DMSO-d6, 2:1 mixture of diastereomers)) δ 10.44 and 10.40 (2s, ratio ca 2:1, 1H), 9.41 and 9.40 (2s, ratio 1:2, 1H), 8.71 and 8.70 (2d, ratio 2:1, 1H), 8.20 (d, 1H), 7.76 and 7.75 (2d, ratio 2:1, 2H), 7.22 (d, 1H), 7.19 (d, 2H), 4.60 and 4.58 |

-continued

| Example | Structure/Name | Inter-mediate 3-x | Inter-mediate 4-x | LC-MS (Method) | 1H NMR |
|---|---|---|---|---|---|
| | | | | | (2dd, ratio 1:2, 1H), 2.85 (q, 2H), 2.72-2.55 (br. m, 1H), 2.44-1.49 (br. m, 6H), 2.08 (s, 3H), 1.97 (s, 3H), 1.18 (t, 3H) ppm. |
| | 3-(4-((2S)-2-(3,3-difluorocyclopentyl)-2-(3-ethylisoxazole-4-carboxamido)acetamido)phenyl)-2,4-dimethylpyridine 1-oxide | | | | |
| 87 | 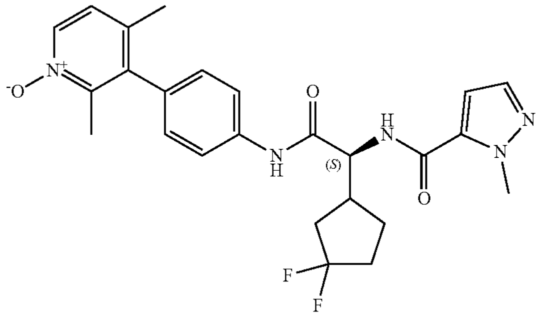 3-(4-((2S)-2-(3,3-difluorocyclopentyl)-2-(1-methyl-1H-pyrazole-5-carboxamido)acetamido)phenyl)-2,4-dimethylpyridine 1-oxide | 3-45 | 1-methyl-1H-pyrazole-5-carboxylic acid | Rt = 0.77 min; MS: m/z = 484.2 $[MH]^+$ (Method 5) | 1H NMR (400 MHz, DMSO-d6) δ 10.4 and 10.39 (2s, ratio 2:1, 1H), 8.73 (t, 1H), 8.19 (d, 1H), 7.76 and 7.75 (2d, ratio 2:1 2H), 7.48 (d, 1H), 7.23 (d, 1H), 7.18 (dd, 2H), 7.05 (t, 1H), 4.66-4.49 (m, 1H), 4.04 (s, 3H), 3.31 (s, 3H), 2.78-2.65 (m, 1H), 2.47-2.21 (m, 1H), 2.29-2.11 (m, 2H), 2.08 (s, 3H), 1.97 (s, 3H) ppm. |
| 88 | 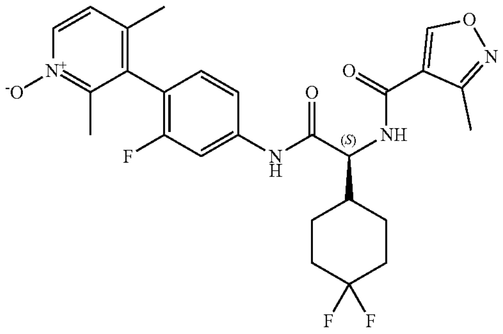 3-(4-((2S)-2-(3,3-difluorocyclopentyl)-2-(1-methyl-1H-pyrazole-5-carboxamido)acetamido)phenyl)-2,4-dimethylpyridine 1-oxide | 3-46 | 3-methyliso-xazole-4-carboxylic acid | Rt = 0.92 min; MS: m/z = 517.3 $[MH]^+$ (Method 2) | 1H NMR (400 MHz, DMSO-d6) δ 10.66 (s, 1H), 9.44 (s, 1H), 8.67 (d, 1H), 8.24 (d, 1H), 7.80 (d, 1H), 7.49 (d, 1H), 7.31-7.25 (m, 2H), 4.50 (dd, 1H), 2.38 (s, 3H), 2.09 (s, 3H), 1.99 (s, 3H), 1.96-1.61 (m, 6H), 1.58-1.18 (m, 3H) ppm |

-continued

| Example | Structure/Name | Intermediate 3-x | Intermediate 4-x | LC-MS (Method) | 1H NMR |
|---|---|---|---|---|---|
| 89 | 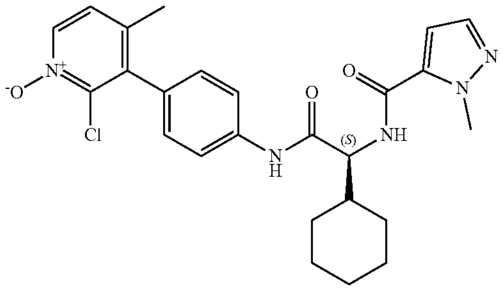 (S)-2-chloro-3-(4-(2-cyclohexyl-2-(1-methyl-1H-pyrazole-5-carboxamido)acetamido)phenyl)-4-methylpyridine 1-oxide | 3-47 | 1-methyl-1H-pyrazole-5-carboxylic acid | Rt = 0.94 min; MS: m/z = 482.3 $[MH]^+$ (Method 2) | 1H NMR (400 MHz, DMSO-d6) δ 10.38 (s, 1H), 8.52 (d, 1H), 8.38 (d, 1H), 7.83-7.72 (m, 2H), 7.46 (d, 1H), 7.37 (dd, 1H), 7.23 (d, 2H), 7.07 (d, 1H), 4.42 (dd, 1H), 4.03 (s, 3H), 2.02 (s, 3H), 1.99 (s, 3H) 1.94-1.57 (m, 6H), 1.04 (m, 2H) ppm |
| 90 | 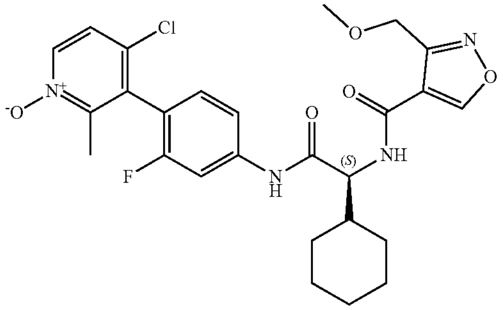 4-chloro-3-(4-((S)-2-cyclohexyl-2-(3-(methoxymethyl)isoxazole-4-carboxamido)acetamido)-2-fluorophenyl)-2-methylpyridine 1-oxide | 3-48 | 3-(methoxy-methyl)1,2 oxazole-4-cabonylic acid | Rt = 1.02; 1.03 min (mixture of atropisomers); MS: m/z = 531 and 533 $[MH]^+$ (Method 3) | 1H NMR (400 MHz, DMSO-d6) δ 10.67 (s, 1H), 9.49 (s, 1H), 8.58 (d, 1H), 8.37 (d, 1H), 7.80 (m, 1H), 7.59 (d, 1H), 7.49 (m, 1H), 7.35 (t, 1H), 4.71 (s, 2H), 4.49 (dd, 1H), 3.36 (s, 3H), 2.15 (s, 3H), 1.83-1.62 (br. m, 6H), 1.26-1.10 (m, 5H) ppm. |
| 91 | 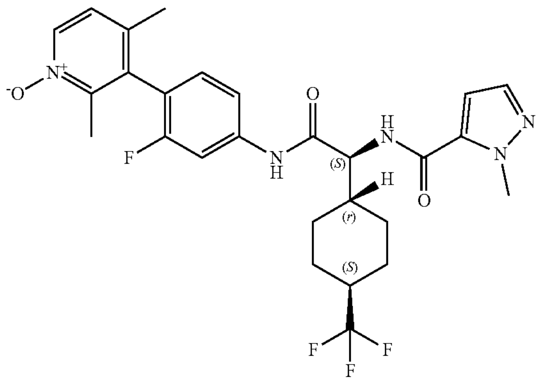 3-(2-fluoro-4-((S)-2-(1-methyl-1H-pyrazole-5-carboxamido)-2-((1r,4S)-4-(trifluoromethyl)cyclohexyl) acetamido)phenyl)-2,4-dimethylpyridine 1-oxide | 3-49 | 1-methyl-1H-pyrazole-5-carboxylic acid | Rt = 1.04 min; MS: m/z = 548 $[MH]^+$ (Method 3) | 1H NMR (400 MHz, DMSO-d6) δ 10.65 (s, 1H), 8.62 (d, 1H), 8.24 (d, 1H), 7.81 (dt, 1H), 7.55-7.44 (m, 2H), 7.31-7.23 (m, 2H), 7.07 (d, 1H), 4.42 (dd, 1H), 4.04 (s, 3H), 2.34-2.19 (br. m, 1H), 2.09 (s, 3H), 1.98 (s, 3H), 1.97-1.83 (br. m, 4H), 1.78-1.71 (br. m, 1H), 1.33-1.09 (m, 4H) ppm. |

-continued

| Example | Structure/Name | Intermediate 3-x | Intermediate 4-x | LC-MS (Method) | 1H NMR |
|---|---|---|---|---|---|
| 92 | 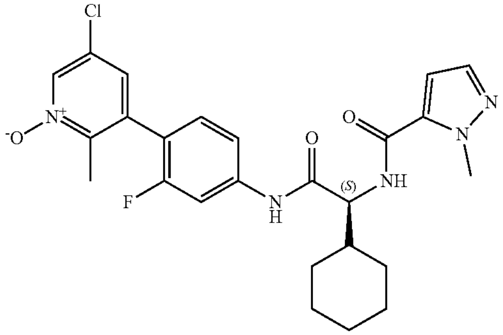 (S)-5-chloro-3-(4-(2-cyclohexyl-2-(1-methyl-1H-pyrazole-5-carboxamido)acetamido)-2-fluorophenyl)-2-methylpyridine 1-oxide | 3-50 | 1-methyl-1H-pyrazole-5-carboxylic acid | Rt = 1.07 min; MS: m/z = 498, and 500 $[MH]^+$ (Method 9) | 1H NMR (400 MHz, DMSO-d6) δ 10.63 (s, 1H), 8.64 (d, 1H), 8.58 (d, 1H), 7.79 (dd, 1H), 7.53-7.36 (m, 4H), 7.07 (d, 1H), 4.39 (dd, 1H), 4.03 (s, 3H), 2.17 (s, 3H), 1.92-1.55 (br. m, 6H), 1.26-0.98 (br. m, 5H) ppm. |
| 93 | 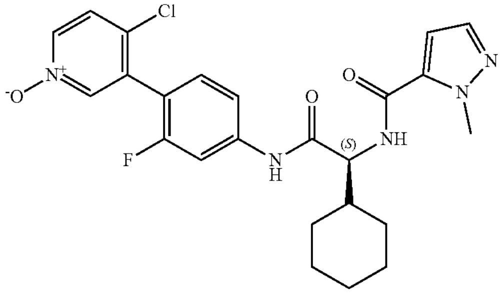 (S)-4-chloro-3-(4-(2-cyclohexyl-2-(1-methyl-1H-pyrazole-5-carboxamido)acetamido)-2-fluorophenyl)pyridine 1-oxide | 3-61 | 1-methyl-1H-pyrazole-5-carboxylic acid | Rt = 1.00 min; MS: m/z = 486.3 $[MH]^+$ (Method 3) | 1H NMR (400 MHz, DMSO-d6) δ 10.64 (s, 1H), 8.58 (d, 1H), 8.35 (d, 1H), 8.27 (dd, 1H), 7.78 (dd, 1H), 7.68 (d, 1H), 7.48 (dd, 2H), 7.42 (m, 1H), 7.07 (d, 1H), 4.39 (dd, 1H), 4.03 (s, 3H), 1.94-1.83 (br. m, 2H), 1.76-1.69 (br. m, 2H), 1.65-1.56 (br. m, 2H), 1.25-0.99 (br. m, 5H) ppm |
| 94 | 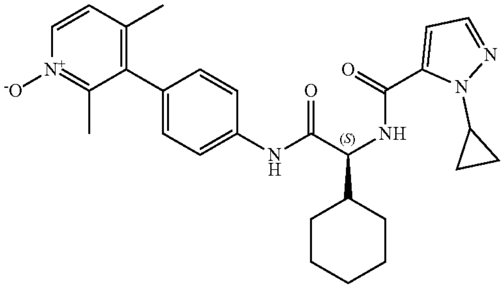 (S)-3-(4-(2-cyclohexyl-2-(1-cyclopropyl-1H-pyrazole-5-carboxamido)acetamido)phenyl)-2,4-dimethylpyridine 1-oxide | 3-48 | 1-cyclopropyl-1H-pyrazole-5-carboxylic acid | Rt = 4.40 min; MS: m/z = 488.3 $[MH]^+$ (Method 4) | 1H NMR (400 MHz, DMSO-d6) δ 10.38 (s, 1H), 8.54 (d, 1H), 8.19 (d, 1H), 7.77 (d, 2H), 7.42 (d, 1H), 7.22 (d, 1H), 7.17 (d, 2H), 6.97 (d, 1H), 4.48-4.37 (m, 2H), 2.08 (s, 3H), 1.97 (s, 3H), 1.93-1.84 (br. m, 2H), 1.77-1.69 (br. m, 2H), 1.67-1.61 (br. m, 2H), 1.23-1.13 (br. m, 4H), 1.16-0.79 (m, 5H). |

-continued

| Example | Structure/Name | Intermediate 3-x | Intermediate 4-x | LC-MS (Method) | 1H NMR |
|---|---|---|---|---|---|
| 95 | 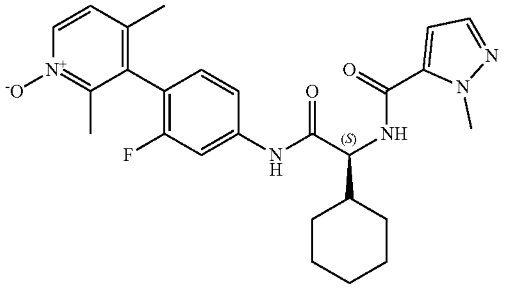 3-(4-((S)-2-cyclohexyl-2-(1-methyl-1H-pyrazole-5-carboxamido)acetamido)-2-fluorophenyl)-2,4-dimethylpyridine 1-oxide | 3-57 | 1-methyl-1H-pyrazole-5-carboxylic acid | Rt = 0.91 min; MS: m/z = 480.2 $[MH]^+$ (Method 1) | 1H NMR (400 MHz, DMSO-d6 ) δ 10.61 (s, 1H), 8.58 (d, 1H), 8.24 (d, 1H), 7.80 (d, 1H), 7.50 (d, 1H), 7.47 (d, 1H), 7.31-7.22 (m, 2H), 7.07 (d, 1H), 4.40 (dd, 1H), 4.03 (s, 3H), 2.09 (d, 3H), 1.98 (s, 3H), 1.91-1.82 (br. m, 2H), 1.77-1.70 (br. m, 2H), 1.67-1.56 (br. m, 2H), 1.24-1.00 (br. m, 5H) ppm. |
| 96 | 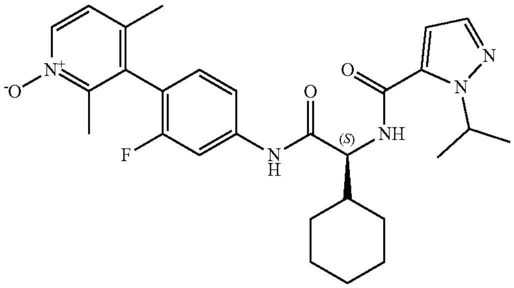 3-(4-((S)-2-cyclohexyl-2-(1-isopropyl-1H-pyrazole-5-carboxamido)acetamido)-2-fluorophenyl)-2,4-dimethylpyridine 1-oxide | 3-56 | 1-isopropyl-1H-pyrazole-5-carboxylic acid | Rt = 1.00 & 1.01 min (Atropisomers); MS: m/z = 508 $[MH]^+$ (Method 1) | 1H NMR (400 MHz, DMSO-d6) δ 10.59 (s, 1H), 8.56 (d, 1H), 8.24 (d, 1H), 7.80 (d, 1H), 7.55-7.47 (m, 2H), 7.34-7.22 (m, 2H), 6.96 (d, 1H), 5.39 (hept, 1H), 4.38 (dd, 1H), 2.10 (s, 3H), 1.99 (s, 3H), 1.93-1.81 (br. m, 2H), 1.77-1.69 (br. m, 2H), 1.66-1.57 (br. m, 2H), 1.37 (d, 3H), 1.35 (d, 3H), 1.19-1.03 (br. m, 5H) ppm. |
| 97 | 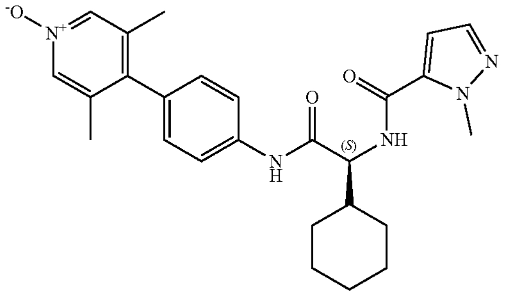 (S)-4-(4-(2-cyclohexyl-2-(1-methyl-1H-pyrazole-5-carboxamido)acetamido)phenyl)-3,5-dimethylpyridine 1-oxide | 3-51 | 1-methyl-1H-pyrazole-5-carboxylic acid | Rt = 0.85 min; MS: m/z = 446.7 $[MH]^+$ (Method 1) | $^1$H NMR (400 MHz, DMSO-$d_6$) δ 10.35 (s, 1H), 8.52 (d, 1H), 8.09 (s, 2H), 7.75 (d, 2H), 7.46 (d, 1H), 7.16 (d, 2H), 7.07 (d, 1H), 4.41 (dt, 1H), 4.03 (s, 3H), 1.94 (s, 6H), 1.89-1.82 (m, 2H), 1.79-1.58 (m, 4H), 1.28-1.12 (m, 4H), 1.12-0.97 (m, 1H) ppm. |

-continued

| Example | Structure/Name | Inter-mediate 3-x | Inter-mediate 4-x | LC-MS (Method) | 1H NMR |
|---|---|---|---|---|---|
| 98 | 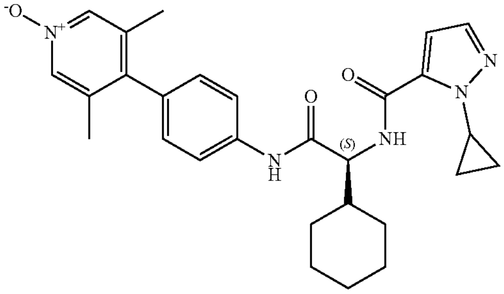 (S)-4-(4-(2-cyclohexyl-2-(1-cyclopropyl-1H-pyrazole-5-carboxamido)acetamido)phenyl)-3,5-dimethylpyridine 1-oxide | 3-51 | 1-cyclopropyl-1H-pyrazole-5-carboxylic acid | Rt = 0.93 min; MS: m/z = 488.4 $[MH]^+$ (Method 1) | $^1$H NMR (400 MHz, DMSO-$d_6$) δ 10.35 (s, 1H), 8.53 (d, 1H), 8.09 (s, 2H), 7.75 (d, 2H), 7.41 (d, 1H), 7.16 (d, 2H), 6.97 (d, 1H), 4.43 (m, 2H), 1.94 (s, 6H), 1.91-1.83 (m, 2H), 1.81-1.55 (m, 4H), 1.31-1.14 (m, 4H), 1.14-0.99 (m, 3H), 0.99-0.86 (m, 2H)ppm. |
| 99 | 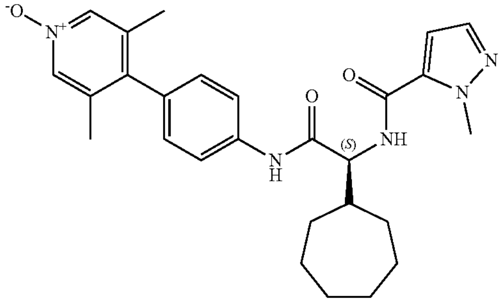 (S)-4-(4-(2-cycloheptyl-2-(1-methyl-1H-pyrazole-5-carboxamido)acetamido)phenyl)-3,5-dimethylpyridine 1-oxide | 3-52 | 1-methyl-1H-pyrazole-5-carboxylic acid | Rt = 0.93 min; MS: m/z = 476.4 $[MH]^+$ (Method 1) | $^1$H NMR (400 MHz, DMSO-$d_6$) δ 10.35 (s, 1H), 8.53 (d, 1H), 8.09 (s, 2H), 7.75 (d, 2H), 7.46 (d, 1H), 7.16 (d, 2H), 7.06 (d, 1H), 4.49 (dd, 1H), 4.04 (s, 3H), 2.22-2.05 (m, 1H), 1.94 (s, 6H), 1.83-1.74 (m, 1H), 1.73-1.62 (m, 3H), 1.61-1.27 (m, 8H) ppm. |
| 100 | 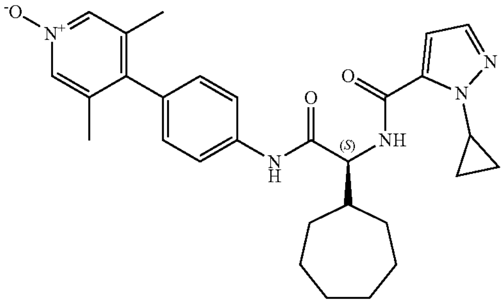 (S)-4-(4-(2-cycloheptyl-2-(1-cyclopropyl-1H-pyrazole-5-carboxamido)acetamido)phenyl)-3,5-dimethylpyridine 1-oxide | 3-52 | 1-cyclopropyl-1H-pyrazole-5-carboxylic acid | Rt = 0.99 min; MS: m/z = 502.2 $[MH]^+$ (Method 2) | $^1$H NMR (400 MHz, DMSO-$d_6$) δ 10.36 (s, 1H), 8.54 (d, 1H), 8.09 (s, 2H), 7.75 (d, 2H), 7.41 (d, 1H), 7.16 (d, 2H), 6.96 (d, 1H), 4.51 (dt, 1H), 4.46-4.36 (m, 1H), 2.20-2.07 (m, 1H), 1.94 (s, 6H), 1.83-1.74 (m, 1H), 1.73-1.63 (m, 3H), 1.62-1.30 (m, 8H), 1.16-1.00 (m, 2H), 0.99-0.85 (m, 2H) ppm. |

-continued

| Example | Structure/Name | Intermediate 3-x | Intermediate 4-x | LC-MS (Method) | 1H NMR |
|---|---|---|---|---|---|
| 101 | 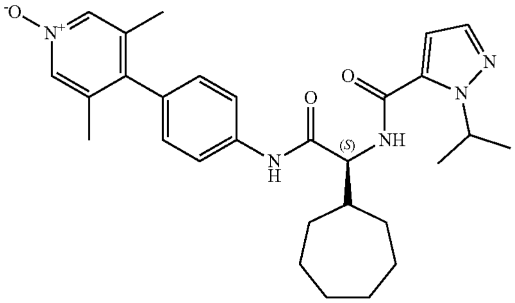 (S)-4-(4-(2-cycloheptyl-2-(1-isopropyl-1H-pyrazole-5-carboxamido)acetamido)phenyl)-3,5-dimethylpyridine 1-oxide | 3-52 | 1-isopropyl-1H-pyrazole-5-carboxylic acid | Rt = 1.03 min; MS: m/z = 504.4 $[MH]^+$ (Method 1) | $^1$H NMR (400 MHz, DMSO-$d_6$) δ 10.34 (s, 1H), 8.51 (d, 1H), 8.09 (s, 2H), 7.75 (d, 2H), 7.49 (d, 1H), 7.16 (d, 2H), 6.94 (d, 1H), 5.39 (hept, 1H), 4.48 (dd, 1H), 2.19-2.06 (m, 1H), 1.94 (s, 6H), 1.83-1.74 (m, 1H), 1.72-1.62 (m, 3H), 1.60-1.38 (m, 8H), 1.37 (d, 3H), 1.34 (d, 3H) ppm |
| 102 | 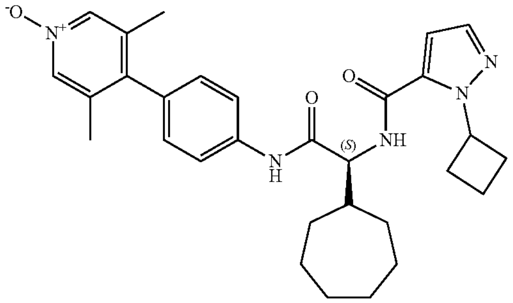 (S)-4-(4-(2-(1-cyclobutyl-1H-pyrazole-5-carboxamido)-2-cycloheptylacetamido)phenyl)-3,5-dimethylpyridine 1-oxide | 3-52 | 1-cyclobutyl-1H-pyrazole-5-carboxylic acid | Rt = 1.07 min; MS: m/z = 516.3 $[MH]^+$ (Method 1) | $^1$H NMR (400 MHz, DMSO-$d_6$) δ 10.33 (s, 1H), 8.52 (d, 1H), 8.09 (s, 2H), 7.75 (d, 2H), 7.54 (d, 1H), 7.16 (d, 2H), 6.98 (d, 1H), 5.66-5.47 (m, 1H), 4.47 (dd, 1H), 2.58-2.44 (m, 2H), 2.39-2.24 (m, 2H), 2.19-2.05 (m, 1H), 1.94 (s, 6H), 1.84-1.60 (m, 6H), 1.58-1.30 (m, 8H) ppm |
| 103 | 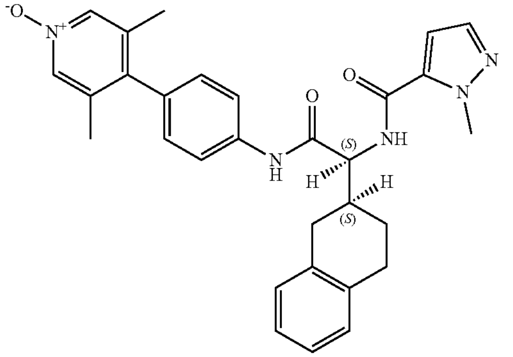 3,5-dimethyl-4-(4-((S)-2-(1-methyl-1H-pyrazole-5-carboxamido)-2-((S)-1,2,3,4-tetrahydronaphthalen-2-yl)acetamido)phenyl)pyridine 1-oxide | 3-53 | 2-12 | Rt = 0.92 min; MS: m/z = 510.1 $[MH]^+$ (Method 1) | $^1$H NMR (400 MHz, DMSO-$d_6$) δ 10.49 (s, 1H), 8.71 (d, 1H), 8.18 (s, 2H), 7.79 (d, 2H), 7.48 (d, 1H), 7.18 (d, 2H), 7.12 (d, 1H), 7.10-7.04 (m, 4H), 4.60 (dd, 1H), 4.06 (s, 3H), 3.01-2.83 (m, 2H), 2.84-2.57 (m, 2H), 2.45-2.28 (br. m, 1H), 1.97 (s, 6H), 1.93-1.85 (br. m, 1H), 1.69-1.49 (m, 1H) ppm |

-continued

| Example | Structure/Name | Inter-mediate 3-x | Inter-mediate 4-x | LC-MS (Method) | 1H NMR |
|---|---|---|---|---|---|
| 104 | 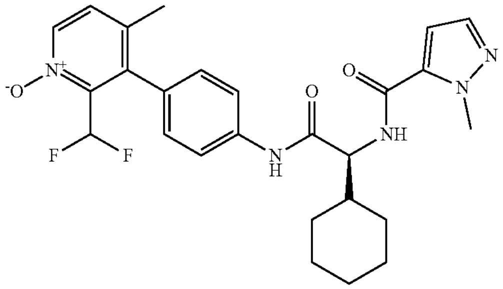 (S)-3-(4-(2-cyclohexyl-2-(1-methyl-1H-pyrazole-5-carboxamido)acetamido)phenyl)-2-(difluoromethyl)-4-methylpyridine 1-oxide | 3-42 | 1-methyl-1H-pyrazole-5-carboxylic acid | Rt = 1.39 min; MS: m/z = 498.4 $[MH]^+$ (Method 14) | 1H NMR (300 MHz, DMSO-d6) δ 8.31 (d, 1H), 7.77-7.70 (m, 2H), 7.54 (d, 1H), 7.47 (m, 1H), 7.27-7.09 (m, 3H), 6.90 (d, 1H), 4.47 (d, 1H), 4.08 (s, 3H), 2.08 (s, 3H), 1.95-1.92 (m, 2H), 1.82-1.72 (m, 4H), 1.31-1.15 (m, 6H). |
| 105 | 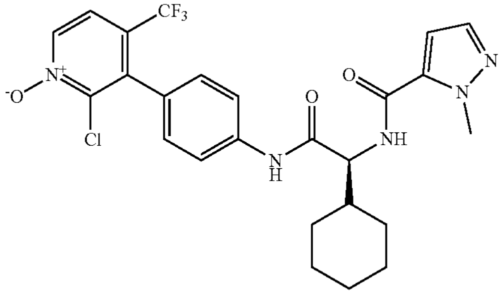 (S)-4-(4-(2-cyclohexyl-2-(1-methyl-1H-pyrazole-5-carboxamido)acetamido)phenyl)-3-methylpyridine 1-oxide | 3-58 | 1-methyl-1H-pyrazole-5-carboxylic acid | Rt = 1.05 min; MS: m/z = 504 and 506 $[MH]^+$ (Method 5) | 1H NMR (300 MHz, DMSO-d6) δ 10.41 (s, 1H), 8.65 (d, 1H), 8.52 (d, 1H), 7.82 (d, 1H), 7.79-7.71 (m, 2H), 7.45 (d, 1H), 7.29 (d, 2H), 7.06 (d, 1H), 4.42 (dd, 1H), 4.03 (s, 3H), 1.94-1.81 (br. m, 2H), 1.73 (br. m, 2H), 1.62 (br. m, 2H), 1.62-0.99 (br. m, 5H) ppm. |
| 106 | 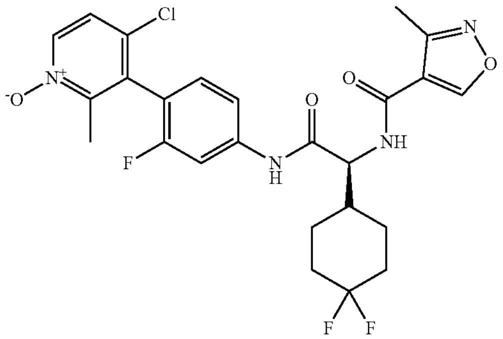 4-chloro-3-(4-((S)-2-(4,4-difluorocyclohexyl)-2-(3-methylisoxazole-4-carboxamido)acetamido)-2-fluorophenyl)-2-methylpyridine 1-oxide | 3-31 | 3-methylisoxazole-4-carboxylic acid | Rt = 0.92 min; MS: m/z = 537 and 539 $[MH]^+$ (Method 5) | 1H NMR (400 MHz, DMSO-d6) δ 10.70 (s, 1H), 9.44 (s, 1H), 8.67 (d, 1H), 8.37 (d, 1H), 7.81 (m, 1H), 7.59 (d, 1H), 7.49 (m, 1H), 7.35 (m, 1H), 4.51 (dd, 1H), 2.37 (s, 3H), 2.14 (s, 3H), 2.10-1.69 (br. m, 7H), 1.50-1.31 (m, 2H) ppm. |

-continued

| Example | Structure/Name | Intermediate 3-x | Intermediate 4-x | LC-MS (Method) | 1H NMR |
|---|---|---|---|---|---|
| 107 | 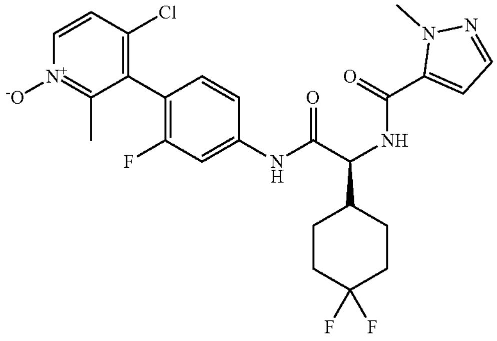<br>4-chloro-3-(4-((S)-2-(4,4-difluorocyclohexyl)-2-(1-methyl-1H-pyrazole-5-carboxamido)acetamido)-2-fluorophenyl)-2-methylpyridine 1-oxide | 3-31 | 1-methyl-1H-pyrazole-5-carboxylic acid | Rt = 0.94 min; MS: m/z = 536 and 538 $[MH]^+$ (Method 3) | 1H NMR (400 MHz, DMSO-d6) δ 10.71 (s, 1H), 8.73 (br. d, 1H), 8.36 (d, 1H), 7.83 (d, 1H), 7.59 (d, 1H), 7.48 (m, 1H), 7.07 (d, 1H), 4.48 (dd, 1H), 4.03 (s, 3H), 2.15 (s, 3H), 2.12-1.67 (br. m, 7H), 1.50-1.28 (m, 2H) ppm. |
| 108 | 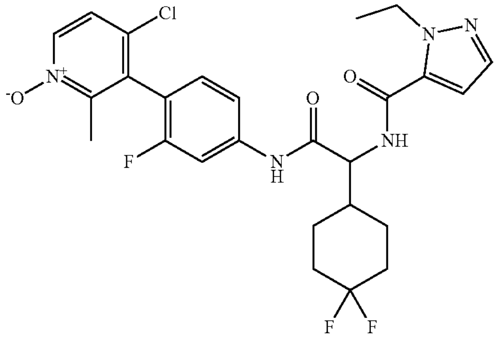<br>4-chloro-3-(4-(2-(4,4-difluorocyclohexyl)-2-(1-ethyl-1H-pyrazole-5-carboxamido)acetamido)-2-fluorophenyl)-2-methylpyridine 1-oxide | 3-31 | 1-ethyl-1H-pyrazole-5-carboxylic acid | Rt = 1.00 min; MS: m/z = 548 and 550 $[MH]^+$ (Method 3) | 1H NMR (400 MHz, DMSO-d6) δ 10.70 (s, 1H), 8.73 (d, 1H), 8.36 (d, 1H), 7.82 (dd, 1H), 7.58 (d, 1H), 7.48 (m, 2H), 7.35 (m, 1H), 7.02 (d, 1H), 4.51-4.43 (m, 3H), 2.12 (s, 3H), 2.12-1.67 (br. m, 7H), 1.51-1.32 (m, 2H), 1.28 (t, 3H) ppm. |
| 109 | 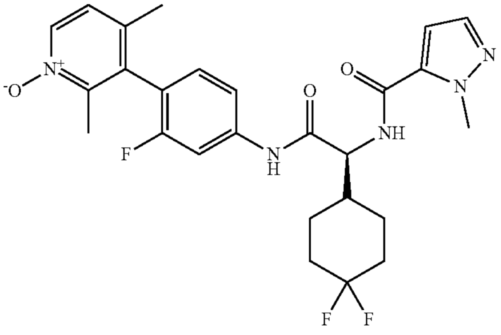<br>3-(4-((S)-2-(4,4-difluorocyclohexyl)-2-(1-methyl-1H-pyrazole-5-carboxamido)acetamido)-2-fluorophenyl)-2,4-dimethylpyridine 1-oxide | 3-46 | 1-methyl-1H-pyrazole-5-carboxylic acid | Rt = 0.91 min; MS: m/z = 516.2 $[MH]^+$ (Method 2) | 1H NMR (400 MHz, DMSO-d6) δ 10.66 (s, 1H), 8.72 (br. d, 1H), 8.24 (d, 1H), 7.80 (d, 1H), 7.49 (m, 2H), 7.29 (d, 1H), 7.26 (d, 1H), 7.07 (d, 1H), 4.48 (dd, 1H), 4.04 (s, 3H), 2.09 (s, 3H), 2.08-2.01 (br. m, 2H), 1.98 (s, 3H), 1.97-1.67 (br. m, 5H), 1.51-1.28 (m, 2H) ppm |

-continued

| Example | Structure/Name | Inter-mediate 3-x | Inter-mediate 4-x | LC-MS (Method) | 1H NMR |
|---|---|---|---|---|---|
| 110 | 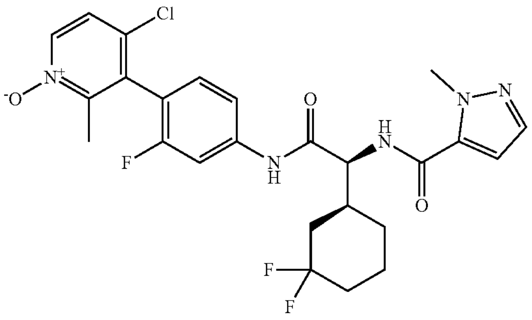 4-chloro-3-(4-((S)-2-((S)-3,3-difluorocyclohexyl)-2-(1-methyl-1H-pyrazole-5-carboxamido)acetamido)-2-fluorophenyl)-2-methylpyridine 1-oxide | 3-56 | 1-methyl-1H-pyrazole-5-carboxylic acid | Rt = 0.91 min; MS: m/z = 516.2 $[MH]^+$ (Method 2) | 1H NMR (400 MHz, DMSO-d6) δ 10.70 (s, 1H), 8.70 (d, 1H), 8.37 (d, 1H), 7.82 (dd, 1H), 7.59 (d, 1H), 7.53-7.46 (m, 2H), 7.36 (m, 1H), 7.10 (d, 1H), 4.59 (dd, 1H), 4.04 (s, 3H), 2.31-2.09 (br. m, 2H), 2.15 (s, 3H), 2.00 (br. m, 1H), 1.90-1.59 (m, 4H), 1.50-1.20 (m, 2H). |

Example 111

(S)-4-(4-(2-cyclohexyl-2-(1-methyl-1H-pyrazole-5-carboxamido)acetamido)phenyl)-3-methylpyridine I-oxide

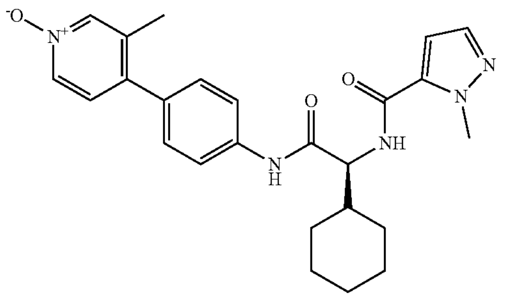

To a solution of (S)-(4-(2-cyclohexyl-2-(1-methyl-1H-pyrazole-5-carboxamido)acetamido)phenyl)boronic acid (Intermediate 4-2; 80 mg, 0.146 mmol) and PdCl2(dppf).DCM (12 mg, 0.015 mmol) in dioxane (1.5 mL) was added 4-bromo-3-methylpyridine 1-oxide (41 mg, 0.22 mmol) and 2M aq. $Na_2CO_3$ (0.3 mL). The mixture was purged with Ar and then heated to 100° C. for 2 h. After cooling, the mixture was diluted with EtOAc and washed successively with sat. $NaHCO_3$, water, and brine. The organic layer was dried ($Na_2SO_4$) and evaporated. The residue was purified by SFC (column: 250x30Reprospher PEI 100 A 5 um, elution with 10-20% MeOH) to yield the title compound (21 mg, 32%) as an off-white solid.

LC-MS: Rt=0.84 min; MS: m/z=448.2 $[MH]^+$ (Method 1).

1H NMR (400 MHz, DMSO-d6) δ 10.37 (s, 1H), 8.52 (d, 1H), 8.22 (d, 1H), 8.09 (dd, 1H), 7.74 (d, 2H), 7.46 (d, 1H), 7.38 (d, 2H), 7.25 (d, 1H), 7.07 (d, 1H), 4.41 (dd, 1H), 4.03 (s, 3H), 2.21 (s, 3H), 1.94-1.81 (br. m, 2H), 1.75-1.69 (br. m, 2H), 0.66-1.57 (br. m, 2H), 1.31-0.95 (br. m, 5H) ppm.

Example 112

(S)-4-chloro-3-(4-(2-cyclohexyl-2-(1-methyl-1H-pyrazole-5-carboxamido)acetamido)phenyl)pyridine 1-oxide

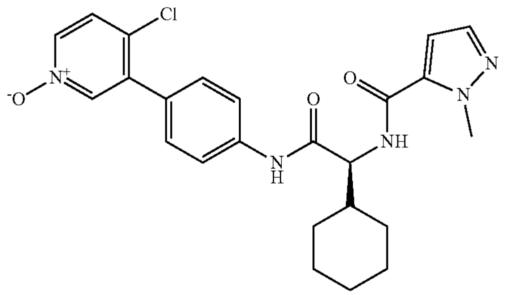

The title compound was prepared by a two-step sequence involving 1.) Suzuki-coupling of Intermediate 4-2 and 3-bromo-4-chloropyridine following a procedure similar to that of Example 111, and 2.) oxidation to the pyridine N-oxide with mCPBA following a procedure similar to that of Example 82, Step 2.

LC-MS: Rt=4.30 min; MS: m/z=468 and 470 $[MH]^+$ (Method 4).

1H NMR (400 MHz, DMSO-d6) δ 10.43 (s, 1H), 8.54 (d, 1H), 8.27 (d, 1H), 8.21 (dd, 1H), 7.77 (d, 2H), 7.65 (d, 1H), 7.46 (dd, 3H), 7.07 (d, 1H), 4.42 (dt, 1H), 4.03 (s, 3H), 1.87 (t, 2H), 1.71 (m, 2H), 1.62 (m, 2H), 1.16 (m, 4H), 1.03 (m, 1H) ppm.

Example 113

(S)-3-(4-(2-cyclohexyl-2-(1-methyl-1H-pyrazole-5-carboxamido)acetamido)phenyl)-2,5-dimethylpyridine 1-oxide

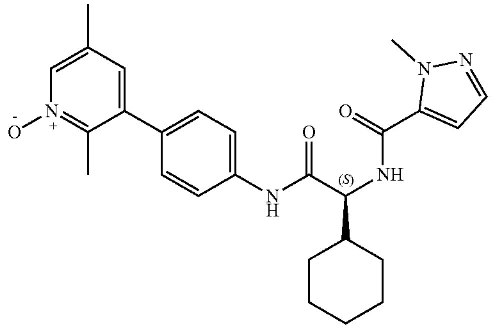

The title compound was prepared by a two-step sequence involving 1.) Suzuki-coupling of Intermediate 4-2 and 3-bromo-2,5-dimethylpyridine following a procedure similar to that of Example 111, and 2.) oxidation to the pyridine N-oxide with mCPBA following a procedure similar to that of Example 82, Step 2.

LC-MS: Rt=0.96 min; MS: m/z=462.5 $[MH]^+$ (Method 3).

1H NMR (400 MHz, DMSO-d6) δ 10.37 (s, 1H), 8.52 (d, 1H), 8.20 (d, 1H), 7.75 (d, 2H), 7.46 (d, 1H), 7.34 (d, 2H), 7.07 (d, 1H), 7.05 (s, 1H), 4.42 (dd, 1H), 4.03 (s, 3H), 2.25 (s, 6H), 1.93-1.81 (m, 2H), 1.74-1.55 (m, 4H), 1.25-1.03 (m, 1H) ppm.

Example 114

(S)-3-(4-(2-cyclohexyl-2-(1-methyl-1H-pyrazole-5-carboxamido)acetamido)phenyl)-2-fluoro-4-methylpyridine 1-oxide

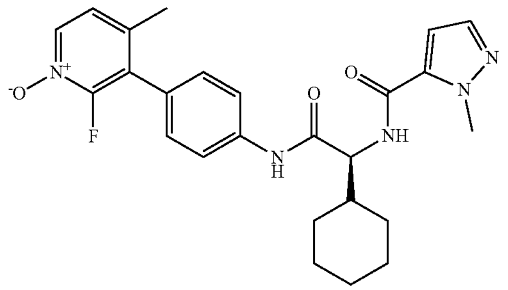

The title compound was prepared by a two-step sequence involving 1.) Suzuki-coupling of Intermediate 4-2 and 3-bromo-2-fluoropyridine following a procedure similar to that of Example 111, and 2.) oxidation to the pyridine N-oxide with mCPBA following a procedure similar to that of Example 82, Step 2.

LC-MS: Rt=4.30 min; MS: m/z=466.3 $[MH]^+$ (Method 4).

1H NMR (400 MHz, DMSO-d6) δ 10.40 (s, 1H), 8.52 (d, 1H), 8.28 (t, 1H), 7.77 (d, 2H), 7.46 (d, 1H), 7.35 (d, 2H), 7.27 (d, 1H), 7.07 (d, 1H), 4.42 (dd, 1H), 4.04 (s, 3H), 2.12 (s, 3H), 1.88 (br. m, 2H), 1.75-1.58 (br. m, 4H) 1.28-1.02 (br. m, 5H) ppm.

Example 115

(S)-3-(4-(2-cyclohexyl-2-(1-methyl-1H-pyrazole-5-carboxamido)acetamido)phenyl)-5-(hydroxymethyl)-2-methylpyridine 1-oxide

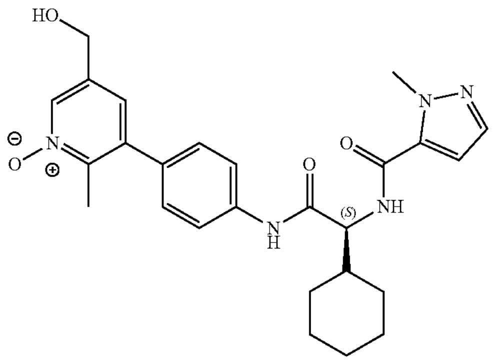

Step 1: (S)—N-(2-((4-(5-(((tert-butyldimethylsilyl)oxy)methyl)-2-methylpyridin-3-yl)phenyl)amino)-1-cyclohexyl-2-oxoethyl)-1-methyl-1H-pyrazole-5-carboxamide The title compound was prepared by Suzuki-coupling of Intermediate 4-2 and Intermediate 4-3 following a procedure similar to that of Example 111.

LC-MS: Rt=1.34 min; MS: m/z=576.5 $[MH]^+$ (Method 3).

Step 2: (S)—N-(1-cyclohexyl-2-((4-(5-(hydroxymethyl)-2-methylpyridin-3-yl)phenyl)amino)-2-oxoethyl)-1-methyl-1H-pyrazole-5-carboxamide (S)—N-(2-((4-(5-(((tert-butyldimethylsilyl)oxy)methyl)-2-methylpyridin-3-yl)phenyl)amino)-1-cyclohexyl-2-oxoethyl)-1-methyl-1H-pyrazole-5-carboxamide (Step 1; 545 mg, 0.946 mmol) was treated with 1 M TBAF in THF (9465 µl, 9.46 mmol). After stirring at RT for 20 h HPLC-MS indicated complete conversion of the starting material The reaction mixture was diluted with EtOAc and extracted with sat. aq. $Na_2CO_3$ solution, and with brine. The aqueous layers were re-extracted with EtOAc and the combined organic layers were evaporated. The residue was purified by column chromatography on silica (column: Redisep 40 g; elution with 0 to 100% EtOAc in DCM, then with 10% MeOH in EtOAc) to yield the title compound (430 mg, 99%) as a colorless solid.

LC-MS: Rt=0.76 min: MS: m/z=462.5 $[MH]^+$ (Method 5)

Step 3: (S)-3-(4-(2-cyclohexyl-2-(1-methyl-1H-pyrazole-5-carboxamido)acetamido)phenyl)-5-(hydroxymethyl)-2-methylpyridine 1-oxide The title compound was prepared from (S)—N-(1-cyclohexyl-2-((4-(5-(hydroxymethyl)-2-methylpyridin-3-yl)phenyl)amino)-2-oxoethyl)-1-methyl-1H-pyrazole-5-carboxamide (Step 2) and mCPBA following a procedure similar to that of Example 82, Step 2.

LC-MS: Rt=0.82 min; MS: m/z=478.3 $[MH]^+$ (Method 5).

1H NMR (400 MHz, DMSO-d6) δ 10.39 (s, 1H), 8.53 (d, 1H), 8.22 (s, 1H), 7.76 (d, 2H), 7.46 (d, 1H), 7.36 (d, 2H), 7.13 (s, 1H), 7.07 (d, 1H), 4.49 (s, 2H), 4.43 (dd, 1H), 4.03 (s, 3H), 2.28 (s, 3H), 1.93-1.80 (br. m, 2H), 1.77-1.68 (br. m, 2H), 1.66-1.56 (br. m, 2H), 1.25-0.98 (br. m, 5H) ppm.

Example 116: (S)-4-(4-(2-cycloheptyl-2-(1,2,3,4-tetrahydropyrrolo[1,2-a]pyrazine-6-carboxamido) acetamido)phenyl)-3,5-dimethylpyridine 1-oxide

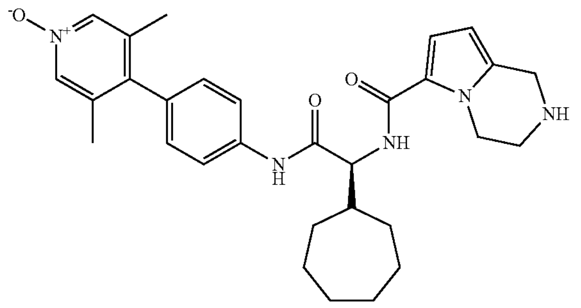

Step 1: (S)-tert-butyl 6-((1-cycloheptyl-2-((4-(3,5-dimethylpyridin-4-yl)phenyl)amino)-2-oxoethyl) carbamoyl)-3,4-dihydropyrrolo[1,2-a]pyrazine-2 (1H)-carboxylate The title compound was prepared from Intermediate 3-52 and 2-Boc-3,4-dihydro-1H-pyrrolo(1,2a)pyrazine-6-carboxylic acid by a procedure similar to that of Example 1.

LC-MS: Rt=1.29 min; MS: m/z=600.4 $[MH]^+$ (Method 1).

$^1$H NMR (400 MHz, DMSO-$d_6$) δ 10.25 (s, 1H), 8.32 (s, 2H), 7.90 (d, 1H), 7.75 (d, 2H), 7.13 (d, 2H), 7.03 (d, 1H), 5.95 (d, 1H), 4.53 (s, 2H), 4.44 (dd, 1H), 4.39-4.23 (m, 2H), 3.73-3.55 (m, 2H), 2.19-2.06 (m, 1H), 1.99 (s, 6H), 1.83-1.72 (m, 1H), 1.71-1.61 (m, 3H), 1.60-1.29 (m, 9H), 1.42 (s, 9H) ppm.

Step 2: (S)-4-(4-(2-(2-(tert-butoxycarbonyl)-1,2,3,4-tetrahydropyrrolo[1,2-a]pyrazine-6-carboxamido)-2-cycloheptylacetamido)phenyl)-3,5-dimethylpyridine 1-oxide To a solution of (S)-tert-butyl 6-((1-cycloheptyl-2-((4-(3,5-dimethylpyridin-4-yl)phenyl)amino)-2-oxoethyl)carbamoyl)-3,4-dihydropyrrolo[1,2-a]pyrazine-2(1H)-carboxylate (Step 1, 81 mg, 0.135 mmol) in THF (2.7 mL) was added dropwise at RT a solution of mCPBA (60 mg, 0.270 mmol) in THF (1.8 mL). After stirring at RT for 2 h the mixture was diluted with EtOAc and washed with sat. aq. $NaHCO_3$ (80 mL), water and brine. The organic phase was dried ($Na_2SO_4$) and concentrated under reduced pressure. The residue was purified by column chromatography on silica (RediSep 12 g; 5% to 100% EtOAc in heptane) to yield the title compound (68 mg, 70%) as a white foam.

LC-MS: Rt=1.20 min; MS: m/z=616.4 $[MH]^+$ (Method 1).

$^1$H NMR (400 MHz, DMSO-$d_6$) δ 10.27 (s, 1H), 8.09 (s, 2H), 7.91 (d, 1H), 7.74 (d, 2H), 7.15 (d, 2H), 7.03 (d, 1H), 5.95 (d, 1H), 4.53 (s, 1H), 4.43 (dd, 1H), 4.39-4.24 (m, 1H), 3.69-3.57 (m, 1H), 2.16-2.02 (m, 1H), 1.94 (s, 7H), 1.82-1.73 (m, 1H), 1.72-1.60 (m, 3H), 1.60-1.27 (m, 10H) 1.42 (s, 9H) ppm.

Step 3: (S)-4-(4-(2-cycloheptyl-2-(1,2,3,4-tetrahydropyrrolo[1,2-a]pyrazine-6-carboxamido)acetamido)phenyl)-3,5-dimethylpyridine 1-oxide To a solution of (S)-4-(4-(2-(2-(tert-butoxycarbonyl)-1,2,3,4-tetrahydropyrrolo[1,2-a]pyrazine-6-carboxamido)-2-cycloheptylacetamido)phenyl)-3,5-dimethylpyridine 1-oxide (Step 2; 60 mg, 0.097 mmol) in DCM (1 mL) was added TFA (75 uL, 0.974 mmol) and the mixture was stirred at RT overnight. The reaction was quenched by addition of sat. aq. $NaHCO_3$ and extracted with DCM/2-propanol. The combined organic phases were dried ($Na_2SO_4$) and evaporated. The residue was purified by SFC (column: 250×30Reprospher PEI 100 A 5 um; gradient: 26-36% MeOH in 10 min) to yield the title compound (14 mg, 26%) as an off-white solid.

LC-MS: Rt=0.72 min; MS: m/z=516.3 $[MH]^+$ (Method 1)

$^1$H NMR (400 MHz, DMSO-$d_6$) δ 10.24 (s, 1H), 8.09 (s, 2H), 7.80-7.70 (m, 3H), 7.15 (d, 2H), 6.96 (d, 1H), 5.78 (d, 1H), 4.42 (t, 1H), 4.24-4.04 (m, 2H), 3.86 (s, 2H), 3.05-2.93 (m, 2H), 2.16-2.03 (m, 1H), 1.94 (s, 6H), 1.82-1.72 (m, 1H), 1.71-1.60 (m, 3H), 1.60-1.28 (m, 9H) ppm.

Example 117: (S)-4-(4-(2-cycloheptyl-2-(2-methyl-1,2,3,4-tetrahydropyrrolo[1,2-a]pyrazine-6-carboxamido)acetamido)phenyl)-3,5-dimethylpyridine 1-oxide

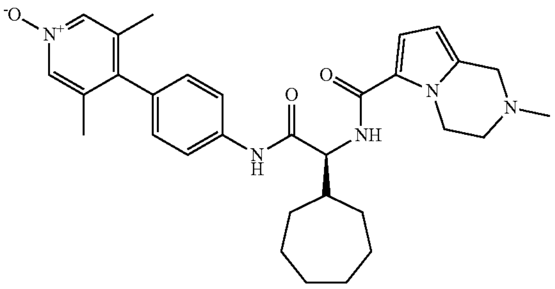

To a solution of (S)-4-(4-(2-cycloheptyl-2-(1,2,3,4-tetrahydropyrrolo[1,2-a]pyrazine-6-carboxamido)acetamido) phenyl)-3,5-dimethylpyridine 1-oxide (Example 116, 60 mg, 0.116 mmol in methanol (1.2 mL) was added 37% aqueous formaldehyde (55 uL, 0.698 mmol, 6 eq). After stirring the mixture for 10 min at RT, sodium cyanoborohydride (37 mg, 0.582 mmol, 5 eq) and acetic acid (13 uL, 0.233 mmol, 2 eq) were added. After stirring at RT for 3 h, the reaction was quenched by addition of aq. sat. $NaHCO_3$ and extracted with DCM/isopropanol 4:1. The combined organic phases were dried ($Na_2SO_4$) and evaporated. The residue was purified by SFC (column: 250×30 Reprosphere PEI 100 A 5 um; gradient: 12-20% MeOH in 10 min) to yield the title compound (13 mg, 21%) as a colorless solid.

LC-MS: Rt=0.74 min; MS: m/z=530.6 $[MH]^+$ (Method 2).

$^1$H NMR (400 MHz, DMSO-$d_6$) δ 10.24 (s, 1H), 8.09 (s, 2H), 7.81 (d, 1H), 7.74 (d, 2H), 7.15 (d, 2H), 6.98 (d, 1H), 5.81 (d, 1H), 4.42 (dd, 1H), 4.35-4.24 (m, 1H), 4.24-4.13 (m,

1H), 3.50 (s, 2H), 2.67 (t, 2H), 2.31 (s, 3H), 2.16-2.02 (m, 1H), 1.94 (s, 6H), 1.84-1.72 (m, 1H), 1.72-1.61 (m, 3H), 1.58-1.27 (m, 8H) ppm.

Example 118

(S)-4-(4-(2-(2-acetyl-1,2,3,4-tetrahydropyrrolo[1,2-a]pyrazine-6-carboxamido)-2-cycloheptylacetamido)phenyl)-3,5-dimethylpyridine 1-oxide

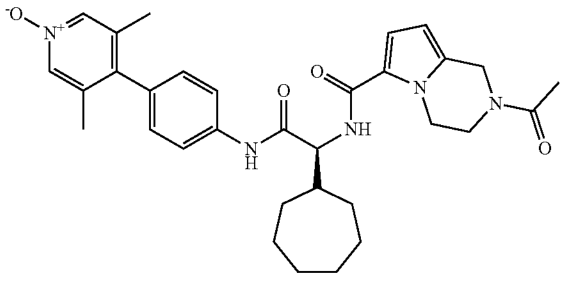

To a cooled (0° C.) solution of (S)-4-(4-(2-cycloheptyl-2-(1,2,3,4-tetrahydropyrrolo[1,2-a]pyrazine-6-carboxamido)acetamido)phenyl)-3,5-dimethylpyridine 1-oxide (Example 116; 60 mg, 0.116 mmol) and N-ethyldiisopropylamine (61 uL, 0.349 mmol) in THF (1 mL) was added dropwise a solution of acetyl chloride (11 uL, 0.151 mmol) in THF (160 uL). After stirring at 0° C. for 2 h, the mixture was was diluted with EtOAc and washed with sat. aq. $NaHCO_3$, water and brine. The organic phase was dried ($Na_2SO_4$) and concentrated under reduced pressure. The residue was purified by SFC (column: 250×30Reprospher PEI 100A 5 um; gradient: 14-22% MeOH in 10 min) to yield the title compound (10 mg, 15%) as a colorless solid.

LC-MS: Rt=0.92 min; MS: m/z=558.4 $[MH]^+$ (Method 2).

$^1H$ NMR (400 MHz, DMSO-$d_6$) δ 10.30 (s, 1H), 8.09 (s, 2H), 7.95 (dd, 1H), 7.75 (d, 2H), 7.15 (d, 2H), 7.04 (m, 1H), 6.01-5.86 (m, 1H), 4.71 (s, 1H), 4.61 (s, 1H), 4.49-4.23 (m, 3H), 3.84-3.67 (m, 2H), 2.18-2.04 (m, 1H), 2.08 (s, 3H), 1.94 (s, 6H), 1.84-1.73 (m, 1H), 1.70-1.61 (m, 3H), 1.60-1.24 (m, 8H) ppm.

The following Examples were prepared by a three step sequence of 1.) amide bond formation of Intermediate 3-X and the corresponding carboxylic acids, 2.) N-Boc deprotection and 3.) reductive amination by procedures similar to that of Example 117.

| Example | Structure/Name | Intermediate 3-x | Carboxylic acid | LC-MS (Method) | 1H NMR |
|---|---|---|---|---|---|
| 119 | 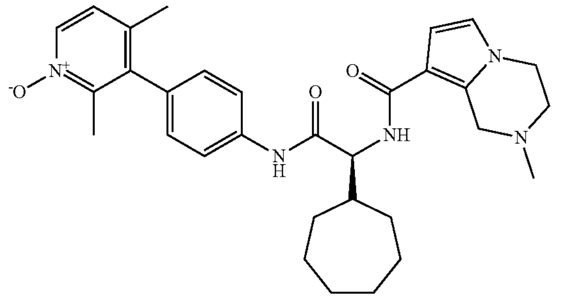 (S)-3-(4-(2-cycloheptyl-2-(2-methyl-1,2,3,4-tetrahydropyrrolo[1,2-a]pyrazine-8-carboxamido)acetamido)phenyl)-2,4-dimethylpyridine 1-oxide | 3-15 | 2-(tert-butoxycarbonyl)-1,2,3,4-tetrahydro-pyrrolo[1,2-a]pyrazine-8-carboxylic acid | Rt = 3.52 min; MS: m/z = 530.2 $[MH]^+$ (Method 4) | 1H NMR (400 MHz, DMSO-d6) δ 10.23 (s, 1H), 8.19 (d, 1H), 7.76 (d, 2H), 7.52 (d, 1H), 7.22 (d, 1H), 7.16 (d, 2H), 6.71 (d, 1H), 6.64 (d, 1H), 4.43 (dd, 1H), 3.93 (t, 2H), 3.74 (d, 2H), 2.69 (t, 2H) 2.35 (s, 3H), 2.08 (s, 4H), 1.96 (s, 3H), 1.24-1.85 (m, 12H) ppm |
| 120 | 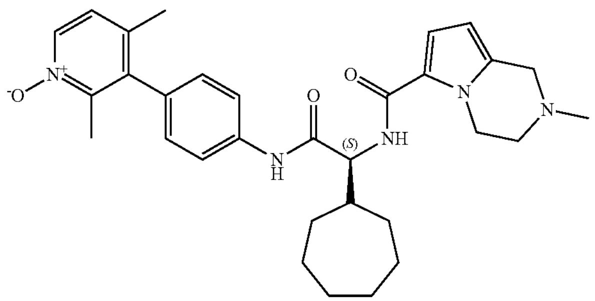 | 3-15 | 2-(tert-butoxycarbonyl)-1,2,3,4-tetrahydro-pyrrolo[1,2-a]pyrazine-6-carboxylic acid | Rt = 3.87 min; MS: m/z = 530.3 $[MH]^+$ (Method 4) | 1H NMR (400 MHz, DMSO-d6) δ ppm 10.26 (s, 1H), 8.19 (d, 1H), 7.80 (d, 1H), 7.76 (d, 2H), 7.21 (d, 1H), 7.16 (d, 2H), 6.99 (d, 1H), 5.81 (d, 1H), 4.43 (dd, 1H) 4.34-4.15 (m, 2H) 3.50 (s, 2H) 3.17 (d, 1H), 2.67 (m, 2H), 2.31 (s, 3H), 2.13-2.05 (m, 1H), 2.08 (s, 3H), 1.96 (s, 3H), 1.84-1.73 (m, 1H), 1.70-1.62 (m, |

-continued

| Example | Structure/Name | Inter-mediate 3-x | Carboxylic acid | LC-MS (Method) | 1H NMR |
|---|---|---|---|---|---|
| | (S)-3-(4-(2-cycloheptyl-2-(2-methyl-1,2,3,4-tetrahydropyrrolo[1,2-a]pyrazine-6-carboxamido)acetamido) phenyl)-2,4-dimethylpyridine 1-oxide | | | | 3H), 1.56-1.29 (m, 7H) ppm |
| 121 | 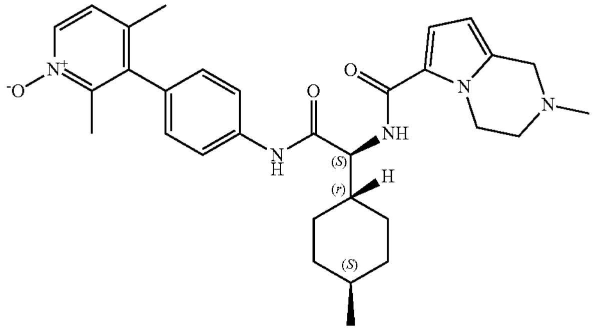 2,4-dimethyl-3-(4-((S)-2-(2-methyl-1,2,3,4-tetrahydropyrrolo[1,2-a]pyrazine-6-carboxamido)-2-((1r,4S)-4-methylcyclohexyl)acetamido) phenyl)pyridine 1-oxide | 3-3 | 2-Boc-3,4-dihydro-1H-pyrrolo(1,2a) pyrazine-6-carboxylic acid | Rt = 0.89 min; MS: m/z = 530.3 $[MH]^+$ (Method 1) | 1H NMR (400 MHz, DMSO-d6) δ 10.28 (s, 1H), 8.19 (d, 1H), 7.84 (d, 1H), 7.76 (d, 2H), 7.22 (d, 1H), 7.17 (d, 2H), 7.00 (d, 1H), 5.81 (d, 1H), 4.37-4.13 (m, 3H), 3.50 (s, 2H), 2.67 (t, 2H), 2.31 (s, 3H), 2.08 (s, 3H), 1.96 (s, 3H), 1.92-1.84 (m, 1H), 1.83-1.77 (m, 1H), 1.73-1.59 (br. m, 3H), 1.30-1.15 (m, 2H), 1.06-0.86 (m, 6H) ppm. |
| 122 | 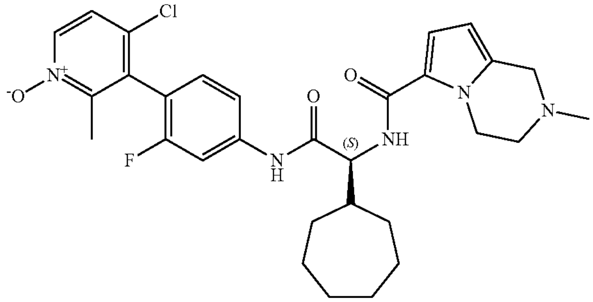 4-chloro-3-(4-((S)-2-cycloheptyl-2-(2-methyl-1,2,3,4-tetrahydropyrrolo[1,2-a]pyrazine-6-carboxamido)acetamido)-2-fluorophenyl)-2-methylpyridine 1-oxide | 3-31 | 2-Boc-3,4-dihydro-1H-pyrrolo(1,2a) pyrazine-6-carboxylic acid | Rt = 3.99 and 4.10 min, 1:1 mixture of atropiso-mers; MS: m/z = 568.3 $[MH]^+$ (Method 4) | 1H NMR (500 MHz, DMSO-d6) δ 10.02 (s, 1H), 8.29 (d, 1H), 7.81-7.64 (m, 1H), 7.50 (dd, 2H), 7.28 (t, 2H), 6.86 (d, 1H), 5.84 (d, 1H), 4.52 (dd, 1H), 4.28 (m, 2H), 3.57 (s, 2H), 2.74 (td, 2H), 2.37 (s, 3H), 2.20 (s, 3H), 2.15 (m, 1H), 1.90-1.67 (m, 4H), 1.67-1.35 (m, 8H) ppm. |

-continued

| Example | Structure/Name | Intermediate 3-x | Carboxylic acid | LC-MS (Method) | 1H NMR |
|---|---|---|---|---|---|
| 123 | 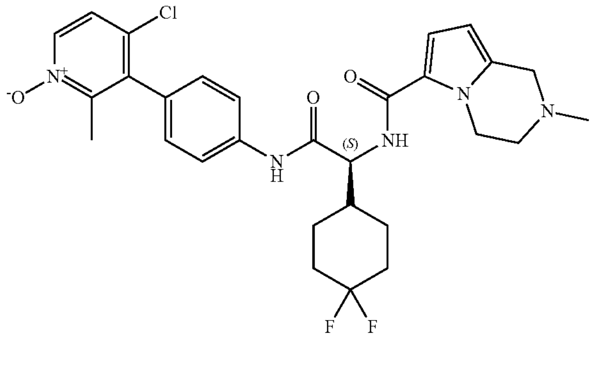 (S)-4-chloro-3-(4-(2-(4,4-difluorocyclohexyl)-2-(2-methyl-1,2,3,4-tetrahydropyrrolo[1,2-a]pyrazine-6-carboxamido)acetamido) phenyl)-2-methylpyridine 1-oxide | 3-23 | 2-Boc-3,4-dihydro-1H-pyrrolo(1,2a) pyrazine-6-carboxylic acid | LC-MS: Rt = 0.76 min; MS: m/z = 572.4 $[MH]^+$ (Method 2) | 1H NMR (400 MHz, DMSO-d6) δ 10.38 (s, 1H), 8.31 (d, 1H), 7.97 (d, 1H), 7.78 (m, 2H), 7.53 (d, 1H), 7.25 (d, 2H), 7.00 (d, 1H), 5.82 (d, 1H), 4.45 (dd, 1H), 4.21-4.17 (m, 2H), 3.50 (s, 2H), 2.71-2.64 (m, 2H), 2.31 (s, 3H), 2.13 (s, 3H), 2.11-1.89 (m, 4H), 1.87-1.68 (m, 3H), 1.50-1.27 (m, 2H) ppm. |
| 124 | 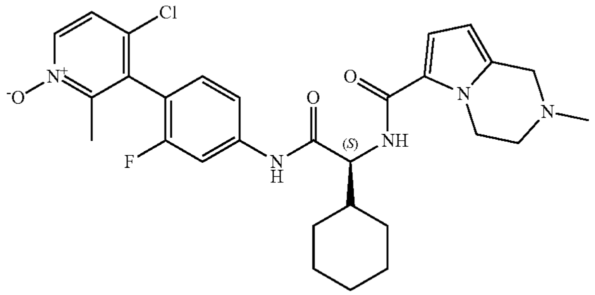 4-chloro-3-(4-((S)-2-cyclohexyl-2-(2-methyl-1,2,3,4-tetrahydropyrrolo[1,2-a]pyrazine-6-carboxamido)acetamido)-2-fluorophenyl)-2-methylpyridine 1-oxide | 3-2 | 2-Boc-3,4-dihydro-1H-pyrrolo(1,2a) pyrazine-6-carboxylic acid | Rt = 3.59 and 3.71 min, 1:1 mixture of atropisomers; MS: m/z = 554.2 $[MH]^+$ (Method 4) | 1H NMR (400 MHz, DMSO-d6) δ 10.53 (s, 1H), 8.36 (d, 1H), 7.92-7.78 (m, 2H), 7.58 (d, 1H), 7.54-7.45 (m, 1H), 7.33 (t, 1H) 7.00 (d, 1H), 5.82 (d, 1H), 4.39-4.03 (m, 3H), 3.50 (s, 2H) 2.67 (t, 2H), 2.36-2.26 (m, 1H), 2.31 (s, 3H), 2.15 (s, 3H), 1.92-1.82 (br. m, 2H), 1.76-1.67 (br. m, 2H), 1.64-1.57 (br. m, 2H), 1.24-0.96 (br. m, 4H) ppm. |

-continued

| Example | Structure/Name | Inter-mediate 3-x | Carboxylic acid | LC-MS (Method) | 1H NMR |
|---|---|---|---|---|---|
| 125 | 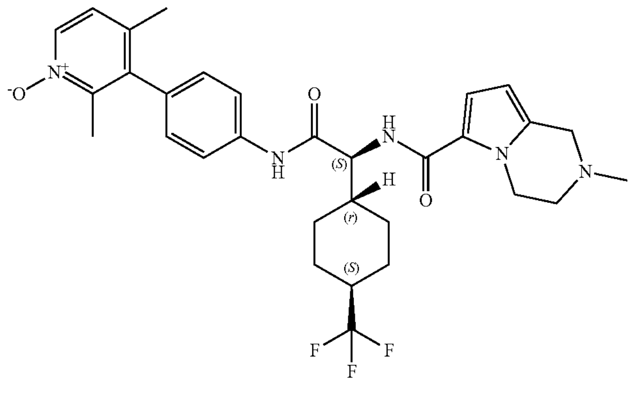 2,4-dimethyl-3-(4-((S)-2-(2-methyl-1,2,3,4-tetrahydropyrrolo[1,2-a]pyrazine-6-carboxamido)-2-((1r,4S)-4-(trifluoromethyl)cyclohexyl) acetamido)phenyl)pyridine 1-oxide | 3-7 | 2-Boc-3,4-dihydro-1H-pyrrolo(1,2a) pyrazine-6-carboxylic acid | Rt = 0.80 min; MS: m/z = 584.4 $[MH]^+$ (Method 1) | 1H NMR (400 MHz, DMSO-d6) δ 10.30 (s, 1H), 8.19 (d, 1H), 7.85 (d, 1H), 7.76 (d, 2H), 7.22 (d, 1H), 7.17 (d, 2H), 7.00 (d, 1H), 5.83 (d, 1H), 4.37 (dd, 1H), 4.33-4.13 (m, 2H), 3.51 (s, 2H), 2.67 (br. m, 2H), 2.32 (s, 3H), 2.30-2.21 (br. m, 1H), 2.08 (s, 3H), 2.00-1.72 (m, 5H), 1.97 (s, 3H), 1.31-1.06 (m, 4H) ppm. |
| 126 | 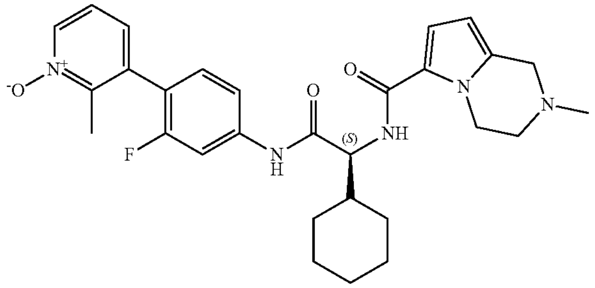 (S)-3-(4-(2-cyclohexyl-2-(2-methyl-1,2,3,4-tetrahydropyrrolo[1,2-a]pyrazine-6-carboxamido)acetamido)-2-fluorophenyl)-2-methylpyridine 1-oxide | 3-41 | 2-Boc-3,4-dihydro-1H-pyrrolo(1,2a) pyrazine-6-carboxylic acid | Rt = 0.81 min; MS: m/z = 520.4 $[MH]^+$ (Method 2) | 1H NMR (400 MHz, DMSO-d6 ) δ 10.50 (s, 1H), 8.33 (d, 1H), 7.86 (d, 1H), 7.78 (d, 1H), 7.48 (dd, 1H), 7.39-7.34 (m, 2H), 7.21 (dd, 1H), 7.01 (d, 1H), 5.82 (d, 1H), 4.37-4.14 (m, 3H), 3.50 (s, 2H), 2.70-2.63 (m, 2H), 2.31 (s, 3H), 2.20 (d, 3H), 1.86 (br. m, 2H), 1.75-1.69 (m , 2H), 1.63-1.56 (br. m, 2H), 1.26-1.00 (m, 5H) ppm |
| 127 | 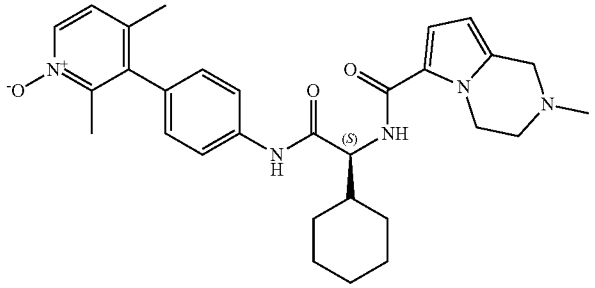 | 3-15 | 2-Boc-3,4-dihydro-1H-pyrrolo(1,2a) pyrazine-6-carboxylic acid | Rt = 3.13 min; MS: m/z = 516.3 $[MH]^+$ | 1H NMR (400 MHz, DMSO-d6) δ 10.27 (s, 1H), 8.19 (d, 1H), 7.81 (d, 1H), 7.76 (d, 2H), 7.22 (d, 1H), 7.16 (d, 2H), 7.00 (d, 1H), 5.81 (d, 1H), 4.37-4.12 (m, 3H), 3.50 (s, 2H), 2.70-2.63 (m, 2H), 2.31 (s, 3H), 2.08 (s, 3H), 1.96 (s, 3H), 1.91-1.81 (br. m, 2H), 1.76-1.67 (br. m, 2H), 1.66- |

-continued

| Example | Structure/Name | Intermediate 3-x | Carboxylic acid | LC-MS (Method) | 1H NMR |
|---|---|---|---|---|---|
| | (S)-3-(4-(2-cyclohexyl-2-(2-methyl-1,2,3,4-tetrahydropyrrolo[1,2-a]pyrazine-6-carboxamido)acetamido) phenyl)-2,4-dimethylpyridine 1-oxide | | | | 1.54 (br. m, 2H), 1.30-0.91 (m, 5H) ppm. |
| 128 | 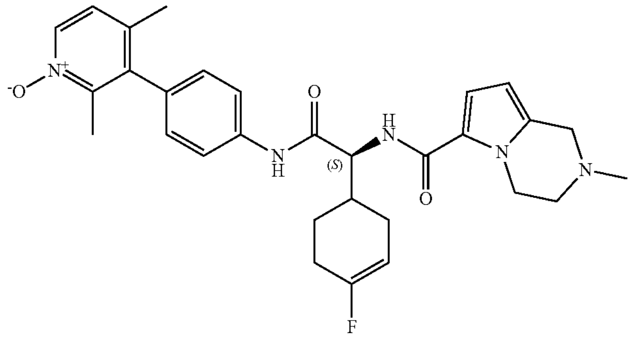 3-(4-((2S)-2-(4-fluorocyclohex-3-en-1-yl)-2-(2-methyl-1,2,3,4-tetrahydropyrrolo[1,2-a]pyrazine-6-carboxamido)acetamido) phenyl)-2,4-dimethylpyridine 1-oxide | 3-10 | 2-Boc-3,4-dihydro-1H-pyrrolo(1,2a) pyrazine-6-carboxylic acid | Rt = 0.67 min; MS: m/z = 532.4 $[MH]^+$ (Method 5) | 1H NMR (400 MHz, DMSO-d6) δ 10.37 and 10.35 (2s, ratio ca 3:2, 1H), 8.20 (d, 1H), 7.98 (d, 1H), 7.77 (m, 2H), 7.22 (d, 1H), 7.17 (d, 2H), 7.01 (dd, 1H), 5.82 (m, 1H), 5.21 (m, 1H) 4.46 and 4.23 (2dt, ratio 1:2, 3H), 3.51 (s, 2H), 2.72-2.56 (br. m, 2H), 2.32 (s, 3H), 2.28-1.79 (br. m, 5H), 2.08 (s, 3H), 2.01 (m, 1H), 1.97 (s, 3H), 1.62-1.42 (m, 1H) ppm. |
| 129 | 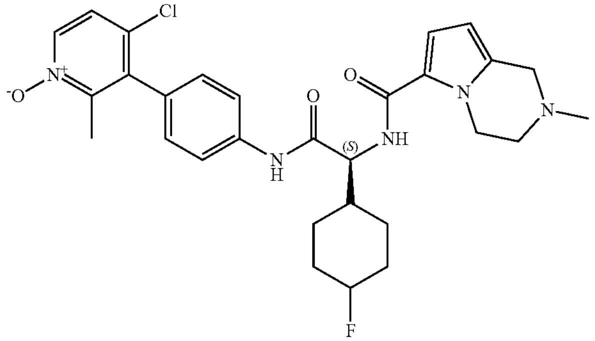 4-chloro-3-(4-((2S)-2-(4-fluorocyclohexyl)-2-(2-methyl-1,2,3,4-tetrahydropyrrolo[1,2-a]pyrazine-6-carboxamido)acetamido) | 3-28 | 2-Boc-3,4-dihydro-1H-pyrrolo(1,2a) pyrazine-6-carboxylic acid | Rt = 0.72 and 0.73 min, 1:1 mixture of isomers; MS: m/z = 554.3 $[MH]^+$ (Method 2) | 1H NMR (400 MHz, DMSO-d6) δ 10.38 and 10.36 (2s, ratio 1:1, 1H), 8.32 and 8.31 (2s, ratio 1:1, 1H), 7.97 (br. m, 1H), 7.80-7.74 (m, 2H), 7.54 (d, 1H), 7.24 (d, 2H), 7.04 (d, 1H), 5.88 (m, 1H), 4.93-4.46 (m, 1H), 4.42-4.22 (m, 3H), 3.71 (br. m, 1H), 2.84 (br. m, 2H), 2.46 (br. m, 1H), 2.13 (s, 3H), 2.07 (br. m, 1H), 2.00-1.84 (br. m, 3H), 1.77-1.66 (br. m, 1H), 1.61-1.09 (m, 5H) ppm |

-continued

| Example | Structure/Name | Inter-mediate 3-x | Carboxylic acid | LC-MS (Method) | 1H NMR |
|---|---|---|---|---|---|
| | phenyl)-2-methylpyridine 1-oxide | | | | |
| 130 | 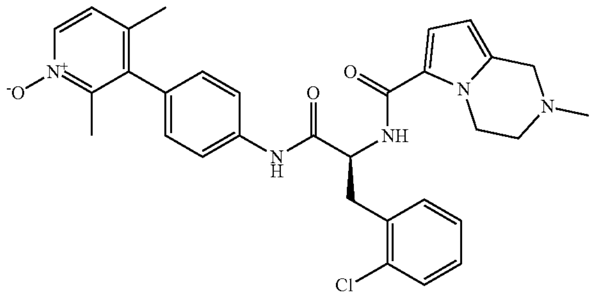 (S)-3-(4-(3-(2-chlorophenyl)-2-(2-methyl-1,2,3,4-tetrahydropyrrolo[1,2-a]pyrazine-6-carboxamido)propanamido)phenyl)-2,4-dimethylpyridine 1-oxide | | 2-Boc-3,4-dihydro-1H-pyrrolo(1,2a) pyrazine-6-carboxylic acid | Rt = 2.96 min, MS: m/z = 558 and 560 $[MH]^+$ (Method 4) | 1H NMR (400 MHz, DMSO-d6) δ 10.90 (br. s, 1H), 10.38 (s, 1H), 8.51 (d, 1H), 8.42 (d, 1H), 7.78 (d, 2H), 7.50-7.40 (m, 3H), 7.27-7.18 (m, 4H), 7.09 (br. s, 1H), 6.07 (d, 1H), 4.90 (br. m, 2H), 4.34-4.19 (br. m, 2H), 3.74 (br. m, 1H), 3.49 (br s, 1H), 3.44-3.22 (m, 2H), 2.91 (s, 3H), 2.17 (s, 3H), 2.04 (s, 3H) ppm. |

Example 131

(S)-3-(4-(2-cyclohexyl-2-(2-cyclopropyl-1,2,3,4-tetrahydropyrrolo[1,2-a]pyrazine-6-carboxamido)acetamido)phenyl)-2,4-dimethylpyridine 1-oxide

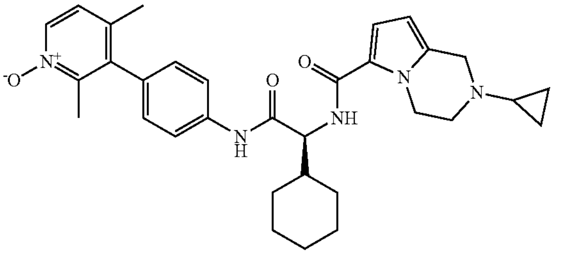

To a solution of (S)-3-(4-(2-cyclohexyl-2-(1,2,3,4-tetrahydropyrrolo[1,2-a]pyrazine-6-carboxamido)acetamido)phenyl)-2,4-dimethylpyridine 1-oxide (precursor to example 138, 50 mg, 0.10 mmol) in DMF (0.5 mL), $Cs_2CO_3$ (97 mg, 0.30 mmol) and cyclopropyl bromide (18.1 mg, 0.15 mmol) were added at RT, and stirred at 60° for 24 h. Another portion of cyclopropyl bromide (300 mg, 2.5 mmol) was added and stirring at 60° continued for 4 days. The mixture was diluted with EtOAc and washed with sat. aq. $NaHCO_3$, water, and brine. The organic phase was dried ($Na_2SO_4$), filtered and concentrated under reduced pressure to afford a yellow oil. Purification by prep. HPLC (column: XBridge-C18 5 um, 30×100 mm, gradient: 15-45% acetonitrile in water+0.1% TFA) yielded the title compound (1.6 mg, 3%) as a white solid.

LC-MS: Rt=1.34 min; MS: m/z=542.5 $[MH]^+$ (Method 5).

1H NMR (400 MHz, $CHCl_3$-d) δ 8.80 (s, 1H) 8.41 (d, 1H) 7.74 (d, 2H) 7.19-7.25 (m, 1H) 7.11 (d, 2H), 6.74 (d, 1H) 6.56 (d, 1H) 5.97-6.08 (m, 2H) 5.44-5.55 (m, 2H) 4.63-4.81 (m, 2H) 4.51 (t, 1H) 4.24 (br s, 2H), 3.71 (m, 1H) 2.36 (s, 4H) 2.11 (s, 3H) 1.64-2.06 (m, 7H) 0.99-1.46 (m, 6H) ppm.

Example 132

2,4-dimethyl-3-(4-((S)-2-(2-(oxetan-3-yl)-1,2,3,4-tetrahydropyrrolo[1,2-a]pyrazine-6-carboxamido)-2-((1r,4S)-4-(trifluoromethyl)cyclohexyl)acetamido)phenyl)pyridine 1-oxide

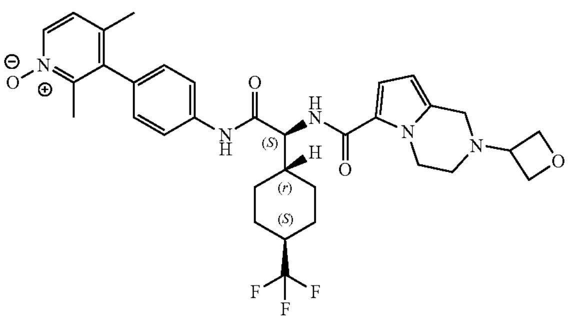

To a solution of 2,4-dimethyl-3-(4-((S)-2-(1,2,3,4-tetrahydropyrrolo[1,2-a]pyrazine-6-carboxamido)-2-((1r,4S)-4-(trifluoromethyl)cyclohexyl)acetamido)phenyl)pyridine 1-oxide (precursor to example 137, 92 mg, 0.162 mmol) in MeOH (5 mL), acetic acid (0.028 mL, 0.485 mmol) and 3-oxetanone (116 mg, 1.615 mmol) was added, and the yellow solution stirred at RT for 45 min. $NaBH(OAc)_3$ (68.5 mg, 0.323 mmol) was added and the reaction mixture stirred at RT for 80 h. All volatiles were removed under reduced pressure, the yellow residue dissolved in EtOAc and washed with sat. aq. $NaHCO_3$ and brine. The aq. phases were re-extracted with EtOAc and the combined organic phases dried ($Na_2SO_4$) and evaporated to afford a yellow solid. Purification by preparative HPLC (column: Sunfire 30×100 mm; gradient: 5-80% acetonitrile in water+0.1% TFA) yielded the title compound (57 mg, 55%) as a colorless solid.

LC-MS: Rt=1.01 min; MS: m/z=626.4 $[MH]^+$ (Method 5).

1H NMR (400 MHz, DMSO-d6) δ 10.32 (s, 1H), 8.19 (d, 1H), 7.88 (d, 1H), 7.77 (d, 2H), 7.22 (d, 1H), 7.17 (d, 2H), 7.02 (d, 1H), 5.85 (d, 1H), 4.59 (t, 2H), 4.49 (t, 2H), 4.38 (dd, 1H), 4.33-4.18 (m, 2H), 3.60 (m, 1H), 3.51 (s, 2H), 2.69-2.61 (m, 2H), 2.30-2.19 (br. m, 1H), 2.08 (s, 3H), 2.03-1.84 (br. m, 4H), 1.96 (s, 3H), 1.78-1.71 (br. m, 1H), 1.31-1.07 (m, 4H) ppm.

Example 133

4-chloro-3-(4-((S)-2-cyclohexyl-2-(2-(oxetan-3-yl)-1,2,3,4-tetrahydropyrrolo[1,2-a]pyrazine-6-carboxamido)acetamido)-2-fluorophenyl)-2-methylpyridine 1-oxide

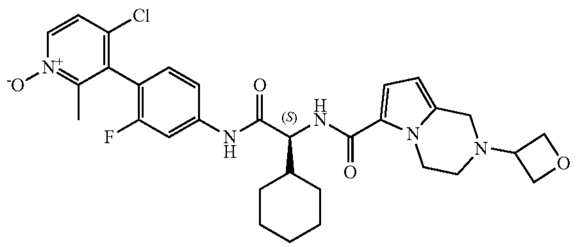

The title compound was prepared as a mixture of atropisomers from 4-chloro-3-(4-((S)-2-cyclohexyl-2-(1,2,3,4-tetrahydropyrrolo[1,2-a]pyrazine-6-carboxamido)acetamido)-2-fluorophenyl)-2-methylpyridine 1-oxide (precursor to example 136) and oxetan-3-one by a procedure similar to that of Example 143. Separation of the two atropisomers by chromatography on chiral stationary phase afforded the title compound as one pure atropisomer.

LC-MS: Rt=1.01 min; MS: m/z=596.4 $[MH]^+$ (Method 2).

1H NMR (400 MHz, DMSO-d6) δ 10.59 (s, 1H), 8.36 (d, 1H), 7.92 (d, 1H), 7.83 (dd, 1H), 7.59 (d, 1H), 7.50 (dd, 1H), 7.33 (t, 1H), 7.03 (d, 1H), 5.84 (d, 1H), 4.59 (t, 2H), 4.49 (td, 2H), 4.41-4.13 (m, 3H), 3.59 (m, 1H), 3.50 (s, 2H), 2.65 (m, 2H), 2.15 (s, 3H), 1.96-1.51 (m, 7H), 1.24 (m, 4H) ppm.

Example 134

3-(4-((S)-2-(2-acetyl-1,2,3,4-tetrahydropyrrolo[1,2-a]pyrazine-6-carboxamido)-2-cycloheptylacetamido)-2-fluorophenyl)-4-chloro-2-methylpyridine 1-oxide

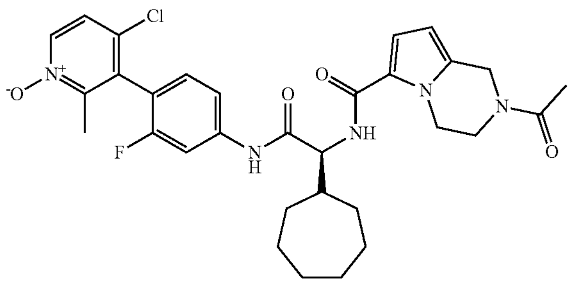

The title compound was prepared from Intermediate 3-30 and Intermediate 4-10 by a procedure similar to that of Example 1.

LC-MS: Rt=1.34 min; MS: m/z=594 $[MH]^+$ (Method 14).

1H NMR (300 MHz, Methanol-d4) δ 8.37 (d, 1H), 7.79 (dd, 1H), 7.59 (d, 1H), 7.47 (d, 1H), 7.26 (t, 1H), 6.91 (d, 1H), 6.01 (dd, 1H), 4.79 (s, 1H), 4.71 (d, 1H), 4.53-4.42 (m, 2H), 4.39 (br. m, 1H), 3.85 (m, 2H), 2.31 (s, 3H), 2.16 (m, 4H), 1.90-1.27 (m, 12H) ppm.

Example 135

(S)-3-(4-(2-cyclohexyl-2-(2-(2-methoxyethyl)-1,2,3,4-tetrahydropyrrolo[1,2-a]pyrazine-6-carboxamido)acetamido)phenyl)-2,4-dimethylpyridine 1-oxide

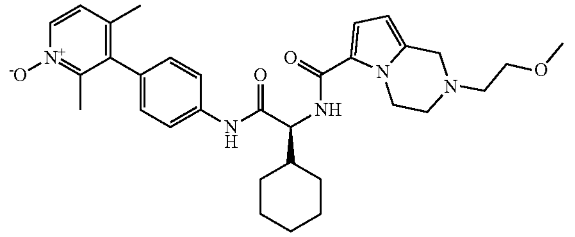

The title compound was prepared from (S)-3-(4-(2-cyclohexyl-2-(1,2,3,4-tetrahydropyrrolo[1,2-a]pyrazine-6-carboxamido)acetamido)phenyl)-2,4-dimethylpyridine 1-oxide (precursor to example 138) and 1-bromo-2-methoxyethane by a procedure similar to that of Example 131.

LC-MS: Rt=3.47 min; MS: m/z=560.5 $[MH]^+$ (Method 5).

1H NMR (400 MHz, DMSO-d6) δ 10.30 (s, 1H), 8.20 (d, 1H), 8.06 (d, 1H) 7.73-7.79 (dd, 2H), 7.23 (d, 1H), 7.18 (d, 2H), 7.15 (d, 1H), 6.07 (br s, 1H), 4.72 (br m, 2H), 4.50-4.89 (m, 2H), 4.38 (br. t, 2H), 3.70 (br s, 2H), 3.33 (s, 3H), 3.30 (br. s, 2H), 2.08 (s, 3H), 1.97 (s, 3H), 1.86 (m, 2H), 1.78 (m, 2H), 1.64 (m, 2H) 0.81-1.30 (m, 8H), ppm.

General Procedure for the Preparation of the Corresponding Pyridines of Examples 1-135

Reference example 136 (corresponding to the N-oxide compound of example 1): N—((S)-2-((4-(2,4-dimethylpyridin-3-yl)phenyl)amino)-2-oxo-1-((S)-1,2,3,4-tetrahydronaphthalen-1-yl)ethyl)-1-methyl-1H-pyrazole-5-carboxamide

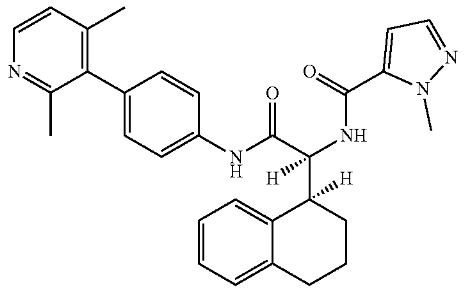 [SMILES: Cc1ccnc(C)c1-c1ccc(NC(=O)[C@@H](NC(=O)c2ccnn2C)[C@H]2CCCc3ccccc32)cc1]

To a solution of 50 mg (2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide (Example 1; 50 mg, 0.078 mmol) in THF (1.2 mL) was added sat. aq. $NH_4Cl$ (1.2 mL) followed by zinc powder (100 mg; 1.4 mmol). After stirring the reaction mixture overnight at RT, HPLC analysis indicated the complete consumption of the starting material. The mixture was diluted with EtOAc, washed with sat $NaHCO_3$, water, and brine, dried ($Na_2SO_4$) and the volatiles were evaporated. The residue was purified by SFC to yield the title compound (26 mg, 67%) as a colorless solid. LC-MS: Rt=0.85 min; MS: m/z=494.4 [MH]+ (Method 8).

The following reference examples were prepared by following the procedure described for reference Example 136:

| Reference Example number | Example number of corresponding N-oxide | Structure | Name | LC-MS |
|---|---|---|---|---|
| 137 | 2 | 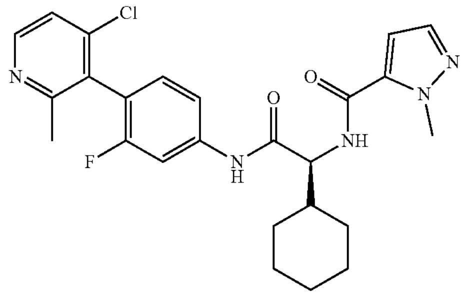 | N-((1S)-2-((4-(4-chloro-2-methylpyridin-3-yl)-3-fluorophenyl)amino)-1-cyclohexyl-2-oxoethyl)-1-methyl-1H-pyrazole-5-carboxamide | Rt = 0.84 min; MS: m/z = 492.4 $[MH]^+$ (Method 8) |
| 138 | 3 | 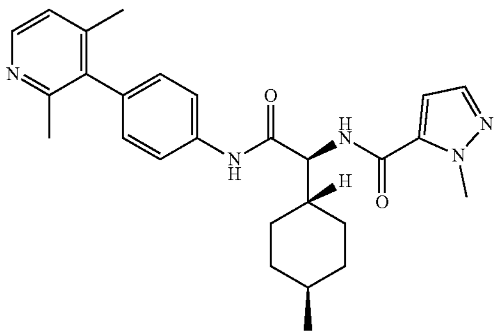 [SMILES: Cc1ccnc(C)c1-c1ccc(NC(=O)[C@@H](NC(=O)c2ccnn2C)[C@H]2CC[C@H](C)CC2)cc1] | N-((S)-2-((4-(2,4-dimethylpyridin-3-yl)phenyl)amino)-1-((1r,4S)-4-methylcyclohexyl)-2-oxoethyl)-1-methyl-1H-pyrazole-5-carboxamide | Rt = 0.89 min; MS: m/z = 460.5 $[MH]^+$ (Method 8) |
| 139 | 5 | 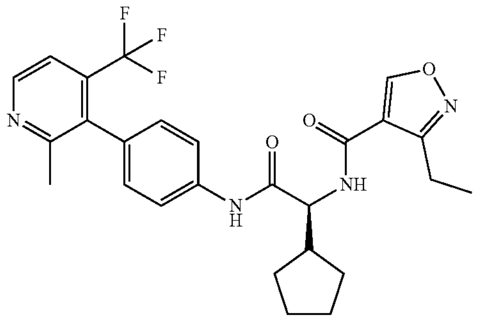 [SMILES: CCc1nocc1C(=O)N[C@H](C(=O)Nc1ccc(-c2c(C(F)(F)F)ccnc2C)cc1)C1CCCC1] | (S)-N-(1-cyclopentyl-2-((4-(2-methyl-4-(trifluoromethyl)pyridin-3-yl)phenyl)amino)-2-oxoethyl)-3-ethylisoxazole-4-carboxamide | Rt = 1.24 min; MS: m/z = 501.3 $[MH]^+$ (Method 5) |

-continued

| Reference Example number | Example number of corresponding N-oxide | Structure | Name | LC-MS |
|---|---|---|---|---|
| 140 | 6 | 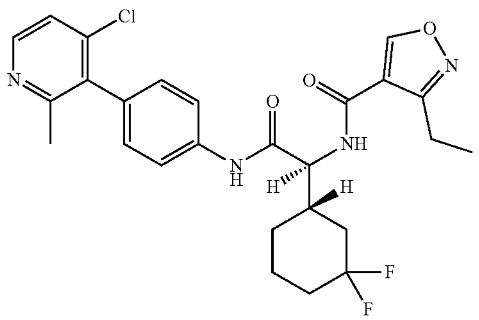 [SMILES: CCc1nocc1C(=O)N[C@H](C(=O)Nc1ccc(-c2c(Cl)ccnc2C)cc1)[C@H]1CCCC(F)(F)C1] | N-((S)-2-((4-(4-chloro-2-methylpyridin-3-yl)phenyl)amino)-1-((S)-3,3-difluorocyclohexyl)-2-oxoethyl)-3-ethylisoxazole-4-carboxamide | Rt = 1.21 min; MS: m/z = 517.3 $[MH]^+$ (Method 5) |
| 141 | 7 | 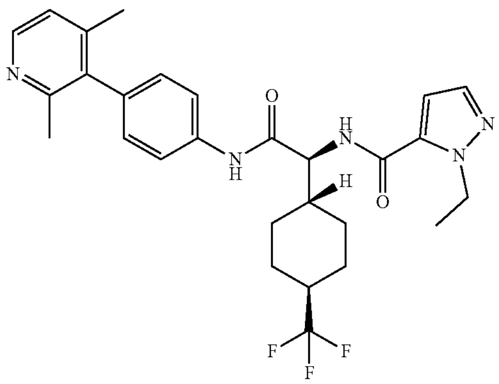 [SMILES: CCn1nccc1C(=O)N[C@H](C(=O)Nc1ccc(-c2c(C)ccnc2C)cc1)[C@H]1CC[C@H](C(F)(F)F)CC1] | N-((S)-2-((4-(2,4-dimethylpyridin-3-yl)phenyl)amino)-2-oxo-1-((1r,4S)-4-(trifluoromethyl)cyclohexyl)ethyl)-1-ethyl-1H-pyrazole-5-carboxamide | Rt = 0.95 min; MS: m/z = 528.4 $[MH]^+$ (Method 8) |
| 142 | 8 | 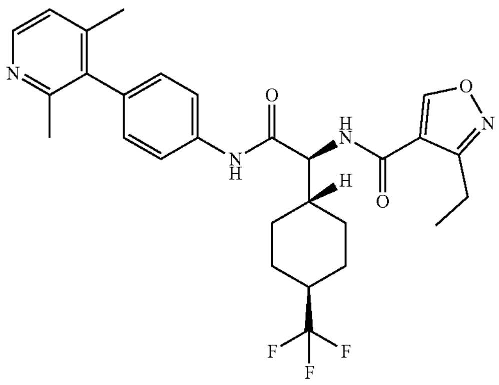 [SMILES: CCc1nocc1C(=O)N[C@H](C(=O)Nc1ccc(-c2c(C)ccnc2C)cc1)[C@H]1CC[C@H](C(F)(F)F)CC1] | N-((S)-2-((4-(2,4-dimethylpyridin-3-yl)phenyl)amino)-2-oxo-1-((1r,4S)-4-(trifluoromethyl)cyclohexyl)ethyl)-3-ethylisoxazole-4-carboxamide | Rt = 0.97 min; MS: m/z = 529.4 $[MH]^+$ (Method 8) |
| 143 | 9 | 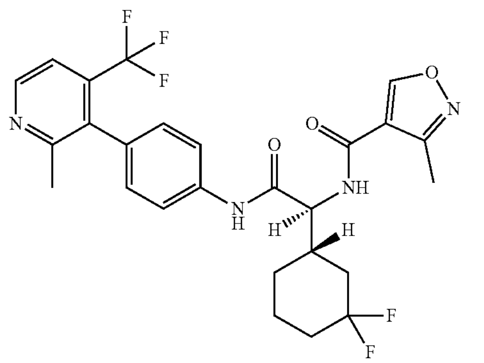 [SMILES: Cc1nocc1C(=O)N[C@H](C(=O)Nc1ccc(-c2c(C(F)(F)F)ccnc2C)cc1)[C@H]1CCCC(F)(F)C1] | N-((S)-1-((S)-3,3-difluorocyclohexyl)-2-((4-(2-methyl-4-(trifluoromethyl)pyridin-3-yl)phenyl)amino)-2-oxoethyl)-3-methylisoxazole-4-carboxamide | Rt = 1.16 min; MS: m/z = 537.4 $[MH]^+$ (Method 8) |

-continued

| Reference Example number | Example number of corresponding N-oxide | Structure | Name | LC-MS |
|---|---|---|---|---|
| 144 | 12 | 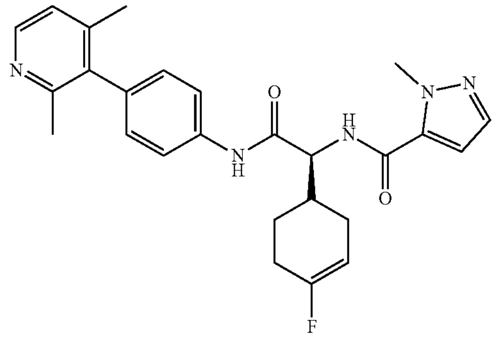 [SMILES: Cc1ccnc(C)c1-c1ccc(NC(=O)[C@@H](NC(=O)c2ccnn2C)C2CC=C(F)CC2)cc1] | N-((S)-2-((4-(2,4-dimethylpyridin-3-yl)phenyl)amino)-1-((S)-4-fluorocyclohex-3-en-1-yl)-2-oxoethyl)-1-methyl-1H-pyrazole-5-carboxamide | Rt = 0.68 min; MS: m/z = 462.3 $[MH]^+$ (Method 8) |

Biological Assays and Data

The activity of a compound according to the present invention can be assessed by the following in vitro methods. A compound of formula (I), or a pharmaceutically acceptable salt thereof, exhibits valuable pharmacological properties, e.g. as indicated in tests as provided in the next sections, and are therefore indicated for therapy related to IL-17.

Expression, Purification, and Labeling of Proteins

Biotinylated Human IL-17A

For the generation of an IL-17A expression construct, the natural leader-hsIL17A (aa24-155)-APP6 insert was amplified by PCR from an existing construct (C #3713, NPL012065, natLeader-hsIL-17 aa24-151-APP/pRS5a; SEQ ID NO: I) using specific primers. Forward primer RS198: 5' CATACGATTTAGGTGA (SEQ ID NO: 2) and reverse primer RS4930; 5'CCTCTAGAGCGGCCGCT-TAGGAGTCGTGACGGAATTCGGCCACATGGTGGA-CAATCGGGG TGACACAGGTGCAC (SEQ ID NO: 3). The PCR product was cloned into the pRS5a expression vector (treated with the appropriate restriction enzymes HindIII and NotI) via the In-Fusion technology to obtain expression plasmid NPL016964 (SEQ ID NO: 4).

The expression of human IL-17A was carried out in HEK293 6E cells using V3 medium (proprietary Novartis cell culture medium, patent: WO2011/134920 A1). Cells were diluted one day before the expression (final density of $1\text{-}2\times10^6$ cells/mL in order to be in the exponential growing phase the next morning. The day of expression, the culture was centrifuged at 300×rpm during 20 minutes and resuspended in fresh V3 medium. The expression was started with a cell density of about $3\times10^6$ cells/mL. One milligram (mg) of plasmid DNA (plasmid NPL016964) per liter (L) (final volume after incubation) was first added to the culture, followed, after mixing, by 4 mg/L of PEI (polyethyleneimine) as transfection reagent. After 4 hours incubation at 120 rpm, 37° C., with 5% $CO_2$, the culture was diluted with fresh V3 medium to a final density of $1.5\times10^6$ cells/mL, in 3 L shake flasks (1 L/flask). Incubation was performed on an orbital shaking platform at 37° C., 5% $CO_2$ and 100 rpm for 5 days. The cultures were then centrifuged at 2000 rpm during 15 minutes and the supernatant concentrated using the Pellicon system (10MWCO membrane). The concentrated sample was loaded onto a CJM112 sepharose 4B column and eluted with 0.1 M glycine-HCl pH 2.7. Said column comprised an anti-IL-17A monoclonal antibody (CJM112, described as XAB4 in WO 2014/122613 A1) coupled to CNBr-activated Sepharose 4B (Pharmacia) at a density of 10 mg/ml resin. The fractions were collected in tubes pre-filled with 10% of 1 M Tris pH 8 buffer. Pooled fractions were concentrated by ultrafiltration (AMICON 10MWCO membrane) and further purified by size exclusion chromatography (Superdex 75 HiLoad 26/60 column, GE Healthcare) in PBS pH 7.4. Fractions were pooled based on SDS-PAGE analysis.

Chemical biotinylation of human IL-17A was performed with a 5-fold excess of EZ-Link-Sulfo-NHS-LC-LC-Biotin (cat. no. 21338; Thermo Scientific) in PBS pH 7.4. After one hour incubation at room temperature, the reaction was stopped with 1 M Tris pH 8 and the excess biotin removed by running the sample on a Zeba Spin Desalting column (Thermo Scientific) in PBS pH 7.4.

AF647-Labeled Human IL-17RA (PN110235)

The FL (full-length) cDNA clone of hsIL17RA was ordered at imaGenes (C #3784, NPL012318; SEQ ID NO: 5). The CD33-hIL17RA (aa33-320)-APP6-Avi insert was amplified via 2-step PCR using primer sets RS3766/3768 for the first step and RS3767/3769 for the second step. Cloning was carried out using the Gateway technology: Initially the insert was cloned via BP reaction in pDON201 (entry clone) and afterwards via LR reaction in pDESTRS5a to obtain expression plasmid NPL012271 (SEQ ID NO: 6).

Sequences of the primers are as follows:

```
Forward primer 1 RS3766:
                                        (SEQ ID NO: 7)
5' CCATGCCCCTGCTCCTGCTGCTGCCCCTGCTGTGGGCCGGAGCCCT

GGCCCTGCGACTCCTGGACCACCGGGCGCTGG,

reverse primer 1 RS3768:
                                        (SEQ ID NO: 8)
5' GCTTCAAAGATATCGTTCAGGCCGCCGCCGGAGTCGTGACGGAATT

CCCACAGGGGCATGTAGTCCGGAATTGG,

forward primer 2 RS3767:
                                        (SEQ ID NO: 9)
5' GGGGACAAGTTTGTACAAAAAAGCAGGCTTGGCCGCCACCATGCCC

CTGCTCCTGCTGCTGCCCCTGCTGG
and

reverse primer 2 RS3769:
                                       (SEQ ID NO: 10)
5' GGGGACCACTTTGTACAAGAAAGCTGGGTTCATTATTCATGCCACT

CAATTTTCTGCGCTTCAAAGATATCGTTCAGGC.
```

Human IL-17RA was expressed in HEK293 6E cells using V3 medium as described above for IL-17A. The recombinant protein was captured on an anti-APP affinity chromatography column and eluted with a one-step gradient of 0.1 M glycine (pH 2.7). Said column comprised an anti-APP monoclonal antibody coupled to CNBr-activated Sepharose 4B (Pharmacia) at a density of 10 mg/ml resin. The aminoacid sequence of the light chain and heavy chain of the used anti-APP antibody comprised SEQ ID NO 11 and 12, respectively. The pH was immediately raised by addition of 1.0 M of Tris (pH 8.5) to the eluted fractions. The isolated protein was then concentrated by ultrafiltration and further purified by size-exclusion chromatography with a High-Load Superdex-200 26/80 equilibrated with PBS pH 7.4.

Before labelling, the IL-17RA concentration was determined by HPLC. A 5-fold excess of Alexa Fluor647 carboxylic acid succinimidyl ester (cat. no. A200066; Invitrogen) was added, and after one hour incubation at room temperature, the sample was purified over a Zeba Spin Desalting column (Thermo Scientific) equilibrated in PBS pH 7.4 The efficiency of the labeling was then deduced from absorbance measurements at 280 nm and 650 nm.

Human IL-17A×IL-17RA TR-FRET Assay

Dilutions of test compounds in DMSO are plated onto white low-volume 384-well plates (Greiner, #784075). Specifically, solutions of graded concentrations (5 mM to 150 nM; sixteen 2-fold dilution steps) are dispensed at 0.2 µL/well to yield final assay concentrations in the range of 100 µM to 3 nM. Each compound concentration is tested in duplicate.

All components of the assay are diluted in PBS containing 0.05% Tween20 (Sigma, #P1379, 5% stock in water), 1 mM EDTA (Invitrogen, #15575-038; 0.5M stock, pH8) and 0.05% bovine serum albumin (Roche; 5% stock in water). The final total assay volume is 10 µL. Reagents are added using a Multidrop Combi device (ThermoFisher, #5840320); between reagents, the instrument is rinsed with buffer:

(i) Biotinylated human IL-17A (PN106276; stock solution: 55.87 µM) is added at 5 µL/well from a 10 nM intermediate dilution to yield a final assay concentration of 5 nM. Each assay plate contains "low controls" where buffer is added in place of IL-17A.

(ii) After 30 minutes of incubation at RT, 2.5 µL/well of AF647-labeled human IL-17RA (PN110235; stock: 2.91 µM) is added from a 120 nM intermediate solution, to yield a final assay concentration of 30 nM.

(iii) Following 30 minutes of incubation at RT, 2.5 µL/well of Eu-Streptavidin (PerkinElmer, #AD0062; stock: 500 µg/mL=8.3 µM) is added from an intermediate dilution of 4 nM to yield a final concentration of 1 nM.

After 30 to 60 minutes of incubation, FRET is measured in an EnVision 2101 Multilabel-Reader (Perkin Elmer) with excitation at 320 nm, and emission at 615 and 665 nm (program "TR-FRET Screening", instrument: NIBR-00013163).

Each plate contains test compounds in columns 1-22 and controls in columns 23 and 24. The neutral control (NC) contains all the assay components, but DMSO instead of test compound. The active control (AC) mimics complete inhibition of the IL-17 ligand interaction, which is achieved by replacing the biotinylated cytokine with buffer. The fluorescence values for emission at 615 nm and 665 nm are loaded to the evaluation software Helios. In a normalization step, reader values are converted to % activity using the formula:

$$\%\ \text{activity} = -100*(x-NC)/(AC-NC)$$

where NC and AC are the median values of the neutral and active control wells on the same plate.

From the activity data at each compound concentration, the IC50 values are obtained using the 4-parameter logistic function ("Hill-slope model") of Helios.

IL-6 Release from NHDF Cells (Normal Human Dermal Fibroblasts)

NHDF cells isolated from normal adult mesoderm, connective tissues were cultured in fibroblast growth medium containing 2% supplement. The cells were detached from plastic using an accutase solution, washed and were seeded in 96-well plates at a density of 5×103/well in fibroblast growth medium lacking the supplements. The cells were allowed to adhere overnight before they were incubated with the compound/cytokine cocktail.

Compound stock solutions (10 mM in DMSO) were serially diluted in 96-well plates in fibroblast growth medium containing 0.2% supplement to give a maximal assay concentration of 10 µM. Diluted compounds were pre-incubated with recombinant human IL-17AA or IL-17AF plus human TNF-α for 30 minutes at room temperature on a shaker. NHDF cells were re-suspended in fibroblast growth medium/0.2% supplement (100 µl/well) followed by addition of the cytokine/compound mix to the cells (100 µl/well) to give a final compound starting concentration of 10 µM. The cells were incubated with the compound/cytokines cocktail for 24 hours at 37° C. (5% $CO_2$). During the culture period, the final concentrations of IL-17AA were 30 pM, IL-17AF were 250 pM, and TNF-α were 6 pM. The final DMSO or plasma concentrations were 0.1% or 20%, respectively. All compound incubations were done in duplicate. The supernatants were collected to quantify IL-6 by ELISA according to the manufacturers instructions. The optical density was measured at 450 nm by an EnVision Multilabel Plate Reader (Perkin Elmer). The IL-6 levels produced after TNF-α stimulation were subtracted from the IL-6 produced after IL-17/TNF-α co-stimulation. These IL-17-specific IL-6 concentrations were used for 050 value calculation. IC50 values for inhibitors were then determined using sigmoidal dose-response curve fitting model (Excel Xlfit, model 205).

The following table provides the potency of Examples 1-135 in the cell and TR-FRET assays:

| Example | Name | IL17AA + TNF IC50 IL-6 [umol I-1] | IL17AA FRET/ IL17Rawt IC50 [umol I-1] |
|---|---|---|---|
| 1 | 2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide | 0.004 | 0.008 |
| 2 | 4-chloro-3-(4-((S)-2-cyclohexyl-2-(1-methyl-1H-pyrazole-5-carboxamido)acetamido)-2-fluorophenyl)-2-methylpyridine 1-oxide (mixture of atropisomers) | 0.015 | 0.024 |
| 2a | 4-chloro-3-(4-((S)-2-cyclohexyl-2-(1-methyl-1H-pyrazole-5-carboxamido)acetamido)-2-fluorophenyl)-2-methylpyridine 1-oxide (single atropisomer) | 0.037 | 0.049 |
| 2b | 4-chloro-3-(4-((S)-2-cyclohexyl-2-(1-methyl-1H-pyrazole-5-carboxamido)acetamido)-2-fluorophenyl)-2-methylpyridine 1-oxide (single atropisomer) | 0.014 | 0.017 |

-continued

| Example | Name | IL17AA + TNF IC50 IL-6 [umol I-1] | IL17AA FRET/ IL17Rawt IC50 [umol I-1] |
|---|---|---|---|
| 3 | 2,4-dimethyl-3-(4-((S)-2-(1-methyl-1H-pyrazole-5-carboxamido)-2-((1r,4S)-4-methylcyclohexyl)acetamido)phenyl) pyridine 1-oxide | 0.007 | 0.024 |
| 4 | 4-chloro-3-(4-((S)-2-(3-ethylisoxazole-4-carboxamido)-2-((1r,4S)-4-(trifluoromethyl)cyclohexyl)acetamido) phenyl)-2-methylpyridine 1-oxide | 0.012 | 0.026 |
| 5 | (S)-3-(4-(2-cyclopentyl-2-(3-ethylisoxazole-4-carboxamido)acetamido)phenyl)-2-methyl-4-(trifluoromethyl)pyridine 1-oxide | 0.009 | 0.028 |
| 6 | 4-chloro-3-(4-((S)-2-((S)-3,3-difluorocyclohexyl)-2-(3-ethylisoxazole-4-carboxamido)acetamido)phenyl)-2-methylpyridine 1-oxide | 0.005 | 0.048 |
| 7 | 3-(4-((S)-2-(1-ethyl-1H-pyrazole-5-carboxamido)-2-((1r,4S)-4-(trifluoromethyl)cyclohexyl)acetamido) phenyl)-2,4-dimethylpyridine 1-oxide | 0.026 | 0.046 |
| 8 | 3-(4-((S)-2-(3-ethylisoxazole-4-carboxamido)-2-((1r,4S)-4-(trifluoromethyl)cyclohexyl)acetamido) phenyl)-2,4-dimethylpyridine 1-oxide | 0.004 | 0.041 |
| 9 | 3-(4-((S)-2-((S)-3,3-difluorocyclohexyl)-2-(3-methylisoxazole-4-carboxamido)acetamido)phenyl)-2-methyl-4-(trifluoromethyl)pyridine 1-oxide | 0.004 | 0.060 |
| 10 | 3-(4-((S)-2-((S)-3,3-difluorocyclohexyl)-2-(1-ethyl-1H-pyrazole-5-carboxamido)acetamido)phenyl)-2-methyl-4-(trifluoromethyl)pyridine 1-oxide | 0.011 | 0.093 |
| 11 | (S)-3-(4-(2-(4,4-difluorocyclohexyl)-2-(1-ethyl-1H-pyrazole-5-carboxamido)acetamido)phenyl)-2-methyl-4-(trifluoromethyl)pyridine 1-oxide | 0.02 | 0.082 |
| 12a | 3-(4-((S)-2-((R)-4-fluorocyclohex-3-en-1-yl)-2-(1-methyl-1H-pyrazole-5-carboxamido)acetamido)phenyl)-2,4-dimethylpyridine 1-oxide or 3-(4-((S)-2-((S)-4-fluorocyclohex-3-en-1-yl)-2-(1-methyl-1H-pyrazole-5-carboxamido)acetamido)phenyl)-2,4-dimethylpyridine 1-oxide | 0.017 | 0.112 |
| 12b | 3-(4-((S)-2-((R)-4-fluorocyclohex-3-en-1-yl)-2-(1-methyl-1H-pyrazole-5-carboxamido)acetamido)phenyl)-2,4-dimethylpyridine 1-oxide or 3-(4-((S)-2-((S)-4-fluorocyclohex-3-en-1-yl)-2-(1-methyl-1H-pyrazole-5-carboxamido)acetamido)phenyl)-2,4-dimethylpyridine 1-oxide | 0.008 | 0.151 |
| 13a | (S)-4-chloro-3-(4-(2-(4,4-difluorocyclohexyl)-2-(1-ethyl-1H-pyrazole-5-carboxamido)acetamido)phenyl)-2-methylpyridine 1-oxide | 0.011 | 0.016 |
| 13b | (R)-4-chloro-3-(4-(2-(4,4-difluorocyclohexyl)-2-(1-ethyl-1H-pyrazole-5-carboxamido)acetamido)phenyl)-2-methylpyridine 1-oxide | n.t. | 30.4 |
| 14 | 4-chloro-3-(4-((S)-2-cyclohexyl-2-(3-methylisoxazole-4-carboxamido)acetamido)-2-fluorophenyl)-2-methylpyridine 1-oxide | 0.009 | 0.024 |
| 15 | 4-chloro-3-(4-((S)-2-cyclohexyl-2-(1-(2-methoxyethyl)-1H-pyrazole-5-carboxamido)acetamido)-2-fluorophenyl)-2-methylpyridine 1-oxide | 0.010 | 0.052 |
| 16 | 4-chloro-3-(4-((S)-2-cyclohexyl-2-(1-(2-hydroxyethyl)-1H-pyrazole-5-carboxamido)acetamido)-2-fluorophenyl)-2-methylpyridine 1-oxide | 0.013 | 0.084 |
| 17 | 4-chloro-3-(4-((S)-2-cyclohexyl-2-(3-methylisothiazole-4-carboxamido)acetamido)-2-fluorophenyl)-2-methylpyridine 1-oxide | 0.018 | 0.118 |
| 18 | 4-chloro-2-methyl-3-(4-((S)-2-(1-methyl-1H-pyrazole-5-carboxamido)-2-((1r,4S)-4-(trifluoromethyl)cyclohexyl)acetamido) phenyl)pyridine 1-oxide | 0.028 | 0.025 |
| 19 | 4-chloro-2-methyl-3-(4-((S)-2-(3-methylisoxazole-4-carboxamido)-2-((1r,4S)-4-(trifluoromethyl)cyclohexyl)acetamido) phenyl)pyridine 1-oxide | 0.020 | 0.026 |
| 20 | 4-chloro-3-(4-((S)-2-(1-ethyl-1H-pyrazole-5-carboxamido)-2-((1r,4S)-4-(trifluoromethyl)cyclohexyl)acetamido) phenyl)-2-methylpyridine 1-oxi | n.t. | 0.68 |
| 21 | (S)-3-(4-(2-cyclopentyl-2-(1-ethyl-1H-pyrazole-5-carboxamido)acetamido)phenyl)-2-methyl-4-(trifluoromethyl)pyridine 1-oxide | 0.031 | 0.039 |
| 22 | (S)-3-(4-(2-cyclopentyl-2-(3-methylisoxazole-4-carboxamido)acetamido)phenyl)-2-methyl-4-(trifluoromethyl)pyridine 1-oxide | 0.066 | 0.059 |
| 23 | 2,4-dimethyl-3-(4-((S)-2-(3-methylisoxazole-4-carboxamido)-2-((1r,4S)-4-(trifluoromethyl)cyclohexyl)acetamido) phenyl)pyridine 1-oxide | 0.006 | 0.060 |
| 24 | 2,4-dimethyl-3-(4-((S)-2-(1-methyl-1H-pyrazole-5-carboxamido)-2-((1r,4S)-4-(trifluoromethyl)cyclohexyl)acetamido) phenyl)pyridine 1-oxide | 0.048 | 0.114 |
| 25 | 3-(4-((S)-2-(3-(methoxymethyl)isoxazole-4-carboxamido)-2-((1r,4S)-4-(trifluoromethyl)cyclohexyl)acetamido) phenyl)-2,4-dimethylpyridine 1-oxide | 0.069 | 0.178 |
| 26 | 3-(4-((S)-2-((S)-3,3-difluorocyclohexyl)-2-(3-ethylisoxazole-4-carboxamido)acetamido)phenyl)-2-methyl-4-(trifluoromethyl)pyridine 1-oxide | 0.014 | 0.044 |
| 27 | (S)-3-(4-(2-(4,4-difluorocyclohexyl)-2-(1-methyl-1H-pyrazole-5-carboxamido)acetamido)phenyl)-2-methyl-4-(trifluoromethyl)pyridine 1-oxide | 0.115 | 0.121 |
| 28 | 3-(4-((S)-2-(3-ethylisoxazole-4-carboxamido)-2-((S)-4-fluorocyclohex-3-en-1-yl)acetamido)phenyl)-2,4-dimethylpyridine 1-oxide | 0.022 | 0.02 |

-continued

| Example | Name | IL17AA + TNF IC50 IL-6 [umol I-1] | IL17AA FRET/ IL17Rawt IC50 [umol I-1] |
|---|---|---|---|
| 29 | 3-(4-((S)-2-((S)-4-fluorocyclohex-3-en-1-yl)-2-(3-methylisoxazole-4-carboxamido)acetamido)phenyl)-2,4-dimethylpyridine 1-oxide | 0.047 | 0.085 |
| 30 | 3-(4-((S)-2-((S)-3,3-difluorocyclohexyl)-2-(3-ethylisoxazole-4-carboxamido)acetamido)phenyl)-2,4-dimethylpyridine 1-oxide | 0.012 | 0.046 |
| 31 | (S)-3-(4-(2-(4,4-difluorocyclohexyl)-2-(3-ethylisoxazole-4-carboxamido)acetamido)phenyl)-2,4-dimethylpyridine 1-oxide | 0.015 | 0.114 |
| 32 | (S)-3-(4-(2-(4,4-difluorocyclohexyl)-2-(1-methyl-1H-pyrazole-5-carboxamido)acetamido)phenyl)-2,4-dimethylpyridine 1-oxide | 0.05 | 0.286 |
| 33 | (S)-3-(4-(2-(4,4-difluorocyclohexyl)-2-(3-(methoxymethyl)isoxazole-4-carboxamido)acetamido)phenyl)-2,4-dimethylpyridine 1-oxide | 0.088 | 1.15 |
| 34 | (S)-3-(4-(2-cyclopentyl-2-(3-ethylisoxazole-4-carboxamido)acetamido)phenyl)-2,4-dimethylpyridine 1-oxide | 0.1 | 0.081 |
| 35 | (S)-3-(4-(2-cyclopentyl-2-(1-ethyl-1H-pyrazole-5-carboxamido)acetamido)phenyl)-2,4-dimethylpyridine 1-oxide | 0.212. | 0.306 |
| 36 | (S)-3-(4-(2-cyclopentyl-2-(1-methyl-1H-pyrazole-5-carboxamido)acetamido)phenyl)-2,4-dimethylpyridine 1-oxide | 0.038 | 1.41 |
| 37 | (S)-3-(4-(2-cyclopentyl-2-(3-methylisoxazole-4-carboxamido)acetamido)phenyl)-2,4-dimethylpyridine 1-oxide | 0.06 | 0.396 |
| 38 | (S)-3-(4-(3-(2-chlorophenyl)-2-(3-methylisoxazole-4-carboxamido)propanamido)phenyl)-2,4-dimethylpyridine 1-oxide | 0.131 | 0.017 |
| 39 | (S)-3-(4-(2-cyclohexyl-2-(1-methyl-1H-pyrazole-5-carboxamido)acetamido)phenyl)-2,4-dimethylpyridine 1-oxide | 0.02 | 0.191 |
| 40 | (S)-3-(4-(2-cycloheptyl-2-(1-isopropyl-1H-pyrazole-5-carboxamido)acetamido)phenyl)-2,4-dimethylpyridine 1-oxide | 0.002 | 0.025 |
| 41 | (S)-3-(4-(2-cycloheptyl-2-(1-methyl-1H-pyrazole-5-carboxamido)acetamido)phenyl)-2,4-dimethylpyridine 1-oxide | 0.009 | 0.024 |
| 42 | (S)-3-(4-(2-cycloheptyl-2-(1-cyclopropyl-1H-pyrazole-5-carboxamido)acetamido)phenyl)-2,4-dimethylpyridine 1-oxide | 0.012 | 0.026 |
| 43 | 2,4-dimethyl-3-(4-(2-(1-methyl-1H-pyrazole-5-carboxamido)-2-(1-methylcyclohexyl)acetamido)phenyl) pyridine 1-oxide | n.t. | 78.9 |
| 44 | (S)-6'-(2-cycloheptyl-2-(3-methylisoxazole-4-carboxamido)acetamido)-2,4-dimethyl-[3,3'-bipyridine] 1-oxide | 0.018 | 0.034 |
| 45 | (S)-4-chloro-3-(4-(2-cyclohexyl-2-(1-methyl-1H-pyrazole-5-carboxamido)acetamid)phenyl)-2-methylpyridine 1-oxide | 0.026 | 0.026 |

-continued

| Example | Name | IL17AA + TNF IC50 IL-6 [umol I-1] | IL17AA FRET/ IL17Rawt IC50 [umol I-1] |
|---|---|---|---|
| 46 | 4-chloro-2-methyl-3-(4-((S)-2-(1-methyl-1H-pyrazole-5-carboxamido)-2-((1r,4S)-4-methylcyclohexyl)acetamido)phenyl) pyridine 1-oxide | 0.004 | 0.018 |
| 47 | (S)-4-chloro-3-(4-(2-cycloheptyl-2-(1-methyl-1H-pyrazole-5-carboxamido)acetamido)phenyl)-2-methylpyridine 1-oxide | 0.007 | 0.017 |
| 48 | (S)-4-chloro-3-(4-(2-cycloheptyl-2-(1-isopropyl-1H-pyrazole-5-carboxamido)acetamido)phenyl)-2-methylpyridine 1-oxide | 0.001 | 0.012 |
| 49 | (S)-4-chloro-3-(4-(2-(4,4-difluorocyclohexyl)-2-(3-methylisoxazole-4-carboxamido)acetamido)phenyl)-2-methylpyridine 1-oxide | 0.031 | 0.058 |
| 50 | 3-(4-((S)-2-(1-isopropyl-1H-pyrazole-5-carboxamido)-2-((S)-1,2,3,4-tetrahydronaphthalen-1-yl)acetamido)phenyl)-2,4-dimethylpyridine 1-oxide | 0.001 | 0.023 |
| 51 | 4-chloro-3-(4-(2-(4,4-difluorocyclohexyl)-2-(3-ethylisoxazole-4-carboxamido)acetamido)phenyl)-2-methylpyridine 1-oxide | 0.062 | 0.066 |
| 52 | (S)-4-chloro-3-(4-(2-(4,4-difluorocyclohexyl)-2-(1-methyl-1H-pyrazole-5-carboxamido)acetamido)phenyl)-2-methylpyridine 1-oxide | 0.08 | 0.043 |
| 53 | (S)-3-(4-(2-cyclohexyl-2-(2-methylfuran-3-carboxamido)acetamido)phenyl)-2,4-dimethylpyridine 1-oxide | 0.086 | 0.016 |
| 54a | 4-chloro-3-(4-((S)-2-((1R,3s,5S)-6,6-difluorobicyclo[3.1.0]hexan-3-yl)-2-(1-methyl-1H-pyrazole-5-carboxamido)acetamido)phenyl)-2-methylpyridine 1-oxide | 0.034 | 0.028 |
| 54b | 4-chloro-3-(4-((R)-2-((1R,3s,5S)-6,6-difluorobicyclo[3.1.0]hexan-3-yl)-2-(1-methyl-1H-pyrazole-5-carboxamido)acetamido)phenyl)-2-methylpyridine 1-oxide | n.t. | 10.9 |
| 55 | 4-chloro-3-(4-((2S)-2-(4-fluorocyclohex-3-en-1-yl)-2-(1-methyl-1H-pyrazole-5-carboxamido)acetamido)phenyl)-2-methylpyridine 1-oxide | 0.027 | 0.038 |
| 56 | 4-chloro-3-(2-fluoro-4-((S)-2-(1-methyl-1H-pyrazole-5-carboxamido)-2-((1r,4S)-4-methylcyclohexyl)acetamido)phenyl)-2-methylpyridine 1-oxide | 0.004 | 0.021 |
| 57 | 3-(4-(2-((1R,3s,5S)-bicyclo[3.1.0]hexan-3-yl)-2-(3-methylisoxazole-4-carboxamido)acetamido)-2-fluorophenyl)-4-chloro-2-methylpyridine 1-oxide | 0.012 | 0.037 |
| 58 | 3-(4-(2-((1R,3s,5S)-bicyclo[3.1.0]hexan-3-yl)-2-(1-ethyl-1H-pyrazole-5-carboxamido)acetamido)-2-fluorophenyl)-4-chloro-2-methylpyridine 1-oxide | 0.012 | 0.044 |
| 59 | (S)-4-chloro-3-(4-(2-cyclohexyl-2-(1-methyl-1H-pyrazole-5-carboxamido)acetamido)-3-fluorophenyl)-2-methylpyridine 1-oxide | 0.056 | 0.049 |

-continued

| Example | Name | IL17AA + TNF IC50 IL-6 [umol I-1] | IL17AA FRET/ IL17Rawt IC50 [umol I-1] |
|---|---|---|---|
| 60 | (S)-4-chloro-6'-(2-cyclohexyl-2-(1-methyl-1H-pyrazole-5-carboxamido)acetamido)-2-methyl-[3,3'-bipyridine] 1-oxide | 0.236 | 0.123 |
| 61 | (S)-4-chloro-3-(4-(2-cyclohexyl-2-(1-methyl-1H-pyrazole-5-carboxamido)acetamido)-2,6-difluorophenyl)-2-methylpyridine 1-oxide | 0.016 | 0.018 |
| 62 | 4-chloro-3-(4-((S)-2-cyclohexyl-2-(1-methyl-1H-pyrazole-5-carboxamido)acetamido)-2,3-difluorophenyl)-2-methylpyridine 1-oxide | 0.007 | 0.015 |
| 63 | 4-chloro-3-(4-((S)-2-cyclohexyl-2-(1-methyl-1H-pyrazole-5-carboxamido)acetamido)-2,5-difluorophenyl)-2-methylpyridine 1-oxide | 0.057 | 0.247 |
| 64 | 3-(4-((S)-2-((1R,3s,5S)-bicyclo[3.1.0]hexan-3-yl)-2-(1-ethyl-1H-pyrazole-5-carboxamido)acetamido)phenyl)-2-methyl-4-(trifluoromethyl)pyridine 1-oxide | 0.025 | 0.074 |
| 65 | 3-(4-((2S)-2-(4-fluorocyclohex-3-en-1-yl)-2-(1-methyl-1H-pyrazole-5-carboxamido)acetamido)phenyl)-2-methyl-4-(trifluoromethyl)pyridine 1-oxide | 0.024 | 0.057 |
| 66 | 3-(4-((S)-2-cyclohexyl-2-(1-methyl-1H-pyrazole-5-carboxamido)acetamido)-2-fluorophenyl)-2-methyl-4-(trifluoromethyl)pyridine 1-oxide | 0.004 | 0.018 |
| 67 | (S)-3-(4-(2-cyclohexyl-2-(1-methyl-1H-pyrazole-5-carboxamido)acetamido)phenyl)-2-methyl-4-(trifluoromethyl)pyridine 1-oxide | 0.015 | 0.124 |
| 68 | (S)-3-(4-(2-(1-isopropyl-1H-pyrazole-5-carboxamido)-3,3-diphenylpropanamido)phenyl)-2,4-dimethylpyridine 1-oxide | 0.016 | 0.076 |
| 69 | (S)-4-chloro-2-methyl-3-(4-(2-(1-methyl-1H-pyrazole-5-carboxamido)-3,3-diphenylpropanamido)phenyl) pyridine 1-oxide | 0.020 | 0.090 |
| 70 | 3-(4-(2-(bicyclo[3.1.0]hexan-3-yl)-2-(1-ethyl-1H-pyrazole-5-carboxamido)acetamido)phenyl)-4-chloro-2-methylpyridine 1-oxide | 0.026 | 0.084 |
| 71 | 3-(4-(2-(bicyclo[3.1.0]hexan-3-yl)-2-(3-methylisoxazole-4-carboxamido)acetamido)phenyl)-4-chloro-2-methylpyridine 1-oxide | 0.035 | 0.086 |
| 72 | (S)-3-(4-(3-(2-fluorophenyl)-2-(3-methylisoxazole-4-carboxamido)propanamido)phenyl)-2,4-dimethylpyridine 1-oxide | 3.4 | 0.454 |
| 73 | (S)-3-(4-(2-cyclopentyl-2-(2-methyl-4-(trifluoromethyl)thiazole-5-carboxamido)acetamido)phenyl)-2-methyl-4-(trifluoromethyl)pyridine 1-oxide | n.t. | 1.41 |
| 74 | (S)-2,4-dimethyl-3-(4-(2-(3-methylisoxazole-4-carboxamido)-3-phenylpropanamido)phenyl)pyridine 1-oxide | >10 | 1.53 |
| 75 | (S)-2,4-dimethyl-3-(4-(2-(1-methyl-1H-pyrazole-5-carboxamido)-3-phenylpropanamido)phenyl)pyridine 1-oxide | >10 | 2.64 |
| 76 | 4-chloro-3-(4-((S)-2-cyclohexyl-2-(1-(2-methoxy-2-oxoethyl)-1H-pyrazole-5-carboxamido)acetamido)-2-fluorophenyl)-2-methylpyridine 1-oxide | n.t. | 0.603 |
| 77 | 4-chloro-3-(4-((S)-2-cyclohexyl-2-(1-(2-(dimethylamino)ethyl)-1H-pyrazole-5-carboxamido)acetamido)-2-fluorophenyl)-2-methylpyridine 1-oxide | 0.151 | 0.436 |
| 78 | 3-(4-((S)-2-(3-(hydroxymethyl)isoxazole-4-carboxamido)-2-((1r,4S)-4-(trifluoromethyl)cyclohexyl)acetamido) phenyl)-2,4-dimethylpyridine 1-oxide | n.t. | 1.69 |
| 79 | (S)-3-(4-(2-(3-(aminomethyl)isoxazole-4-carboxamido)-2-cyclohexylacetamido)phenyl)-2,4-dimethylpyridine 1-oxide | n.t. | 0.918 |
| 80 | (S)-3-(4-(2-cyclohexyl-2-(3-((dimethylamino)methyl)isoxazole-4-carboxamido)acetamido)phenyl)-2,4-dimethylpyridine 1-oxide | n.t. | 4.45 |
| 81 | (S)-3-(4-(2-cyclohexyl-2-(1-methyl-1H-pyrazole-5-carboxamido)acetamido)phenyl)-4-methylpyridine 1-oxide | n.t. | 3.74 |
| 82 | (S)-3-(4-(2-cyclohexyl-2-(1-isopropyl-1H-pyrazole-5-carboxamido)acetamido)-2-fluorophenyl)-2-methylpyridine 1-oxide | 0.035 | 0.085 |
| 83 | (S)-3-(4-(2-cyclohexyl-2-(1-methyl-1H-pyrazole-5-carboxamido)acetamido)-2-fluorophenyl)-2-methylpyridine 1-oxide | 0.115 | 1.98 |
| 84 | 3-(2-fluoro-4-((S)-2-(1-methyl-1H-pyrazole-5-carboxamido)-2-((1r,4S)-4-methylcyclohexyl)acetamido)phenyl)-2,4-dimethylpyridine 1-oxide | 0.008 | 0.014 |
| 85 | (S)-4-chloro-3-(3-chloro-4-(2-cyclohexyl-2-(1-methyl-1H-pyrazole-5-carboxamido)acetamido)phenyl)-2-methylpyridine 1-oxide | n.t. | 20.9 |
| 86 | 3-(4-((2S)-2-(3,3-difluorocyclopentyl)-2-(3-ethylisoxazole-4-carboxamido)acetamido)phenyl)-2,4-dimethylpyridine 1-oxide | 0.232 | 0.119 |
| 87 | 3-(4-((2S)-2-(3,3-difluorocyclopentyl)-2-(1-methyl-1H-pyrazole-5-carboxamido)acetamido)phenyl)-2,4-dimethylpyridine 1-oxide | 0.504 | 0.489 |
| 88 | 3-(4-((2S)-2-(3,3-difluorocyclopentyl)-2-(1-methyl-1H-pyrazole-5-carboxamido)acetamido)phenyl)-2,4-dimethylpyridine 1-oxide | 0.298 | 0.45 |
| 89 | (S)-2-chloro-3-(4-(2-cyclohexyl-2-(1-methyl-1H-pyrazole-5-carboxamido)acetamido)phenyl)-4-methylpyridine 1-oxide | 0.083 | 0.286 |
| 90 | 4-chloro-3-(4-((S)-2-cyclohexyl-2-(3-(methoxymethyl)isoxazole-4-carboxamido)acetamido)-2-fluorophenyl)-2-methylpyridine 1-oxide | 0.005 | 0.065 |
| 91 | 3-(2-fluoro-4-((S)-2-(1-methyl-1H-pyrazole-5-carboxamido)-2-((1r,4S)-4-(trifluoromethyl)cyclohexyl)acetamido) phenyl)-2,4-dimethylpyridine 1-oxide | 0.039 | 0.134 |

-continued

| Example | Name | IL17AA + TNF IC50 IL-6 [umol I-1] | IL17AA FRET/ IL17Rawt IC50 [umol I-1] |
|---|---|---|---|
| 92 | (S)-5-chloro-3-(4-(2-cyclohexyl-2-(1-methyl-1H-pyrazole-5-carboxamido)acetamido)-2-fluorophenyl)-2-methylpyridine 1-oxide | 0.028 | 0.372 |
| 93 | (S)-4-chloro-3-(4-(2-cyclohexyl-2-(1-methyl-1H-pyrazole-5-carboxamido)acetamido)-2-fluorophenyl)pyridine 1-oxide | 0.058 | 0.601 |
| 94 | (S)-3-(4-(2-cyclohexyl-2-(1-cyclopropyl-1H-pyrazole-5-carboxamido)acetamido)phenyl)-2,4-dimethylpyridine 1-oxide | 0.047 | 0.128 |
| 95 | 3-(4-((S)-2-cyclohexyl-2-(1-methyl-1H-pyrazole-5-carboxamido)acetamido)-2-fluorophenyl)-2,4-dimethylpyridine 1-oxide | 0.019 | 0.125 |
| 96 | 3-(4-((S)-2-cyclohexyl-2-(1-isopropyl-1H-pyrazole-5-carboxamido)acetamido)-2-fluorophenyl)-2,4-dimethylpyridine 1-oxide | 0.007 | 0.070 |
| 97 | (S)-4-(4-(2-cyclohexyl-2-(1-methyl-1H-pyrazole-5-carboxamido)acetamido)phenyl)-3,5-dimethylpyridine 1-oxide | n.t. | 1.73 |
| 98 | (S)-4-(4-(2-cyclohexyl-2-(1-cyclopropyl-1H-pyrazole-5-carboxamido)acetamido)phenyl)-3,5-dimethylpyridine 1-oxide | n.t. | 1.4 |
| 99 | (S)-4-(4-(2-cycloheptyl-2-(1-methyl-1H-pyrazole-5-carboxamido)acetamido)phenyl)-3,5-dimethylpyridine 1-oxide | 0.081 | 0.208 |
| 100 | (S)-4-(4-(2-cycloheptyl-2-(1-cyclopropyl-1H-pyrazole-5-carboxamido)acetamido)phenyl)-3,5-dimethylpyridine 1-oxide | 0.046 | 0.243 |
| 101 | (S)-4-(4-(2-cycloheptyl-2-(1-isopropyl-1H-pyrazole-5-carboxamido)acetamido)phenyl)-3,5-dimethylpyridine 1-oxide | 0.022 | 0.085 |
| 102 | (S)-4-(4-(2-(1-cyclobutyl-1H-pyrazole-5-carboxamido)-2-cycloheptylacetamido)phenyl)-3,5-dimethylpyridine 1-oxide | 0.017 | 0.123 |
| 103 | 3,5-dimethyl-4-(4-((S)-2-(1-methyl-1H-pyrazole-5-carboxamido)-2-((S)-1,2,3,4-tetrahydronaphthalen-2-yl)acetamido)phenyl)pyridine 1-oxide | 0.045 | 0.072 |
| 104 | (S)-3-(4-(2-cyclohexyl-2-(1-methyl-1H-pyrazole-5-carboxamido)acetamido)phenyl)-2-(difluoromethyl)-4-methylpyridine 1-oxide | 0.139 | 1.6 |
| 105 | (S)-4-(4-(2-cyclohexyl-2-(1-methyl-1H-pyrazole-5-carboxamido)acetamido)phenyl)-3-methylpyridine 1-oxide | 0.022 | 0.041 |
| 106 | 4-chloro-3-(4-((S)-2-(4,4-difluorocyclohexyl)-2-(3-methylisoxazole-4-carboxamido)acetamido)-2-fluorophenyl)-2-methylpyridine 1-oxide | 0.018 | 0.05 |
| 107 | 4-chloro-3-(4-((S)-2-(4,4-difluorocyclohexyl)-2-(1-methyl-1H-pyrazole-5-carboxamido)acetamido)-2-fluorophenyl)-2-methylpyridine 1-oxide | 0.015 | 0.019 |

-continued

| Example | Name | IL17AA + TNF IC50 IL-6 [umol I-1] | IL17AA FRET/ IL17Rawt IC50 [umol I-1] |
|---|---|---|---|
| 108 | 4-chloro-3-(4-(2-(4,4-difluorocyclohexyl)-2-(1-ethyl-1H-pyrazole-5-carboxamido)acetamido)-2-fluorophenyl)-2-methylpyridine 1-oxide | 0.007 | 0.03 |
| 109 | 3-(4-((S)-2-(4,4-difluorocyclohexyl)-2-(1-methyl-1H-pyrazole-5-carboxamido)acetamido)-2-fluorophenyl)-2,4-dimethylpyridine 1-oxide | 0.084 | 0.164 |
| 110 | 4-chloro-3-(4-((S)-2-((S)-3,3-difluorocyclohexyl)-2-(1-methyl-1H-pyrazole-5-carboxamido)acetamido)-2-fluorophenyl)-2-methylpyridine 1-oxide | 0.008 | 0.023 |
| 111 | (S)-4-(4-(2-cyclohexyl-2-(1-methyl-1H-pyrazole-5-carboxamido)acetamido)phenyl)-3-methylpyridine 1-oxide | n.t. | 4.78 |
| 112 | (S)-4-chloro-3-(4-(2-cyclohexyl-2-(1-methyl-1H-pyrazole-5-carboxamido)acetamido)phenyl) pyridine 1-oxide | 0.162 | 1.04 |
| 113 | (S)-3-(4-(2-cyclohexyl-2-(1-methyl-1H-pyrazole-5-carboxamido)acetamido)phenyl)-2,5-dimethylpyridine 1-oxide | 0.038 | 0.339 |
| 114 | (S)-3-(4-(2-cyclohexyl-2-(1-methyl-1H-pyrazole-5-carboxamido)acetamido)phenyl)-2-fluoro-4-methylpyridine 1-oxide | n.t. | 2.79 |
| 115 | (S)-3-(4-(2-cyclohexyl-2-(1-methyl-1H-pyrazole-5-carboxamido)acetamido)phenyl)-5-(hydroxymethyl)-2-methylpyridine 1-oxide | 0.201 | 1.38 |
| 116 | (S)-4-(4-(2-cycloheptyl-2-(1,2,3,4-tetrahydropyrrolo[1,2-a]pyrazine-6-carboxamido)acetamido)phenyl)-3,5-dimethylpyridine 1-oxide | 0.118 | 0.304 |
| 117 | (S)-4-(4-(2-cycloheptyl-2-(2-methyl-1,2,3,4-tetrahydropyrrolo[1,2-a]pyrazine-6-carboxamido)acetamido)phenyl)-3,5-dimethylpyridine 1-oxide | 0.121 | 0.161 |
| 118 | (S)-4-(4-(2-(2-acetyl-1,2,3,4-tetrahydropyrrolo[1,2-a]pyrazine-6-carboxamido)-2-cycloheptylacetamido)phenyl)-3,5-dimethylpyridine 1-oxide | 0.02 | 0.183 |
| 119 | (S)-3-(4-(2-cycloheptyl-2-(2-methyl-1,2,3,4-tetrahydropyrrolo[1,2-a]pyrazine-8-carboxamido)acetamido)phenyl)-2,4-dimethylpyridine 1-oxide | 0.015 | 0.13 |
| 120 | (S)-3-(4-(2-cycloheptyl-2-(2-methyl-1,2,3,4-tetrahydropyrrolo[1,2-a]pyrazine-6-carboxamido)acetamido)phenyl)-2,4-dimethylpyridine 1-oxide | 0.004 | 0.094 |
| 121 | 2,4-dimethyl-3-(4-((S)-2-(2-methyl-1,2,3,4-tetrahydropyrrolo[1,2-a]pyrazine-6-carboxamido)-2-((1r,4S)-4-methylcyclohexyl)acetamido)phenyl) pyridine 1-oxide | 0.017 | 0.111 |
| 122 | 4-chloro-3-(4-((S)-2-cycloheptyl-2-(2-methyl-1,2,3,4-tetrahydropyrrolo[1,2-a]pyrazine-6-carboxamido)acetamido)-2-fluorophenyl)-2-methylpyridine 1-oxide | 0.009 | 0.128 |

-continued

| Example | Name | IL17AA + TNF IC50 IL-6 [umol I-1] | IL17AA FRET/ IL17Rawt IC50 [umol I-1] |
|---|---|---|---|
| 123 | (S)-4-chloro-3-(4-(2-(4,4-difluorocyclohexyl)-2-(2-methyl-1,2,3,4-tetrahydropyrrolo[1,2-a]pyrazine-6-carboxamido)acetamido)phenyl)-2-methylpyridine 1-oxide | 0.059 | 0.15 |
| 124 | 4-chloro-3-(4-((S)-2-cyclohexyl-2-(2-methyl-1,2,3,4-tetrahydropyrrolo[1,2-a]pyrazine-6-carboxamido)acetamido)-2-fluorophenyl)-2-methylpyridine 1-oxide | 0.008 | 0.172 |
| 125 | 2,4-dimethyl-3-(4-((S)-2-(2-methyl-1,2,3,4-tetrahydropyrrolo[1,2-a]pyrazine-6-carboxamido)-2-((1r,4S)-4-(trifluoromethyl)cyclohexyl)acetamido) phenyl)pyridine 1-oxide | 0.018 | 0.174 |
| 126 | (S)-3-(4-(2-cyclohexyl-2-(2-methyl-1,2,3,4-tetrahydropyrrolo[1,2-a]pyrazine-6-carboxamido)acetamido)-2-fluorophenyl)-2-methylpyridine 1-oxide | 0.062 | 0.228 |
| 127 | (S)-3-(4-(2-cyclohexyl-2-(2-methyl-1,2,3,4-tetrahydropyrrolo[1,2-a]pyrazine-6-carboxamido)acetamido)phenyl)-2,4-dimethylpyridine 1-oxide | 0.012 | 0.2355 |
| 128 | 3-(4-((2S)-2-(4-fluorocyclohex-3-en-1-yl)-2-(2-methyl-1,2,3,4-tetrahydropyrrolo[1,2-a]pyrazine-6-carboxamido)acetamido)phenyl)-2,4-dimethylpyridine 1-oxide | 0.054 | 0.299 |
| 129 | 4-chloro-3-(4-((2S)-2-(4-fluorocyclohexyl)-2-(2-methyl-1,2,3,4-tetrahydropyrrolo[1,2-a]pyrazine-6-carboxamido)acetamido)phenyl)-2-methylpyridine 1-oxide | n.t. | 0.382 |
| 130 | (S)-3-(4-(3-(2-chlorophenyl)-2-(2-methyl-1,2,3,4-tetrahydropyrrolo[1,2-a]pyrazine-6-carboxamido)propanamido)phenyl)-2,4-dimethylpyridine 1-oxide | 0.956 | 0.124 |
| 131 | (S)-3-(4-(2-cyclohexyl-2-(2-cyclopropyl-1,2,3,4-tetrahydropyrrolo[1,2-a]pyrazine-6-carboxamido)acetamido)phenyl)-2,4-dimethylpyridine 1-oxide | n.t. | 0.102 |
| 132 | 2,4-dimethyl-3-(4-((S)-2-(2-(oxetan-3-yl)-1,2,3,4-tetrahydropyrrolo[1,2-a]pyrazine-6-carboxamido)-2-((1r,4S)-4-(trifluoromethyl)cyclohexyl)acetamido) phenyl)pyridine 1-oxide | n.t. | 0.866 |
| 133 | 4-chloro-3-(4-((S)-2-cyclohexyl-2-(2-(oxetan-3-yl)-1,2,3,4-tetrahydropyrrolo[1,2-a]pyrazine-6-carboxamido)acetamido)-2-fluorophenyl)-2-methylpyridine 1-oxide | 0.017 | 0.099 |
| 134 | 3-(4-((S)-2-(2-acetyl-1,2,3,4-tetrahydropyrrolo[1,2-a]pyrazine-6-carboxamido)-2-cycloheptylacetamido)-2-fluorophenyl)-4-chloro-2-methylpyridine 1-oxide | 0.007 | 0.0728 |
| 135 | (S)-3-(4-(2-cyclohexyl-2-(2-(2-methoxyethyl)-1,2,3,4-tetrahydropyrrolo[1,2-a]pyrazine-6-carboxamido)acetamido)phenyl)-2,4-dimethylpyridine 1-oxide | n.t. | 0.451 |

The following table provides the potency of reference examples 136-144 in the cell and TR-FRET assays:

| Reference Name | | | |
|---|---|---|---|
| Reference Example | Name | IL 17AA + TNF $IC_{50}$ IL-6 [umol I-1] | IL17AA FRET/ IL17RAwt $IC_{50}$ [umol I-1] |
| 136 | N-((S)-2-((4-(2,4-dimethylpyridin-3-yl)phenyl)amino)-2-oxo-1-((S)-1,2,3,4-tetrahydronaphthalen-1-yl)ethyl)-1-methyl-1H-pyrazole-5-carboxamide | 0.05 | 0.117 |
| 137 | N-((1S)-2-((4-(4-chloro-2-methylpyridin-3-yl)-3-fluorophenyl)amino)-1-cyclohexyl-2-oxoethyl)-1-methyl-1H-pyrazole-5-carboxamide | 0.578 | 3.79 |
| 138 | N-((S)-2-((4-(2,4-dimethylpyridin-3-yl)phenyl)amino)-1-((1r,4S)-4-methylcyclohexyl)-2-oxoethyl)-1-methyl-1H-pyrazole-5-carboxamide | 0.055 | 0.552 |
| 139 | (S)-N-(1-cyclopentyl-2-((4-(2-methyl-4-(trifluoromethyl)pyridin-3-yl)phenyl)amino)-2-oxoethyl)-3-ethylisoxazole-4-carboxamide | 0.152 | 0.899 |
| 140 | N-((S)-2-((4-(4-chloro-2-methylpyridin-3-yl)phenyl)amino)-1-((S)-3,3-difluorocyclohexyl)-2-oxoethyl)-3-ethylisoxazole-4-carboxamide | n.t. | 1.22 |
| 141 | N-((S)-2-((4-(2,4-dimethylpyridin-3-yl)phenyl)amino)-2-oxo-1-((1r,4S)-4-(trifluoromethyl)cyclohexyl)ethyl)-1-ethyl-1H-pyrazole-5-carboxamide | n.t. | 2.63 |
| 142 | N-((S)-2-((4-(2,4-dimethylpyridin-3-yl)phenyl)amino)-2-oxo-1-((1r,4S)-4-(trifluoromethyl)cyclohexyl)ethyl)-3-ethylisoxazole-4-carboxamide | n.t. | 4.38 |
| 143 | N-((S)-1-((S)-3,3-difluorocyclohexyl)-2-((4-(2-methyl-4-(trifluoromethyl)pyridin-3-yl)phenyl)amino)-2-oxoethyl)-3-methylisoxazole-4-carboxamide | n.t. | 0.851 |
| 144 | N-((S)-2-((4-(2,4-dimethylpyridin-3-yl)phenyl)amino)-1-((S)-4-fluorocyclohex-3-en-1-yl)-2-oxoethyl)-1-methyl-1H-pyrazole-5-carboxamide | 0.715 | 4.18 |

The following table provides the potency of additional Examples 145-225 which have been prepared by following the procedures described for Examples 1 to 135 in the cell- and TR-FRET assays:

| Ex. | Structure | Name | IL17AA + TNF IC50 IL-6 [umol I-1] | IL17AA FRET/ IL17Rawt IC50 [umol I-1] |
|---|---|---|---|---|
| 145 | 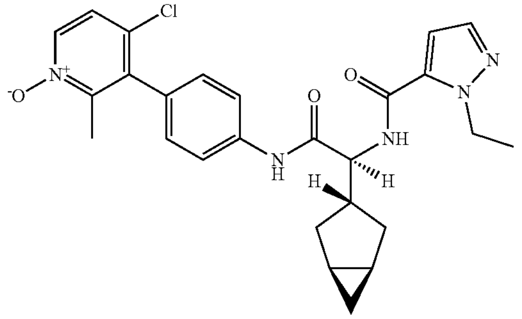 | 3-(4-((S)-2-((1R,3s,5S)-bicyclo[3.1.0]hexan-3-yl)-2-(1-ethyl-1H-pyrazole-5-carboxamido)acetamido) phenyl)-4-chloro-2-methylpyridine 1-oxide | 0.0235 | 0.024 |
| 146 | 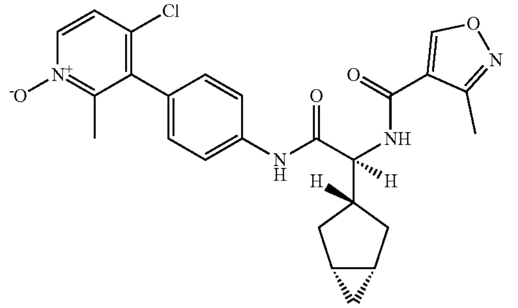 | 3-(4-((S)-2-((1R,3r,5S)-bicyclo[3.1.0]hexan-3-yl)-2-(3-methylisoxazole-4-carboxamido)acetamido) phenyl)-4-chloro-2-methylpyridine 1-oxide | 0.057 | 0.0863 |
| 147 | 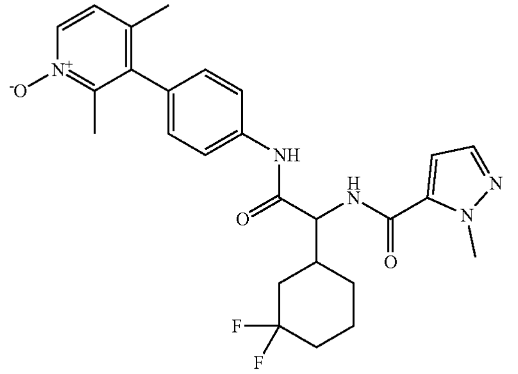 | 3-(4-(2-(3,3-difluorocyclohexyl)-2-(1-methyl-1H-pyrazole-5-carboxamido)acetamido) phenyl)-2,4-dimethylpyridine 1-oxide | 0.193 | 0.513 |
| 148 | 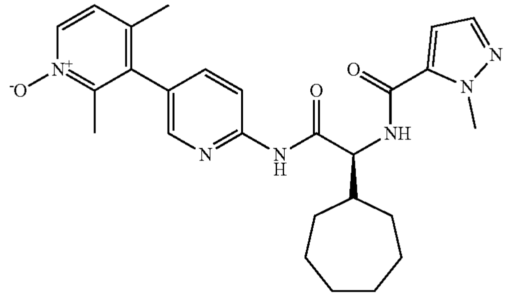 | (S)-6'-(2-cycloheptyl-2-(1-methyl-1H-pyrazole-5-carboxamido)acetamido)-2,4-dimethyl-[3,3'-bipyridine] 1-oxide | 0.131 | 0.125 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 149 | 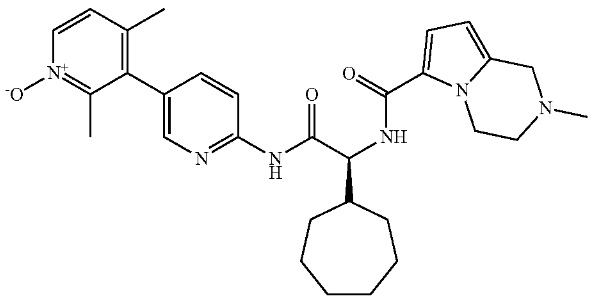 | (S)-6'-(2-cycloheptyl-2-(2-methyl-1,2,3,4-tetrahydropyrrolo[1,2-a]pyrazine-6-carboxamido)acetamido)-2,4-dimethyl-[3,3'-bipyridine] 1-oxide | 0.059 | 0.118 |
| 150 | 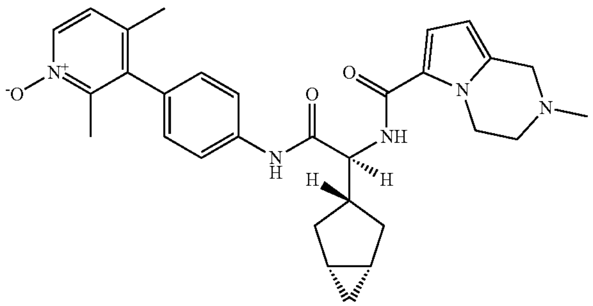 | 3-(4-((S)-2-((1R,3r,5S)-bicyclo[3.1.0]hexan-3-yl)-2-(2-methyl-1,2,3,4-tetrahydropyrrolo[1,2-a]pyrazine-6-carboxamido)acetamido) phenyl)-2,4-dimethylpyridine 1-oxide | n.t. | 0.464 |
| 151 | 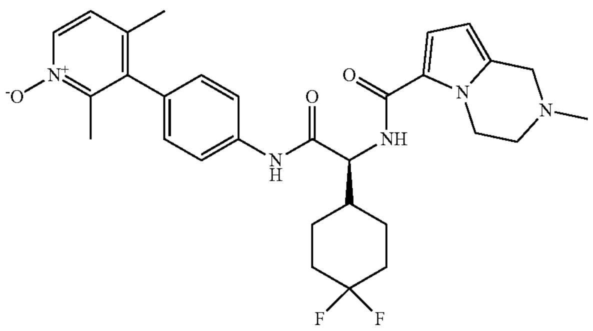 | (S)-3-(4-(2-(4,4-difluorocyclohexyl)-2-(2-methyl-1,2,3,4-tetrahydropyrrolo[1,2-a]pyrazine-6-carboxamido)acetamido) phenyl)-2,4-dimethylpyridine 1-oxide | 0.057 | 0.26 |
| 152 | 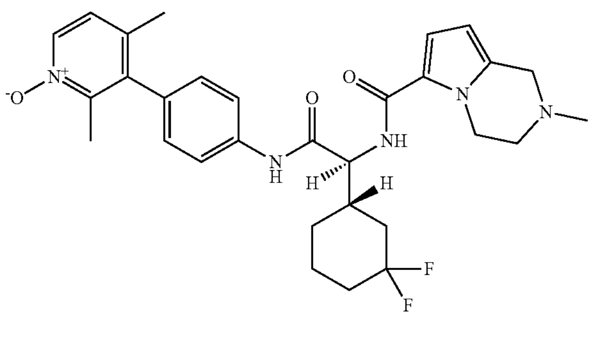 | 3-(4-((S)-2-((S)-3,3-difluorocyclohexyl)-2-(2-methyl-1,2,3,4-tetrahydropyrrolo[1,2-a]pyrazine-6-carboxamido)acetamido) phenyl)-2,4-dimethylpyridine 1-oxide | n.t. | 0.391 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 153 | 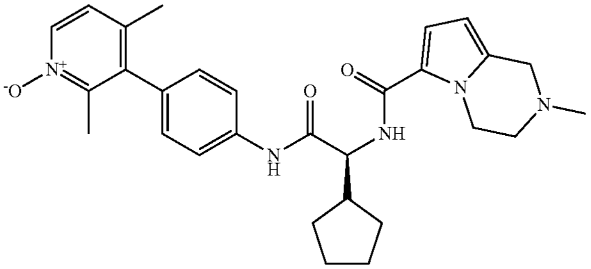 | (S)-3-(4-(2-cyclopentyl-2-(2-methyl-1,2,3,4-tetrahydropyrrolo[1,2-a]pyrazine-6-carboxamido)acetamido) phenyl)-2,4-dimethylpyridine 1-oxide | n.t. | 0.798 |
| 154 | 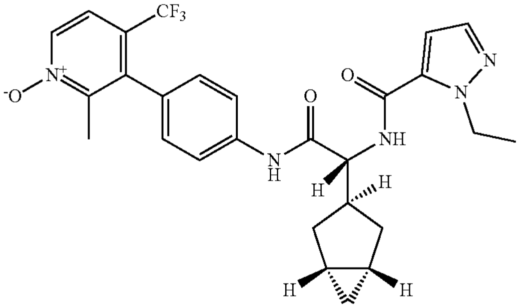 | 3-(4-((R)-2-((1R,3s,5S)-bicyclo[3.1.0]hexan-3-yl)-2-(1-ethyl-1H-pyrazole-5-carboxamido)acetamido) phenyl)-2-methyl-4-(trifluoromethyl)pyridine 1-oxide | n.t. | 6.3 |
| 155 | 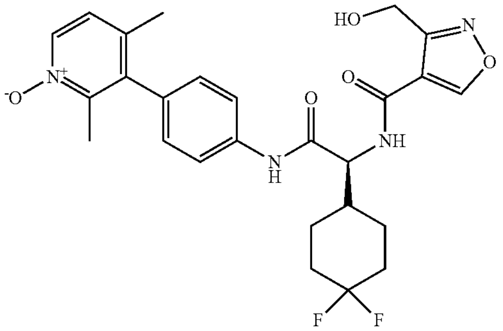 | (S)-3-(4-(2-(4,4-difluorocyclohexyl)-2-(3-(hydroxymethyl)isoxazole-4-carboxamido)acetamido) phenyl)-2,4-dimethylpyridine 1-oxide | n.t. | 1.15 |
| 156 | 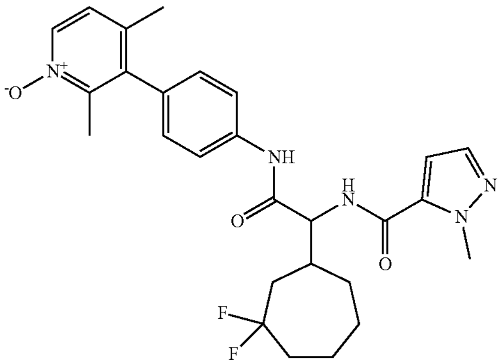 | 3-(4-(2-(3,3-difluorocycloheptyl)-2-(1-methyl-1H-pyrazole-5-carboxamido)acetamido) phenyl)-2,4-dimethylpyridine 1-oxide | 0.0515 | 0.11 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 157 | 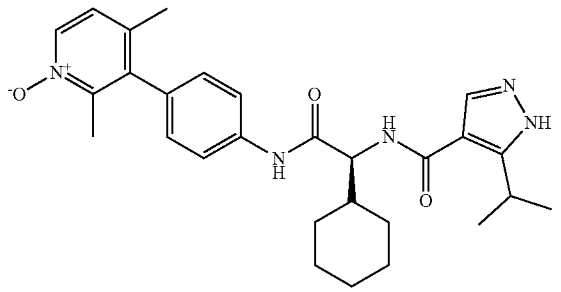 | (S)-3-(4-(2-cyclohexyl-2-(5-isopropyl-1H-pyrazole-4-carboxamido)acetamido) phenyl)-2,4-dimethylpyridine 1-oxide | 0.105 | 0.17 |
| 158 | 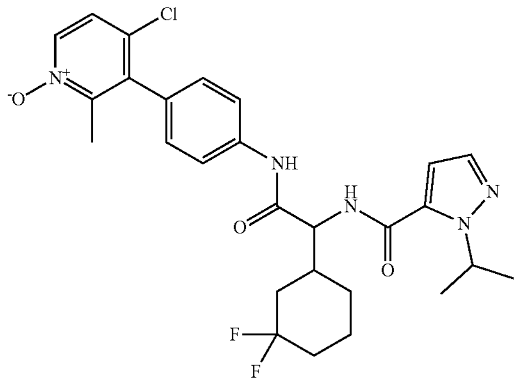 | 4-chloro-3-(4-(2-(3,3-difluorocyclohexyl)-2-(1-isopropyl-1H-pyrazole-5-carboxamido)acetamido) phenyl)-2-methylpyridine 1-oxide | 0.0155 | <0.0061 |
| 159 | 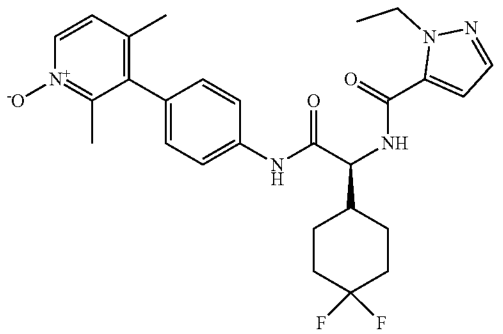 | (S)-3-(4-(2-(4,4-difluorocyclohexyl)-2-(1-ethyl-1H-pyrazole-5-carboxamido)acetamido) phenyl)-2,4-dimethylpyridine 1-oxide | 0.031 | 0.1 |
| 160 | 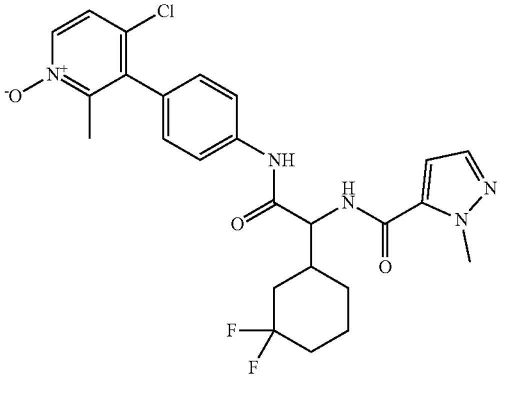 | 4-chloro-3-(4-(2-(3,3-difluorocyclohexyl)-2-(1-methyl-1H-pyrazole-5-carboxamido)acetamido) phenyl)-2-methylpyridine 1-oxide | 0.0523333 | 0.0895 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 161 | 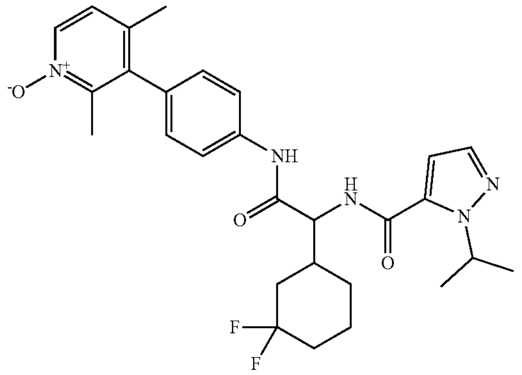 | 3-(4-(2-(3,3-difluorocyclohexyl)-2-(1-isopropyl-1H-pyrazole-5-carboxamido)acetamido) phenyl)-2,4-dimethylpyridine 1-oxide | 0.0205 | 0.13 |
| 162 | 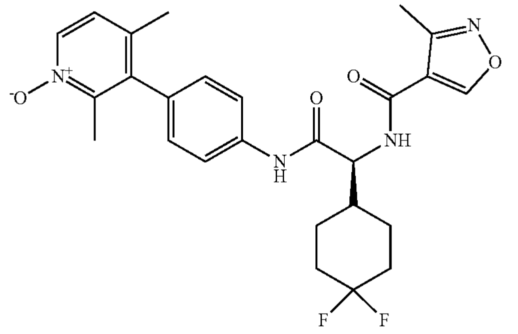 | (S)-3-(4-(2-(4,4-difluorocyclohexyl)-2-(3-methylisoxazole-4-carboxamido)acetamido) phenyl)-2,4-dimethylpyridine 1-oxide | 0.044 | 0.186 |
| 163 | 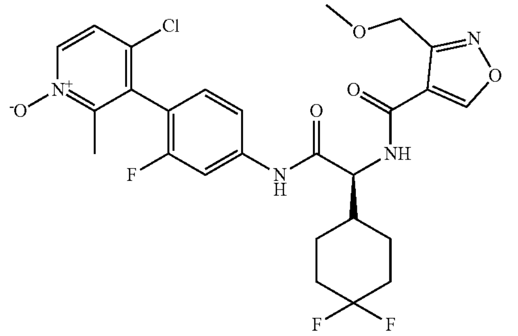 | 4-chloro-3-(4-((S)-2-(4,4-difluorocyclohexyl)-2-(3-(methoxymethyl)isoxazole-4-carboxamido)acetamido)-2-fluorophenyl)-2-methylpyridine 1-oxide | 0.068 | 0.191 |
| 164 | 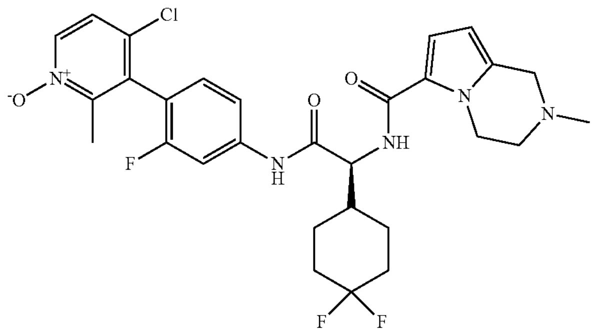 | 4-chloro-3-(4-((S)-2-(4,4-difluorocyclohexyl)-2-(2-methyl-1,2,3,4-tetrahydropyrrolo[1,2-a]pyrazine-6-carboxamido)acetamido)-2-fluorophenyl)-2-methylpyridine 1-oxide | 0.045 | 0.199 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 165 | 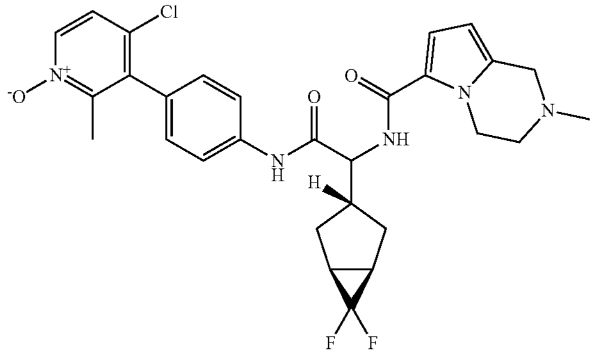 | 4-chloro-3-(4-(2-((1R,3s,5S)-6,6-difluorobicyclo[3.1.0]hexan-3-yl)-2-(2-methyl-1,2,3,4-tetrahydropyrrolo[1,2-a]pyrazine-6-carboxamido)acetamido)phenyl)-2-methylpyridine 1-oxide | n.t. | 0.301 |
| 166 | 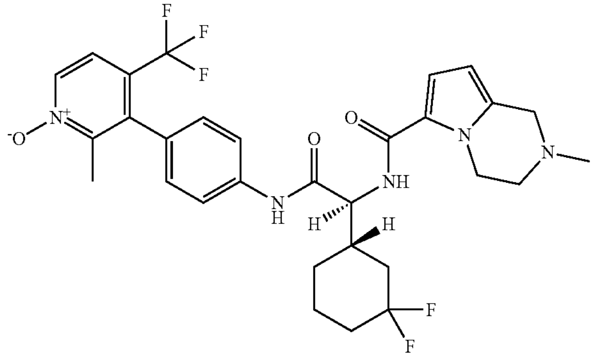 | 3-(4-((S)-2-((S)-3,3-difluorocyclohexyl)-2-(2-methyl-1,2,3,4-tetrahydropyrrolo[1,2-a]pyrazine-6-carboxamido)acetamido)phenyl)-2-methyl-4-(trifluoromethyl)pyridine 1-oxide | n.t. | 0.358 |
| 167 | 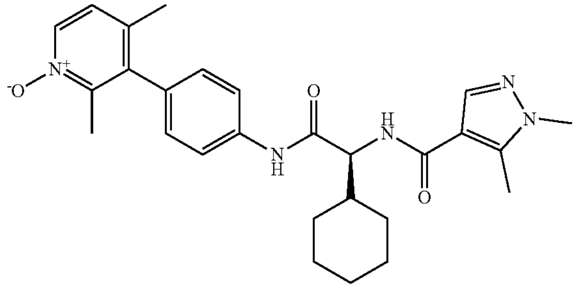 | (S)-3-(4-(2-cyclohexyl-2-(1,5-dimethyl-1H-pyrazole-4-carboxamido)acetamido)phenyl)-2,4-dimethylpyridine 1-oxide | 0.21 | 0.155 |
| 168 | 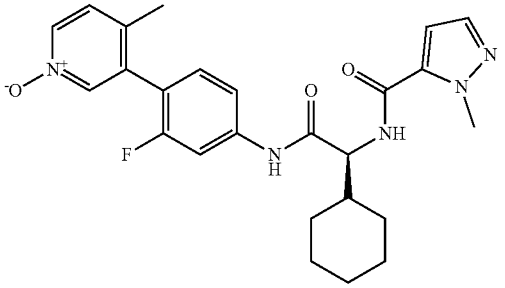 | (S)-3-(4-(2-cyclohexyl-2-(1-methyl-1H-pyrazole-5-carboxamido)acetamido)-2-fluorophenyl)-4-methylpyridine 1-oxide | n.t. | 1.47 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 169 | 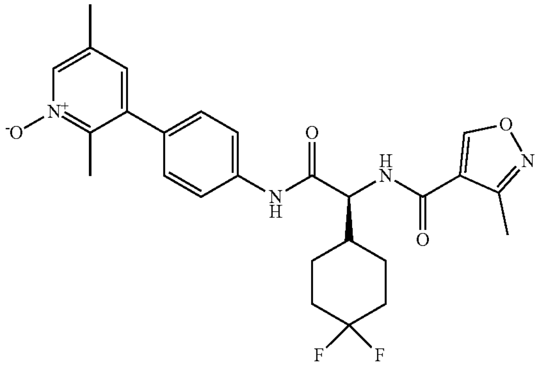 | (S)-3-(4-(2-(4,4-difluorocyclohexyl)-2-(3-methylisoxazole-4-carboxamido)acetamido) phenyl)-2,5-dimethylpyridine 1-oxide | 0.339 | 0.391 |
| 170 | 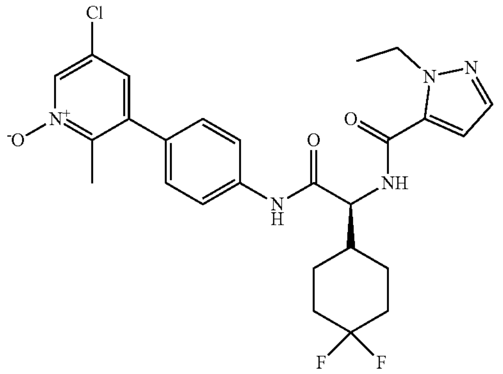 | (S)-5-chloro-3-(4-(2-(4,4-difluorocyclohexyl)-2-(1-ethyl-1H-pyrazole-5-carboxamido)acetamido) phenyl)-2-methylpyridine 1-oxide | 0.231 | 0.402 |
| 171 | 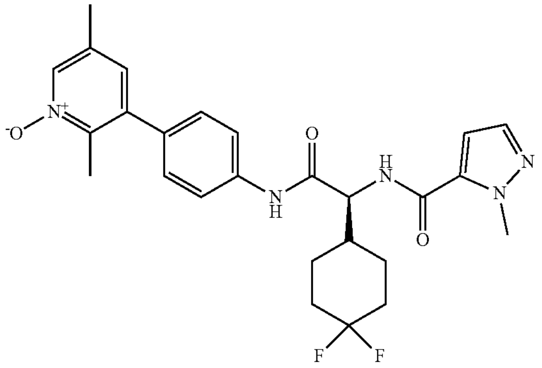 | (S)-3-(4-(2-(4,4-difluorocyclohexyl)-2-(1-methyl-1H-pyrazole-5-carboxamido)acetamido) phenyl)-2,5-dimethylpyridine 1-oxide | 0.398 | 0.465 |
| 172 | 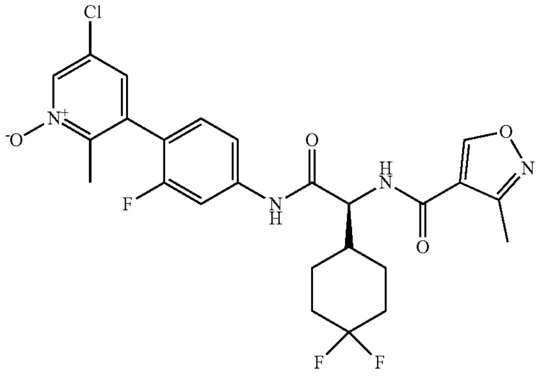 | (S)-5-chloro-3-(4-(2-(4,4-difluorocyclohexyl)-2-(3-methylisoxazole-4-carboxamido)acetamido)-2-fluorophenyl)-2-methylpyridine 1-oxide | 0.531 | 0.596 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 173 | 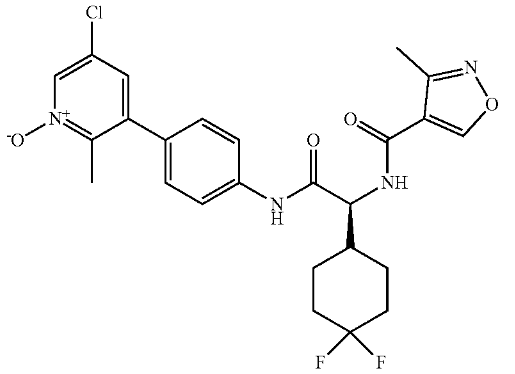 | (S)-5-chloro-3-(4-(2-(4,4-difluorocyclohexyl)-2-(3-methylisoxazole-4-carboxamido)acetamido) phenyl)-2-methylpyridine 1-oxide | 1.681 | 0.659 |
| 174 | 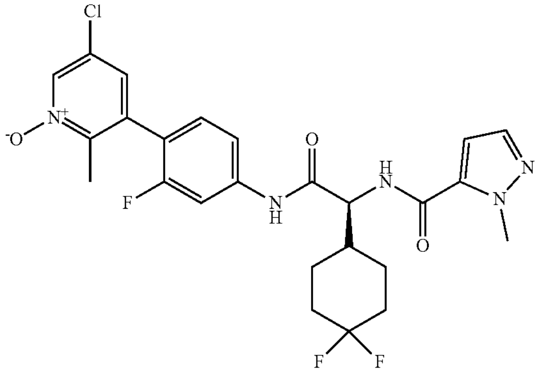 | (S)-5-chloro-3-(4-(2-(4,4-difluorocyclohexyl)-2-(1-methyl-1H-pyrazole-5-carboxamido)acetamido)-2-fluorophenyl)-2-methylpyridine 1-oxide | 0.286 | 0.683 |
| 175 | 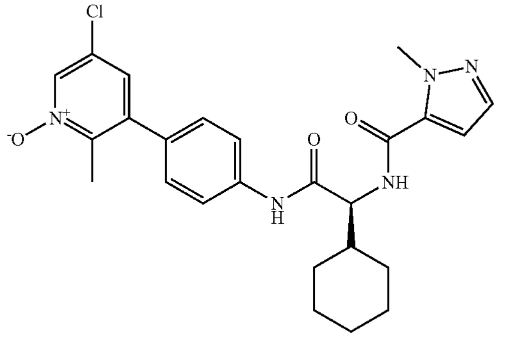 | (S)-5-chloro-3-(4-(2-cyclohexyl-2-(1-methyl-1H-pyrazole-5-carboxamido)acetamido) phenyl)-2-methylpyridine 1-oxide | 0.13 | 0.846 |
| 176 | 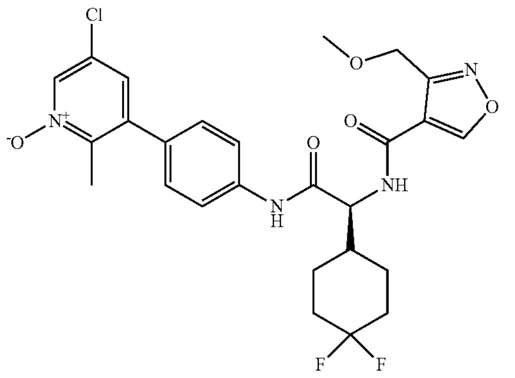 | (S)-5-chloro-3-(4-(2-(4,4-difluorocyclohexyl)-2-(3-(methoxymethyl)isoxazole-4-carboxamido)acetamido) phenyl)-2-methylpyridine 1-oxide | n.t. | 1.61 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 177 | 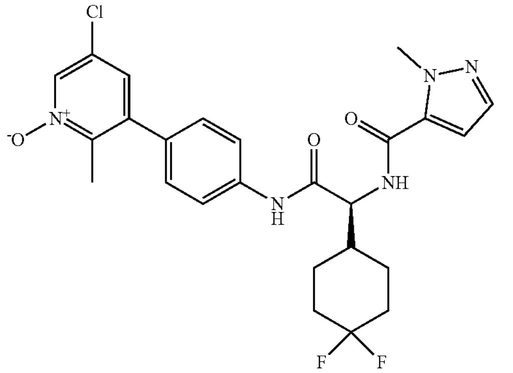 | (S)-5-chloro-3-(4-(2-(4,4-difluorocyclohexyl)-2-(1-methyl-1H-pyrazole-5-carboxamido)acetamido) phenyl)-2-methylpyridine 1-oxide | n.t. | 2.11 |
| 178 | 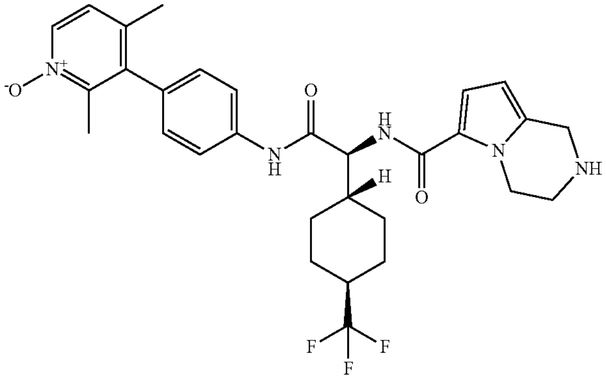 | 2,4-dimethyl-3-(4-((S)-2-(1,2,3,4-tetrahydropyrrolo[1,2-a]pyrazine-6-carboxamido)-2-((1r,4S)-4-(trifluoromethyl) cyclohexyl) acetamido)phenyl) pyridine 1-oxide | 0.03 | 0.00896 |
| 179 | 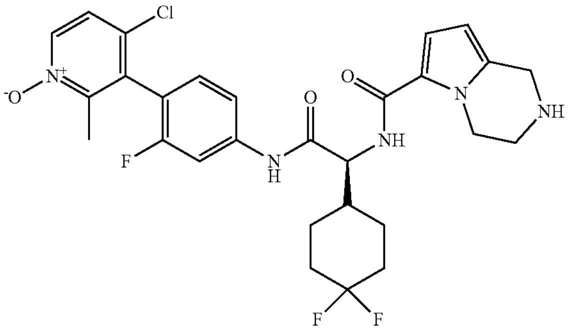 | 4-chloro-3-(4-((S)-2-(4,4-difluorocyclohexyl)-2-(1,2,3,4-tetrahydropyrrolo[1,2-a]pyrazine-6-carboxamido)acetamido)-2-fluorophenyl)-2-methylpyridine 1-oxide | 0.06 | 0.0139 |
| 180 | 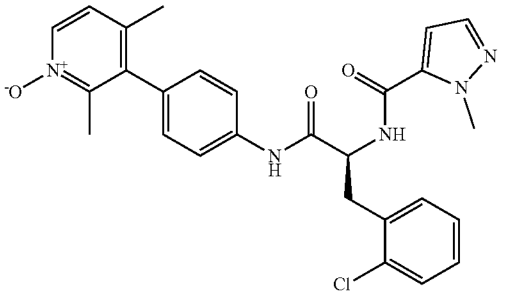 | (S)-3-(4-(3-(2-chlorophenyl)-2-(1-methyl-1H-pyrazole-5-carboxamido)propanamido) phenyl)-2,4-dimethylpyridine 1-oxide | 0.372 | 0.052 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 181 | 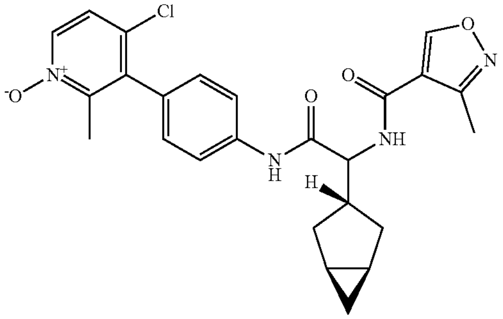 | 3-(4-(2-((1R,3s,5S)-bicyclo[3.1.0]hexan-3-yl)-2-(3-methylisoxazole-4-carboxamido)acetamido) phenyl)-4-chloro-2-methylpyridine 1-oxide | 0.064 | 0.0548 |
| 182 | 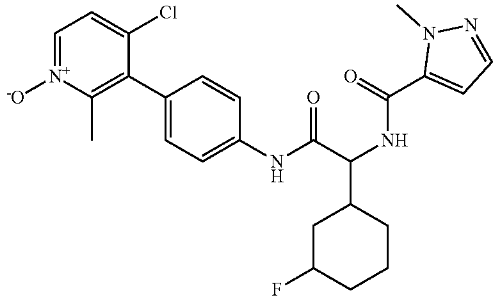 | 4-chloro-3-(4-(2-(3-fluorocyclohexyl)-2-(1-methyl-1H-pyrazole-5-carboxamido)acetamido) phenyl)-2-methylpyridine 1-oxide | 0.0445 | 0.0612 |
| 183 | 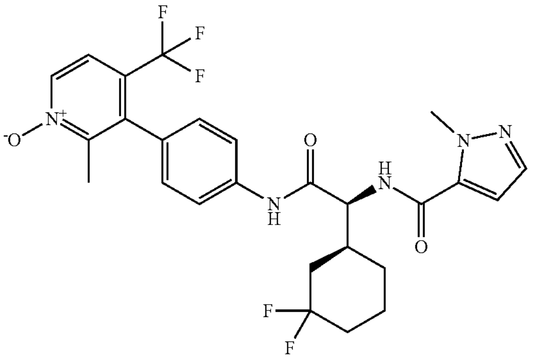 | 3-(4-((S)-2-((S)-3,3-difluorocyclohexyl)-2-(1-methyl-1H-pyrazole-5-carboxamido)acetamido) phenyl)-2-methyl-4-(trifluoromethyl)pyridine 1-oxide | 0.042 | 0.0541 |
| 184 | 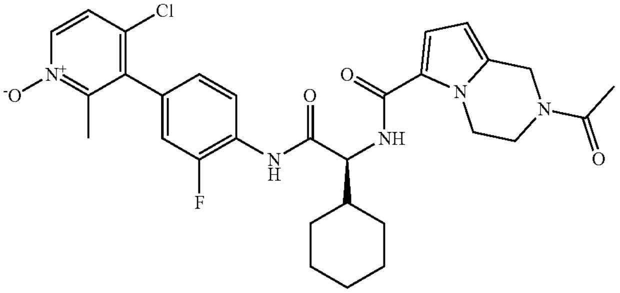 | (S)-3-(4-(2-(2-acetyl-1,2,3,4-tetrahydropyrrolo[1,2-a]pyrazine-6-carboxamido)-2-cyclohexylacetamido)-3-fluorophenyl)-4-chloro-2-methylpyridine 1-oxide | 0.011 | 0.0599 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 185 | 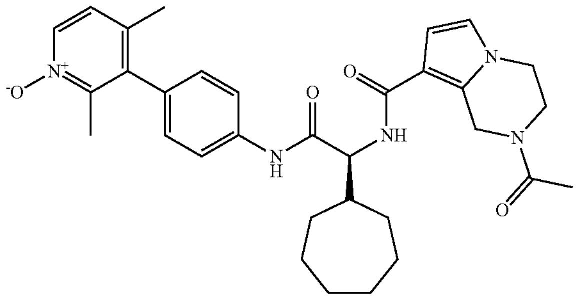 | (S)-3-(4-(2-(2-acetyl-1,2,3,4-tetrahydropyrrolo[1,2-a]pyrazine-8-carboxamido)-2-cycloheptylacetamido) phenyl)-2,4-dimethylpyridine 1-oxide | 0.00975 | 0.0771 |
| 186 | 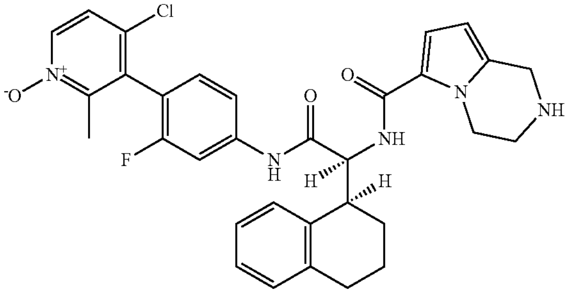 | 4-chloro-3-(2-fluoro-4-((S)-2-((S)-1,2,3,4-tetrahydronaphthalen-1-yl)-2-(1,2,3,4-tetrahydropyrrolo[1,2-a]pyrazine-6-carboxamido)acetamido) phenyl)-2-methylpyridine 1-oxide | 0.034 | 0.0815 |
| 187 | 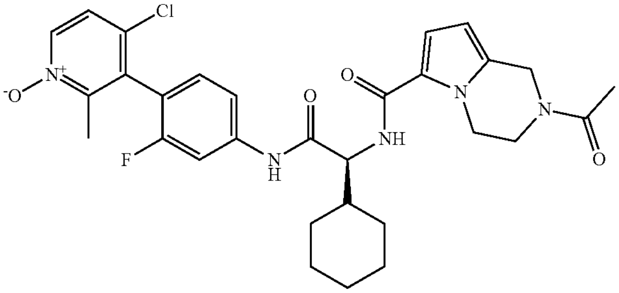 | 3-(4-((S)-2-(2-acetyl-1,2,3,4-tetrahydropyrrolo[1,2-a]pyrazine-6-carboxamido)-2-cyclohexylacetamido)-2-fluorophenyl)-4-chloro-2-methylpyridine 1-oxide | 0.017 | 0.0854 |
| 188 | 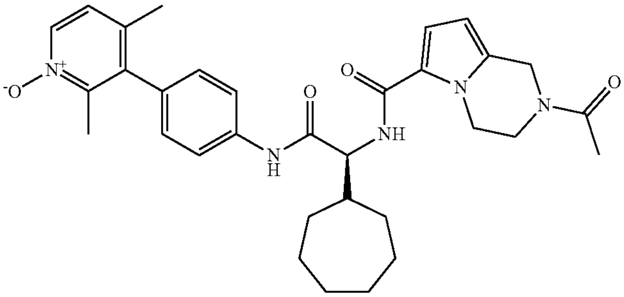 | (S)-3-(4-(2-(2-acetyl-1,2,3,4-tetrahydropyrrolo[1,2-a]pyrazine-6-carboxamido)-2-cycloheptylacetamido) phenyl)-2,4-dimethylpyridine 1-oxide | 0.00605 | 0.104 |
| 189 | 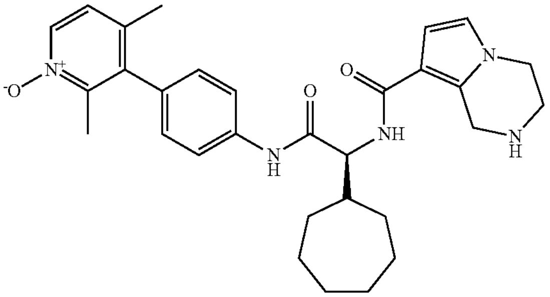 | (S)-3-(4-(2-cycloheptyl-2-(1,2,3,4-tetrahydropyrrolo[1,2-a]pyrazine-8-carboxamido)acetamido) phenyl)-2,4-dimethylpyridine 1-oxide | 0.0155 | 0.118 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 190 | 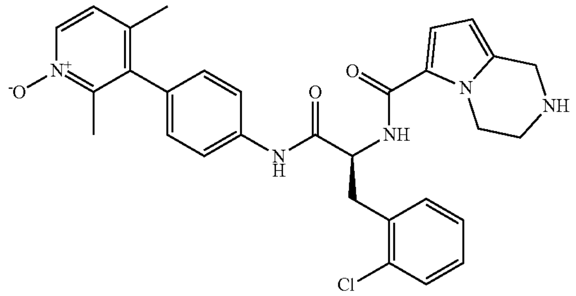 | (S)-3-(4-(3-(2-chlorophenyl)-2-(1,2,3,4-tetrahydropyrrolo[1,2-a]pyrazine-6-carboxamido) propanamido) phenyl)-2,4-dimethylpyridine 1-oxide | 0.278 | 0.123 |
| 191 | 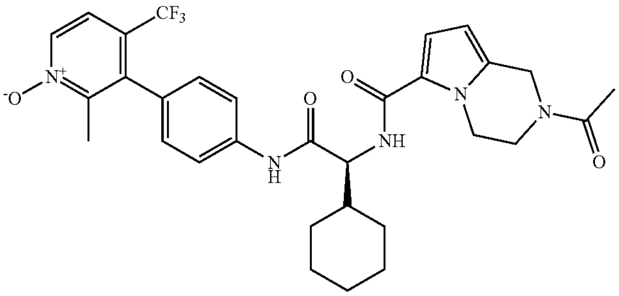 | (S)-3-(4-(2-(2-acetyl-1,2,3,4-tetrahydropyrrolo[1,2-a]pyrazine-6-carboxamido)-2-cyclohexylacetamido) phenyl)-2-methyl-4-(trifluoromethyl)pyridine 1-oxide | 0.0185 | 0.128 |
| 192 | 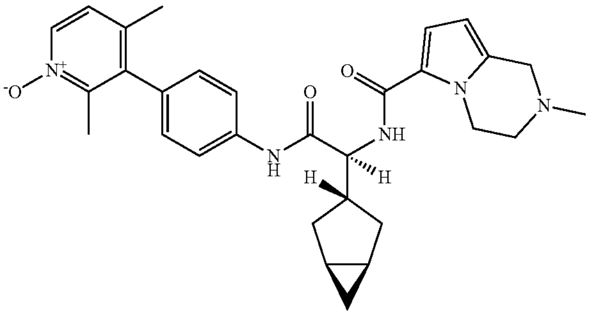 | 3-(4-((S)-2-((1R,3s,5S)-bicyclo[3.1.0]hexan-3-yl)-2-(2-methyl-1,2,3,4-tetrahydropyrrolo[1,2-a]pyrazine-6-carboxamido)acetamido) phenyl)-2,4-dimethylpyridine 1-oxide | 0.142 | 0.151 |
| 193 | 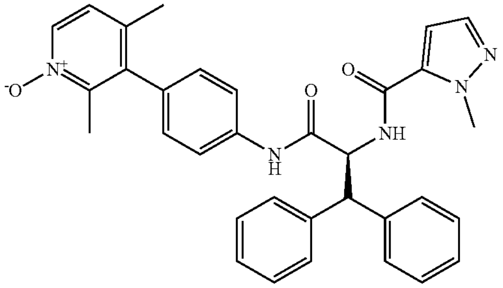 | (S)-2,4-dimethyl-3-(4-(2-(1-methyl-1H-pyrazole-5-carboxamido)-3,3-diphenylpropanamido) phenyl)pyridine 1-oxide | 0.047 | 0.0973 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 194 | 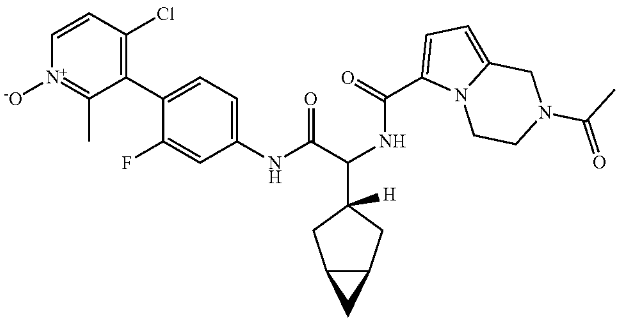 | 3-(4-(2-(2-acetyl-1,2,3,4-tetrahydropyrrolo[1,2-a]pyrazine-6-carboxamido)-2-((1R,3s,5S)-bicyclo[3.1.0]hexan-3-yl)acetamido)-2-fluorophenyl)-4-chloro-2-methylpyridine 1-oxide | 0.047 | 0.165 |
| 195 | 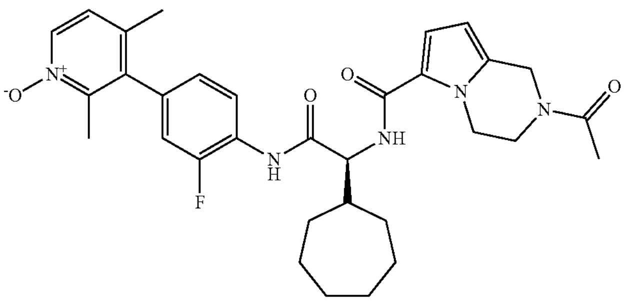 | (S)-3-(4-(2-(2-acetyl-1,2,3,4-tetrahydropyrrolo[1,2-a]pyrazine-6-carboxamido)-2-cycloheptylacetamido)-3-fluorophenyl)-2,4-dimethylpyridine 1-oxide | 0.0285 | 0.178 |
| 196 | 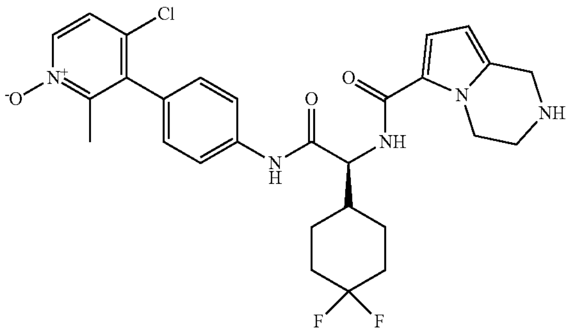 | (S)-4-chloro-3-(4-(2-(4,4-difluorocyclohexyl)-2-(1,2,3,4-tetrahydropyrrolo[1,2-a]pyrazine-6-carboxamido)acetamido)phenyl)-2-methylpyridine 1-oxide | 0.0126 | 0.181 |
| 197 | 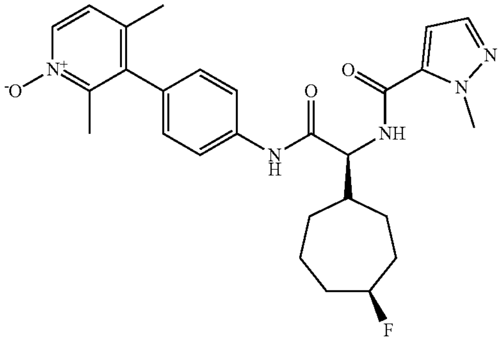 | 3-(4-((S)-2-((1S,4S)-4-fluorocycloheptyl)-2-(1-methyl-1H-pyrazole-5-carboxamido)acetamido)phenyl)-2,4-dimethylpyridine 1-oxide | 0.1215 | 0.213 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 198 | 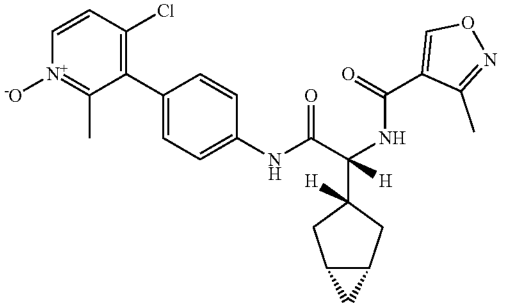 | 3-(4-((R)-2-((1R,3r,5S)-bicyclo[3.1.0]hexan-3-yl)-2-(3-methylisoxazole-4-carboxamido)acetamido) phenyl)-4-chloro-2-methylpyridine 1-oxide | 0.094 | 0.222 |
| 199 | 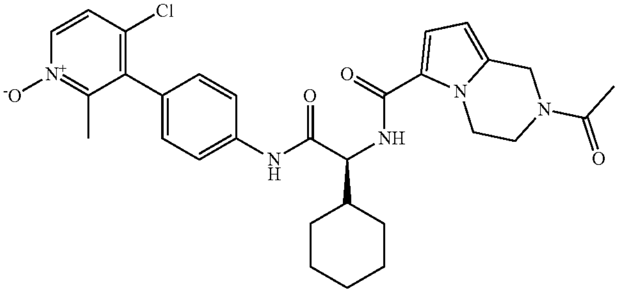 | (S)-3-(4-(2-(2-acetyl-1,2,3,4-tetrahydropyrrolo[1,2-a]pyrazine-6-carboxamido)-2-cyclohexylacetamido) phenyl)-4-chloro-2-methylpyridine 1-oxide | 0.0115 | 0.237 |
| 200 | 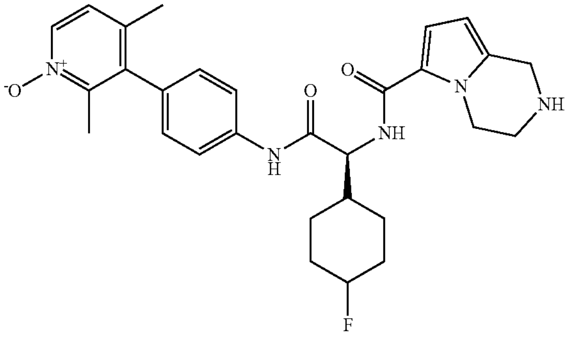 | 3-(4-((2S)-2-(4-fluorocyclohexyl)-2-(1,2,3,4-tetrahydropyrrolo[1,2-a]pyrazine-6-carboxamido)acetamido) phenyl)-2,4-dimethylpyridine 1-oxide | 0.416 | 0.246 |
| 201 | 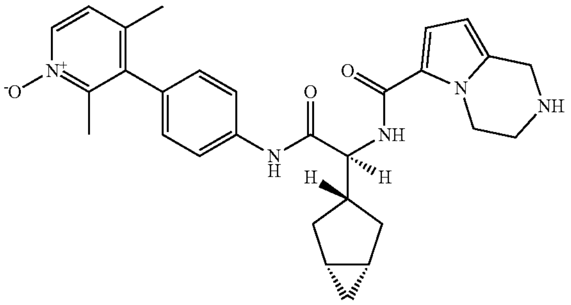 | 3-(4-((S)-2-((1R,3r,5S)-bicyclo[3.1.0]hexan-3-yl)-2-(1,2,3,4-tetrahydropyrrolo[1,2-a]pyrazine-6-carboxamido)acetamido) phenyl)-2,4-dimethylpyridine 1-oxide | 0.061 | 0.252 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 202 | 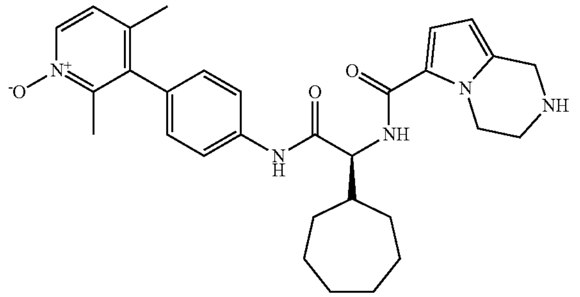 | (S)-3-(4-(2-cycloheptyl-2-(1,2,3,4-tetrahydropyrrolo[1,2-a]pyrazine-6-carboxamido)acetamido) phenyl)-2,4-dimethylpyridine 1-oxide | 0.073 | 0.257 |
| 203 | 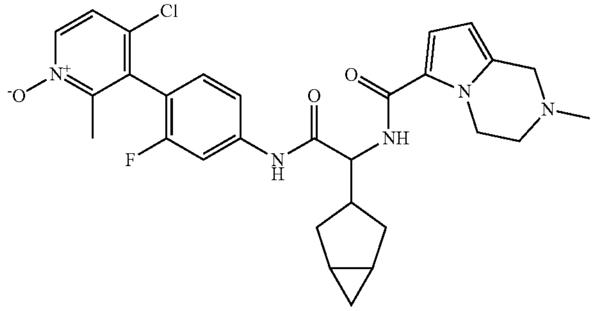 | 3-(4-(2-(bicyclo[3.1.0]hexan-3-yl)-2-(2-methyl-1,2,3,4-tetrahydropyrrolo[1,2-a]pyrazine-6-carboxamido)acetamido)-2-fluorophenyl)-4-chloro-2-methylpyridine 1-oxide | 0.039 | 0.257 |
| 204 | 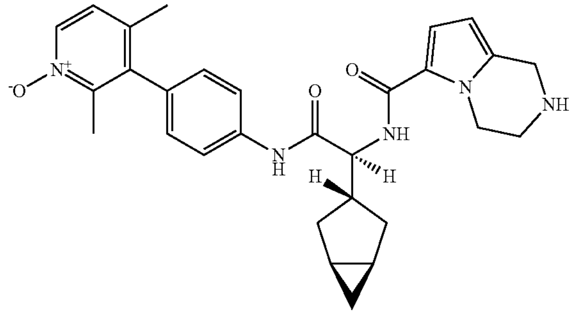 | 3-(4-((S)-2-((1R,3s,5S)-bicyclo[3.1.0]hexan-3-yl)-2-(1,2,3,4-tetrahydropyrrolo[1,2-a]pyrazine-6-carboxamido)acetamido) phenyl)-2,4-dimethylpyridine 1-oxide | 0.095 | 0.278 |
| 205 | 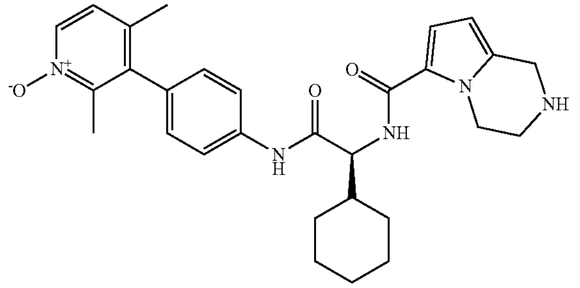 | (S)-3-(4-(2-cyclohexyl-2-(1,2,3,4-tetrahydropyrrolo[1,2-a]pyrazine-6-carboxamido)acetamido) phenyl)-2,4-dimethylpyridine 1-oxide | 0.058 | 0.287 |
| 206 | 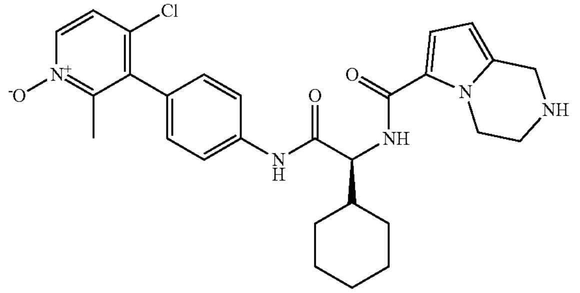 | (S)-4-chloro-3-(4-(2-cyclohexyl-2-(1,2,3,4-tetrahydropyrrolo[1,2-a]pyrazine-6-carboxamido)acetamido) phenyl)-2-methylpyridine 1-oxide | 0.063 | 0.296 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 207 | 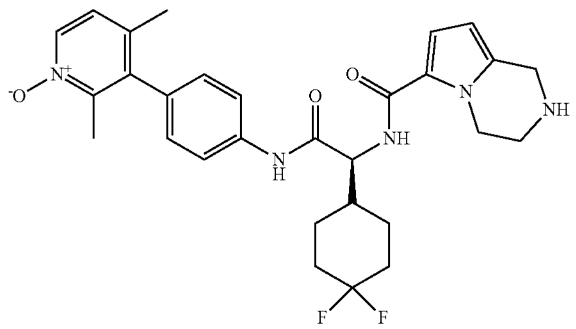 | (S)-3-(4-(2-(4,4-difluorocyclohexyl)-2-(1,2,3,4-tetrahydropyrrolo[1,2-a]pyrazine-6-carboxamido)acetamido) phenyl)-2,4-dimethylpyridine 1-oxide | 0.069 | 0.303 |
| 208 | 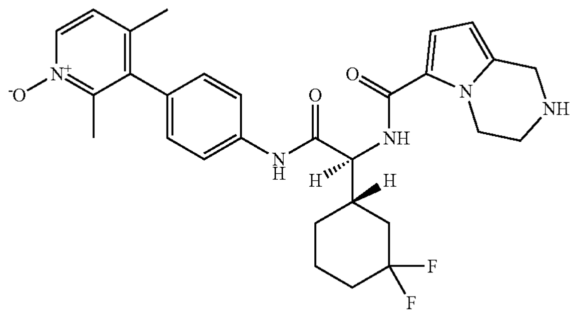 | 3-(4-((S)-2-((S)-3,3-difluorocyclohexyl)-2-(1,2,3,4-tetrahydropyrrolo[1,2-a]pyrazine-6-carboxamido)acetamido) phenyl)-2,4-dimethylpyridine 1-oxide | n.t. | 0.316 |
| 209 | 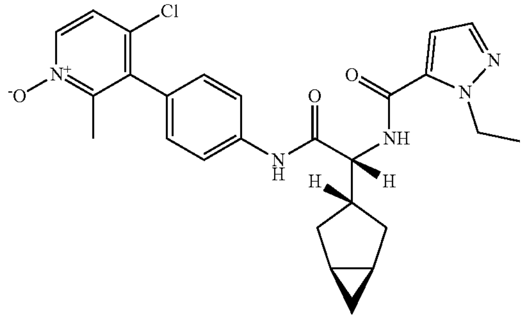 | 3-(4-((R)-2-((1R,3s,5S)-bicyclo[3.1.0]hexan-3-yl)-2-(1-ethyl-1H-pyrazole-5-carboxamido)acetamido) phenyl)-4-chloro-2-methylpyridine 1-oxide | 0.175 | 0.381 |
| 210 | 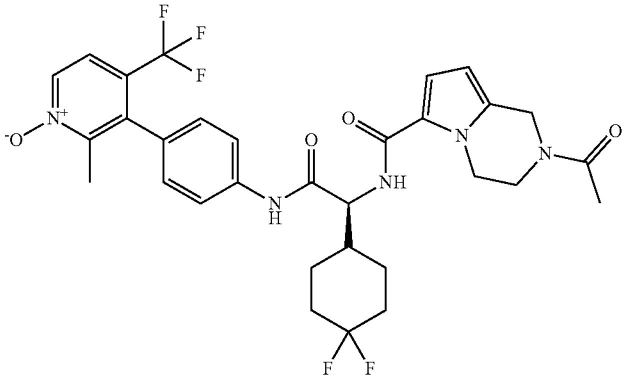 | (S)-3-(4-(2-(2-acetyl-1,2,3,4-tetrahydropyrrolo[1,2-a]pyrazine-6-carboxamido)-2-(4,4-difluorocyclohexyl) acetamido)phenyl)-2-methyl-4-(trifluoromethyl) pyridine 1-oxide | n.t. | 0.478 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 211 | 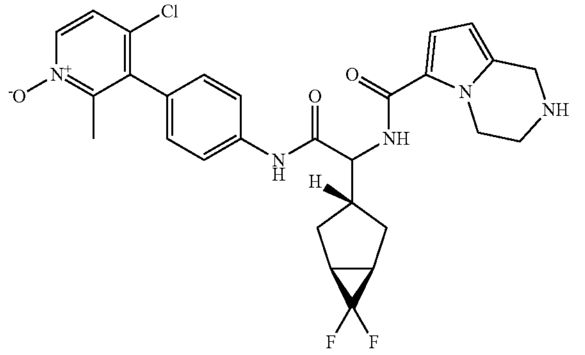 | 4-chloro-3-(4-(2-((1R,3s,5S)-6,6-difluorobicyclo[3.1.0]hexan-3-yl)-2-(1,2,3,4-tetrahydropyrrolo[1,2-a]pyrazine-6-carboxamido)acetamido)phenyl)-2-methylpyridine 1-oxide | n.t. | 0.499 |
| 212 | 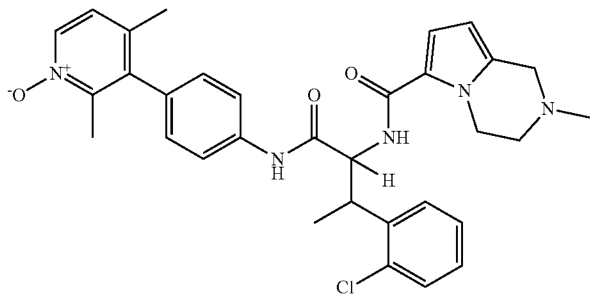 | 3-(4-(3-(2-chlorophenyl)-2-(2-methyl-1,2,3,4-tetrahydropyrrolo[1,2-a]pyrazine-6-carboxamido)butanamido)phenyl)-2,4-dimethylpyridine 1-oxide | n.t. | 0.502 |
| 213 | 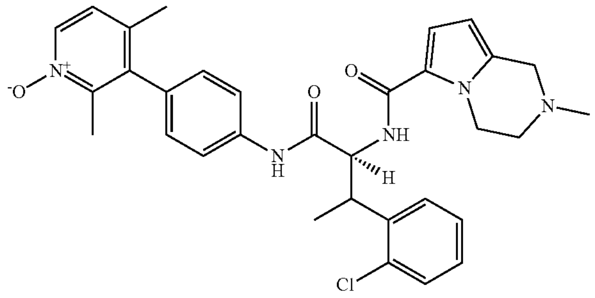 | 3-(4-((2S)-3-(2-chlorophenyl)-2-(2-methyl-1,2,3,4-tetrahydropyrrolo[1,2-a]pyrazine-6-carboxamido)butanamido)phenyl)-2,4-dimethylpyridine 1-oxide | 2.584 | 0.533 |
| 214 | 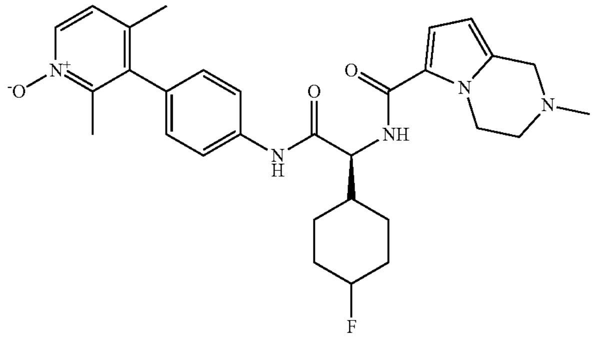 | 3-(4-((2S)-2-(4-fluorocyclohexyl)-2-(2-methyl-1,2,3,4-tetrahydropyrrolo[1,2-a]pyrazine-6-carboxamido)acetamido)phenyl)-2,4-dimethylpyridine 1-oxide | n.t. | 0.69 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 215 | 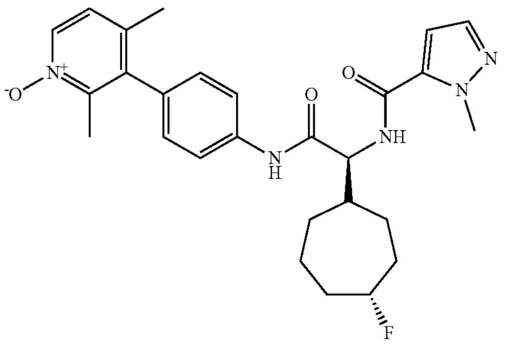 | 3-(4-((S)-2-((1S,4R)-4-fluorocycloheptyl)-2-(1-methyl-1H-pyrazole-5-carboxamido)acetamido) phenyl)-2,4-dimethylpyridine 1-oxide | 0.138 | 0.755 |
| 216 | 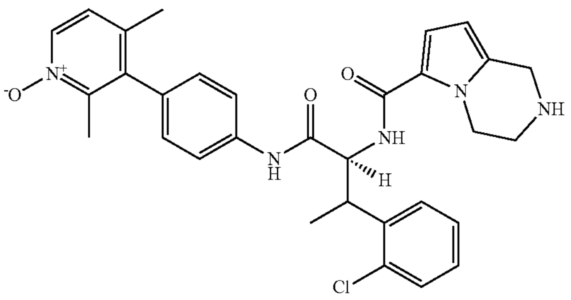 | 3-(4-((2S)-3-(2-chlorophenyl)-2-(1,2,3,4-tetrahydropyrrolo[1,2-a]pyrazine-6-carboxamido) butanamido) phenyl)-2,4-dimethylpyridine 1-oxide | n.t. | 0.796 |
| 217 | 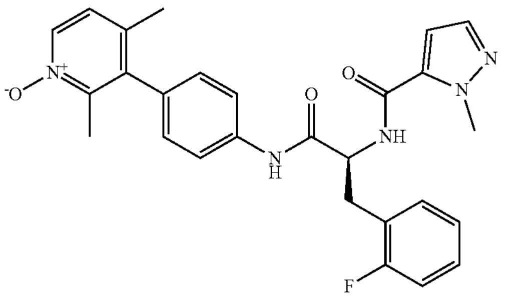 | (S)-3-(4-(3-(2-fluorophenyl)-2-(1-methyl-1H-pyrazole-5-carboxamido) propanamido) phenyl)-2,4-dimethylpyridine 1-oxide | 2.959 | 1.1 |
| 218 | 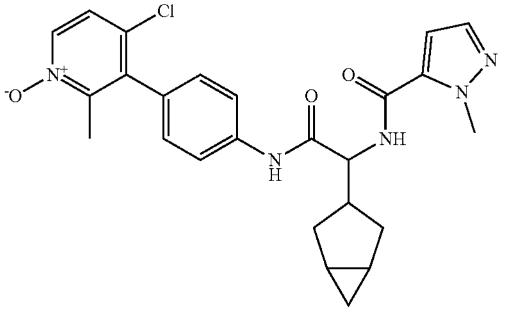 | 3-(4-(2-(bicyclo[3.1.0]hexan-3-yl)-2-(1-methyl-1H-pyrazole-5-carboxamido)acetamido) phenyl)-4-chloro-2-methylpyridine 1-oxide | 0.0195 | 0.0675 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 219 | 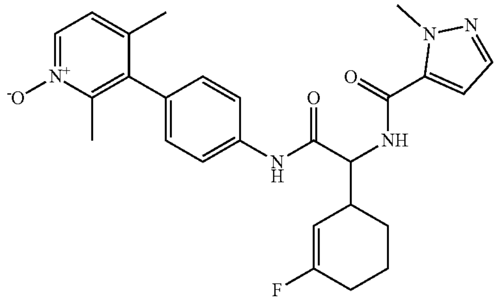 | 3-(4-(2-(3-fluorocyclohex-2-en-1-yl)-2-(1-methyl-1H-pyrazole-5-carboxamido)acetamido) phenyl)-2,4-dimethylpyridine 1-oxide | 0.142 | 2.29 |
| 220 | 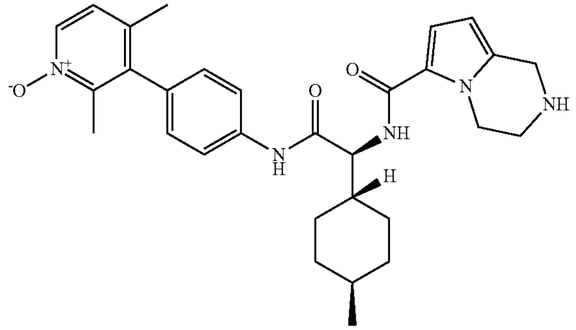 | 2,4-dimethyl-3-(4-((S)-2-((1r,4S)-4-methylcyclohexyl)-2-(1,2,3,4-tetrahydropyrrolo[1,2-a]pyrazine-6-carboxamido)acetamido) phenyl)pyridine 1-oxide | n.t | 2.31 |
| 221 | 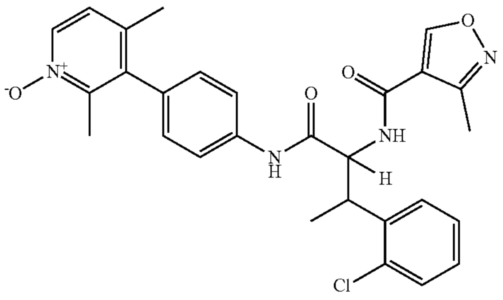 | 3-(4-(3-(2-chlorophenyl)-2-(3-methylisoxazole-4-carboxamido)butanamido) phenyl)-2,4-dimethylpyridine 1-oxide | 0.264 | 0.0719 |
| 222 | 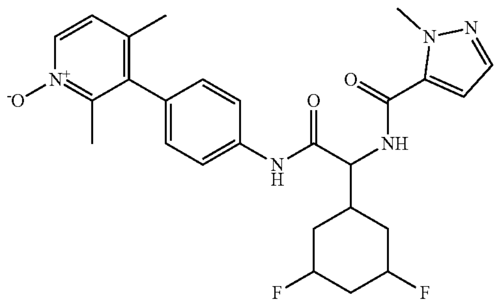 | 3-(4-(2-(3,5-difluorocyclohexyl)-2-(1-methyl-1H-pyrazole-5-carboxamido)acetamido) phenyl)-2,4-dimethylpyridine 1-oxide | n.t. | 7.29 |

-continued

| Ex. | Structure | Name | IL17AA + TNF IC50 IL-6 [umol I-1] | IL17AA FRET/ IL17Rawt IC50 [umol I-1] |
|---|---|---|---|---|
| 223 | 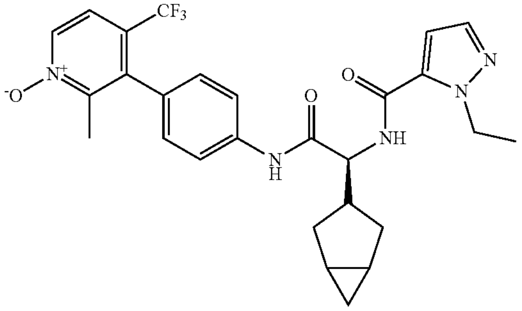 | 3-(4-((2S)-2-(bicyclo[3.1.0]hexan-3-yl)-2-(1-ethyl-1H-pyrazole-5-carboxamido)acetamido) phenyl)-2-methyl-4-(trifluoromethyl)pyridine 1-oxide | n.t. | 9.08 |
| 224 | 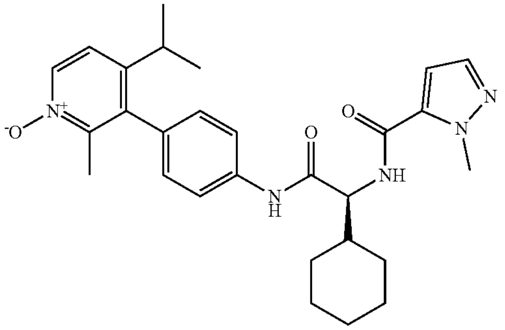 | (S)-3-(4-(2-cyclohexyl-2-(1-methyl-1H-pyrazole-5-carboxamido)acetamido) phenyl)-4-isopropyl-2-methylpyridine 1-oxide | 0.108 | 2.19 |
| 225 | 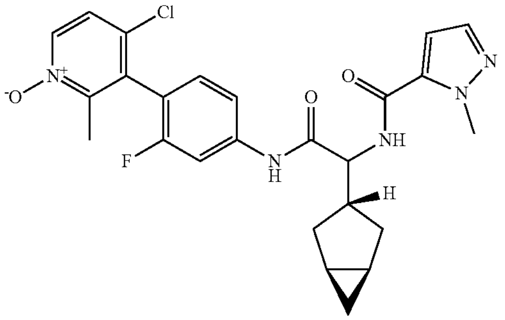 | 3-(4-(2-((1R,3s,5S)-bicyclo[3.1.0]hexan-3-yl)-2-(1-methyl-1H-pyrazole-5-carboxamido)acetamido)-2-fluorophenyl)-4-chloro-2-methylpyridine 1-oxide | 0.012 | 0.029 |

The invention claimed is:

1. A compound that is 2,4-dimethyl-3-(4-((S)-2-(1-methyl-1H-pyrazole-5-carboxamido)-2-((S)-1,2,3,4-tetrahydronaphthalen-1-yl)acetamido)phenyl)pyridine 1-oxide, or a pharmaceutically acceptable salt thereof.

2. A pharmaceutical composition comprising a compound, or a pharmaceutically acceptable salt thereof, according to claim 1, and a pharmaceutically acceptable carrier.

3. A combination comprising a compound, or a pharmaceutically acceptable salt thereof, according to claim 1, and one or more therapeutically active agents.

4. A method of treating an IL-17 mediated disease or condition, comprising administering to a subject a therapeutically effective amount of the compound, or a pharmaceutically acceptable salt thereof, according to claim 1, wherein the IL-17 mediated disease or condition is psoriasis, psoriatic arthritis, or rheumatoid arthritis.

* * * * *